United States Patent
Luo et al.

(10) Patent No.: US 9,718,804 B2
(45) Date of Patent: Aug. 1, 2017

(54) GSK-3 INHIBITORS

(71) Applicant: BRISTOL-MYERS SQUIBB COMPANY, Princeton, NJ (US)

(72) Inventors: Guanglin Luo, Madison, CT (US); Ling Chen, Middletown, CT (US); Gene M. Dubowchik, Middlefield, CT (US); Swanee E. Jacutin-Porte, Madison, CT (US); Vivekananda M. Vrudhula, Brier, WA (US); Senliang Pan, Woodbridge, CT (US); Prasanna Sivaprakasam, Middletown, CT (US); John E. Macor, Washington Crossing, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/033,813

(22) PCT Filed: Nov. 3, 2014

(86) PCT No.: PCT/US2014/063691
§ 371 (c)(1),
(2) Date: May 2, 2016

(87) PCT Pub. No.: WO2015/069594
PCT Pub. Date: May 14, 2015

(65) Prior Publication Data
US 2016/0272621 A1   Sep. 22, 2016

Related U.S. Application Data

(60) Provisional application No. 61/900,465, filed on Nov. 6, 2013.

(51) Int. Cl.
| C07D 213/02 | (2006.01) |
| C07D 401/14 | (2006.01) |
| C07D 405/14 | (2006.01) |
| C07D 413/14 | (2006.01) |
| C07D 417/14 | (2006.01) |
| C07D 487/04 | (2006.01) |
| C07D 471/04 | (2006.01) |

(52) U.S. Cl.
CPC ......... *C07D 401/14* (2013.01); *C07D 405/14* (2013.01); *C07D 413/14* (2013.01); *C07D 417/14* (2013.01); *C07D 471/04* (2013.01); *C07D 487/04* (2013.01)

(58) Field of Classification Search
CPC .................................. C07D 213/02

USPC .................................................. 546/255
See application file for complete search history.

(56) References Cited

U.S. PATENT DOCUMENTS

| 6,756,385 B2 | 6/2004 | Sanner et al. |
| 7,273,865 B2 | 9/2007 | Norcross |
| 7,531,556 B2 | 5/2009 | Green |
| 2007/0225292 A1 | 9/2007 | Amin et al. |
| 2008/0146536 A1 | 6/2008 | Cole et al. |
| 2016/0289210 A1 | 10/2016 | Luo et al. |

FOREIGN PATENT DOCUMENTS

| WO | WO 2009/007751 A2 | 1/2009 |
| WO | WO 2009/106209 A1 | 9/2009 |
| WO | WO 2012/116586 A1 | 9/2012 |
| WO | 2014049578 | * 4/2014 |

OTHER PUBLICATIONS

Database Registry [Online] Chemical Abstracts Service, Columbus, Ohio, Jan. 2010 (Jan. 24, 2010), retrieved from STN Database accession No. 1203187-94-3.

Helal, C.J., "Discovery and SAR of 2-amkinothiazole inhibitors of cyclin-dependent kinase 5/p25 as a potential treatment of Alzheimer's disease," Bioorganic & Medicinal Chemistry Letters, 14, pp. 5521-5525, (2004).

Yoshida, Ken-ichi, et al., "MexAB-OprM specific efflux pump inhibitors in *Pseudomonas aeruginosa*. Part 7: Highly soluble and in vivo active quaternary ammonium analogue D13-9001, a potential preclinical candidate," Bioorganic & Medicinal Chemistry, 15, pp. 7087-7097 (2007).

* cited by examiner

*Primary Examiner* — Niloofar Rahmani
(74) *Attorney, Agent, or Firm* — James Epperson

(57) ABSTRACT

The disclosure generally relates to compounds of formula I, including their salts, as well as compositions and methods of using the compounds to treat disorders associated with GSK-3.

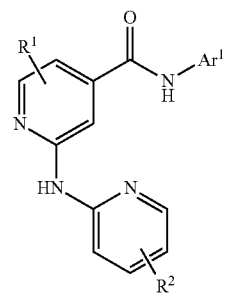

6 Claims, No Drawings

GSK-3 INHIBITORS

CROSS-REFERENCE TO RELATED APPLICATIONS

This application claims priority to Provisional Patent Application U.S. Ser. No. 61/900,465 filed Nov. 6, 2013, hereby incorporated by reference in its entirety.

BACKGROUND OF THE INVENTION

The disclosure generally relates to compounds of formula I, including their salts, as well as compositions and methods of using the compounds. The compounds inhibit GSK-3 and may be useful for the treatment of various disorders of the central nervous system.

GSK-3 is a proline directed serine/threonine kinase that carries out the phosphorylation of multiple protein substrates. Many of these proteins are involved in the regulation of numerous diverse cellular functions, including metabolism, differentiation, proliferation and apoptosis. GSK-3 is constitutively active, with its base level of activity being positively modulated by phosphorylation on Tyr216/219, depending on isoform. GSK-3 has a unique substrate selectivity profile that is distinguished by the strong preference for the presence of a phosphorylated residue optimally located four amino acids C-terminal to the site of GSK-3 phosphorylation. Most commonly, GSK-3 activity is associated with inducing a loss of substrate function, such that GSK-3 inhibition will frequently result in increased downstream substrate activity.

GSK-3 exists in two isoforms, GSK-3α (51 kDa) and GSK-3β (47 kDa), that share 84% overall identity and greater than 98% identity within their respective catalytic domains. Both primary isoforms are ubiquitously expressed, with high levels observed in the brain, particularly in the cortex and hippocampus. In most brain areas, GSK-3β is the predominant isoform. However, some studies suggest that GKS-3α and GSK-3β share very similar, if not entirely redundant functions in a number of cellular processes. The activity of GSK-3β is significantly reduced by phosphorylation at Ser9 in the N-terminal domain, most notably by protein kinase B (PKB or AKT). This inhibitory pathway has been proposed to result in neuroprotection, neurogenesis, and favorable outcomes following pharmacological treatment in various mood disorders.

Alzheimer's disease (AD) pathology is prominently associated with the formation of beta-amyloid (Aβ) plaques, soluble forms of Aβ such as Aβ1-42 that are associated with increased neuronal toxicity, and neurofibrillary tangles (NFTs). There is evidence to suggest that certain pathological mechanisms in AD, such as Aβ1-42, cause increases in GSK-3 activity in the brain. A principal consequence of this dysregulation is the hyperphosphorylation of the microtubule associated protein tau. This function of GSK-3 has been demonstrated both in cell culture, and in in vivo studies looking at tau and NFT formation. Hyper-phosphorylated tau disengages from microtubules resulting in structural destabilization of microtubules with concomitant negative effects on intracellular structures and transport mechanisms. In addition, the uncomplexed hyperphosphorylated tau assembles into paired helical filaments (PHFs) that aggregate to produce the stereotypic intracellular NFTs associated with AD. Other potential pathological consequences of over-activation of GSK-3 include neuroinflammation and neuronal apoptosis. In addition, GSK-3 has been demonstrated to be involved in mechanisms underlying memory and learning, and dysregulation of GSK-3 function may explain some of the early cognitive deficits observed in AD.

GSK-3 is also known to play a key role in glucose metabolism, and was first identified as the enzyme responsible for effecting the inhibitory phosphorylation of glycogen synthase, the result of which is to reduce the rate of conversion of glucose to glycogen, giving rise to elevated blood glucose levels. This function of GSK-3 is controlled by insulin. Binding of insulin to its receptor leads indirectly to the activation of AKT and subsequent inhibitory Ser9 phosphorylation of GSK-3.

These results and observations suggest that modulation of GSK-3 activity may be useful in the treatment of both the neuropathologic and symptomatic aspects of Alzheimer's disease, as well as other neurodegenerative diseases. These include, but are not limited to, tauopathies (for example, frontotemporal dementia, progressive supranuclear palsy, argyophilic grain disease, corticobasal degeneration, Pick's disease), Parkinson's disease, amyotrophic lateral schlerosis, stroke, Huntington's disease, peripheral neuropathies, traumatic brain injury, spinal cord trauma, and vascular dementias.

Compounds that inhibit GSK-3 may also have utility in the treatment of diabetes, inflammatory diseases such as rheumatoid arthritis and osteoarthritis, treatment-resistant depression, schizophrenia, bipolar disorder, manic depression, osteoporosis, cardioprotection, and various cancers such as gliomas, non-small cell lung cancer, pancreatic cancer, breast cancer, T- or B-cell leukemia, and multiple myeloma.

Recent reviews on the functions of GSK-3, potential therapeutic applications, and other compounds that inhibit the enzyme are listed below:

Kaidanovich-Beilin O and Woodgett J R (2011) GSK-3: functional insights from cell biology and animal models. *Front. Mol. Neurosci.* 4:40. doi: 10.3389/fnmol.2011.00040.

"Glycogen Synthase Kinase 3 (GSK-3) and Its Inhibitors", Martinez, Ana/Castro, Ana/Medina, Miguel (eds.), John Wiley and Sons (2006).

Gentles, R G, Hu, S. and Dubowchik, G M (2009) Recent Advances in the Discovery of GSK-3 Inhibitors and a Perspective on their Utility for the Treatment of Alzheimer's Disease. *Annual Reports in Medicinal Chemistry* 44, 3-26.

The invention provides technical advantages, for example, the compounds are novel inhibitors of GSK-3 and may be useful for the treatment of various disorders of the central nervous system. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

The invention encompasses compounds of Formula I, including pharmaceutically acceptable salts, pharmaceutical compositions, and their use in treating disorders associated with GSK-3.

One aspect of the invention is a compound of formula I

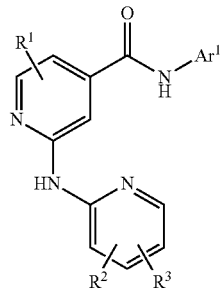

where:
R¹ is hydrogen, cyano, halo, alkyl, haloalkyl, alkoxy, or haloalkoxy;
R² is hydrogen, cyano, halo, alkyl, cyanoalkyl, haloalkyl, cycloalkyl, cyanocycloalkyl, (alkoxycarbonyl)alkenyl, alkoxy, haloalkoxy, alkylthio, haloalkylthio, cycloalkylthio, alkylcarbonyl, alkoxycarbonyl, aminocarbonyl, alkylsulfinyl, cycloalkylsulfinyl, phenylsulfinyl, alkylsulfonyl, haloalkylsulfonyl, cycloalkylsulfonyl, alkylcarbonylamino, morpholinyl, $SO_2N(R^4)(R^5)$;
R³ is hydrogen, cyano, halo, alkyl, haloalkyl, alkoxy, or haloalkoxy;
or R² and R³ taken together is —CH=CH—CH=CH—;
R⁴ is hydrogen or alkyl;
R⁵ is hydrogen or alkyl;
or $N(R^4)(R^5)$ taken together is azetidinyl, pyrrolidinyl, piperidinyl, piperazinyl, morpholinyl, and is substituted with 0-4 halo or alkyl substituents;
Ar¹ is 3-pyridinyl, 2-pyrazinyl, 4-pyridazinyl, 4-pyrimidinyl, 4-pyrazolyl, 4-isothiazolyl, or 3-imidazopyridazinyl, and is substituted with 1 substituent selected from hydrogen, cyano, halo, alkyl, haloalkyl, hydroxyalkyl, (cycloalkyl)hydroxyalkyl, (dicycloalkyl)hydroxyalkyl, (hydroxy)haloalkyl, alkoxyalkyl, $(N(R^4)(R^5))$alkyl, cycloalkyl, hydroxycycloalkyl, cycloalkenyl, alkoxy, haloalkoxy, (cycloalkyl)alkoxy, ((alkyl)cycloalkyl)alkoxy, alkylcarbonyl, cycloalkylcarbonyl, tetrahydrofuranyl, (alkyl)tetrahydrofuranyl, dioxolanyl, (alkyl)dioxolanyl, (cycloalkyl)dioxolanyl, (phenyl)dioxolanyl, (dialkyl)dioxolanyl, (haloalkyl)(alkyl)dioxolanyl, (trialkyl)dioxolanyl, dihydropyranyl, tetrahydropyranyl, hydroxytetrahydropyranyl, $N(R^4)(R^5)$, and Ar²; and is also substituted with 0-1 substituent selected from hydrogen, cyano, halo, alkyl, haloalkyl, alkoxy, and haloalkoxy;
Ar² is phenyl, pyridinyl, or pyrazolyl, and is substituted with 0-3 substituents selected from the group consisting of cyano, halo, alkyl, haloalkyl, alkoxy, and haloalkoxy;
or a pharmaceutically acceptable salt thereof.

Another aspect of the invention is a compound of formula I where R¹ is hydrogen or halo.

Another aspect of the invention is a compound of formula I where R² is haloalkyl.

Another aspect of the invention is a compound of formula I where Ar¹ is 3-pyridinyl substituted with 1 substituent selected from hydrogen, cyano, halo, alkyl, haloalkyl, hydroxyalkyl, (cycloalkyl)hydroxyalkyl, (dicycloalkyl)hydroxyalkyl, (hydroxy)haloalkyl, alkoxyalkyl, $(N(R^4)(R^5))$alkyl, cycloalkyl, hydroxycycloalkyl, cycloalkenyl, alkoxy, haloalkoxy, (cycloalkyl)alkoxy, ((alkyl)cycloalkyl)alkoxy, alkylcarbonyl, cycloalkylcarbonyl, tetrahydrofuranyl, (alkyl)tetrahydrofuranyl, dioxolanyl, (alkyl)dioxolanyl, (cycloalkyl)dioxolanyl, (phenyl)dioxolanyl, (dialkyl)dioxolanyl, (haloalkyl)(alkyl)dioxolanyl, (trialkyl)dioxolanyl, dihydropyranyl, tetrahydropyranyl, hydroxytetrahydropyranyl, $N(R^4)(R^5)$, and Ar²; and is also substituted with 0-1 substituent selected from hydrogen, cyano, halo, alkyl, haloalkyl, alkoxy, and haloalkoxy.

Another aspect of the invention is a compound of formula I where is phenyl substituted with 0-3 substituents selected from the group consisting of cyano, halo, alkyl, haloalkyl, alkoxy, and haloalkoxy.

For a compound of formula I, the scope of any instance of a variable substituent, including R¹, R², R³, R⁴, R⁵, Ar¹, and Ar², can be used independently with the scope of any other instance of a variable substituent. As such, the invention includes combinations of the different aspects.

Unless specified otherwise, these terms have the following meanings "Halo" includes fluoro, chloro, bromo, and iodo. "Alkyl" means a straight or branched alkyl group composed of 1 to 6 carbons. "Alkenyl" means a straight or branched alkyl group composed of 2 to 6 carbons with at least one double bond. "Alkynyl" means a straight or branched alkyl group composed of 2 to 6 carbons with at least one triple bond. "Cycloalkyl" means a monocyclic ring system composed of 3 to 7 carbons. "Haloalkyl" and "haloalkoxy" include all halogenated isomers from monohalo to perhalo. Terms with a hydrocarbon moiety (e.g. alkoxy) include straight and branched isomers for the hydrocarbon portion. "Aryl" means a monocyclic or bicyclic aromatic hydrocarbon groups having 6 to 12 carbon atoms, or a bicyclic fused ring system wherein one or both of the rings is a phenyl group. Bicyclic fused ring systems consist of a phenyl group fused to a four- to six-membered aromatic or non-aromatic carbocyclic ring. Representative examples of aryl groups include, but are not limited to, indanyl, indenyl, naphthyl, phenyl, and tetrahydronaphthyl. "Heteroaryl" means a 5 to 7 membered monocyclic or 8 to 11 membered bicyclic aromatic ring system with 1-5 heteroatoms independently selected from nitrogen, oxygen, and sulfur. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some Formula I compounds contain at least one asymmetric carbon atom, an example of which is shown below. The invention includes all stereoisomeric forms of the compounds, both mixtures and separated isomers. Mixtures of stereoisomers can be separated into individual isomers by methods known in the art.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Synthetic Methods

Compounds of Formula I may be made by methods known in the art including those described below and including variations within the skill of the art. Some reagents and intermediates are known in the art. Other reagents and intermediates can be made by methods known in the art using readily available materials. The variables (e.g. numbered "R" substituents) used to describe the synthesis of the compounds are intended only to illustrate how to make the compounds and are not to be confused with variables used in the claims or in other sections of the specification. The following methods are for illustrative purposes and are not intended to limit the scope of the invention. The schemes encompass reasonable variations known in the art.

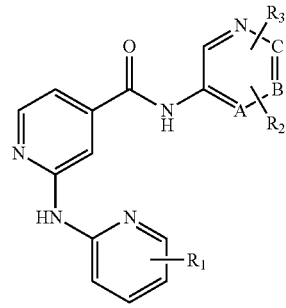

Formula I

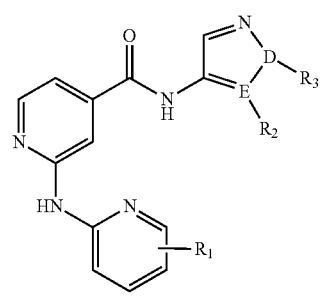

Compounds of Formula I can be synthesized through the following general scheme. Starting from either 2-chloro-isonicotinic acid or isonicotinic acid dichloride, reaction with commercially available or prepared 3-amino heterocycles can afford 2-chloro-isonicotinamides of formula II. Reaction of Formula II compounds with substituted 2-amino pyridines can obtain Formula I compounds. Direct amination of 2-chloro-isonicotinic acid with substituted 2-amino pyridines can afford intermediate acids of Formula III, which after amide formation reaction with various 3-amino heterocycles can also lead to Formula I compounds.

General Scheme I:

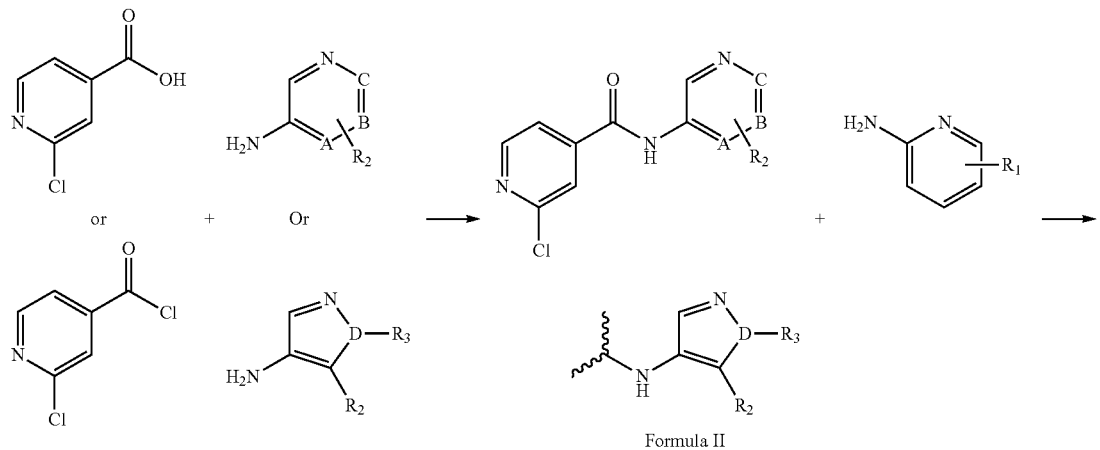

Formula II

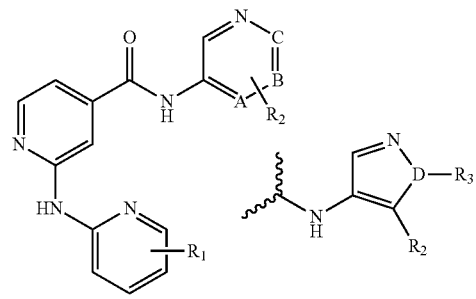
Formula I
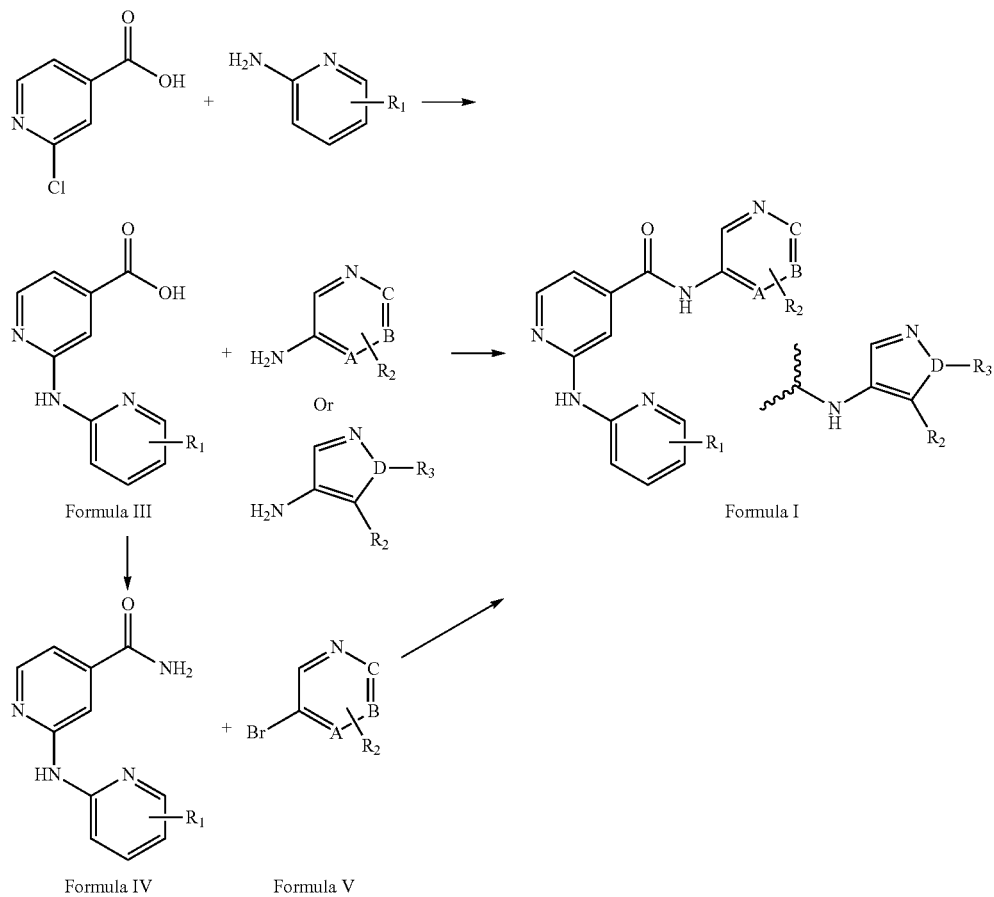
The variously substituted 3-amino heterocycles could be prepared through different approaches shown in General Scheme II.
General Scheme II: Representative amine intermediates.
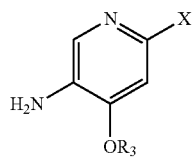
Amine A
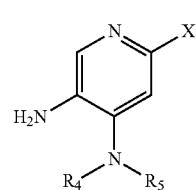
Amine B
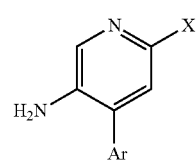
Amine C Amine D 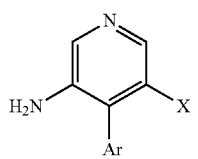

Amine E 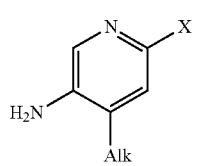

Amine F 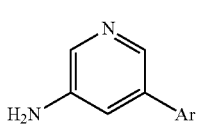

Amine G 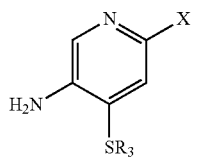

Amine H 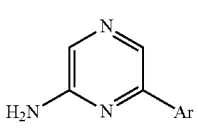

Amine I 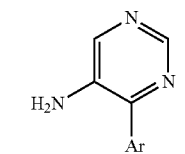

Amine J 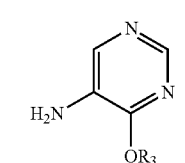

Amine K 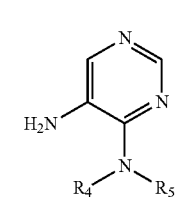

Amine L 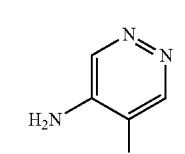

Amine M 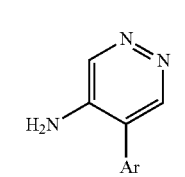

Amine N 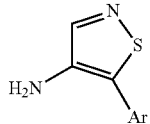

Amine O 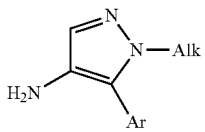

Amine 9 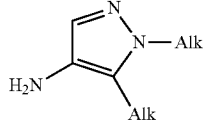

X = H, F, Cl, Me, etc.

Biological Methods

The kinase assay was performed in V-bottom 384-well plates. The final assay volume was 30 μl prepared from 15 μl additions of enzyme, substrates (fluoresceinated peptide FL-KRREILSRRP[ps]ERYR-NH2 and ATP) and test compounds in assay buffer (100 mM HEPES pH 7.4, 10 mM $MgCl_2$, 25 mM Beta-Glycerolphosphate, 0.015% Brij35 and 0.25 mM DTT). The reaction was incubated at room temperature for 20 hours and terminated by adding 45 μl of 35 mM EDTA to each sample. The reaction mixture was analyzed on the Caliper LabChip3000 (Caliper, Hopkinton, Mass.) by electrophoretic separation of the unphosphorylated substrate and phosphorylated product. Inhibition data were calculated by comparison of the no enzyme control reactions for 100% inhibition and vehicle-only reactions for 0% inhibition. The final concentration of reagents in the assay were 250 pM GSK3α or GSK3β, 20 uM ATP, 1.5 uM FL-KRREILSRRP[ps]ERYR-NH2, and 1.6% DMSO. Dose response curves were generated to determine the concentration required to inhibit 50% of the kinase activity ($IC_{50}$). Compounds were dissolved at 10 mM in dimethylsulfoxide (DMSO) and evaluated at eleven concentrations. $IC_{50}$ values were derived by non-linear regression analysis.

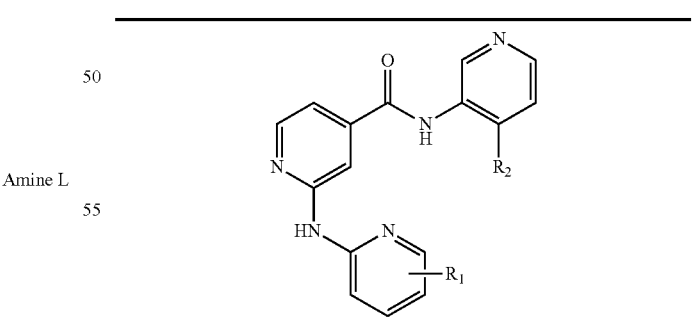

| Example | R1 | R2 | GSK3β/α (nM) | pTau (nM) |
|---|---|---|---|---|
| 1 | H | Ph | 3.4/2.6 | 213 |
| 2 | 6-CF3 | Ph | 6.8/7.3 | 574 |
| 3 | 4-CF3 | Ph | 9.0/8.7 | 705 |
| 4 | 5-CF3 | Ph | | |
| 5 | 5-Me | Ph | 0.77/4.8 | 183 |

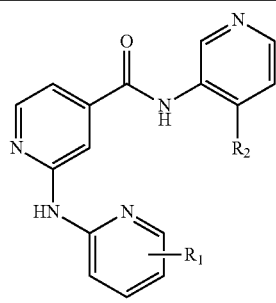

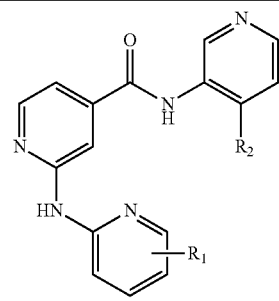

| Example | R1 | R2 | GSK3β/α (nM) | pTau (nM) |
|---|---|---|---|---|
| 6 | 4-Me | Ph | 1.1/1.3 | 164 |
| 7 | 6-F | Ph | 8.5/5.9 | 249 |
| 8 | 5-F | Ph | 4.1/1.9 | 132 |
| 9 | 4-Me-5-F | Ph | 4.1/2.5 | 110 |
| 10 | 5-CN | Ph | 0.98/0.58 | 27 |
| 11 | H | OEt | 8.9/2.8 | 294 |
| 12 | 3,4-Benzo | OEt | 5.9/35 | 5400 |
| 13 | 4-Me | OEt | 1.4/2.3 | 154 |
| 14 | 5-Me | OEt | 0.47/1.5 | 125 |
| 15 | 5-CF₃ | OEt | 1.3/0.56 | 42 |
| 16 | 5-CN | OEt | 1.1/0.62 | 12 |
| 17 | 5-CF₃ | OCH₂tBu | 1.6/0.89 | 43 |
| 18 | 5-CF₃ | OCH₂CF₃ | 0.71/0.42 | 13 |
| 19 | 5-CF₃ | OiPr | 1.6/0.55 | 16 |
| 20 | 5-CF₃ | 4-(3S-Me)-morpholinyl | 0.10/0.09 | 0.66 |
| 21 | 5-CF₃ | 4-(3R-Me)-morpholinyl | 0.70/0.28 | 9.1 |
| 22 | 5-CF₃ | 4-(2,2-Me₂)-morpholinyl | 0.48/0.31 | 18 |
| 23 | 5-CF₃ | 1-piperidinyl | 0.24/0.15 | 6.5 |
| 24 | 5-CF₃ | 1-(4,4-F₂)-piperidinyl | 0.69/0.49 | 4.6 |
| 25 | 5-CN | OCH₂tBu | 4.3/2.0 | 30 |
| 26 | 5-CN | Me | 14/8.2 | 670 |
| 27 | 5-CN | 1-piperidinyl | 0.42/0.18 | 5.2 |
| 28 | 5-CN | 4-(2,2-Me₂)-morpholinyl | 0.55/0.37 | 16 |
| 29 | 5-CN | OCH₂CF₃ | 0.69/0.62 | 16 |
| 30 | 5-S(O)2NMe2 | OCH₂CF₃ | 0.50/0.31 | 24 |
| 31 | 5-Cl | OCH₂CF₃ | 0.74/0.30 | 22 |
| 32 | 5-CF₃ | (3,6-dihydro-2H-pyran-4-yl) | 2.3/0.78 | 71 |
| 33 | 5-CF₃ | (2-methyl-1,3-dioxolan-2-yl) | 0.29/0.18 | 0.55 |
| 34 | 5-CF₃ | (1-hydroxypropan-2-yl) | 3.2/1.4 | 37 |
| 35 | 5-CF₃ | (tetrahydro-2H-pyran-4-yl) | 16/8.7 | 760 |
| 36 | 5-CF₃ | (cyclohex-1-en-1-yl) | 2.9/1.4 | 130 |
| 37 | 5-CF₃ | (3-oxobutan-2-yl) | 3.3/1.5 | 130 |
| 38 | 5-CF₃ | (1-hydroxycyclohexyl) | 1.1/0.71 | 8.8 |
| 39 | 5-CF₃ | (3,4-dihydro-2H-pyran-6-yl) | 1.2/0.93 | 140 |
| 40 | 5-CF₃ | (1,3-dioxolan-2-yl) | 23/46 | 3300 |
| 41 | 5-CF₃ | (tetrahydro-2H-pyran-2-yl) | 13/— | 120 |

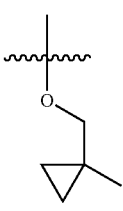 [SMILES: *OCC1(C)CC1]
| Example | R1 | R2 | GSK3β/α (nM) | pTau (nM) |
|---|---|---|---|---|
| 42 | 5-CF₃ | OCH₂CHF₂ | 0.49/0.27 | 21 |
| 43 | 5-CF₃ | 4-(2-Pyridine) | 0.77/0.59 | — |
| 44 | 5-CF₃ | 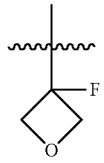 [SMILES: *C1(F)COC1] | 1.4/0.33 | 52 |
| 45 | 5-CF₃ | 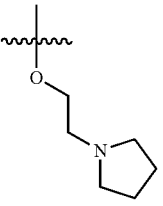 [SMILES: *OCCN1CCCC1] | 17/11 | 150 |
| 46 | 5-CF₃ | 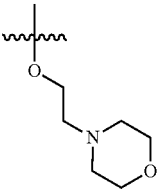 [SMILES: *OCCN1CCOCC1] | 150/75 | 4300 |
| 47 | 5-CF₃ | 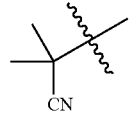 | 18/5.6 | 420 |
| 48 | 6-Cl | 4-(4-F-Ph) | 2.9/1.9 | 270 |
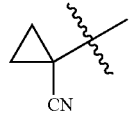
| Examples | R1 | R2 | GSK3β/α (nM) | pTau (nM) |
|---|---|---|---|---|
| 49 | CF₃ | 2-F | 0.65/0.32 | 53 |
| 50 | CF₃ | 4-F | 2.1/0.86 | 54 |
| 51 | CF₃ | 4-Cl | 9.9/6.9 | 266 |
| 52 | CF₃ | 2-F-4-CN | 3.6/1.5 | 35 |
| 53 | CF₃ | 2-CF3-4-F | 0.51/0.57 | 8.3 |
| 54 | CF₃ | 2-F-4-F | 2.8/0.96 | 57 |
| 55 | CF₃ | 2-F-4-OMe | 3.2/0.89 | 86 |
| 56 | CN | 4-F | 2.4/0.98 | 36 |
| 57 | CN | 2-F-4-F | 1.3/0.59 | 19 |
| 58 | Cl | 4-F | 0.86/0.36 | 57 |
| 59 | Cl | H | 0.90/0.39 | 45 |
| 60 | Cl | 4-Cl | 2.7/1.2 | 270 |
| 61 | 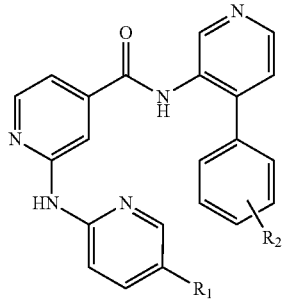 | H | 1.5/0.54 | 150 |
| 62 | 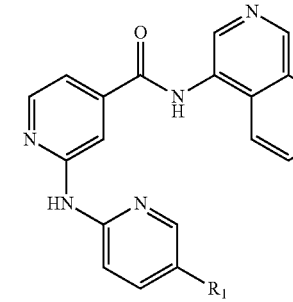 | H | 0.62/0.29 | 37 |
| 63 | Br | H | 9.3/3.4 | 150 |
| Examples | R1 | GSK3β/α (nM) | pTau (nM) |
|---|---|---|---|
| 64 | CF₃ | 10/3.1 | 610 |
| 65 | CN | 8.5/3.2 | 420 |

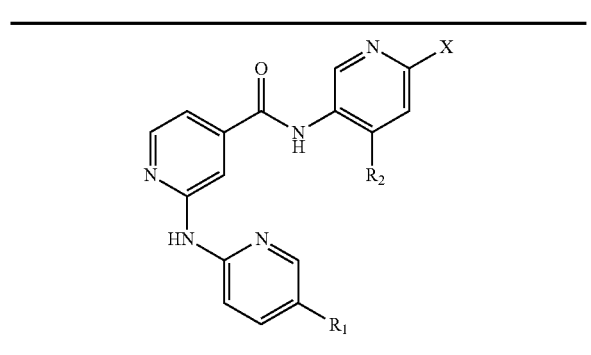

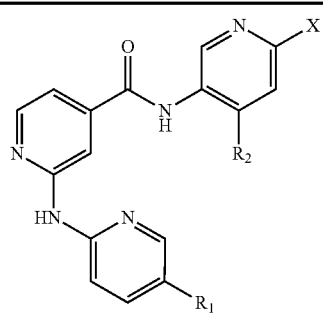

| Examples | R1 | R2 | X | GSK3β/α (nM) | pTau (nM) |
|---|---|---|---|---|---|
| 66 | CF₃ | Ph | Cl | 61/29 | 5849 |
| 67 | CF₃ | Ph | F | 7.0/4.0 | 524 |
| 68 | CF₃ | Ph | Me | 12/5.7 | 1011 |
| 69 | CF₃ | OCH₂CF₃ | F | 2.6/— | 165 |
| 70 | CF₃ | 4,4-difluoropiperidin-1-yl | Cl | 7.6/2.6 | 564 |
| 71 | CF₃ | 4,4-difluoropiperidin-1-yl | F | 1.3/0.36 | 60 |
| 72 | CF₃ | 4,4-difluoropiperidin-1-yl | Me | 3.5/0.76 | 120 |
| 73 | CF₃ | morpholin-4-yl | F | 1.0/0.6 | 43 |
| 74 | CF₃ | 4-hydroxytetrahydropyran-4-yl | Cl | 3.4/2.5 | 180 |
| 75 | CF₃ | neopentyloxymethyl | F | 5.1/2.4 | 830 |
| 76 | CF₃ | 2-methyl-1,3-dioxolan-2-yl | Cl | 0.32/0.20 | 13 |
| 77 | CF₃ | 2-methyltetrahydrofuran-2-yl | Cl | 0.63/0.35 | 31 |
| 78 | CF₃ | 2,4,5-trimethyl-1,3-dioxolan-2-yl | Cl | 4.5/3.2 | 170 |
| 79 | CF₃ | 2-ethyl-1,3-dioxolan-2-yl | Cl | 0.31/0.17 | 33 |
| 80 | CF₃ | OCH₂CHF₂ | F | 6.2/3.3 | 86 |
| 81 | CF₃ | 2-ethyl-4,5-dimethyl-1,3-dioxolan-2-yl | Cl | 6.7/4.0 | 1900 |

-continued

| Examples | R1 | R2 | X | GSK3β/α (nM) | pTau (nM) |
|---|---|---|---|---|---|
| 82 | CF$_3$ | 2-methyl-1,3-dioxolan-2-yl | F | 7.1/1.9 | 230 |
| 83 | CF$_3$ | 2-isopropyl-1,3-dioxolan-2-yl | Cl | 1.1/0.55 | 57 |
| 84 | CF$_3$ | 2-methyl-1,3-dioxolan-2-yl | O(CH$_2$)$_2$OH | 9.2/5.0 | 350 |
| 85 | CF$_3$ | 2-ethyl-4-(trifluoromethyl)-1,3-dioxolan-2-yl | Cl | 64/35 | 5500 |
| 86 | CF$_3$ | 2-ethyl-4-(trifluoromethyl)-1,3-dioxolan-2-yl | Cl | 12/2.4 | 510 |
| 87 | CF$_3$ | 1,4-dioxaspiro[4.2]heptan-5-yl | Cl | 0.04/0.17 | 6.6 |

-continued

| Examples | R1 | R2 | X | GSK3β/α (nM) | pTau (nM) |
|---|---|---|---|---|---|
| 88 | CF$_3$ | 2-propyl-1,3-dioxolan-2-yl | Cl | 0.69/0.23 | 80 |
| 89 | CF$_3$ | 2-ethyl-4-methyl-1,3-dioxolan-2-yl | Cl | 1.6/1.7 | 340 |
| 90 | CF$_3$ | 2-ethyl-4-methyl-1,3-dioxolan-2-yl | Cl | 2.0/0.94 | 150 |
| 91 | CF$_3$ | 2-methyl-1,3-dioxolan-2-yl | OMe | 3.9/20 | 1200 |
| 92 | CF$_3$ | cyclopropyl ketone | Cl | 8.8/4.0 | 1400 |
| 93 | CF$_3$ | hydroxy(cyclopropyl)methyl | Cl | 2.6/0.78 | 110 |
| 94 | CF$_3$ | 1,4-dioxaspiro[4.2]heptan-5-yl | F | 0.06/0.03 | 1.2 |

-continued

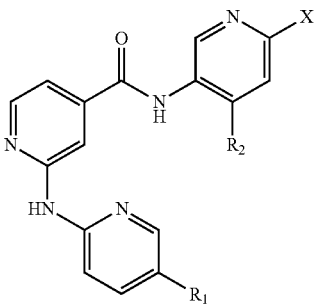

| Examples | R1 | R2 | X | GSK3β/α (nM) | pTau (nM) |
|---|---|---|---|---|---|
| 95 | CF₃ | (1-phenyl-1,3-dioxolan-2-yl methyl) | Cl | 10/5.5 | 910 |
| 96 | CF₃ | (spiro cyclopropane dioxolane with methyl) | Cl | 0.29/0.16 | 39 |
| 97 | CF₃ | (ethyl methyl dioxolane with methyl) | Cl | 1.5/0.56 | 84 |
| 98 | CF₃ | (HO, cyclopropyl, methyl) | Cl | 3.7/4.0 | 230 |
| 99 | CF₃ | (HO, dicyclopropyl) | Cl | 6.4/4.6 | 430 |
| 100 | CF₃ | (HO, propyl methyl) | Cl | 11/8.4 | 500 |

-continued

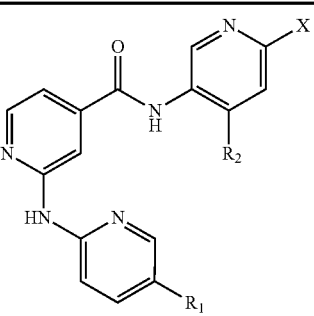

| Examples | R1 | R2 | X | GSK3β/α (nM) | pTau (nM) |
|---|---|---|---|---|---|
| 101 | CF₃ | (HO, cyclopropyl, ethyl, methyl) | Cl | 11/7.4 | 660 |
| 102 | CF₃ | (HO, cyclopropyl, isopropyl, methyl) | Cl | 43/30 | 1200 |
| 103 | CF₃ | (HO, isopropyl, methyl) | Cl | 6.7/3.9 | 540 |
| 104 | CF₃ | (HO, t-butyl, methyl) | Cl | 18/9.9 | 280 |
| 105 | CF₃ | (spiro cyclopropane dioxolane with methyl) | Me | —/— | 2.0 |
| 106 | CF₃ | (HO, cyclopropyl, methyl) | Me | 0.25/0.49 | 22 |
| 107 | CF₃ | (HO, cyclopropyl, methyl) | Me | 0.92/0.75 | 94 |

-continued

| Examples | R1 | R2 | X | GSK3β/α (nM) | pTau (nM) |
|---|---|---|---|---|---|
| 108 | H | 2-ethyl-1,3-dioxolan-2-yl | Cl | 1.4/0.95 | 30 |
| 109 | Me | 2-ethyl-1,3-dioxolan-2-yl | Cl | 1.8/1.2 | 45 |
| 110 | Cl | OCH₂CF₃ | F | 3.8/0.51 | 170 |
| 111 | Cl | 4-hydroxytetrahydropyran-4-yl | Cl | 2.6/1.4 | 530 |
| 112 | Cl | OCH₂C(CH₃)₃ | F | 5.0/3.0 | 850 |
| 113 | F | 2-ethyl-1,3-dioxolan-2-yl | Cl | 1.7/0.04 | 14 |
| 114 | F | OCH₂CHF₂ | F | 4.4/1.5 | 220 |

| Examples | GSK3β/α (nM) | pTau (nM) |
|---|---|---|
| 115 | 0.97/0.65 | 297 |

| Examples | GSK3β/α (nM) | pTau (nM) |
|---|---|---|
| 116 | 7.8/3.9 | 610 |

| Examples | GSK3β/α (nM) | pTau (nM) |
|---|---|---|
| 117 | 3.0/1.4 | 254 |

23

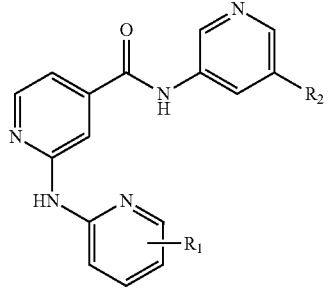

| Examples | R1 | R2 | GSK3β/α (nM) | pTau (nM) |
|---|---|---|---|---|
| 118 | 5-CF₃ | pyrazole-4-CN | 7.3/— | 360 |
| 119 | 5-CF₃ | 4-methylpyrazole | | |
| 120 | 5-CF₃ | pyrazole-4-CF₃ | 29/14 | 1500 |
| 121 | 5-CF₃ | morpholine | 25/12 | 1500 |
| 122 | 6-CF₃ | pyrazole-4-CN | 6.9/2.2 | 2000 |
| 123 | 6-CF₃ | OCH₂CF₃ | 7.4/3.2 | 520 |
| 124 | 6-CF₃ | OCH₂-cyclopropyl | 9.4/3.5 | 3600 |
| 125 | 6-CF₃ | OCH₂-(1-methylcyclopropyl) | 12/3.8 | 2200 |
| 126 | 6-CF₃ | OCH₂-(2-methylcyclopropyl) | 9.7/4.8 | 3200 |

24

| Examples | R1 | R2 | GSK3β/α (nM) | pTau (nM) |
|---|---|---|---|---|
| 127 | 5-CF₃ | 2-F | 11/6.0 | 1753 |
| 128 | 5-CF₃ | 2-Cl | 12/16 | 2176 |
| 129 | 5-CF₃ | 2,5-di-F | 18/9.8 | 2100 |
| 130 | 5-CF₃ | 2,3-di-F | 42/20 | 2600 |
| 131 | 5-F | 2-F | 6.1/3.0 | 640 |
| 132 | 4-Me | 2-F | 9.0/6.2 | 1900 |
| 133 | 5-Me | 2-F | 7.3/3.4 | 1400 |
| 134 | 6-CF₃ | 2-F | 3.9/1.5 | 470 |
| 135 | 5-CN | 2-F | 3.0/1.7 | 670 |
| 136 | 6-F | 2-F | 11/2.7 | 1100 |
| 137 | 6-Me | 2-F | 7.1/5.6 | 2700 |
| 138 | 6-Et | 2-F | 3.5/2.2 | 4700 |
| 139 | 6-OMe | 2-F | 5.4/3.2 | 1300 |
| 140 | 5-(N-morpholino) | 2-F | 6.7/10 | 980 |
| 141 | 5-OMe | 2-F | 3.5/1.8 | 680 |
| 142 | 5,6-(phenyl fused) | 2-F | 23/5.6 | 2100 |
| 143 | 5,6-di-Me | 2-F | 8.7/6.0 | 2800 |
| 144 | 6-CF₃ | H | 10/39 | 910 |
| 145 | 6-CF₃ | 2-Cl | 6.4/4.4 | 730 |
| 146 | 6-CF₃ | 2,5-di-F | 5.1/3.2 | 1400 |
| 147 | 6-CF₃ | 2,3-di-F | 2.3/44 | 380 |
| 148 | 6-Et, 5-CN | 2-F | 4.5/— | 360 |
| 149 | 6-CO₂Me | 2-F | 2.7/— | 1700 |
| 150 | 6-Cl | 2-F | 3.5/— | 1100 |
| 151 | 6,5-di-MeO | 2-F | 6.0/2.4 | 510 |
| 152 | 6-CN | 2-F | 1.6/0.87 | 260 |
| 153 | 5,6-(phenyl fused) | 2-F | 1.5/0.45 | 200 |
| 154 | 6-NHC(O)tBu | 2-F | 9.2/2.2 | 1100 |
| 155 | 5-CN-6-Me | 2-F | 3.6/1.2 | 570 |
| 156 | 5-S(O)₂NH₂ | 2-F | 3.0/1.6 | 5600 |
| 157 | 5-S(O)₂NMe₂ | 2-F | 3.6/1.6 | 750 |
| 158 | 5-C(O)Me | 2-F | 6.0/3.0 | 690 |
| 159 | 5-S(O)₂N(CH₂)₅ | 2-F | 3.9/1.9 | 960 |
| 160 | 5-C(O)NH₂ | 2-F | 16/7.6 | — |
| 161 | 5-CH=CHCO₂Me | 2-F | 23/8.0 | — |
| 162 | 6-CN | 4-CN | 3.5/2.4 | — |
| 163 | 1-CN-cyclopropyl (at 5) | 2-F | 3.2/1.1 | 610 |

-continued

| Examples | R1 | R2 | GSK3β/α (nM) | pTau (nM) |
|---|---|---|---|---|
| 164 | (2,2-dimethyl-CN group) | 2-F | 4.9/2.4 | 3100 |
| 165 | 6-CN | 3-F-4-CN | 1.2/0.40 | 84 |
| 166 | 6-CN | 2-CN-3-F | 0.91/0.28 | 390 |

| Examples | R | GSK3β/α (nM) | pTau (nM) |
|---|---|---|---|
| 167 | Ph | 1.8/0.55 | 230 |
| 168 | OCH$_2$CF$_3$ | 1.5/0.73 | — |

| Examples | R | GSK3β/α (nM) | pTau (nM) |
|---|---|---|---|
| 169 | OCH$_2$CF$_3$ | 28/10 | 3898 |

| Examples | R | X | GSK3β/α (nM) | pTau (nM) |
|---|---|---|---|---|
| 170 | n-Pr | H | 0.75/0.21 | 49 |
| 171 | CH$_2$CF$_3$ | H | 1.2/0.61 | 47 |
| 172 | Ph | H | 5.6/1.1 | 240 |
| 173 | 2-Pr | H | 0.52/0.19 | 48 |
| 174 | t-Bu | H | 0.14/0.08 | 27 |
| 175 | i-Bu | H | 1.1/0.40 | 78 |
| 176 | Cyclopropyl | Cl | 11/7.0 | 1100 |

| Examples | R | X | GSK3β/α (nM) | pTau (nM) |
|---|---|---|---|---|
| 177 | Ph | H | 3.9/1.1 | 760 |
| 178 | t-Bu | H | 0.12/1.2 | 13 |
| 179 | 2-Pr | H | 4.3/1.2 | — |
| 180 | Cyclopropyl | Cl | 15/7.6 | 790 |

| Examples | R | X | GSK3β/α (nM) | pTau (nM) |
|---|---|---|---|---|
| 181 | Me | H | 1.2/0.77 | — |
| 182 | n-Pr | H | 5.2/2.1 | 15 |
| 183 | Ph | H | 2.2/0.75 | 200 |
| 184 | CH$_2$CF$_3$ | H | 120/4.8 | 130 |
| 185 | i-Bu | H | 0.51/4.8 | 49 |
| 186 | 2-Pr | H | 1.2/0.04 | 2.0 |
| 187 | t-Bu | H | 0.40/0.07 | 1.1 |

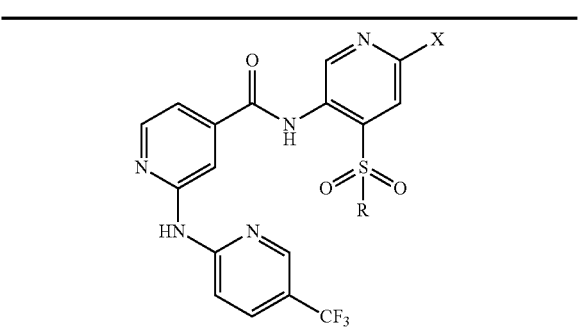
| Examples | R | X | GSK3β/α (nM) | pTau (nM) |
|---|---|---|---|---|
| 188 | Cyclopropyl | Cl | 5.0/3.3 | 150 |
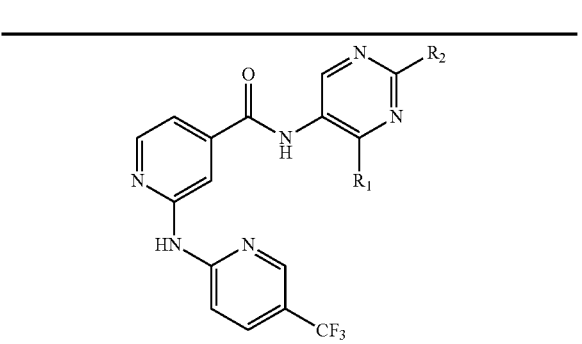
| Examples | R | GSK3β/α (nM) | pTau (nM) |
|---|---|---|---|
| 189 | H | 11/4.3 | 1030 |
| 190 | 2-F-Ph | 68/29 | 10000 |
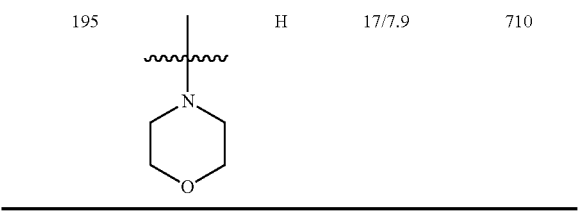
| Examples | R1 | R2 | GSK3β/α (nM) | pTau (nM) |
|---|---|---|---|---|
| 191 | H | H | 17/9 | 1600 |
| 192 | Br | H | 23/9.3 | 520 |
| 193 | Ph | H | 3.6/1.9 | 165 |
| 194 | OCH2CF3 | H | 3.2/1.6 | 140 |
| 195 | morpholinyl | H | 17/7.9 | 710 |
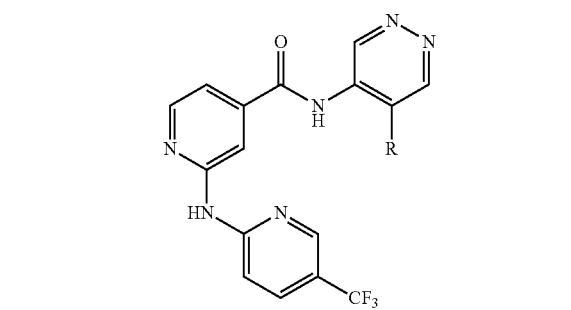
| Examples | R | GSK3β/α (nM) | pTau (nM) |
|---|---|---|---|
| 196 | H | 80/25 | 7400 |
| 197 | Br | 70/22 | 3500 |
| 198 | Ph | 6.7/2.9 | 180 |
| 199 | 4-(allyloxy)phenyl | 8.7/— | 470 |
| 200 | 2-methyl-1,3-dioxolan-2-yl | 0.62/0.39 | 3.2 |
| 201 | 2-(3-chloropropyl)-2-methyl-1,3-dioxolan-2-yl | 0.19/0.40 | 28 |
| 202 | cyclopropanecarbonyl (isopropyl) | 2.9/1.1 | — |
| 203 | 1-cyclopropyl-1-hydroxyethyl | 1.2/0.94 | 10000 |

| Examples | GSK3β/α (nM) | pTau (nM) |
|---|---|---|
| 204 | 3.0/1.7 | 300 |

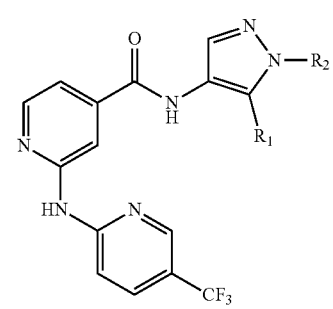

| Examples | R1 | R2 | GSK3β/α (nM) | pTau (nM) |
|---|---|---|---|---|
| 205 | Ph | H | 28/20 | 10000 |
| 206 | | Me | 3.1/2.7 | 400 |
| 207 | | Me | 0.09/0.10 | 1.4 |
| 208 | 2OH) | Me | 3.0/3.6 | 120 |
| 209 | OH) | Me | 0.30/0.21 | 21 |

| Examples | GSK3β/α (nM) | pTau (nM) |
|---|---|---|
| 210 | 33/11 | 2300 |

Pharmaceutical Compositions and Methods of Treatment

Compounds of formula I can be useful in treating neurological or psychiatric disorders. Therefore, another aspect of the invention is a composition comprising a compound of formula I or a pharmaceutically acceptable salt thereof, and a pharmaceutically acceptable carrier.

Another aspect of the invention is a method for the treatment for modulation of GSK-3 activity may be useful in the treatment of both the neuropathologic and symptomatic aspects of Alzheimer's disease, as well as other neurodegenerative diseases. These include, but are not limited to, tauopathies (for example, frontotemporal dementia, progressive supranuclear palsy, argyophilic grain disease, corticobasal degeneration, Pick's disease), Parkinson's disease, amyotrophic lateral sclerosis, stroke, Huntington's disease, peripheral neuropathies, traumatic brain injury, spinal cord trauma, and vascular dementias, which comprises administering to a patient a therapeutically affective amount of a compound of formula I.

Another aspect of the invention is a method for the treatment for diabetes, inflammatory diseases such as rheumatoid arthritis and osteoarthritis, treatment-resistant depression, schizophrenia, bipolar disorder, manic depression, osteoporosis, cardioprotection, and various cancers such as gliomas, non-small cell lung cancer, pancreatic cancer, breast cancer, T- or B-cell leukemia, and multiple myeloma, which comprises administering to a patient a therapeutically affective amount of a compound of formula I.

Another aspect of the invention is a method for the treatment of Alzheimer's disease which comprises administering to a patient a therapeutically affective amount of a compound of formula I.

Another aspect of the invention is the use of a compound of formula I in the manufacture of a medicament for the treatment of Alzheimer's disease.

"Patient" means a person suitable for therapy as understood by practitioners in the field of affective disorders and neurodegenerative disorders.

"Treatment," "therapy," and related terms are used as understood by practitioners in the field of neurological and psychiatric disorders.

The compounds of this invention are generally given as pharmaceutical compositions comprised of a therapeutically effective amount of a compound or its pharmaceutically acceptable salt and a pharmaceutically acceptable carrier and may contain conventional excipients. Pharmaceutically acceptable carriers are those conventionally known carriers having acceptable safety profiles. Compositions encompass all common solid and liquid forms including for example capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, Mack Publishing Company, Easton, Pa., 17th edition, 1985.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

DESCRIPTION OF SPECIFIC EMBODIMENTS

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC" for t-butoxycarbonyl, "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for CF$_3$(CF$_2$)$_3$SO$_2$—; and "TMOF" for trimethylorthoformate.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

General Synthesis of Formula II

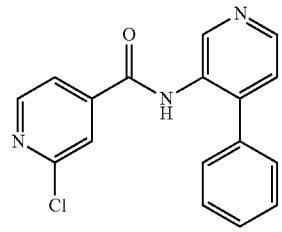 [SMILES: O=C(Nc1cnccc1-c1ccccc1)c1ccnc(Cl)c1]

2-Chloro-N-(4-phenylpyridin-3-yl)isonicotinamide

In a 100 mL round-bottom flask was added 2-chloroisonicotinoyl chloride (556 mg, 3.16 mmol) and 4-phenylpyridin-3-amine dihydrochloride (384 mg, 1.58 mmol) in methylene chloride (14 mL) to give a tan suspension. DIEA (0.910 mL, 5.21 mmol) was added dropwise. The solids dissolved and the resulting greenish solution was stirred at rt for two days. To this was added 12 mL of 1.0 N NaOH (7.6 equiv.), and the mixture was stirred at rt for 5 h. LCMS showed complete conversion to the desired product. The mixture was partitioned between ethyl acetate and water. The layers were separated. The organic layer was washed with brine, dried, and concentrated. The residue was purified by flash column chromatography on silica gel, eluting with 8% methanol/methylene chloride, to afford the desired product (470 mg, 96%) as a tan foam: $^1$H NMR (400 MHz, CDCl3) δ 9.45 (s, 1H), 8.69-8.36 (m, 2H), 8.22 (s, 1H), 7.55 (s, 4H), 7.43 (d, J=6.3 Hz, 2H), 7.37 (d, J=3.7 Hz, 1H), 7.28 (d, J=4.0 Hz, 1H).

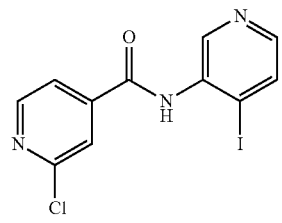 [SMILES: O=C(Nc1cnccc1I)c1ccnc(Cl)c1]

2-Chloro-N-(4-iodopyridin-3-yl)isonicotinamide

MS (ESI) (m/z): 360.0 (M+H)⁺.

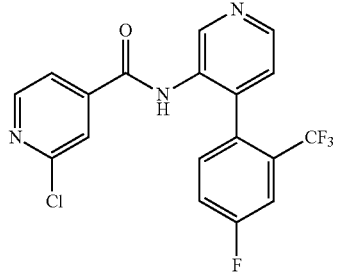 [SMILES: O=C(Nc1cnccc1-c1ccc(F)cc1C(F)(F)F)c1ccnc(Cl)c1]

2-Chloro-N-(4-(4-fluoro-2-(trifluoromethyl)phenyl)pyridin-3-yl)isonicotinamide

A mixture of PdCl2(dppf) (0.013 g, 0.018 mmol), sodium carbonate (0.296 mL, 0.591 mmol), (4-fluoro-2-(trifluoromethyl)phenyl)boronic acid (0.123 g, 0.591 mmol) and 2-chloro-N-(4-iodopyridin-3-yl)isonicotinamide (0.1063 g, 0.296 mmol) was heated for 1 h at 80° C. LCMS showed the desired product. The reaction was filtered through a celite cartridge and washed with methylene chloride. The filtrate was concentrated and the product purified by flash chromatography on silica gel, eluting with ethyl acetate in hexane from 0 to 50% to 100%, to afford the desired product (41 mg, 35%): MS (ESI) (m/z): 396.1 (M+H)⁺; ¹H NMR (500 MHz, CHLOROFORM-d) δ 9.25 (s, 1H), 8.54 (d, J=5.0 Hz, 1H), 8.46 (dd, J=5.1, 0.7 Hz, 1H), 7.68 (br. s., 1H), 7.56 (d, J=8.4 Hz, 1H), 7.48 (dd, J=1.4, 0.7 Hz, 1H), 7.40 (dd, J=6.4, 1.5 Hz, 2H), 7.28-7.26 (m, 1H), 7.23 (d, J=4.9 Hz, 1H).

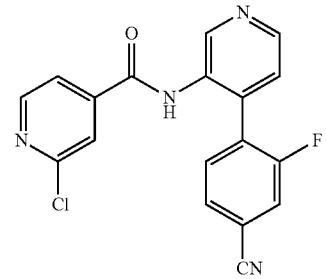

2-Chloro-N-(4-(4-cyano-2-fluorophenyl)pyridin-3-yl)isonicotinamide

MS (ESI) (m/z): 353.1 (M+H)⁺; ¹H NMR (400 MHz, CHLOROFORM-d) δ 9.01 (s, 1H), 8.62 (d, J=5.0 Hz, 1H), 8.51 (d, J=5.0 Hz, 1H), 8.31 (br. s., 1H), 7.64-7.59 (m, 2H), 7.57-7.49 (m, 2H), 7.46 (dd, J=5.1, 1.4 Hz, 1H), 7.33 (d, J=5.0 Hz, 1H); ¹⁹F NMR (376 MHz, CHLOROFORM-d) δ −111.21 (s, 1F).

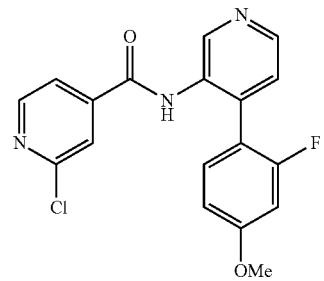 [SMILES: COc1ccc(-c2ccncc2NC(=O)c2ccnc(Cl)c2)c(F)c1]

2-Chloro-N-(4-(4-methoxy-2-fluorophenyl)pyridin-3-yl)isonicotinamide

MS (ESI) (m/z): 358.1 (M+H)⁺.

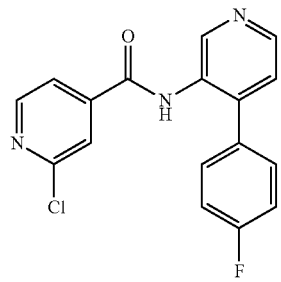 [SMILES: O=C(Nc1cnccc1-c1ccc(F)cc1)c1ccnc(Cl)c1]

2-Chloro-N-(4-(4-fluorophenyl)pyridin-3-yl)isonicotinamide

MS (ESI) (m/z): 328.1 (M+H)⁺.

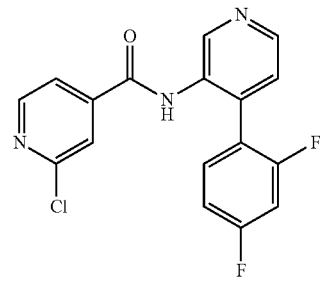 [SMILES: O=C(Nc1cnccc1-c1ccc(F)cc1F)c1ccnc(Cl)c1]

2-Chloro-N-(4-(2,4-difluorophenyl)pyridin-3-yl)isonicotinamide

MS (ESI) (m/z): 346.1 (M+H)⁺.

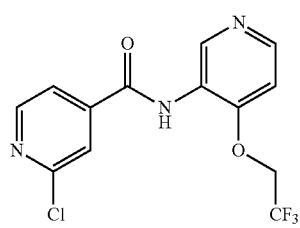 [SMILES: O=C(Nc1cnccc1OCC(F)(F)F)c1ccnc(Cl)c1]

2-Chloro-N-(4-(2,2,2-trifluoroethoxy)pyridin-3-yl)
isonicotinamide

MS (ESI) (m/z): 332 (M+H)+.

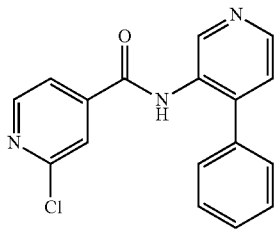 [SMILES: O=C(Nc1cnccc1-c1ccccc1)c1ccnc(Cl)c1]

2-Chloro-N-(4-phenylpyridin-3-yl)isonicotinamide
(alternative synthesis)

To 4-phenylpyridin-3-amine (0.5 g, 2.94 mmol) and 2-chloroisonicotinic acid (0.486 g, 3.08 mmol) in EtOAc (10 mL) was added DIEA (2.57 mL, 14.69 mmol) followed by T3P, 50% in EtOAc (2 mL, 3.43 mmol). The reaction was stirred at rt overnight. It was diluted with EtOAc and washed with water, brine and dried over sodium sulfate. The crude product was dissolved in a small amount of dichloromethane and charged to a 120 g silica gel cartridge which was eluted with 0-15% dichloromethane/methanol over a period of 40 mins. The desired fractions were combined and dried under vacuo to give 2-chloro-N-(4-phenylpyridin-3-yl)isonicotinamide (0.75 g, 2.421 mmol, 82% yield). MS (ESI) (m/z): 310.0 (M+H)+.

Example 1

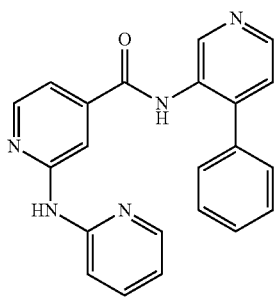 [SMILES: O=C(Nc1cnccc1-c1ccccc1)c1ccnc(Nc2ccccn2)c1]

N-(4-Phenylpyridin-3-yl)-2-(pyridin-2-ylamino)
isonicotinamide

In a 5 mL vial was added 2-chloro-N-(4-phenylpyridin-3-yl)isonicotinamide (31.7 mg, 0.102 mmol), pyridin-2-amine (11.6 mg, 0.123 mmol), and Cs$_2$CO$_3$ (50.0 mg, 0.154 mmol) in dioxane (0.6 mL) to give a tan suspension under nitrogen. PdOAc$_2$ (0.919 mg, 4.09 µmol) and XANTPHOS (3.55 mg, 6.14 µmol) were added under nitrogen. The vial was sealed under nitrogen, and the mixture was heated at 100° C. overnight. After 18 h, LCMS showed ca 60% conversion to the desired product. The mixture was diluted with water and ethyl acetate. The layers were separated. The organic layer was dried and concentrated. The residue was dissolved in 1.5 ml DMF and purified by prep-HPLC (13.4 mg, 36%): MS (ESI) (m/z): 368.2 (M+H)+; $^1$H NMR (500 MHz, DMSO) δ 10.35 (s, 1H), 9.91 (s, 1H), 8.65 (s, 1H), 8.58 (d, J=5.0 Hz, 1H), 8.35 (d, J=5.2 Hz, 1H), 8.25 (dd, J=4.9, 1.3 Hz, 1H), 8.13 (s, 1H), 7.69 (d, J=2.9 Hz, 2H), 7.57-7.52 (m, 2H), 7.52-7.45 (m, 3H), 7.44-7.39 (m, 1H), 7.18 (d, J=4.8 Hz, 1H), 6.95-6.88 (m, 1H).

Example 2

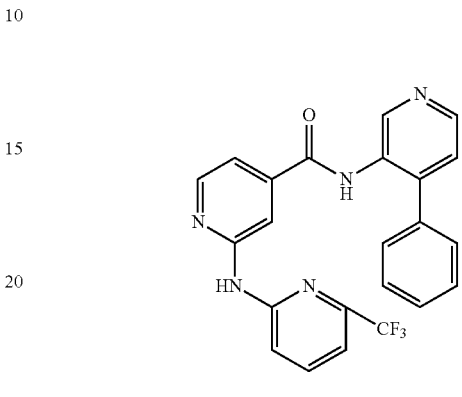

N-(4-Phenylpyridin-3-yl)-2-((6-(trifluoromethyl)
pyridin-2-yl)amino)isonicotinamide MS (ESI) (m/z): 436.2 (M+H)+; $^1$H NMR (500 MHz, DMSO-d$_6$) δ 0.42-10.36 (m, 2H), 8.65 (s, 1H), 8.59 (d, J=4.9 Hz, 1H), 8.51 (d, J=5.2 Hz, 1H), 8.43 (d, J=5.2 Hz, 1H), 8.17 (s, 1H), 8.05 (s, 1H), 7.54 (d, J=7.3 Hz, 2H), 7.52-7.45 (m, 3H), 7.44-7.39 (m, 1H), 7.27 (d, J=4.6 Hz, 1H), 7.23 (d, J=5.2 Hz, 1H).

Example 3

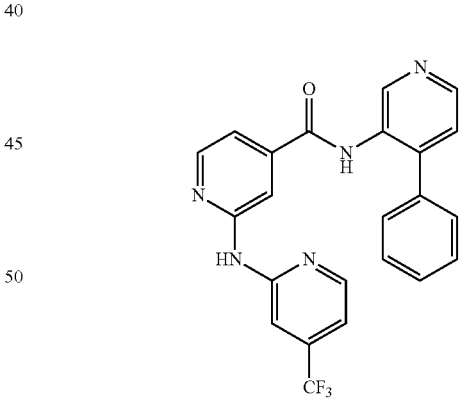

N-(4-Phenylpyridin-3-yl)-2-((4-(trifluoromethyl)
pyridin-2-yl)amino)isonicotinamide MS (ESI) (m/z): 436.2 (M+H)+; $^1$H NMR (500 MHz, DMSO-d$_6$) δ 10.42 (s, 1H), 10.39 (s, 1H), 8.62 (s, 1H), 8.59 (d, J=5.2 Hz, 1H), 8.40 (d, J=5.2 Hz, 1H), 8.12 (d, J=8.5 Hz, 1H), 8.03 (s, 1H), 7.96 (t, J=7.9 Hz, 1H), 7.54 (d, J=7.3 Hz, 2H), 7.50 (d, J=5.2 Hz, 1H), 7.46 (t, J=7.5 Hz, 2H), 7.42-7.37 (m, 2H), 7.25 (d, J=5.2 Hz, 1H).

Example 5

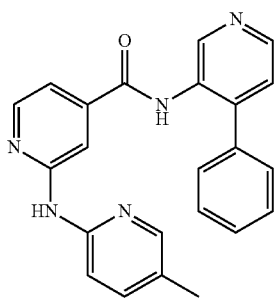 [SMILES: Cc1ccc(Nc2cc(C(=O)Nc3cnccc3-c3ccccc3)ccn2)nc1]

2-((5-Methylpyridin-2-yl)amino)-N-(4-phenylpyridin-3-yl)isonicotinamide

MS (ESI) (m/z): 382.2 (M+H)$^+$.

Example 6

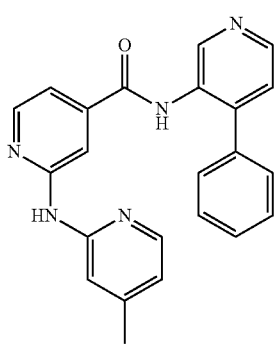 [SMILES: Cc1ccnc(Nc2cc(C(=O)Nc3cnccc3-c3ccccc3)ccn2)c1]

2-((4-Methylpyridin-2-yl)amino)-N-(4-phenylpyridin-3-yl)isonicotinamide

MS (ESI) (m/z): 382.2 (M+H)$^+$; $^1$H NMR (500 MHz, DMSO-d$_6$) δ 10.33 (s, 1H), 9.81 (s, 1H), 8.65 (s, 1H), 8.59 (d, J=5.2 Hz, 1H), 8.35 (d, J=5.2 Hz, 1H), 8.16-8.08 (m, 2H), 7.57-7.36 (m, 7H), 7.16 (d, J=4.6 Hz, 1H), 6.77 (d, J=5.2 Hz, 1H), 2.29 (s, 3H).

Example 7

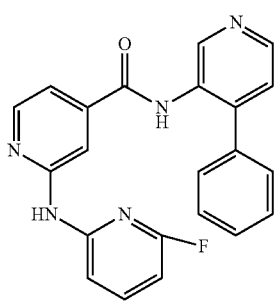 [SMILES: O=C(Nc1cnccc1-c1ccccc1)c1ccnc(Nc2cccc(F)n2)c1]

2-((6-Fluoropyridin-2-yl)amino)-N-(4-phenylpyridin-3-yl)isonicotinamide

MS (ESI) (m/z): 386.3 (M+H)$^+$.

Example 8

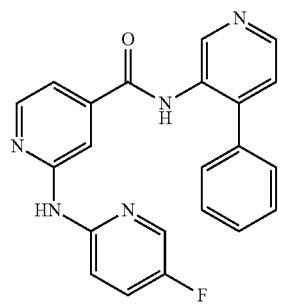

2-((5-Fluoropyridin-2-yl)amino)-N-(4-phenylpyridin-3-yl)isonicotinamide

MS (ESI) (m/z): 386.2 (M+H)$^+$.

Example 9

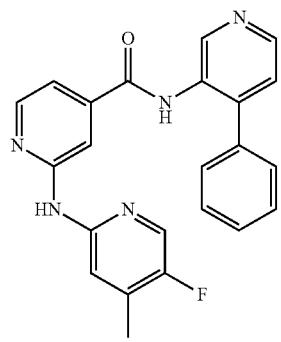 [SMILES: Cc1cc(Nc2cc(C(=O)Nc3cnccc3-c3ccccc3)ccn2)ncc1F]

2-((5-Fluoro-4-methylpyridin-2-yl)amino)-N-(4-phenylpyridin-3-yl)isonicotinamide MS (ESI) (m/z): 400.2 (M+H)$^+$; $^1$H NMR (500 MHz, DMSO-d$_6$) δ 10.33 (s, 1H), 9.87 (s, 1H), 8.64 (s, 1H), 8.58 (d, J=5.2 Hz, 1H), 8.34 (d, J=5.2 Hz, 1H), 8.13 (s, 1H), 7.96 (s, 1H), 7.69 (d, J=5.5 Hz, 1H), 7.56-7.52 (m, 2H), 7.51-7.45 (m, 3H), 7.44-7.38 (m, 1H), 7.16 (d, J=4.9 Hz, 1H), 2.28 (s, 3H).

Example 10

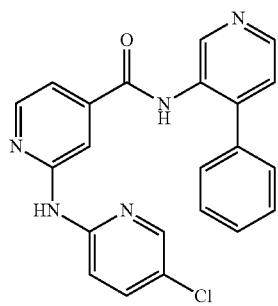

2-((5-Cyanopyridin-2-yl)amino)-N-(4-phenylpyridin-3-yl)isonicotinamide

MS (ESI) (m/z): 393.2 (M+H)$^+$; $^1$H NMR (500 MHz, DMSO-d$_6$) δ 10.58 (br. s., 1H), 10.42 (br. s., 1H), 8.69 (d, J=2.4 Hz, 1H), 8.66 (s, 1H), 8.58 (d, J=4.9 Hz, 1H), 8.45 (d, J=5.2 Hz, 1H), 8.14-8.06 (m, 2H), 7.87 (d, J=8.9 Hz, 1H), 7.54 (d, J=7.6 Hz, 2H), 7.51-7.44 (m, 3H), 7.43-7.38 (m, 1H), 7.33 (d, J=4.9 Hz, 1H).

Example 115

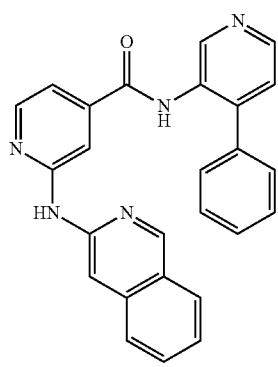 [SMILES: O=C(Nc1cnccc1-c1ccccc1)c1ccnc(Nc2cc3ccccc3cn2)c1]

2-(Isoquinolin-3-ylamino)-N-(4-phenylpyridin-3-yl)isonicotinamide

MS (ESI) (m/z): 418.2 (M+H)$^+$; $^1$H NMR (500 MHz, DMSO-d$_6$) δ 10.36 (s, 1H), 10.05 (s, 1H), 9.11 (s, 1H), 8.65 (s, 1H), 8.60 (d, J=4.9 Hz, 1H), 8.47 (s, 1H), 8.43 (d, J=5.2 Hz, 1H), 8.01 (d, J=7.9 Hz, 1H), 7.82 (d, J=8.5 Hz, 1H), 7.71 (s, 1H), 7.66 (s, 1H), 7.57-7.53 (m, 2H), 7.53-7.38 (m, 5H), 7.17 (d, J=5.2 Hz, 1H).

Example 116

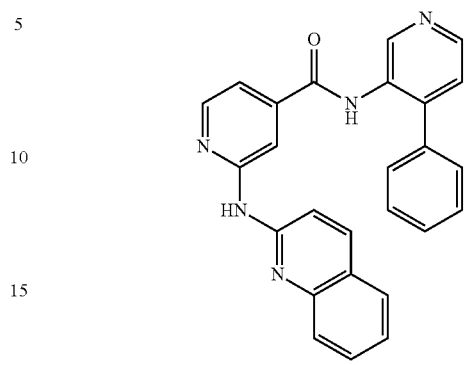

N-(4-Phenylpyridin-3-yl)-2-(quinolin-2-ylamino)isonicotinamide

MS (ESI) (m/z): 418.3 (M+H)$^+$; $^1$H NMR (500 MHz, DMSO-d$_6$) δ 10.46 (s, 1H), 10.31 (s, 1H), 8.94 (s, 1H), 8.67 (s, 1H), 8.61 (d, J=5.2 Hz, 1H), 8.42 (d, J=4.9 Hz, 1H), 8.19 (d, J=8.9 Hz, 1H), 7.81 (d, J=7.6 Hz, 1H), 7.74-7.70 (m, 1H), 7.68-7.63 (m, 1H), 7.59 (s, 2H), 7.56 (d, J=9.2 Hz, 1H), 7.52 (d, J=5.2 Hz, 1H), 7.45 (t, J=7.6 Hz, 2H), 7.39 (dd, J=7.0, 2.1 Hz, 2H), 7.27 (d, J=4.6 Hz, 1H).

Example 11

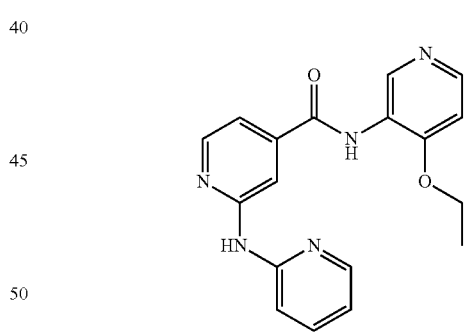

N-(4-Ethoxypyridin-3-yl)-2-(pyridin-2-ylamino)isonicotinamide

MS (ESI) (m/z): 336.2 (M+H)$^+$; $^1$H NMR (500 MHz, DMSO-d$_6$) δ 9.94 (s, 1H), 9.86 (s, 1H), 8.67 (s, 1H), 8.40 (d, J=5.2 Hz, 1H), 8.35 (d, J=5.8 Hz, 1H), 8.29-8.25 (m, 1H), 8.23 (s, 1H), 7.76-7.66 (m, 2H), 7.34 (d, J=4.6 Hz, 1H), 7.18 (d, J=5.5 Hz, 1H), 6.92 (ddd, J=6.5, 5.0, 1.7 Hz, 1H), 4.21 (q, J=6.9 Hz, 2H), 1.37 (t, J=6.9 Hz, 3H).

Example 12

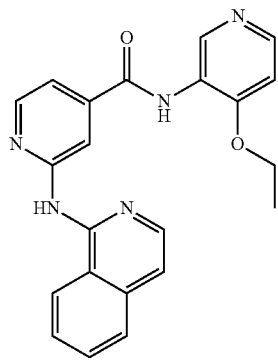 [SMILES: CCOc1ccncc1NC(=O)c1ccnc(Nc2nccc3ccccc23)c1]

N-(4-Ethoxypyridin-3-yl)-2-(isoquinolin-1-ylamino)isonicotinamide

MS (ESI) (m/z): 386.2 (M+H)+; 1H NMR (500 MHz, DMSO-d6) δ 10.00 (s, 1H), 9.90 (br. s., 1H), 8.70 (s, 1H), 8.67 (s, 1H), 8.61 (d, J=8.5 Hz, 1H), 8.51 (d, J=4.9 Hz, 1H), 8.35 (d, J=5.5 Hz, 1H), 8.14 (d, J=5.8 Hz, 1H), 7.91 (d, J=7.9 Hz, 1H), 7.77 (t, J=7.5 Hz, 1H), 7.65 (t, J=7.3 Hz, 1H), 7.46 (br. s., 1H), 7.40 (d, J=5.8 Hz, 1H), 7.18 (d, J=5.8 Hz, 1H), 4.21 (q, J=6.8 Hz, 2H), 1.37 (t, J=7.0 Hz, 3H).

Example 13

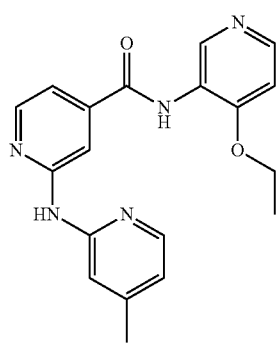 [SMILES: CCOc1ccncc1NC(=O)c1ccnc(Nc2cc(C)ccn2)c1]

N-(4-Ethoxypyridin-3-yl)-2-((4-methylpyridin-2-yl)amino)isonicotinamide

MS (ESI) (m/z): 350.2 (M+H)+; 1H NMR (500 MHz, DMSO-d6) δ 9.84 (d, J=6.7 Hz, 2H), 8.67 (s, 1H), 8.40 (d, J=4.9 Hz, 1H), 8.34 (d, J=5.8 Hz, 1H), 8.24 (s, 1H), 8.13 (d, J=5.2 Hz, 1H), 7.53 (s, 1H), 7.32 (d, J=4.3 Hz, 1H), 7.17 (d, J=5.5 Hz, 1H), 6.77 (d, J=4.9 Hz, 1H), 4.21 (q, J=6.9 Hz, 2H), 2.30 (s, 3H), 1.37 (t, J=6.9 Hz, 3H).

Example 14

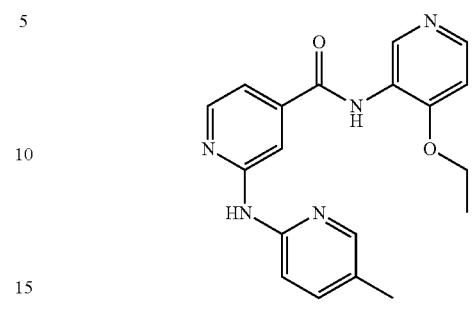

N-(4-Ethoxypyridin-3-yl)-2-((5-methylpyridin-2-yl)amino)isonicotinamide

MS (ESI) (m/z): 350.3 (M+H)+; 1H NMR (500 MHz, DMSO-d6) δ 9.82 (s, 1H), 8.67 (s, 1H), 8.38 (d, J=5.2 Hz, 1H), 8.34 (d, J=5.8 Hz, 1H), 8.12 (d, J=19.2 Hz, 2H), 7.67 (d, J=8.5 Hz, 1H), 7.54 (dd, J=8.5, 2.1 Hz, 1H), 7.29 (d, J=4.3 Hz, 1H), 7.17 (d, J=5.8 Hz, 1H), 4.21 (q, J=6.8 Hz, 2H), 2.24 (s, 3H), 1.37 (t, J=7.0 Hz, 3H).

Example 15

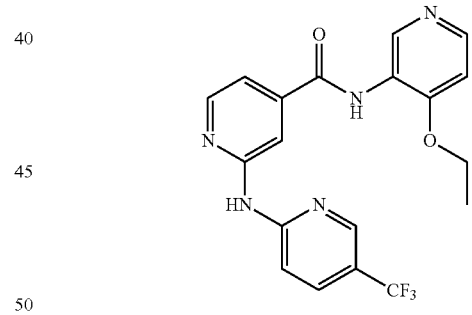

N-(4-Ethoxypyridin-3-yl)-2-((5-trifluoromethylpyridin-2-yl)amino)isonicotinamide MS (ESI) (m/z): 404.2 (M+H)+; 1H NMR (500 MHz, DMSO-d6) δ 10.50 (s, 1H), 9.91 (s, 1H), 8.64 (d, J=15.9 Hz, 2H), 8.48 (d, J=5.2 Hz, 1H), 8.35 (d, J=5.8 Hz, 1H), 8.22 (s, 1H), 8.06 (dd, J=8.9, 2.4 Hz, 1H), 7.94 (d, J=8.9 Hz, 1H), 7.45 (d, J=4.3 Hz, 1H), 7.18 (d, J=5.5 Hz, 1H), 4.21 (q, J=6.8 Hz, 2H), 1.37 (t, J=6.9 Hz, 3H).

Example 16

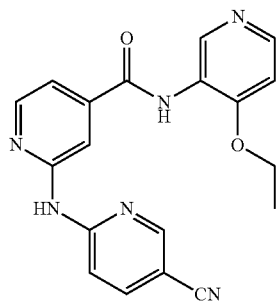 [SMILES: CCOc1ccncc1NC(=O)c1ccnc(Nc2ccc(C#N)cn2)c1]

N-(4-Ethoxypyridin-3-yl)-2-((5-cyanopyridin-2-yl)amino)isonicotinamide

MS (ESI) (m/z): 361.3 (M+H)$^+$; $^1$H NMR (500 MHz, DMSO-d$_6$) δ 10.62 (br. s., 1H), 9.95 (br. s., 1H), 8.71 (d, J=2.4 Hz, 1H), 8.65 (s, 1H), 8.50 (d, J=5.2 Hz, 1H), 8.35 (d, J=5.5 Hz, 1H), 8.21 (s, 1H), 8.11 (dd, J=8.9, 2.4 Hz, 1H), 7.90 (d, J=8.9 Hz, 1H), 7.49 (d, J=4.6 Hz, 1H), 7.18 (d, J=5.8 Hz, 1H), 4.21 (q, J=6.8 Hz, 2H), 1.37 (t, J=7.0 Hz, 3H).

Example 30

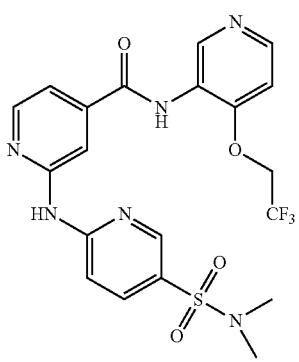 [SMILES: CN(C)S(=O)(=O)c1ccc(Nc2cc(C(=O)Nc3cnccc3OCC(F)(F)F)ccn2)nc1]

2-((5-(N,N-Dimethylsulfamoyl)pyridin-2-yl)amino)-N-(4-(2,2,2-trifluoroethoxy)pyridin-3-yl)isonicotinamide MS (ESI) (m/z): 497.2 (M+H)$^+$; $^1$H NMR (500 MHz, DMSO-d$_6$) δ 10.63 (s, 1H), 10.17 (br. s., 1H), 8.61 (s, 1H), 8.57 (d, J=2.4 Hz, 1H), 8.50 (d, J=5.2 Hz, 1H), 8.45 (d, J=5.5 Hz, 1H), 8.28 (s, 1H), 8.03 (dd, J=9.0, 2.6 Hz, 1H), 7.92 (d, J=9.2 Hz, 1H), 7.45 (d, J=4.9 Hz, 1H), 7.33 (d, J=5.5 Hz, 1H), 4.98 (q, J=8.5 Hz, 2H), 2.65 (s, 6H).

Example 50

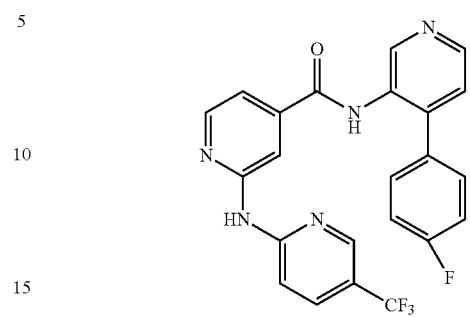

N-(4-(4-Fluorophenyl)pyridin-3-yl)-2-((5-(trifluoromethyl)pyridin-2-yl)amino)isonicotinamide MS (ESI) (m/z): 454.2 (M+H)$^+$; $^1$H NMR (500 MHz, DMSO-d$_6$) δ 10.43 (s, 2H), 8.64 (s, 1H), 8.57 (d, J=4.9 Hz, 2H), 8.42 (d, J=4.9 Hz, 1H), 8.08 (s, 1H), 8.03 (dd, J=9.0, 2.6 Hz, 1H), 7.86 (d, J=8.9 Hz, 1H), 7.57 (dd, J=8.5, 5.5 Hz, 2H), 7.49 (d, J=4.9 Hz, 1H), 7.36-7.24 (m, 3H).

Example 52

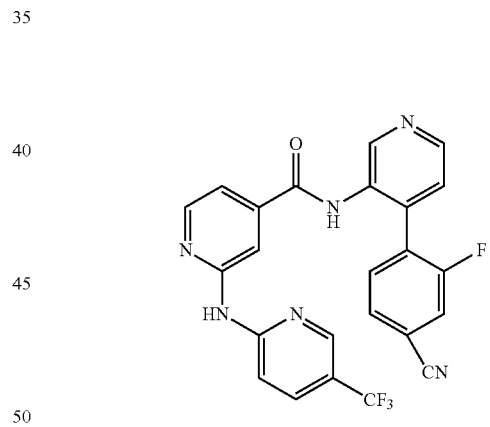

N-(4-(2-Fluoro-4-cyano-phenyl)pyridin-3-yl)-2-((5-(trifluoromethyl)pyridin-2-yl)amino)isonicotinamide MS (ESI) (m/z): 479.2 (M+H)$^+$; $^1$H NMR (500 MHz, DMSO-d$_6$) δ 10.52 (br. s., 1H), 10.46 (s, 1H), 8.77 (s, 1H), 8.63 (d, J=4.9 Hz, 1H), 8.60 (s, 1H), 8.43 (d, J=4.9 Hz, 1H), 8.07-7.95 (m, 3H), 7.89 (d, J=8.9 Hz, 1H), 7.80 (dd, J=7.9, 1.2 Hz, 1H), 7.65 (t, J=7.5 Hz, 1H), 7.54 (d, J=5.2 Hz, 1H), 7.23 (d, J=4.9 Hz, 1H).

Example 53

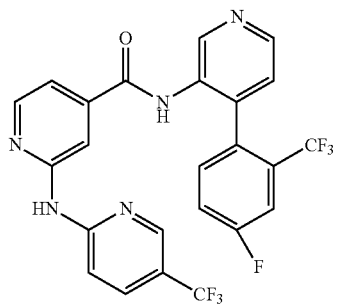 [SMILES: O=C(Nc1cnccc1-c1ccc(F)cc1C(F)(F)F)c1ccnc(Nc2ccc(C(F)(F)F)cn2)c1]

N-(4-(2-Trifluoromethyl-4-fluoro-phenyl)pyridin-3-yl)-2-((5-(trifluoromethyl)pyridin-2-yl)amino)isonicotinamide MS (ESI) (m/z): 522.3 (M+H)$^+$; $^1$H NMR (500 MHz, DMSO-d$_6$) δ 10.44 (s, 1H), 10.21 (br. s., 1H), 8.77 (s, 1H), 8.57 (d, J=4.9 Hz, 2H), 8.39 (d, J=4.9 Hz, 1H), 8.04 (dd, J=9.2, 2.4 Hz, 1H), 7.99 (s, 1H), 7.84 (d, J=9.2 Hz, 1H), 7.77 (dd, J=9.3, 2.6 Hz, 1H), 7.63 (td, J=8.5, 2.6 Hz, 1H), 7.49 (dd, J=8.5, 5.5 Hz, 1H), 7.38 (d, J=4.9 Hz, 1H), 7.12 (dd, J=5.2, 1.2 Hz, 1H).

Example 54

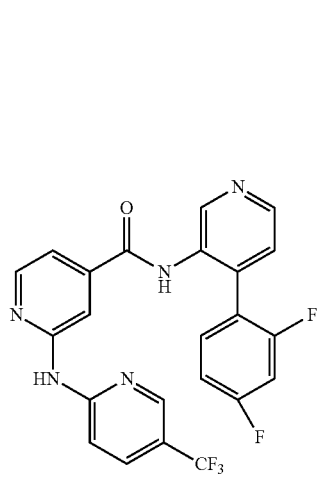 [SMILES: O=C(Nc1cnccc1-c1ccc(F)cc1F)c1ccnc(Nc2ccc(C(F)(F)F)cn2)c1]

N-(4-(2, 4-Difluoro-phenyl)pyridin-3-yl)-2-((5-(trifluoromethyl)pyridin-2-yl)amino)isonicotinamide MS (ESI) (m/z): 472.2 (M+H)$^+$; $^1$H NMR (500 MHz, DMSO-d$_6$) δ 10.46 (s, 1H), 10.40 (br. s., 1H), 8.74 (s, 1H), 8.62-8.56 (m, 2H), 8.42 (d, J=5.2 Hz, 1H), 8.09-8.02 (m, 2H), 7.87 (d, J=8.9 Hz, 1H), 7.53-7.47 (m, 2H), 7.44-7.34 (m, 1H), 7.27-7.16 (m, 2H).

Example 55

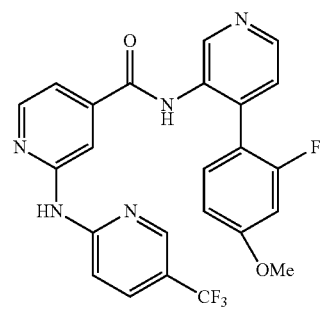 [SMILES: COc1ccc(-c2ccncc2NC(=O)c2ccnc(Nc3ccc(C(F)(F)F)cn3)c2)c(F)c1]

N-(4-(2-Fluoro-4-methoxy-phenyl)pyridin-3-yl)-2-((5-(trifluoromethyl)pyridin-2-yl)amino)isonicotinamide MS (ESI) (m/z): 484.3 (M+H)$^+$; $^1$H NMR (500 MHz, DMSO-d$_6$) δ 10.47 (s, 1H), 10.33 (br. s., 1H), 8.70 (s, 1H), 8.58 (s, 1H), 8.55 (d, J=4.9 Hz, 1H), 8.43 (d, J=4.9 Hz, 1H), 8.11 (s, 1H), 8.04 (dd, J=8.9, 2.4 Hz, 1H), 7.87 (d, J=8.9 Hz, 1H), 7.45 (d, J=4.9 Hz, 1H), 7.37 (t, J=8.7 Hz, 1H), 7.27 (d, J=4.6 Hz, 1H), 6.95 (dd, J=12.4, 2.3 Hz, 1H), 6.88 (dd, J=8.5, 2.4 Hz, 1H), 3.78 (s, 3H).

Example 56

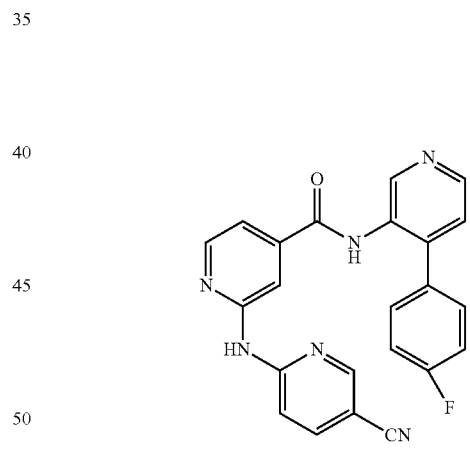

2-((5-Cyanopyridin-2-yl)amino)-N-(4-(4-fluorophenyl)pyridin-3-yl)isonicotinamide MS (ESI) (m/z): 411.2 (M+H)$^+$; $^1$H NMR (500 MHz, DMSO-d$_6$) δ 10.55 (s, 1H), 10.43 (br. s., 1H), 8.68-8.62 (m, 2H), 8.57 (d, J=5.2 Hz, 1H), 8.44 (d, J=4.9 Hz, 1H), 8.10-8.02 (m, 2H), 7.83 (d, J=9.5 Hz, 1H), 7.60-7.53 (m, 2H), 7.49 (d, J=5.2 Hz, 1H), 7.35-7.26 (m, 3H).

Example 57

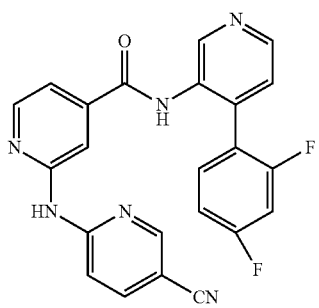 [SMILES: N#Cc1ccc(Nc2cc(C(=O)Nc3cnccc3-c3ccc(F)cc3F)ccn2)nc1]

2-((5-Cyanopyridin-2-yl)amino)-N-(4-(2,4-difluoro-phenyl)pyridin-3-yl)isonicotinamide MS (ESI) (m/z): 429.2 (M+H)+; $^1$H NMR (500 MHz, DMSO-d$_6$) δ 10.58 (s, 1H), 10.44 (br. s., 1H), 8.74 (s, 1H), 8.68 (d, J=2.4 Hz, 1H), 8.57 (d, J=5.2 Hz, 1H), 8.44 (d, J=5.2 Hz, 1H), 8.09 (dd, J=8.9, 2.1 Hz, 1H), 8.06 (s, 1H), 7.85 (d, J=8.9 Hz, 1H), 7.54-7.46 (m, 2H), 7.42-7.35 (m, 1H), 7.28 (d, J=5.2 Hz, 1H), 7.20 (td, J=8.5, 2.6 Hz, 1H).

Example 63

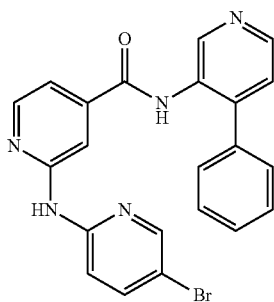 [SMILES: O=C(Nc1cnccc1-c1ccccc1)c1ccnc(Nc2ccc(Br)cn2)c1]

2-((5-Bromopyridin-2-yl)amino)-N-(4-phenylpyridin-3-yl)isonicotinamide

MS (ESI) (m/z): 448.2 (M+H)+; $^1$H NMR (400 MHz, METHANOL-d$_4$) δ ppm 8.85 (s, 1H) 8.52 (d, J=5.27 Hz, 1H) 8.33 (d, J=5.77 Hz, 2H) 7.81-7.92 (m, 2H) 7.41-7.50 (m, 7H) 7.37 (d, J=9.04 Hz, 1H) 7.30 (br. s., 1H).

General Synthesis of Formula III

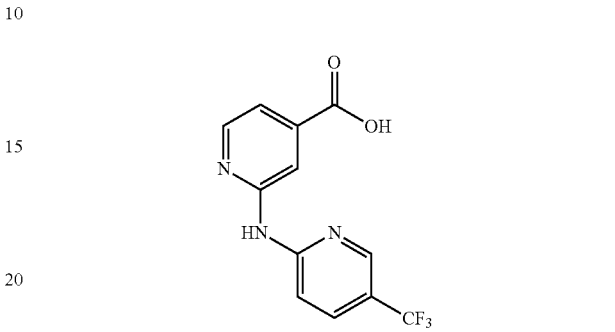

2-((5-(Trifluoromethyl)pyridin-2-yl)amino)isonicotinic acid

To an oven-dried vial containing a stir bar, Brettphos precatalyst (0.101 g, 0.127 mmol), Brettphos (0.068 g, 0.127 mmol), 2-chloroisonicotinic acid (2.0 g, 13 mmol), 5-(trifluoromethyl)pyridin-2-amine (2.68 g, 16.5 mmol) and K$_2$CO$_3$ (2.63 g, 19.0 mmol) were added. The solid mixture was purged with N$_2$ (degassed and flushed) three times. Then tert-butanol (30 mL) was added. The vial was degassed and flushed with N$_2$ three times and the vessel was capped and placed in a preheated oil bath at 110° C. for 10 h. The sample was cooled to rt, diluted with ethyl acetate, and washed with water. The aqueous layer was acidified to pH 5-6 and extracted with ethyl acetate. The organic extracts were combined, dried over sodium sulfate and concentrated in vacuo to give the desired product (1.35 g, 4.77 mmol, 38% yield). The solid was collected by filtration and dried under vacuo to give more of the desired product (1.9 g, 6.71 mmol, 53% yield). Total yield was 91%: MS (ESI) (m/z): 284.1 (M+H)+; $^1$H NMR (400 MHz, DMSO-d$_6$) δ ppm 13.69 (br. s., 1H) 10.48 (s, 1H) 8.58-8.67 (m, 1H) 8.44 (d, J=5.14 Hz, 1H) 8.25 (s, 1H) 8.04 (dd, J=9.05, 2.45 Hz, 1H) 7.94 (d, J=9.05 Hz, 1H) 7.38 (dd, J=5.14, 1.22 Hz, 1H); $^{19}$F NMR (376 MHz, DMSO-d$_6$) δ ppm −59.78 (s, 3F).

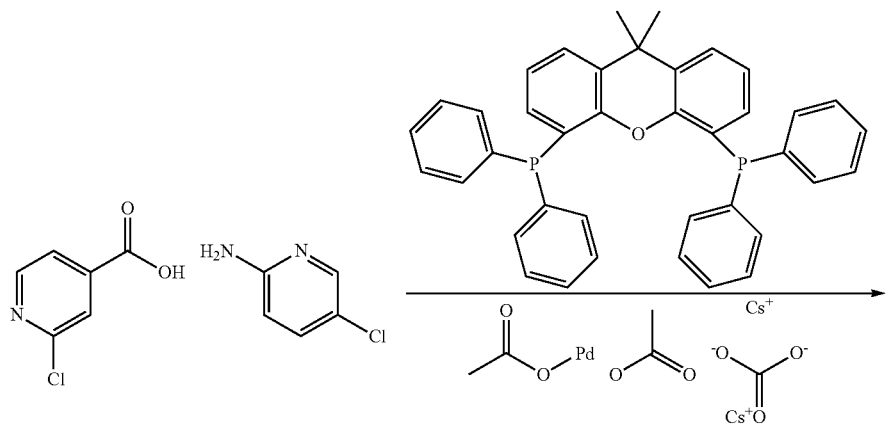

2-((5-Chloropyridin-2-yl)amino)isonicotinic acid

The mixture of XANTPHOS (0.055 g, 0.095 mmol), cesium carbonate (0.414 g, 1.269 mmol), palladium acetate (0.014 g, 0.063 mmol), 2-chloroisonicotinic acid (0.1 g, 0.635 mmol) and 5-chloropyridin-2-amine (0.082 g, 0.635 mmol) in Dioxane (1.5 mL) was heat at 110° C. for over night under N2. The reaction was partitioned between ethyl acetate and water. The aqueous was separated and washed with ethyl acetate two more times. The ethyl acetate layer was discarded. The aqueous was adjust to PH ~4 by adding 1N HCl. The aqueous was extract three more times with ethyl acetate. The ethyl acetate layer was combined, dried (Na2SO4), filtered and concentrated to give the crude as a yellow solid (116.5 mg, 74% yield). MS (ES+) m/e 250 [M+H]⁺.

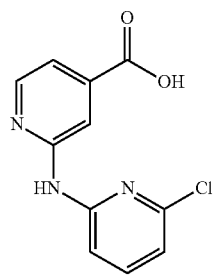 [SMILES: O=C(O)c1ccnc(Nc2cccc(Cl)n2)c1]

2-((6-Chloropyridin-2-yl)amino)isonicotinic acid

MS[ES+] m/e 250 [M+H]⁺.

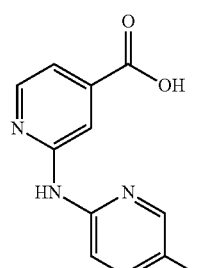

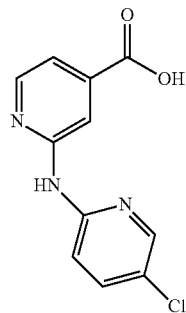

2-((5-Cyanopyridin-2-yl)amino)isonicotinic acid

MS[ES+] m/e 241 [M+H]⁺.

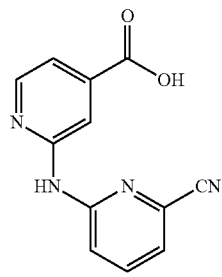 [SMILES: N#Cc1cccc(Nc2cc(C(=O)O)ccn2)n1]

2-((6-Cyanopyridin-2-yl)amino)isonicotinic acid

MS[ES+] m/e 241 [M+H]⁺.

2-(6-Chloropyridin-3-yl)-2-methylpropanenitrile

To 2-(6-chloropyridin-3-yl)acetonitrile (1.0 g, 6.55 mmol) in NaOH, 10 M (19.66 ml, 197 mmol) was N-benzyl-N,N-diethylethanaminium chloride (0.373 g, 1.638 mmol) followed by iodomethane (0.943 ml, 15.07 mmol)). The reaction mixture was placed on an oil bath preheated to 60° C. and stirred for 3 hrs. Ethylacetate and 1N HCl was added. The layers were separated and the org layer was washed with brine and dried over sodium sulfate. The solvent was removed and the residue was dissolved in a small amount of dichloromethane and charged to a 120 g silica gel cartridge which was eluted with 0-60% ethyl acetate/hexanes over a period of 50 mins. The desired fractions were combined and dried under vacuo to give 2-(6-chloropyridin-3-yl)-2-methylpropanenitrile (0.7 g, 3.88 mmol, 59.1% yield). ¹H NMR (400 MHz, CHLOROFORM-d) δ ppm 8.54 (dd, J=2.81, 0.61 Hz, 1H) 7.80 (dd, J=8.31, 2.69 Hz, 1H) 7.40 (dd, J=8.44, 0.61 Hz, 1H) 1.79 (s, 6H). MS (ESI) (m/z): 181.0 (M+H)⁺.

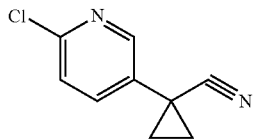 [SMILES: N#CC1(c2ccc(Cl)nc2)CC1]

1-(6-Chloropyridin-3-yl)cyclopropanecarbonitrile $^1$H NMR (400 MHz, CHLOROFORM-d) δ ppm 8.36 (d, J=2.20 Hz, 1H) 7.63 (dd, J=8.56, 2.69 Hz, 1H) 7.36 (dd, J=8.44, 0.61 Hz, 1H) 1.80-1.89 (m, 2H) 1.42-1.50 (m, 2H). MS (ESI) (m/z): 179.0 (M+H)⁺.

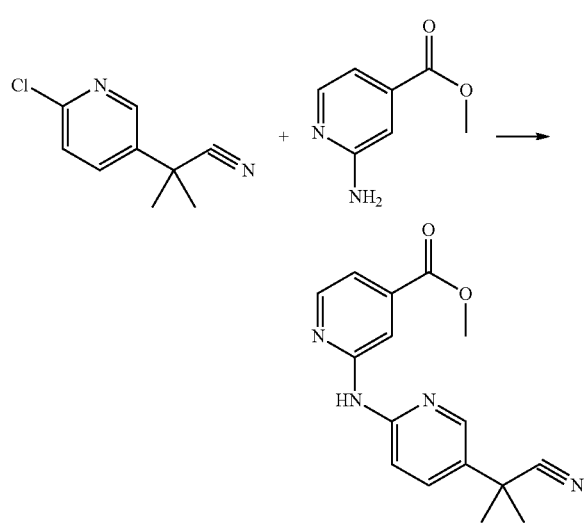 [SMILES: CC(C)(C#N)c1ccc(Cl)nc1 ; COC(=O)c1ccnc(N)c1 ; COC(=O)c1ccnc(Nc2ccc(C(C)(C)C#N)cn2)c1]

Methyl 2-((5-(2-cyanopropan-2-yl)pyridin-2-yl)amino)isonicotinate

To an oven dried vial with a stir bar, brettphos (5.83 mg, 0.011 mmol), brettphos precatalyst (8.84 mg, 0.011 mmol), 2-(6-chloropyridin-3-yl)-2-methylpropanenitrile (0.2 g, 1.107 mmol), methyl 2-aminoisonicotinate (0.168 g, 1.107 mmol) and K2CO3 (0.230 g, 1.661 mmol) were added. The solid mixture was purged with N2 (degassed and flushed) (3×). Then tBuOH (5 mL) was added. The vial was degassed and flushed with N2 (3×) and the vessel was capped and placed in a preheated oil bath at 110° C. for 3 hrs. The reaction mixture was cooled, diluted with ethyl acetate and satd ammonium chloride. The org layer was washed with brine and dried over sodium sulfate and evaporated. The residue was dried under vacuo to give methyl 2-((5-(2-cyanopropan-2-yl)pyridin-2-yl)amino)isonicotinate (0.32 g, 1.080 mmol, 98% yield). Taken to the next step without further purification. MS (ESI) (m/z): 297.5 (M+H)⁺.

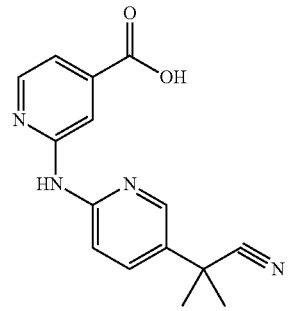 [SMILES: CC(C)(C#N)c1ccc(Nc2cc(C(=O)O)ccn2)nc1]

2-((5-(2-Cyanopropan-2-yl)pyridin-2-yl)amino)isonicotinic acid

To methyl 2-((5-(2-cyanopropan-2-yl)pyridin-2-yl)amino)isonicotinate (0.3 g, 1.012 mmol) in THF (2 mL) and MeOH (0.5 mL) was added LiOH, 2N (3 ml, 6.00 mmol). The reaction was stirred at rt for 2 hr. The solvent was removed and the residue was redissolved in ethyl acetate. 1NHCl was added (til pH 5-6) and the org layer was collected and dried over sodium sulfate. The residue was dried under vacuo to give 2-((5-(2-cyanopropan-2-yl)pyridin-2-yl)amino)isonicotinic acid (0.15 g, 0.531 mmol, 52.5% yield). $^1$H NMR (400 MHz, DMSO-d$_6$) δ ppm 13.49 (br. s., 1H) 10.08 (s, 1H) 8.35-8.42 (m, 2H) 8.26 (s, 1H) 7.82-7.89 (m, 1H) 7.74-7.80 (m, 1H) 7.29 (dd, J=5.14, 1.22 Hz, 1H) 1.72 (s, 6H). MS (ESI) (m/z): 283.5 (M+H)⁺.

1-(6-Aminopyridin-3-yl)cyclopropanecarbonitrile

A mixture of 1-(6-chloropyridin-3-yl)cyclopropanecarbonitrile (0.5 g, 2.80 mmol), BINAP (0.174 g, 0.280 mmol) and TRIS(DIBENZYLIDENEACETONE)DIPALLADIUM(0) (2.56 g, 2.80 mmol) in Toluene (15 mL) was degassed with N2 for 10 min. To this mixture was added diphenylmethanimine (0.515 mL, 3.08 mmol) and SODIUM TERT-BUTOXIDE (0.350 g, 3.64 mmol)). The mixture was heated at 90° C. for 4.0 h. LCMS showed desired M+H. The mixture was then diluted with EtOAc/water/brine (brine for better separation), filtered through a pad of wet celite to remove insoluble material. The organic layer was collected and washed with brine, dried over sodium sulfate and concentrated to give the crude imine. The crude imine was dissolved in THF (12 mL) and was treated with 6.0 N HCl for 30 min. The reaction was left stirring at rt overnight. The mixture was then diluted with EtOAc, the aqueous was collected (through a filter to remove insoluble material) and the organic was further extracted with 4.0 N HCl (2×10 mL). The aqueous layers were combined and treated at 0° C. with 8.0 N NaOH to adjust the pH to 12-13, expecting precipitation of product. However, no precipitate formed. It was then extracted with THF/EtOAc (much better than CH$_2$Cl$_2$ for solubility reason), washed with brine and dried over sodium sulfate. After evaporation of solvent, 1-(6-aminopyridin-3-yl)cyclopropanecarbonitrile was obtained as a dark brown solid. MS (ESI) (m/z): 160.1 (M+H)⁺.

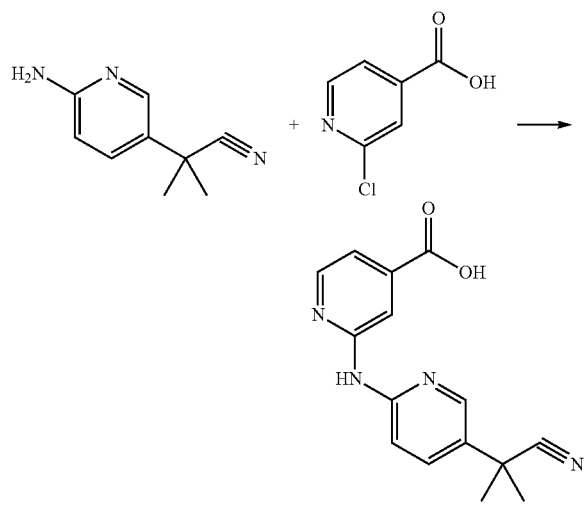

2-((5-(1-Cyanocyclopropyl)pyridin-2-yl)amino) isonicotinic acid

To an oven dried vial with a stir bar, brettphos precatalyst (10.14 mg, 0.013 mmol), brettphos (6.81 mg, 0.013 mmol), 2-chloroisonicotinic acid (0.2 g, 1.269 mmol), 1-(6-aminopyridin-3-yl)cyclopropanecarbonitrile (0.263 g, 1.650 mmol) and K2CO3 (0.263 g, 1.904 mmol) were added. The solid mixture was purged with N2 (degassed and flushed) (3x). Then tBuOH (2 mL) was added. The vial was degassed and flushed with N2 (3x) and the vessel was capped and placed in a preheated oil bath at 110° C. for 10 hrs. The sample was cooled to rm temp, diluted with ethyl acetate and washed with water. The aq layer was acidified to pH5-6 and extracted with ethyl acetate. The org extracts were combined and dried over sodium sulfate. The solid collected between layers were filtered and dried and combined with the dried org layer to give 2-((5-(1-cyanocyclopropyl)pyridin-2-yl) amino)isonicotinic acid (0.15 g, 0.535 mmol, 42.2% yield). MS (ESI) (m/z): 281.1 (M+H)⁺.

Example 4

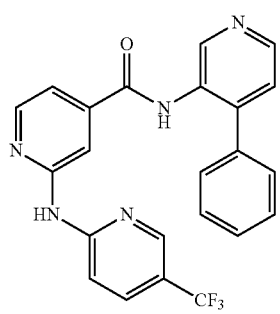 [SMILES: O=C(Nc1cnccc1-c1ccccc1)c1ccnc(Nc2ccc(C(F)(F)F)cn2)c1]

N-(4-Phenylpyridin-3-yl)-2-((5-(trifluoromethyl) pyridin-2-yl)amino)isonicotinamide To 3-amino-4-phenyl-pyridine (2.65 g, 15.6 mmol) and 2-((5-(trifluoromethyl)pyridin-2-yl)amino)isonicotinic acid (4.2 g, 15 mmol) in ethyl acetate (50 mL) was added DIEA (12.9 mL, 74.2 mmol) followed by 1-propanephosphonic acid cyclic anhydride, 50% (by weight) in ethyl acetate (18.9 g, 29.7 mmol) dropwise. The reaction was stirred at rt overnight. The reaction was diluted with ethyl acetate and saturated sodium bicarbonate. A solid formed between the layers. This was filtered, collected and washed with dichloromethane. The solid was further triturated with dichloromethane, filtered and dried in vacuo to obtain the desired product (4.77 g, 73%) as a white solid: MS (ESI) (m/z): 436.2 (M+H)⁺; ¹H NMR (400 MHz, DMSO-d₆) δ ppm 10.48 (s, 1H) 10.40 (s, 1H) 8.65 (s, 1H) 8.56-8.61 (m, 2H) 8.42 (d, J=5.38 Hz, 1H) 8.12 (s, 1H) 8.04 (dd, J=9.05, 2.45 Hz, 1H) 7.90 (d, J=8.80 Hz, 1H) 7.36-7.56 (m, 6H) 7.29 (d, J=4.89 Hz, 1H); ¹⁹F NMR (376 MHz, DMSO-d₆) δ ppm −59.80 (s, 3F). For the following examples that were soluble in EtOAc, the products were generally purified by flash column chromotography.

Example 17

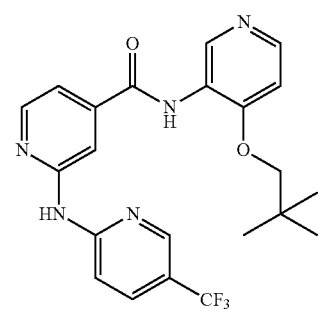 [SMILES: CC(C)(C)COc1ccncc1NC(=O)c1ccnc(Nc2ccc(C(F)(F)F)cn2)c1]

N-(4-(Neopentyloxy)pyridin-3-yl)-2-((5-(trifluoromethyl)pyridin-2-yl)amino)isonicotinamide MS (ESI) (m/z): 446.3 (M+H)⁺; ¹H NMR (500 MHz, DMSO-d₆) δ 10.47 (s, 1H), 10.00 (s, 1H), 8.57 (s, 1H), 8.51-8.45 (m, 2H), 8.35 (d, J=5.5 Hz, 1H), 8.24 (s, 1H), 8.04 (dd, J=9.2, 2.4 Hz, 1H), 7.86 (d, J=8.9 Hz, 1H), 7.40 (d, J=4.6 Hz, 1H), 7.16 (d, J=5.5 Hz, 1H), 3.76 (s, 2H), 0.95 (s, 9H).

Example 18

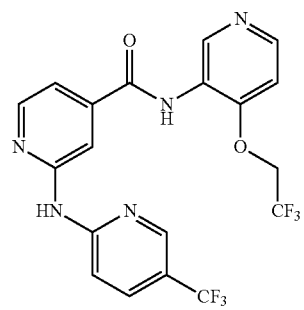 [SMILES: O=C(Nc1cnccc1OCC(F)(F)F)c1ccnc(Nc2ccc(C(F)(F)F)cn2)c1]

N-(4-(Trifluoroethoxy)pyridin-3-yl)-2-((5-(trifluoromethyl)pyridin-2-yl)amino)isonicotinamide MS (ESI) (m/z): 458.2 (M+H)$^+$; $^1$H NMR (500 MHz, DMSO-d$_6$) δ 10.52 (s, 1H), 10.17 (br. s., 1H), 8.61 (s, 2H), 8.49 (d, J=5.2 Hz, 1H), 8.45 (d, J=5.5 Hz, 1H), 8.25 (s, 1H), 8.06 (dd, J=8.9, 2.4 Hz, 1H), 7.91 (d, J=9.2 Hz, 1H), 7.43 (d, J=4.9 Hz, 1H), 7.33 (d, J=5.8 Hz, 1H), 4.98 (q, J=8.9 Hz, 2H).

Example 19

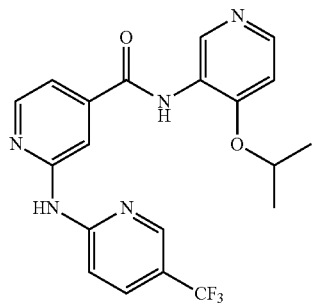 [SMILES: CC(C)Oc1ccncc1NC(=O)c1ccnc(Nc2ccc(C(F)(F)F)cn2)c1]

N-(4-(Isopropoxy)pyridin-3-yl)-2-((5-(trifluoromethyl)pyridin-2-yl)amino)isonicotinamide MS (ESI) (m/z): 418.2 (M+H)$^+$.

Example 20

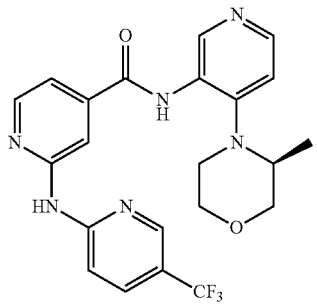 [SMILES: C[C@H]1COCCN1c1ccncc1NC(=O)c1ccnc(Nc2ccc(C(F)(F)F)cn2)c1]

(S)—N-(4-(3-Methylmorpholino)pyridin-3-yl)-2-((5-(trifluoromethyl)pyridin-2-yl)amino)isonicotinamide MS (ESI) (m/z): 459.3 (M+H)$^+$; $^1$H NMR (500 MHz, DMSO-d$_6$) δ 10.56 (s, 1H), 9.95 (s, 1H), 8.76 (s, 1H), 8.62 (s, 1H), 8.51 (d, J=5.2 Hz, 1H), 8.33 (d, J=5.5 Hz, 1H), 8.24 (s, 1H), 8.07 (dd, J=8.9, 2.4 Hz, 1H), 7.94 (d, J=9.2 Hz, 1H), 7.44 (d, J=4.6 Hz, 1H), 7.20 (d, J=5.5 Hz, 1H), 3.78 (dd, J=11.0, 2.7 Hz, 2H), 3.74-3.67 (m, 1H), 3.60-3.52 (m, 1H), 3.45 (dd, J=11.0, 5.5 Hz, 1H), 3.19 (ddd, J=12.2, 6.9, 2.9 Hz, 1H), 2.90 (br. s., 1H), 0.93 (d, J=6.1 Hz, 3H).

Example 21

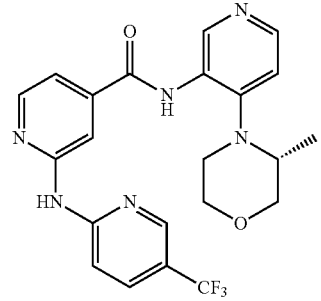 [SMILES: C[C@@H]1COCCN1c1ccncc1NC(=O)c1ccnc(Nc2ccc(C(F)(F)F)cn2)c1]

(R)—N-(4-(3-Methylmorpholino)pyridin-3-yl)-2-((5-(trifluoromethyl)pyridin-2-yl)amino)isonicotinamide MS (ESI) (m/z): 459.3 (M+H)$^+$; $^1$H NMR (500 MHz, DMSO-d$_6$) δ 10.55 (s, 1H), 9.95 (s, 1H), 8.76 (s, 1H), 8.62 (s, 1H), 8.51 (d, J=5.2 Hz, 1H), 8.33 (d, J=5.2 Hz, 1H), 8.24 (s, 1H), 8.07 (dd, J=8.9, 2.4 Hz, 1H), 7.94 (d, J=9.2 Hz, 1H), 7.44 (d, J=4.6 Hz, 1H), 7.20 (d, J=5.5 Hz, 1H), 3.78 (dd, J=10.8, 2.9 Hz, 2H), 3.74-3.66 (m, 1H), 3.60-3.52 (m, 1H), 3.45 (dd, J=11.0, 5.5 Hz, 1H), 3.19 (ddd, J=12.1, 6.8, 3.1 Hz, 1H), 2.90 (d, J=7.9 Hz, 1H), 0.93 (d, J=6.4 Hz, 3H).

Example 22

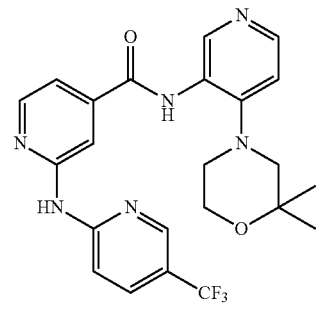 [SMILES: CC1(C)CN(c2ccncc2NC(=O)c2ccnc(Nc3ccc(C(F)(F)F)cn3)c2)CCO1]

N-(4-(2,2-Dimethylmorpholino)pyridin-3-yl)-2-((5-(trifluoromethyl)pyridin-2-yl)amino)isonicotinamide MS (ESI) (m/z): 473.3 (M+H)$^+$; $^1$H NMR (500 MHz, DMSO-d$_6$) δ 10.52 (s, 1H), 10.11 (s, 1H), 8.61 (s, 1H), 8.50 (d, J=4.9 Hz, 1H), 8.35 (s, 1H), 8.31 (d, J=5.8 Hz, 1H), 8.27 (s, 1H), 8.06 (dd, J=8.9, 2.4 Hz, 1H), 7.93 (d, J=8.9 Hz, 1H), 7.49 (d, J=4.6 Hz, 1H), 7.05 (d, J=5.8 Hz, 1H), 3.74-3.69 (m, 2H), 3.10 (br. s., 2H), 2.95 (s, 2H), 1.15 (s, 6H).

Example 23

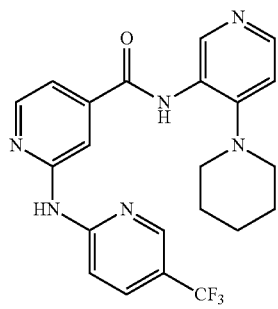 [SMILES: O=C(Nc1cnccc1N1CCCCC1)c1ccnc(Nc2ccc(C(F)(F)F)cn2)c1]

N-(4-(Piperidin-1-yl)pyridin-3-yl)-2-((5-(trifluoromethyl)pyridin-2-yl)amino)isonicotinamide MS (ESI) (m/z): 443.2 (M+H)$^+$; $^1$H NMR (500 MHz, DMSO-d$_6$) δ 10.52 (s, 1H), 9.93 (s, 1H), 8.61 (s, 1H), 8.50 (d, J=5.2 Hz, 1H), 8.46 (s, 1H), 8.30-8.24 (m, 2H), 8.06 (dd, J=8.9, 2.4 Hz, 1H), 7.92 (d, J=8.9 Hz, 1H), 7.48 (d, J=4.3 Hz, 1H), 7.02 (d, J=5.5 Hz, 1H), 3.10-3.04 (m, 4H), 1.63 (d, J=3.7 Hz, 4H), 1.55 (d, J=4.9 Hz, 2H).

Example 24

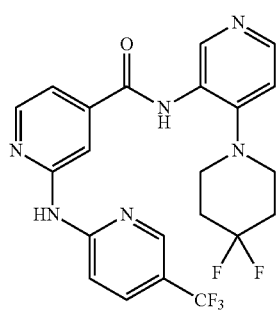 [SMILES: O=C(Nc1cnccc1N1CCC(F)(F)CC1)c1ccnc(Nc2ccc(C(F)(F)F)cn2)c1]

N-(4-(4,4-Difluoropiperidin-1-yl)pyridin-3-yl)-2-((5-(trifluoromethyl)pyridin-2-yl)amino)isonicotinamide MS (ESI) (m/z): 479.2 (M+H)$^+$; $^1$H NMR (500 MHz, DMSO-d$_6$) δ 10.52 (s, 1H), 9.82 (s, 1H), 8.68 (s, 1H), 8.49 (s, 1H), 8.49 (d, J=4.9 Hz, 1H), 8.33 (d, J=5.5 Hz, 1H), 8.22 (s, 1H), 8.06 (dd, J=8.9, 2.4 Hz, 1H), 7.94 (d, J=8.9 Hz, 1H), 7.43 (d, J=4.0 Hz, 1H), 7.19 (d, J=5.8 Hz, 1H), 4.82 (dt, J=12.0, 6.1 Hz, 1H), 1.33 (d, J=5.8 Hz, 7H).

Example 25

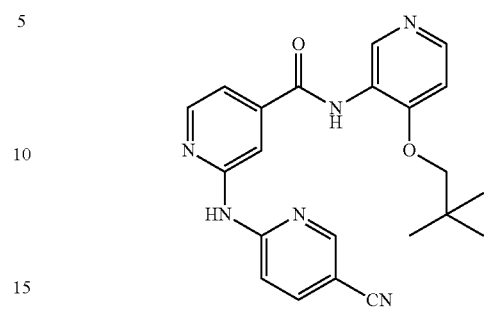

2-((5-Cyanopyridin-2-yl)amino)-N-(4-(neopentyloxy)pyridin-3-yl)isonicotinamide

MS (ESI) (m/z): 403.2 (M+H)$^+$; $^1$H NMR (500 MHz, DMSO-d$_6$) δ 10.63 (s, 1H), 10.03 (s, 1H), 8.69 (d, J=1.8 Hz, 1H), 8.51 (d, J=5.2 Hz, 1H), 8.48 (s, 1H), 8.37 (d, J=5.8 Hz, 1H), 8.23 (s, 1H), 8.11 (dd, J=8.9, 2.4 Hz, 1H), 7.88 (d, J=8.9 Hz, 1H), 7.46 (d, J=4.6 Hz, 1H), 7.17 (d, J=5.5 Hz, 1H), 3.78 (s, 2H), 0.97 (s, 9H).

Example 26

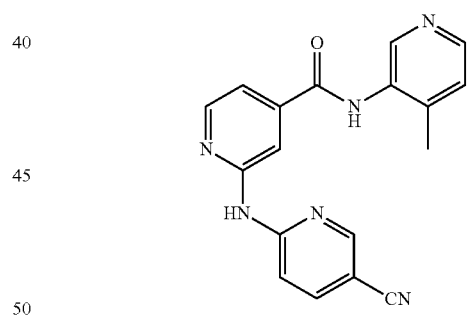

2-((5-Cyanopyridin-2-yl)amino)-N-(4-methylpyridin-3-yl)isonicotinamide

MS (ESI) (m/z): 331.2 (M+H)$^+$; $^1$H NMR (500 MHz, DMSO-d$_6$) δ 10.63 (br. s., 1H), 10.39 (br. s., 1H), 8.72 (d, J=2.1 Hz, 1H), 8.56-8.48 (m, 2H), 8.36 (d, J=4.9 Hz, 1H), 8.26 (s, 1H), 8.11 (dd, J=9.0, 2.3 Hz, 1H), 7.93 (d, J=8.9 Hz, 1H), 7.53 (d, J=4.9 Hz, 1H), 7.36 (d, J=4.9 Hz, 1H), 2.29 (s, 3H).

Example 27

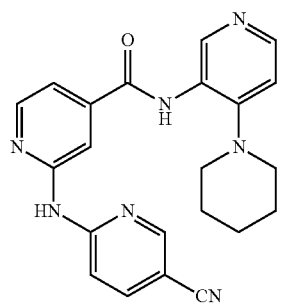 [SMILES: N#Cc1ccc(Nc2cc(C(=O)Nc3cnccc3N3CCCCC3)ccn2)nc1]

2-((5-Cyanopyridin-2-yl)amino)-N-(4-(piperidin-1-yl)pyridin-3-yl)isonicotinamide MS (ESI) (m/z): 400.3 (M+H)$^+$; $^1$H NMR (500 MHz, DMSO-d$_6$) δ 10.65 (br. s., 1H), 10.00 (br. s., 1H), 8.70 (d, J=2.4 Hz, 1H), 8.51 (d, J=5.2 Hz, 1H), 8.43 (s, 1H), 8.26 (d, J=5.5 Hz, 2H), 8.11 (dd, J=8.9, 2.4 Hz, 1H), 7.90 (d, J=8.9 Hz, 1H), 7.52 (d, J=4.6 Hz, 1H), 7.02 (d, J=5.5 Hz, 1H), 3.07 (m, 4H), 1.64-1.51 (m, 6H).

Example 29

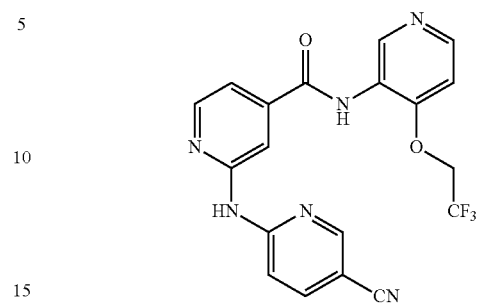

2-((5-Cyanopyridin-2-yl)amino)-N-(4-(2,2,2-trifluoroethoxy)pyridin-3-yl)isonicotinamide MS (ESI) (m/z): 415.3 (M+H)$^+$; $^1$H NMR (500 MHz, DMSO-d$_6$) δ 10.64 (br. s., 1H), 10.22 (br. s., 1H), 8.70 (d, J=2.1 Hz, 1H), 8.60 (s, 1H), 8.51 (d, J=5.2 Hz, 1H), 8.45 (d, J=5.8 Hz, 1H), 8.23 (s, 1H), 8.11 (dd, J=8.9, 2.1 Hz, 1H), 7.89 (d, J=8.9 Hz, 1H), 7.46 (d, J=5.2 Hz, 1H), 7.33 (d, J=5.5 Hz, 1H), 4.98 (q, J=8.7 Hz, 2H).

Example 28

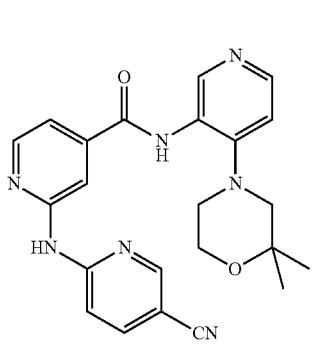 [SMILES: CC1(C)CN(c2ccncc2NC(=O)c2ccnc(Nc3ccc(C#N)cn3)c2)CCO1]

2-((5-Cyanopyridin-2-yl)amino)-N-(4-(2,2-dimethylmorpholino)pyridin-3-yl)isonicotinamide MS (ESI) (m/z): 430.3 (M+H)$^+$; $^1$H NMR (500 MHz, DMSO-d$_6$) δ 10.66 (s, 1H), 10.16 (br. s., 1H), 8.70 (d, J=2.4 Hz, 1H), 8.51 (d, J=4.9 Hz, 1H), 8.33 (s, 1H), 8.31 (d, J=5.5 Hz, 1H), 8.27 (s, 1H), 8.11 (dd, J=8.9, 2.1 Hz, 1H), 7.91 (d, J=8.9 Hz, 1H), 7.53 (d, J=5.2 Hz, 1H), 7.02 (d, J=5.8 Hz, 1H), 3.72-3.68 (m, 2H), 3.09-3.04 (m, 2H), 2.91 (s, 2H), 1.14 (s, 6H).

Example 46

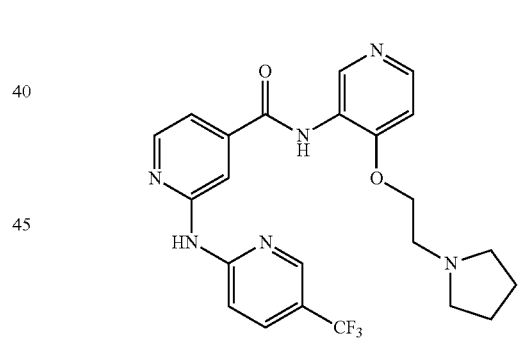

N-(4-(2-(Pyrrolidin-1-yl)ethoxy)pyridin-3-yl)-2-((5-(trifluoromethyl)pyridin-2-yl)amino)isonicotinamide MS (ESI) (m/z): 471 (M+H)$^+$; $^1$H NMR (500 MHz, DMSO-d$_6$) δ 10.49 (s, 1H), 10.00 (s, 1H), 8.67 (s, 1H), 8.62 (s, 1H), 8.47 (d, J=5.3 Hz, 1H), 8.35 (d, J=5.6 Hz, 1H), 8.24 (s, 1H), 8.04 (d, J=8.3 Hz, 1H), 7.89 (d, J=9.0 Hz, 1H), 7.42 (d, J=5.4 Hz, 1H), 7.20 (d, J=5.8 Hz, 1H), 4.22 (t, J=5.8 Hz, 2H), 2.80 (t, J=5.8 Hz, 2H), 2.47 (d, J=5.9 Hz, 4H), 1.57 (d, J=5.5 Hz, 4H).

Example 47

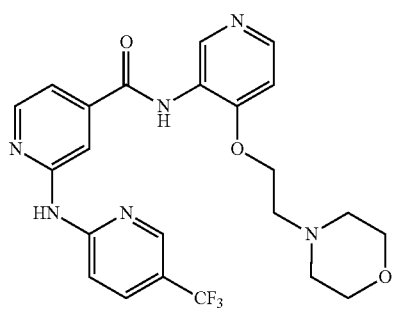 [SMILES: O=C(Nc1cnccc1OCCN1CCOCC1)c1ccnc(Nc2ccc(C(F)(F)F)cn2)c1]

N-(4-(2-Morpholinoethoxy)pyridin-3-yl)-2-((5-(trifluoromethyl)pyridin-2-yl)amino)isonicotinamide MS (ESI) (m/z): 487 (M+H)$^+$; $^1$H NMR (500 MHz, DMSO-d$_6$) δ 10.50 (s, 1H), 10.04-9.90 (m, 1H), 8.62 (s, 2H), 8.47 (d, J=4.2 Hz, 1H), 8.40-8.30 (m, 1H), 8.23 (s, 1H), 8.05 (d, J=9.1 Hz, 1H), 7.95-7.82 (m, 1H), 7.50-7.37 (m, 1H), 7.21 (d, J=5.4 Hz, 1H), 4.24 (s, 2H), 3.47 (d, J=4.8 Hz, 4H), 2.71 (s, 2H), 2.43 (s, 4H).

Example 42

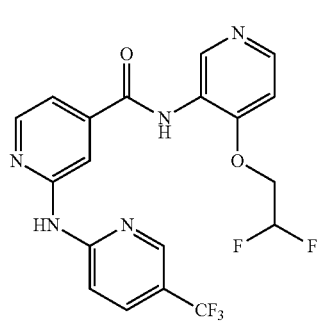 [SMILES: O=C(Nc1cnccc1OCC(F)F)c1ccnc(Nc2ccc(C(F)(F)F)cn2)c1]

N-(4-(2,2-Difluoroethoxy)pyridin-3-yl)-2-((5-(trifluoromethyl)pyridin-2-yl)amino)isonicotinamide MS (ESI) (m/z): 440.3 (M+H)$^+$; $^1$H NMR (500 MHz, DMSO-d$_6$) δ ppm 10.48 (br. s., 1H) 10.04 (br. s., 1H) 8.67 (br. s., 1H) 8.61 (br. s., 1H) 8.47 (br. s., 1H) 8.39 (br. s., 1H) 8.23 (br. s., 1H) 8.05 (d, J=8.24 Hz, 1H) 7.91 (d, J=8.24 Hz, 1H) 7.42 (br. s., 1H) 7.28 (br. s., 1H) 6.25-6.54 (m, 1H) 4.51 (t, J=13.28 Hz, 2H) 2.51 (br. s., 4H).

Example 43

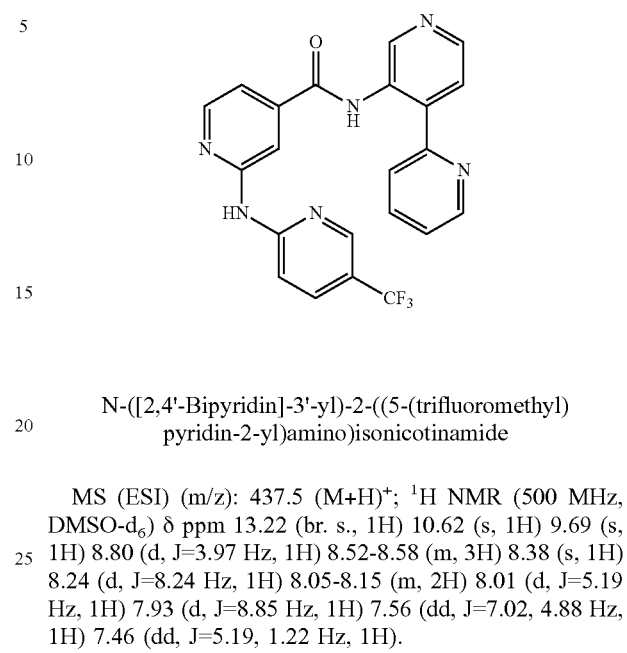

N-([2,4'-Bipyridin]-3'-yl)-2-((5-(trifluoromethyl)pyridin-2-yl)amino)isonicotinamide MS (ESI) (m/z): 437.5 (M+H)$^+$; $^1$H NMR (500 MHz, DMSO-d$_6$) δ ppm 13.22 (br. s., 1H) 10.62 (s, 1H) 9.69 (s, 1H) 8.80 (d, J=3.97 Hz, 1H) 8.52-8.58 (m, 3H) 8.38 (s, 1H) 8.24 (d, J=8.24 Hz, 1H) 8.05-8.15 (m, 2H) 8.01 (d, J=5.19 Hz, 1H) 7.93 (d, J=8.85 Hz, 1H) 7.56 (dd, J=7.02, 4.88 Hz, 1H) 7.46 (dd, J=5.19, 1.22 Hz, 1H).

Example 44

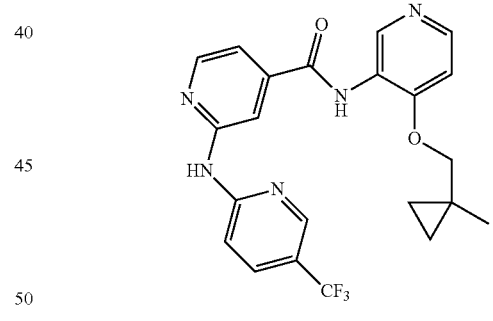

N-(4-((1-Methylcyclopropyl)methoxy)pyridin-3-yl)-2-((5-(trifluoromethyl)pyridin-2-yl)amino)isonicotinamide MS (ESI) (m/z): 444.4 (M+H)$^+$; $^1$H NMR (500 MHz, DMSO-d$_6$) δ ppm 10.49 (br. s., 1H) 9.94 (br. s., 1H) 8.60 (br. s., 1H) 8.54 (br. s., 1H) 8.48 (d, J=4.27 Hz, 1H) 8.34 (d, J=5.19 Hz, 1H) 8.25 (br. s., 1H) 8.04 (d, J=8.54 Hz, 1H) 7.90 (d, J=8.85 Hz, 1H) 7.42 (br. s., 1H) 7.12 (d, J=5.49 Hz, 1H) 3.92 (br. s., 2H) 1.14 (s, 3H) 0.54 (br. s., 2H) 0.34 (br. s., 2H).

Example 45

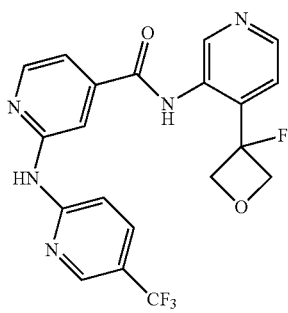 [SMILES: O=C(Nc1cnccc1C1(F)COC1)c1ccnc(Nc2ccc(C(F)(F)F)cn2)c1]

N-(4-(3-Fluorooxetan-3-yl)pyridin-3-yl)-2-((5-(trifluoromethyl)pyridin-2-yl)amino)isonicotinamide MS (ESI) (m/z): 433.9 (M+H)$^+$.

Example 49

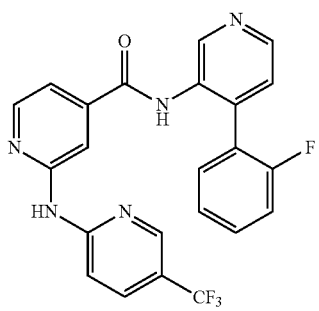 [SMILES: O=C(Nc1cnccc1-c1ccccc1F)c1ccnc(Nc2ccc(C(F)(F)F)cn2)c1]

N-(4-(2-Fluorophenyl)pyridin-3-yl)-2-((5-(trifluoromethyl)pyridin-2-yl)amino)isonicotinamide MS (ESI) (m/z): 454.2 (M+H)$^+$; $^1$H NMR (500 MHz, DMSO-d$_6$) δ 10.45 (s, 1H), 10.39 (br. s., 1H), 8.73 (s, 1H), 8.58 (d, J=4.9 Hz, 2H), 8.41 (d, J=5.2 Hz, 1H), 8.08 (s, 1H), 8.04 (dd, J=8.9, 2.4 Hz, 1H), 7.89 (d, J=8.9 Hz, 1H), 7.52-7.41 (m, 3H), 7.34-7.27 (m, 2H), 7.22 (d, J=4.9 Hz, 1H).

Example 51

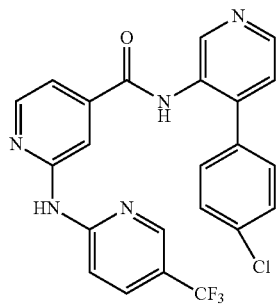

N-(4-(4-Cholorophenyl)pyridin-3-yl)-2-((5-(trifluoromethyl)pyridin-2-yl)amino)isonicotinamide MS (ESI) (m/z): 470.1 (M+H)$^+$; $^1$H NMR (500 MHz, DMSO-d$_6$) δ 10.47 (s, 1H), 8.68 (s, 1H), 8.63-8.55 (m, 2H), 8.44 (d, J=5.2 Hz, 1H), 8.12 (s, 1H), 8.05 (dd, J=8.9, 2.4 Hz, 1H), 7.90 (d, J=8.9 Hz, 1H), 7.62-7.52 (m, 4H), 7.50 (d, J=4.9 Hz, 1H), 7.32 (d, J=4.9 Hz, 1H).

Example 64

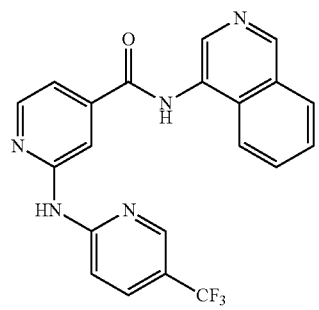 [SMILES: O=C(Nc1cncc2ccccc12)c1ccnc(Nc2ccc(C(F)(F)F)cn2)c1]

N-(Isoquinolin-4-yl)-2-((5-(trifluoromethyl)pyridin-2-yl)amino)isonicotinamide

MS (ESI) (m/z): 410.2 (M+H)$^+$; $^1$H NMR (500 MHz, DMSO-d$_6$) δ 10.81 (br. s., 1H), 10.56 (s, 1H), 9.29 (s, 1H), 8.69-8.62 (m, 2H), 8.54 (d, J=5.2 Hz, 1H), 8.33 (s, 1H), 8.23 (d, J=7.9 Hz, 1H), 8.11-7.99 (m, 3H), 7.90-7.83 (m, 1H), 7.80-7.74 (m, 1H), 7.62 (d, J=4.6 Hz, 1H).

Example 65

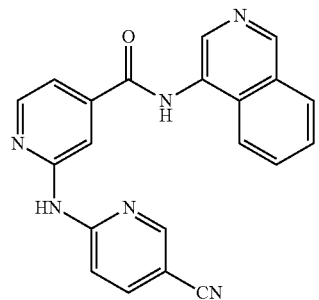 [SMILES: N#Cc1ccc(Nc2cc(C(=O)Nc3cncc4ccccc34)ccn2)nc1]

2-((5-Cyanopyridin-2-yl)amino)-N-(isoquinolin-4-yl)isonicotinamide

MS (ESI) (m/z): 367.2 (M+H)$^+$; $^1$H NMR (500 MHz, DMSO-d$_6$) δ 10.65 (br. s., 1H), 9.30 (s, 1H), 8.73 (s, 1H), 8.67 (s, 1H), 8.56 (d, J=4.9 Hz, 1H), 8.31 (s, 1H), 8.24 (d, J=8.2 Hz, 1H), 8.13 (dd, J=8.7, 2.3 Hz, 1H), 8.04 (d, J=8.5 Hz, 1H), 7.95 (d, J=8.9 Hz, 1H), 7.87 (t, J=7.6 Hz, 1H), 7.80-7.74 (m, 1H), 7.66 (br. s., 1H).

Example 66

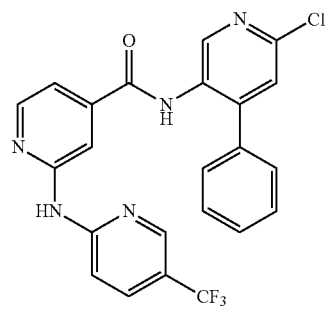 [SMILES: O=C(Nc1cnc(Cl)cc1-c1ccccc1)c1ccnc(Nc2ccc(C(F)(F)F)cn2)c1]

N-(6-Chloro-4-phenylpyridin-3-yl)-2-((5-(trifluoromethyl)pyridin-2-yl)amino)isonicotinamide MS (ESI) (m/z): 470.0 (M+H)[+]; $^1$H NMR (500 MHz, DMSO) δ 10.49 (s, 1H), 10.45 (s, 1H), 8.60 (s, 1H), 8.54 (s, 1H), 8.43 (d, J=5.1 Hz, 1H), 8.12 (s, 1H), 8.05 (dd, J=8.9, 2.4 Hz, 1H), 7.89 (d, J=8.9 Hz, 1H), 7.64 (s, 1H), 7.57 (d, J=7.3 Hz, 2H), 7.46 (dt, J=23.5, 7.2 Hz, 3H), 7.28 (d, J=4.9 Hz, 1H).

Example 67

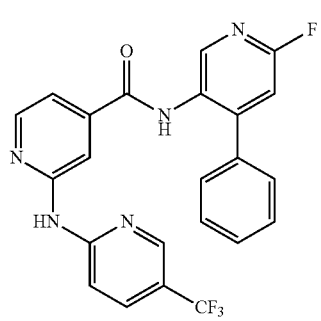

N-(6-Fluoro-4-phenylpyridin-3-yl)-2-((5-(trifluoromethyl)pyridin-2-yl)amino)isonicotinamide MS (ESI) (m/z): 454.1 (M+H)[+]; $^1$H NMR (500 MHz, DMSO) δ 10.47 (s, 1H), 10.39 (s, 1H), 8.43 (d, J=5.2 Hz, 1H), 8.34 (s, 1H), 8.12 (s, 1H), 8.05 (dd, J=8.9, 2.5 Hz, 1H), 7.90 (d, J=8.8 Hz, 1H), 7.58 (d, J=7.2 Hz, 2H), 7.54-7.40 (m, 3H), 7.35 (d, J=1.7 Hz, 1H), 7.29 (d, J=4.4 Hz, 1H).

Example 68

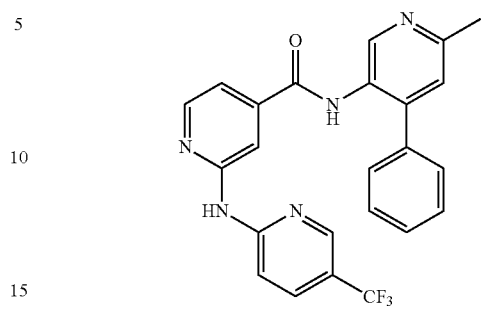

N-(6-Methyl-4-phenylpyridin-3-yl)-2-((5-(trifluoromethyl)pyridin-2-yl)amino)isonicotinamide MS (ESI) (m/z): 450.0 (M+H)[+]; $^1$H NMR (500 MHz, DMSO-$d_6$) δ 10.46 (s, 1H), 10.28 (s, 1H), 8.62-8.56 (m, 1H), 8.49 (s, 1H), 8.42 (d, J=5.2 Hz, 1H), 8.11 (s, 1H), 8.04 (dd, J=8.9, 2.6 Hz, 1H), 7.90 (d, J=8.9 Hz, 1H), 7.53 (d, J=7.0 Hz, 2H), 7.46 (t, J=7.6 Hz, 2H), 7.42-7.34 (m, 2H), 7.29 (dd, J=5.2, 1.5 Hz, 1H), 2.57 (s, 3H).

Example 69

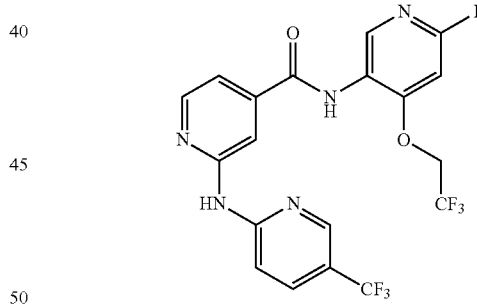

N-(6-Fluoro-4-(2,2,2-trifluoroethoxy)pyridin-3-yl)-2-((5-(trifluoromethyl)pyridin-2-yl)amino)isonicotinamide MS (ESI) (m/z): 476.1 (M+H)[+]; $^1$H NMR (500 MHz, DMSO-$d_6$) δ 10.52 (s, 1H), 10.22 (br. s., 1H), 8.61 (s, 1H), 8.49 (d, J=5.2 Hz, 1H), 8.28-8.22 (m, 2H), 8.06 (dd, J=8.9, 2.4 Hz, 1H), 7.91 (d, J=8.9 Hz, 1H), 7.42 (d, J=4.9 Hz, 1H), 7.19 (s, 1H), 5.03 (q, J=8.9 Hz, 2H).

Example 70

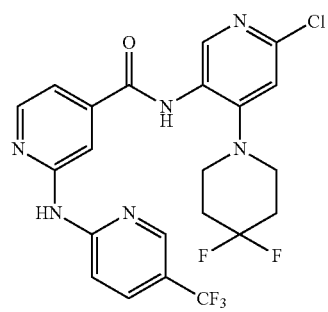 [SMILES: O=C(Nc1cnc(Cl)cc1N1CCC(F)(F)CC1)c1ccnc(Nc2ccc(C(F)(F)F)cn2)c1]

N-(6-Chloro-4-(4,4-difluoropiperidin-1-yl)pyridin-3-yl)-2-((5-(trifluoromethyl)pyridin-2-yl)amino)isonicotinamide MS (ESI) (m/z): 514.9 (M+H)$^+$; $^1$H NMR (500 MHz, DMSO) δ 10.53 (s, 1H), 10.15 (s, 1H), 8.61 (s, 1H), 8.50 (d, J=5.1 Hz, 1H), 8.31 (s, 1H), 8.27 (s, 1H), 8.06 (dd, J=9.0, 2.4 Hz, 1H), 7.89 (d, J=8.8 Hz, 1H), 7.46 (d, J=4.7 Hz, 1H), 7.16 (s, 1H), 3.34-3.29 (m, 4H), 2.17-2.04 (m, 4H).

Example 71

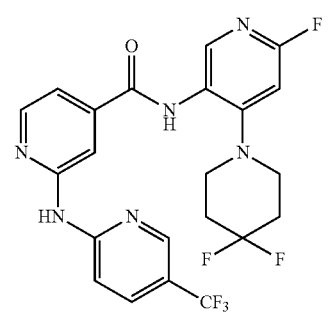

N-(6-Fluoro-4-(4,4-difluoropiperidin-1-yl)pyridin-3-yl)-2-((5-(trifluoromethyl)pyridin-2-yl)amino)isonicotinamide MS (ESI) (m/z): 497.0 (M+H)$^+$; $^1$H NMR (500 MHz, DMSO) δ 10.53 (s, 1H), 10.15 (s, 1H), 8.61 (s, 1H), 8.49 (d, J=5.0 Hz, 1H), 8.27 (s, 1H), 8.09 (s, 1H), 8.06 (dd, J=8.9, 2.2 Hz, 1H), 7.90 (d, J=8.8 Hz, 1H), 7.47 (d, J=4.7 Hz, 1H), 6.82 (s, 1H), 3.35 (obscured by solvent peak), 2.10 (dd, J=16.4, 10.7 Hz, 4H).

Example 72

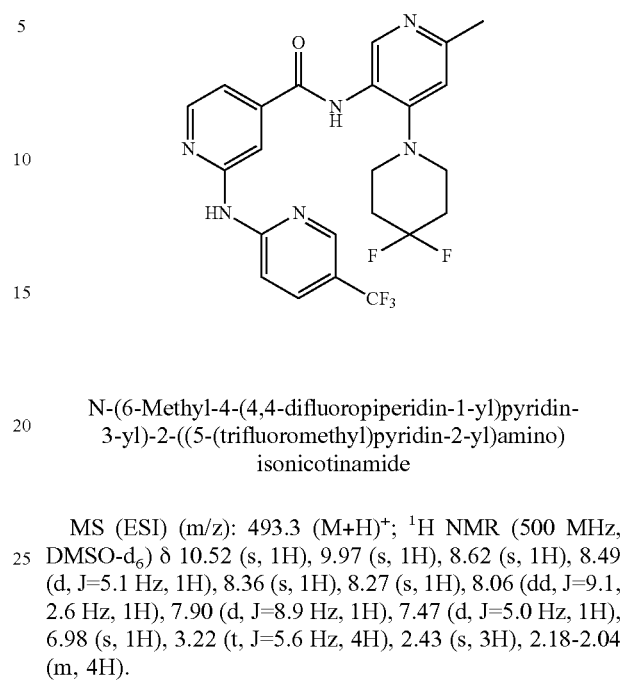

N-(6-Methyl-4-(4,4-difluoropiperidin-1-yl)pyridin-3-yl)-2-((5-(trifluoromethyl)pyridin-2-yl)amino)isonicotinamide MS (ESI) (m/z): 493.3 (M+H)$^+$; $^1$H NMR (500 MHz, DMSO-d$_6$) δ 10.52 (s, 1H), 9.97 (s, 1H), 8.62 (s, 1H), 8.49 (d, J=5.1 Hz, 1H), 8.36 (s, 1H), 8.27 (s, 1H), 8.06 (dd, J=9.1, 2.6 Hz, 1H), 7.90 (d, J=8.9 Hz, 1H), 7.47 (d, J=5.0 Hz, 1H), 6.98 (s, 1H), 3.22 (t, J=5.6 Hz, 4H), 2.43 (s, 3H), 2.18-2.04 (m, 4H).

Example 73

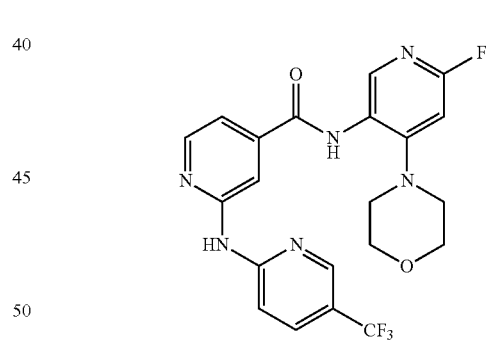

N-(6-Fluoro-4-morpholinopyridin-3-yl)-2-((5-(trifluoromethyl)pyridin-2-yl)amino)isonicotinamide MS (ESI) (m/z): 463.2 (M+H)$^+$; $^1$H NMR (500 MHz, DMSO-d$_6$) δ 10.53 (s, 1H), 10.15 (s, 1H), 8.62 (d, J=2.3 Hz, 1H), 8.49 (d, J=5.2 Hz, 1H), 8.22 (s, 1H), 8.07 (dd, J=8.9, 2.6 Hz, 1H), 8.03 (s, 1H), 7.95 (d, J=8.9 Hz, 1H), 7.50-7.40 (m, 1H), 6.75 (s, 1H), 3.70 (t, J=4.7 Hz, 4H), 3.22 (t, J=4.6 Hz, 4H).

Example 58

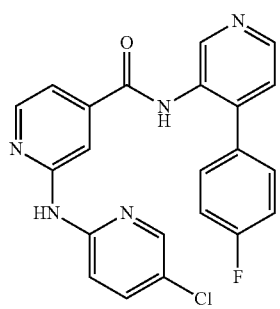 [SMILES: O=C(Nc1cnccc1-c1ccc(F)cc1)c1ccnc(Nc2ccc(Cl)cn2)c1]

2-((5-Chloropyridin-2-yl)amino)-N-(4-(4-fluorophenyl)pyridin-3-yl)isonicotinamide MS (ESI) (m/z): 420 (M+H)$^+$; $^1$H NMR (500 MHz, DMSO-d6) δ 10.38 (s, 1H), 10.12 (s, 1H), 8.65 (s, 1H), 8.59 (d, J=5.2 Hz, 1H), 8.38 (d, J=5.2 Hz, 1H), 8.27 (d, J=2.1 Hz, 1H), 7.97 (s, 1H), 7.86-7.78 (m, 2H), 7.58 (dd, J=8.5, 5.5 Hz, 2H), 7.50 (d, J=5.2 Hz, 1H), 7.32 (t, J=9.0 Hz, 2H), 7.22 (d, J=4.6 Hz, 1H).

Example 59

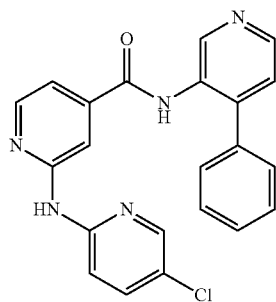 [SMILES: O=C(Nc1cnccc1-c1ccccc1)c1ccnc(Nc2ccc(Cl)cn2)c1]

2-((5-Chloropyridin-2-yl)amino)-N-(4-phenylpyridin-3-yl)isonicotinamide

MS (ESI) (m/z): 402 (M+H)$^+$; $^1$H NMR (500 MHz, DMSO-d$_6$) δ 10.36 (s, 1H), 10.12 (s, 1H), 8.65 (s, 1H), 8.59 (d, J=5.2 Hz, 1H), 8.37 (d, J=4.9 Hz, 1H), 8.27 (d, J=1.8 Hz, 1H), 7.99 (s, 1H), 7.85-7.77 (m, 2H), 7.57-7.38 (m, 6H), 7.21 (d, J=4.9 Hz, 1H).

Example 31

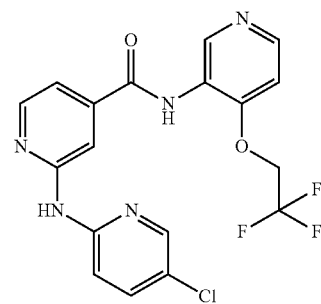

2-((5-Chloropyridin-2-yl)amino)-N-(4-(2,2,2-trifluoroethoxy)pyridin-3-yl)isonicotinamide MS (ESI) (m/z): 424 (M+H)$^+$; $^1$H NMR (500 MHz, DMSO-d6) S δ 10.16 (s, 1H), 10.11 (s, 1H), 8.60 (s, 1H), 8.44 (dd, J=9.2, 5.5 Hz, 2H), 8.28 (d, J=1.8 Hz, 1H), 8.10 (s, 1H), 7.87-7.79 (m, 2H), 7.37-7.31 (m, 2H), 4.98 (q, J=8.6 Hz, 2H).

Example 110

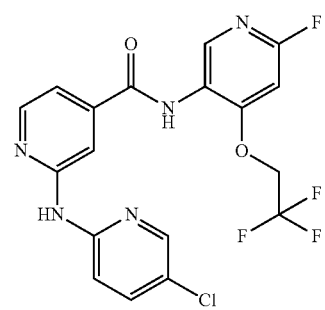

2-((5-Chloropyridin-2-yl)amino)-N-(6-fluoro-4-(2,2,2-trifluoroethoxy)pyridin-3-yl)isonicotinamide MS (ESI) (m/z): 442 (M+H)$^+$; $^1$H NMR (500 MHz, DMSO-d$_6$) δ 10.18-10.13 (m, 2H), 8.44 (d, J=5.2 Hz, 1H), 8.28 (d, J=2.4 Hz, 1H), 8.24 (s, 1H), 8.10 (s, 1H), 7.87-7.79 (m, 2H), 7.34 (d, J=4.6 Hz, 1H), 7.20 (s, 1H), 5.03 (q, J=8.5 Hz, 2H).

Example 60

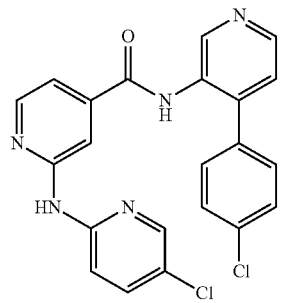 [SMILES: O=C(Nc1cnccc1-c1ccc(Cl)cc1)c1ccnc(Nc2ccc(Cl)cn2)c1]

N-(4-(4-Chlorophenyl)pyridin-3-yl)-2-((5-chloro-pyridin-2-yl)amino)isonicotinamide MS (ESI) (m/z): 436 (M+H)+; 1H NMR (500 MHz, DMSO-d6) δ 10.40 (br. s., 1H), 10.12 (s, 1H), 8.66 (s, 1H), 8.59 (d, J=5.2 Hz, 1H), 8.39 (d, J=4.9 Hz, 1H), 8.27 (s, 1H), 7.98 (s, 1H), 7.83-7.78 (m, 2H), 7.58-7.49 (m, 5H), 7.23 (d, J=4.9 Hz, 1H).

Example 61

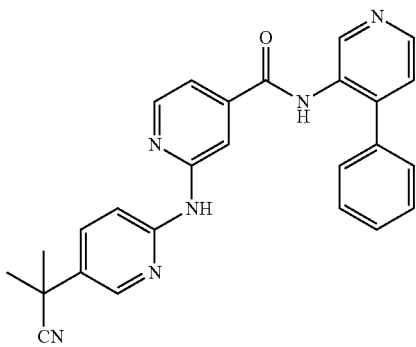 [SMILES: CC(C)(C#N)c1ccc(Nc2cc(C(=O)Nc3cnccc3-c3ccccc3)ccn2)nc1]

2-((5-(2-Cyanopropan-2-yl)pyridin-2-yl)amino)-N-(4-phenylpyridin-3-yl)isonicotinamide MS (ESI) (m/z): 435 (M+H)+; 1H NMR (500 MHz, DMSO-d6) δ 10.33 (s, 1H) 10.06 (s, 1H) 8.65 (s, 1H) 8.59 (d, J=5.19 Hz, 1H) 8.33-8.41 (m, 2H) 8.11 (s, 1H) 7.85 (dd, J=8.85, 2.75 Hz, 1H) 7.74 (d, J=8.85 Hz, 1H) 7.53-7.57 (m, 2H) 7.45-7.52 (m, 3H) 7.41-7.45 (m, 1H) 7.20 (d, J=5.19 Hz, 1H) 1.72 (s, 6H).

Example 62

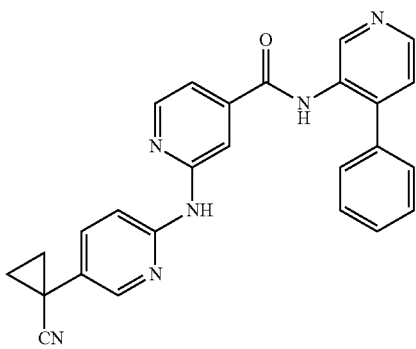 [SMILES: N#CC1(c2ccc(Nc3cc(C(=O)Nc4cnccc4-c4ccccc4)ccn3)nc2)CC1]

2-((5-(1-Cyanocyclopropyl)pyridin-2-yl)amino)-N-(4-phenylpyridin-3-yl)isonicotinamide MS (ESI) (m/z): 433 (M+H)+; 1H NMR (500 MHz, DMSO-d6) δ 10.34 (s, 1H) 10.06 (s, 1H) 8.65 (s, 1H) 8.59 (d, J=4.88 Hz, 1H) 8.36 (d, J=4.88 Hz, 1H) 8.27 (d, J=2.44 Hz, 1H) 8.07 (s, 1H) 7.70-7.74 (m, 1H) 7.64-7.68 (m, 1H) 7.52-7.57 (m, 2H) 7.39-7.51 (m, 4H) 7.20 (d, J=4.58 Hz, 1H) 1.70-1.76 (m, 2H) 1.48-1.54 (m, 2H).

Example 75

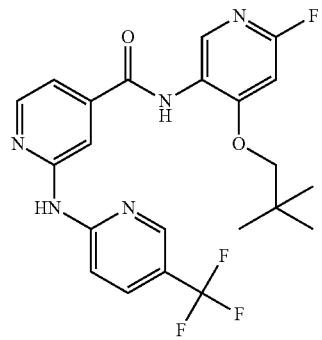 [SMILES: CC(C)(C)COc1cc(F)ncc1NC(=O)c1ccnc(Nc2ccc(C(F)(F)F)cn2)c1]

N-(6-Fluoro-4-(neopentyloxy)pyridin-3-yl)-2-((5-(trifluoromethyl)pyridin-2-yl)amino)isonicotinamide MS (ESI) (m/z): 464 (M+H)+; 1H NMR (500 MHz, DMSO-d6) δ 10.51 (s, 1H), 10.04 (s, 1H), 8.60 (s, 1H), 8.49 (d, J=5.2 Hz, 1H), 8.25 (s, 1H), 8.13 (s, 1H), 8.08-8.04 (m, J=8.9, 2.4 Hz, 1H), 7.90 (d, J=8.9 Hz, 1H), 7.42 (d, J=4.6 Hz, 1H), 6.98 (s, 1H), 3.82 (s, 2H), 0.96 (s, 9H).

Example 112

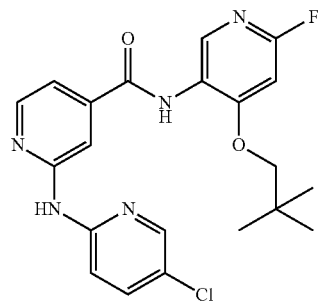 [SMILES: CC(C)(C)COc1cc(F)ncc1NC(=O)c1ccnc(Nc2ccc(Cl)cn2)c1]

2-((5-Chloropyridin-2-yl)amino)-N-(6-fluoro-4-(neopentyloxy)pyridin-3-yl)isonicotinamide MS (ESI) (m/z): 430 (M+H)+; 1H NMR (500 MHz, DMSO-d6) δ 10.16 (s, 1H), 10.01 (s, 1H), 8.43 (d, J=5.2 Hz, 1H), 8.27 (d, J=1.8 Hz, 1H), 8.11 (s, 2H), 7.85-7.79 (m, 2H), 7.34 (d, J=5.2 Hz, 1H), 6.98 (s, 1H), 3.82 (s, 2H), 0.96 (s, 9H).

Example 117

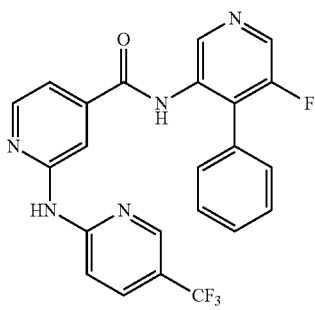 [SMILES: O=C(Nc1cncc(F)c1-c1ccccc1)c1ccnc(Nc2ccc(C(F)(F)F)cn2)c1]

N-(5-Fluoro-4-phenylpyridin-3-yl)-2-((5-(trifluoromethyl)pyridin-2-yl)amino)isonicotinamide MS (ESI) (m/z): 454.2 (M+H)$^+$; $^1$H NMR (500 MHz, DMSO-d$_6$) δ 10.45 (s, 1H), 10.38 (s, 1H), 8.65 (s, 1H), 8.63 (s, 1H), 8.59 (s, 1H), 8.40 (d, J=5.2 Hz, 1H), 8.09-8.02 (m, 2H), 7.88 (d, J=9.1 Hz, 1H), 7.52-7.40 (m, 6H), 7.21 (s, 1H).

Example 111

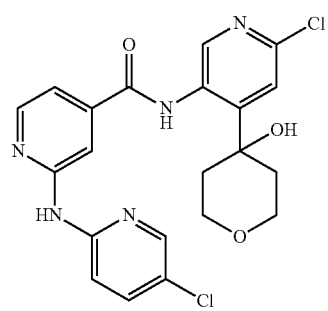 [SMILES: O=C(Nc1cnc(Cl)cc1C1(O)CCOCC1)c1ccnc(Nc2ccc(Cl)cn2)c1]

N-(6-Chloro-4-(4-hydroxytetrahydro-2H-pyran-4-yl)pyridin-3-yl)-2-((5-chloropyridin-2-yl)amino)isonicotinamide MS (ESI) (m/z): 460 (M+H)$^+$.

Example 48

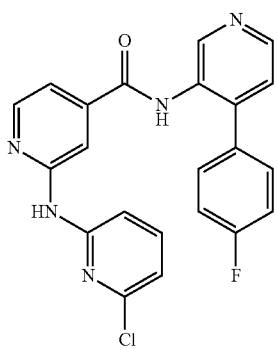 [SMILES: O=C(Nc1cnccc1-c1ccc(F)cc1)c1ccnc(Nc2cccc(Cl)n2)c1]

2-((6-Chloropyridin-2-yl)amino)-N-(4-(4-fluorophenyl)pyridin-3-yl)isonicotinamide MS (ESI) (m/z): 420 (M+H)$^+$; $^1$H NMR (500 MHz, DMSO-d$_6$) δ 10.42 (s, 1H), 10.29 (s, 1H), 8.63 (s, 1H), 8.59 (d, J=5.2 Hz, 1H), 8.40 (d, J=5.2 Hz, 1H), 7.92-7.84 (m, 2H), 7.76 (t, J=7.9 Hz, 1H), 7.59 (dd, J=8.7, 5.6 Hz, 2H), 7.50 (d, J=4.9 Hz, 1H), 7.31 (t, J=8.9 Hz, 2H), 7.24 (d, J=4.6 Hz, 1H), 7.00 (d, J=7.3 Hz, 1H).

Example 32

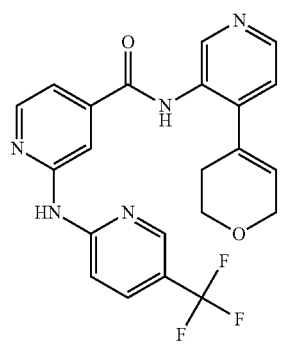 [SMILES: O=C(Nc1cnccc1C1=CCOCC1)c1ccnc(Nc2ccc(C(F)(F)F)cn2)c1]

N-(4-(3,6-Dihydro-2H-pyran-4-yl)pyridin-3-yl)-2-((5-(trifluoromethyl)pyridin-2-yl)amino)isonicotinamide MS (ESI) (m/z): 442 (M+H)$^+$; $^1$H NMR (500 MHz, DMSO-d$_6$) δ 10.52 (s, 1H), 10.33 (s, 1H), 8.63 (s, 1H), 8.57 (s, 1H), 8.48 (dd, J=9.2, 5.2 Hz, 2H), 8.22 (s, 1H), 8.06 (dd, J=9.0, 2.6 Hz, 1H), 7.93 (d, J=8.9 Hz, 1H), 7.43-7.37 (m, 2H), 6.00 (br. s., 1H), 4.17 (d, J=2.7 Hz, 2H), 3.79 (t, J=5.3 Hz, 2H), 3.18 (d, J=5.2 Hz, 2H).

Example 35

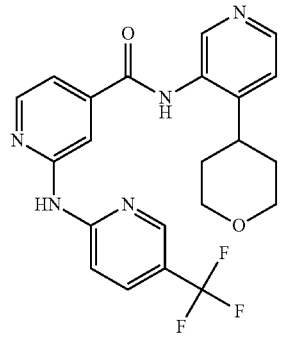 [SMILES: O=C(Nc1cnccc1C1CCOCC1)c1ccnc(Nc2ccc(C(F)(F)F)cn2)c1]

N-(4-(Tetrahydro-2H-pyran-4-yl)pyridin-3-yl)-2-((5-(trifluoromethyl)pyridin-2-yl)amino)isonicotinamide MS (ESI) (m/z): 444 (M+H)$^+$; $^1$H NMR (500 MHz, DMSO-d$_6$) δ 10.53 (s, 1H), 10.37 (s, 1H), 8.63 (s, 1H), 8.51 (d, J=5.2 Hz, 1H), 8.48 (d, J=2.4 Hz, 2H), 8.22 (s, 1H), 8.07 (dd, J=8.9, 2.4 Hz, 1H), 7.98 (d, J=8.9 Hz, 1H), 7.50-7.45

(m, 2H), 3.99-3.93 (m, 2H), 3.43-3.38 (m, 1H), 3.06 (t, J=11.1 Hz, 1H), 1.75-1.64 (m, 3H).

Example 36

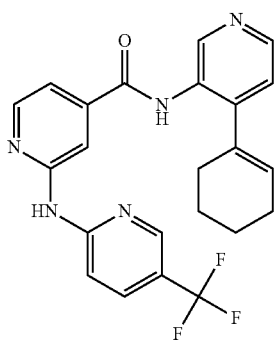 [SMILES: O=C(Nc1cnccc1C1=CCCCC1)c1ccnc(Nc2ccc(C(F)(F)F)cn2)c1]

N-(4-(Cyclohex-1-en-1-yl)pyridin-3-yl)-2-((5-(trifluoromethyl)pyridin-2-yl)amino)isonicotinamide MS (ESI) (m/z): 440 (M+H)$^+$; $^1$H NMR (500 MHz, DMSO-d$_6$) δ 10.52 (s, 1H), 10.21 (s, 1H), 8.61 (s, 1H), 8.55 (s, 1H), 8.49 (d, J=5.2 Hz, 1H), 8.43 (d, J=5.2 Hz, 1H), 8.20 (s, 1H), 8.06 (dd, J=8.7, 2.6 Hz, 1H), 7.92 (d, J=8.9 Hz, 1H), 7.39 (d, J=4.6 Hz, 1H), 7.30 (d, J=5.2 Hz, 1H), 5.87-5.83 (m, 1H), 2.28 (br. s., 2H), 2.10 (d, J=3.7 Hz, 2H), 1.71-1.65 (m, 2H), 1.62-1.56 (m, 2H).

Example 37

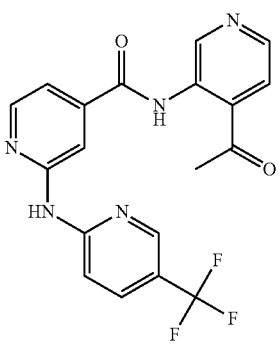 [SMILES: CC(=O)c1ccncc1NC(=O)c1ccnc(Nc2ccc(C(F)(F)F)cn2)c1]

N-(4-Acetylpyridin-3-yl)-2-((5-(trifluoromethyl)pyridin-2-yl)amino)isonicotinamide MS (ESI) (m/z): 402 (M+H)$^+$.

Example 33

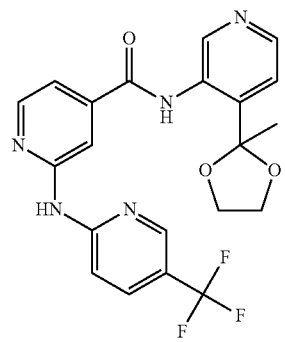 [SMILES: CC1(c2ccncc2NC(=O)c2ccnc(Nc3ccc(C(F)(F)F)cn3)c2)OCCO1]

N-(4-(2-Methyl-1,3-dioxolan-2-yl)pyridin-3-yl)-2-((5-(trifluoromethyl)pyridin-2-yl)amino)isonicotinamide MS (ESI) (m/z): 446 (M+H)$^+$; $^1$H NMR (500 MHz, DMSO-d$_6$) δ 10.60 (s, 1H), 10.09 (s, 1H), 9.16 (s, 1H), 8.63 (s, 1H), 8.54 (d, J=5.2 Hz, 1H), 8.47 (d, J=5.2 Hz, 1H), 8.35 (s, 1H), 8.07 (dd, J=9.2, 2.4 Hz, 1H), 7.91 (d, J=8.9 Hz, 1H), 7.50 (d, J=4.9 Hz, 1H), 7.42 (dd, J=5.2, 1.2 Hz, 1H), 4.13-4.08 (m, 2H), 3.85-3.80 (m, 2H), 1.64 (s, 3H).

Example 34

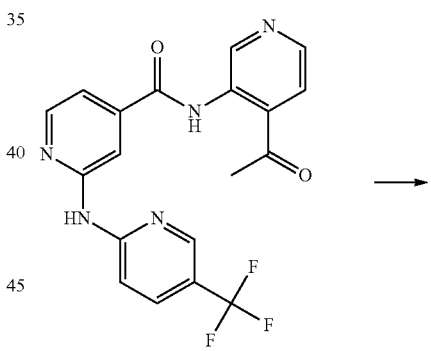

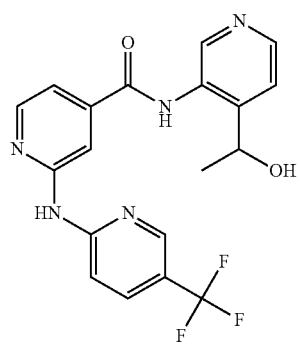

N-(4-(1-Hydroxyethyl)pyridin-3-yl)-2-((5-(trifluoromethyl)pyridin-2-yl)amino)isonicotinamide Sodiumborohydride (2.357 mg, 0.062 mmol) was added to the MeOH (3 mL) solution of N-(4-acetylpyridin-3-yl)-

2-((5-(trifluoromethyl)pyridin-2-yl)amino)isonicotinamide (5 mg, 0.012 mmol) at rt. The reaction was stirred for 20 min. The solvent was removed via vacuum and the product was purified via SCP. MS(ES+) m/e 404 MS[M+H]⁺; ¹H NMR (500 MHz, DMSO-d₆) δ 10.58-10.50 (m, 1H), 8.83 (s, 1H), 8.64 (s, 1H), 8.52 (d, J=4.9 Hz, 1H), 8.45 (d, J=4.9 Hz, 1H), 8.34 (s, 1H), 8.07 (dd, J=9.0, 2.6 Hz, 1H), 7.91 (d, J=8.9 Hz, 1H), 7.51 (d, J=5.2 Hz, 1H), 7.44 (d, J=4.0 Hz, 1H), 5.91 (br. s., 1H), 5.02 (q, J=6.4 Hz, 1H), 1.36 (d, J=6.4 Hz, 3H).

Example 74

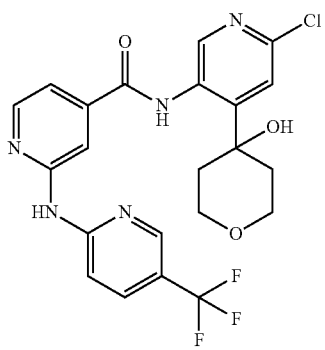 [SMILES: O=C(Nc1cnc(Cl)cc1C1(O)CCOCC1)c1ccnc(Nc2ccc(C(F)(F)F)cn2)c1]

N-(6-Chloro-4-(4-hydroxytetrahydro-2H-pyran-4-yl)pyridin-3-yl)-2-((5-(trifluoromethyl)pyridin-2-yl)amino)isonicotinamide MS (ESI) (m/z) 494 (M+H)⁺; ¹H NMR (500 MHz, DMSO-d₆) δ 11.34 (br. s., 1H), 10.63 (s, 1H), 9.30 (s, 1H), 8.70 (s, 1H), 8.58-8.54 (m, 2H), 8.07 (dd, J=8.9, 2.4 Hz, 1H), 7.76 (d, J=8.9 Hz, 1H), 7.54 (s, 1H), 7.39 (dd, J=5.2, 1.5 Hz, 1H), 6.83 (br. s., 1H), 3.86-3.71 (m, 4H), 2.12 (td, J=12.6, 5.0 Hz, 2H), 1.83 (d, J=13.1 Hz, 2H).

Example 76

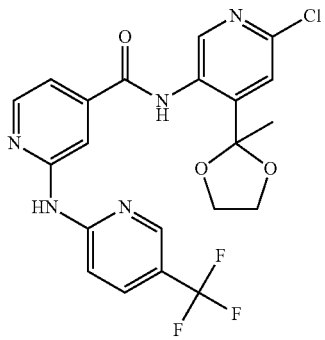 [SMILES: CC1(c2cc(Cl)ncc2NC(=O)c2ccnc(Nc3ccc(C(F)(F)F)cn3)c2)OCCO1]

N-(6-Chloro-4-(2-methyl-1,3-dioxolan-2-yl)pyridin-3-yl)-2-((5-(trifluoromethyl)pyridin-2-yl)amino)isonicotinamide MS (ESI) (m/z) 480 (M+H)⁺; ¹H NMR (500 MHz, DMSO-d₆) δ 10.59 (s, 1H), 10.10 (s, 1H), 9.00 (s, 1H), 8.61 (s, 1H), 8.53 (d, J=5.2 Hz, 1H), 8.33 (s, 1H), 8.06 (dd, J=8.9, 2.1 Hz, 1H), 7.89 (d, J=8.9 Hz, 1H), 7.52 (s, 1H), 7.41-7.36 (m, 1H), 4.12-4.07 (m, 2H), 3.87-3.82 (m, 2H), 1.64 (s, 3H).

Example 38

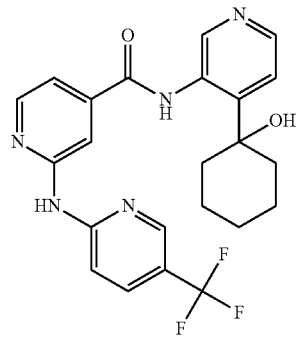 [SMILES: O=C(Nc1cnccc1C1(O)CCCCC1)c1ccnc(Nc2ccc(C(F)(F)F)cn2)c1]

N-(4-(1-Hydroxycyclohexyl)pyridin-3-yl)-2-((5-(trifluoromethyl)pyridin-2-yl)amino)isonicotinamide MS (ESI) (m/z) 458 (M+H)⁺; ¹H NMR (500 MHz, DMSO-d₆) δ 11.62 (s, 1H), 10.59 (s, 1H), 9.51 (s, 1H), 8.70 (s, 1H), 8.64 (s, 1H), 8.54 (d, J=5.2 Hz, 1H), 8.35 (d, J=5.2 Hz, 1H), 8.09-8.02 (m, J=8.9, 2.1 Hz, 1H), 7.71 (d, J=8.9 Hz, 1H), 7.43-7.39 (m, J=4.0, 4.0 Hz, 2H), 6.45 (s, 1H), 1.98-1.91 (m, J=9.2 Hz, 2H), 1.81-1.72 (m, J=9.8 Hz, 4H), 1.67-1.59 (m, J=12.2 Hz, 1H), 1.58-1.49 (m, 2H), 1.30-1.19 (m, J=10.1 Hz, 1H).

Example 39

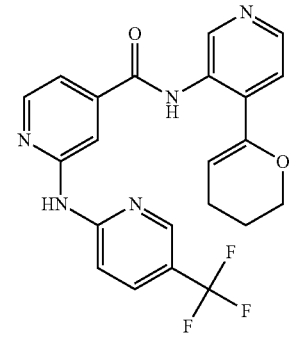 [SMILES: O=C(Nc1cnccc1C1=CCCCO1)c1ccnc(Nc2ccc(C(F)(F)F)cn2)c1]

N-(4-(3,4-Dihydro-2H-pyran-6-yl)pyridin-3-yl)-2-((5-(trifluoromethyl)pyridin-2-yl)amino)isonicotinamide MS (ESI) (m/z) 442 (M+H)⁺; ¹H NMR (500 MHz, DMSO-d₆) δ 10.53-10.44 (m, 1H), 10.20 (br. s., 1H), 8.84-8.74 (m, 1H), 8.63-8.54 (m, 1H), 8.52-8.45 (m, 1H), 8.44-8.35 (m, 1H), 8.25-8.15 (m, 1H), 8.02 (d, J=8.9 Hz, 1H), 7.97-7.86 (m, 1H), 7.49-7.33 (m, 2H), 5.46-5.36 (m, 1H), 4.14-4.01 (m, 2H), 2.13 (d, J=4.6 Hz, 2H), 1.87-1.73 (m, 2H).

Example 77

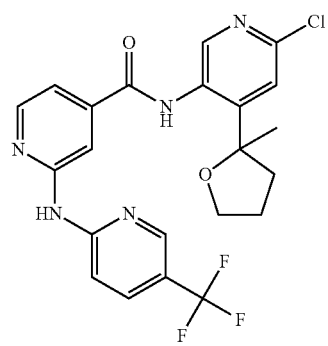

N-(6-Chloro-4-(2-methyltetrahydrofuran-2-yl)pyridin-3-yl)-2-((5-(trifluoromethyl)pyridin-2-yl)amino)isonicotinamide MS (ESI) (m/z) 478 (M+H)+; 1H NMR (500 MHz, DMSO-d6) δ 10.70 (br. s., 1H), 10.56 (s, 1H), 8.84 (s, 1H), 8.59 (s, 1H), 8.51 (d, J=5.2 Hz, 1H), 8.32 (s, 1H), 8.05 (dd, J=8.7, 2.0 Hz, 1H), 7.88 (d, J=8.9 Hz, 1H), 7.58 (s, 1H), 7.38 (d, J=4.9 Hz, 1H), 4.00 (td, J=7.9, 4.9 Hz, 1H), 3.81 (q, J=7.5 Hz, 1H), 2.34-2.26 (m, 1H), 2.19 (ddd, J=12.7, 7.7, 5.5 Hz, 1H), 2.01 (dt, J=12.1, 7.7 Hz, 1H), 1.89-1.80 (m, 1H), 1.48 (s, 3H).

Example 41

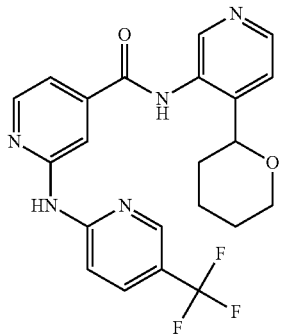 [SMILES: O=C(Nc1cnccc1C1CCCCO1)c1ccnc(Nc2ccc(C(F)(F)F)cn2)c1]

N-(4-(Tetrahydro-2H-pyran-2-yl)pyridin-3-yl)-2-((5-(trifluoromethyl)pyridin-2-yl)amino)isonicotinamide MS (ESI) (m/z) 444 (M+H)+; 1H NMR (500 MHz, DMSO-d6) δ 10.49 (s, 1H), 10.36 (br. s., 1H), 8.67 (s, 1H), 8.60 (br. s., 1H), 8.50 (d, J=4.6 Hz, 1H), 8.46 (d, J=5.2 Hz, 1H), 8.22 (s, 1H), 8.04 (d, J=7.0 Hz, 1H), 7.90 (d, J=9.2 Hz, 1H), 7.47 (d, J=4.9 Hz, 1H), 7.41 (d, J=4.6 Hz, 1H), 4.59 (d, J=11.0 Hz, 1H), 4.07 (d, J=10.1 Hz, 1H), 1.87-1.79 (m, J=9.2 Hz, 2H), 1.54 (br. s., 3H), 1.38 (d, J=10.4 Hz, 1H).

Example 78

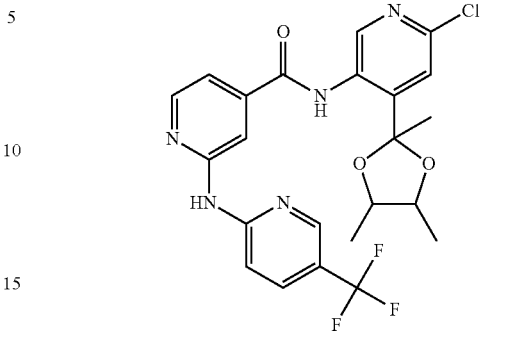

N-(6-Chloro-4-(2,4,5-trimethyl-1,3-dioxolan-2-yl)pyridin-3-yl)-2-((5-(trifluoromethyl)pyridin-2-yl)amino)isonicotinamide MS (ESI) (m/z) 508 (M+H)+.

Example 80

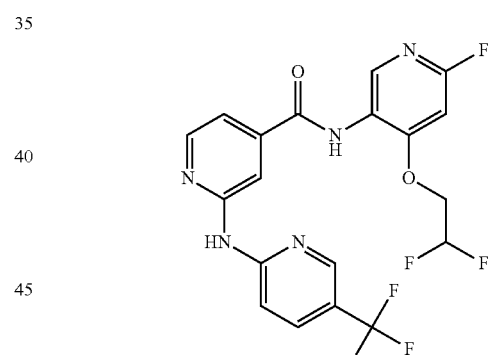

N-(4-(2,2-Difluoroethoxy)-6-fluoropyridin-3-yl)-2-((5-(trifluoromethyl)pyridin-2-yl)amino)isonicotinamide MS (ESI) (m/z) 458 (M+H)+; 1H NMR (500 MHz, DMSO-d6) δ 10.48 (s, 1H), 10.08 (s, 1H), 8.60 (br. s., 1H), 8.48 (d, J=4.9 Hz, 1H), 8.28 (s, 1H), 8.22 (br. s., 1H), 8.04 (d, J=9.2 Hz, 1H), 7.89 (d, J=9.2 Hz, 1H), 7.41 (d, J=3.7 Hz, 1H), 7.13 (s, 1H), 6.53-6.27 (m, 1H), 4.56 (t, J=14.3 Hz, 2H).

Example 79

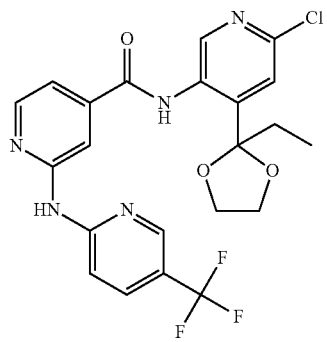 [SMILES: CCC1(c2cc(Cl)ncc2NC(=O)c2ccnc(Nc3ccc(C(F)(F)F)cn3)c2)OCCO1]

N-(6-Chloro-4-(2-ethyl-1,3-dioxolan-2-yl)pyridin-3-yl)-2-((5-(trifluoromethyl)pyridin-2-yl)amino)isonicotinamide MS (ESI) (m/z) 458 (M+H)$^+$; $^1$H NMR (500 MHz, DMSO-d$_6$) δ 10.59 (s, 1H), 10.11 (br. s., 1H), 9.03 (s, 1H), 8.61 (br. s., 1H), 8.53 (d, J=5.2 Hz, 1H), 8.35 (s, 1H), 8.06 (d, J=7.3 Hz, 1H), 7.86 (d, J=8.9 Hz, 1H), 7.47 (s, 1H), 7.38 (d, J=4.0 Hz, 1H), 4.13-4.06 (m, 2H), 3.91-3.85 (m, 2H), 1.94-1.88 (m, 2H), 0.82 (t, J=7.3 Hz, 3H).

Example 83

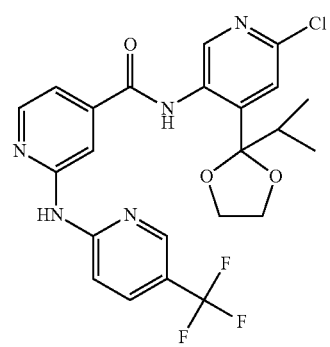

N-(6-Chloro-4-(2-isopropyl-1,3-dioxolan-2-yl)pyridin-3-yl)-2-((5-(trifluoromethyl)pyridin-2-yl)amino)isonicotinamide MS (ESI) (m/z) 508 (M+H)$^+$; $^1$H NMR (500 MHz, DMSO-d$_6$) δ 10.60 (br. s., 1H), 10.16 (br. s., 1H), 9.08 (s, 1H), 8.65-8.49 (m, 2H), 8.36 (br. s., 1H), 8.06 (d, J=8.2 Hz, 1H), 7.85 (d, J=8.5 Hz, 1H), 7.43 (s, 1H), 7.41-7.34 (m, 1H), 4.14-4.03 (m, 2H), 3.96-3.82 (m, 2H), 2.24-2.13 (m, 1H), 0.85 (d, J=6.4 Hz, 6H).

Example 81

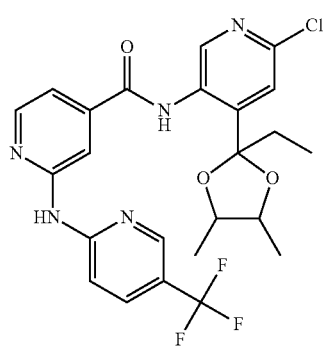 [SMILES: CCC1(c2cc(Cl)ncc2NC(=O)c2ccnc(Nc3ccc(C(F)(F)F)cn3)c2)OC(C)C(C)O1]

N-(6-Chloro-4-(2-ethyl-4,5-dimethyl-1,3-dioxolan-2-yl)pyridin-3-yl)-2-((5-(trifluoromethyl)pyridin-2-yl)amino)isonicotinamide MS (ESI) (m/z) 522 (M+H)$^+$.

Example 85

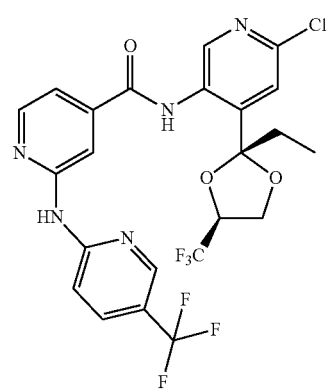 [SMILES: CC[C@@]1(c2cc(Cl)ncc2NC(=O)c2ccnc(Nc3ccc(C(F)(F)F)cn3)c2)OC[C@@H](C(F)(F)F)O1]

N-(6-Chloro-4-((2R,4S)-2-ethyl-4-(trifluoromethyl)-1,3-dioxolan-2-yl)pyridin-3-yl)-2-((5-(trifluoromethyl)pyridin-2-yl)amino)isonicotinamide MS (ESI) (m/z) 562 (M+H)$^+$.

Example 86

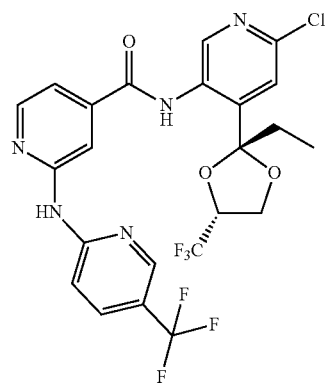 [SMILES: CC[C@@]1(c2cc(Cl)ncc2NC(=O)c2ccnc(Nc3ccc(C(F)(F)F)cn3)c2)OC[C@H](C(F)(F)F)O1]

N-(6-Chloro-4-((2R,4R)-2-ethyl-4-(trifluoromethyl)-1,3-dioxolan-2-yl)pyridin-3-yl)-2-((5-(trifluoromethyl)pyridin-2-yl)amino)isonicotinamide MS (ESI) (m/z) 562 (M+H)$^+$; $^1$H NMR (500 MHz, DMSO-d$_6$) δ 10.56 (br. s., 1H), 8.83 (br. s., 1H), 8.59 (br. s., 1H), 8.51 (br. s., 1H), 8.41 (br. s., 1H), 8.05 (d, J=8.5 Hz, 1H), 7.80 (d, J=8.5 Hz, 1H), 7.54 (br. s., 1H), 7.40 (br. s., 1H), 4.93 (br. s., 1H), 4.32 (d, J=10.1 Hz, 1H), 4.00-3.93 (m, 1H), 2.02 (d, J=6.4 Hz, 2H), 0.89-0.80 (m, 3H).

Example 87

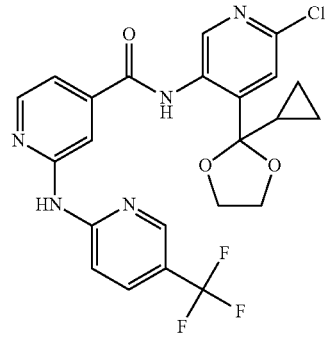 [SMILES: O=C(Nc1cnc(Cl)cc1C1(C2CC2)OCCO1)c1ccnc(Nc2ccc(C(F)(F)F)cn2)c1]

N-(6-Chloro-4-(2-cyclopropyl-1,3-dioxolan-2-yl)pyridin-3-yl)-2-((5-(trifluoromethyl)pyridin-2-yl)amino)isonicotinamide MS (ESI) (m/z) 506 (M+H)$^+$; $^1$H NMR (500 MHz, DMSO-d$_6$) δ 10.62-10.58 (m, 1H), 10.16 (br. s., 1H), 9.12-9.06 (m, 1H), 8.61 (br. s., 1H), 8.55-8.51 (m, J=4.9 Hz, 1H), 8.39 (br. s., 1H), 8.09-8.03 (m, J=8.2 Hz, 1H), 7.89-7.83 (m, J=9.2 Hz, 1H), 7.46-7.39 (m, 2H), 4.10-4.03 (m, 2H), 3.92-3.83 (m, 2H), 1.52-1.41 (m, 1H), 0.53-0.41 (m, 4H).

Example 88

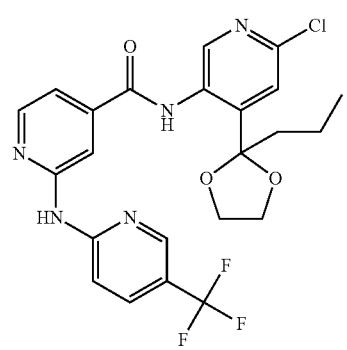 [SMILES: CCCC1(c2cc(Cl)ncc2NC(=O)c2ccnc(Nc3ccc(C(F)(F)F)cn3)c2)OCCO1]

N-(6-Chloro-4-(2-propyl-1,3-dioxolan-2-yl)pyridin-3-yl)-2-((5-(trifluoromethyl)pyridin-2-yl)amino)isonicotinamide MS (ESI) (m/z) 508 (M+H)$^+$; $^1$H NMR (500 MHz, DMSO-d$_6$) δ 10.57 (s, 1H), 10.12 (br. s., 1H), 9.02 (s, 1H), 8.59 (br. s., 1H), 8.52 (d, J=5.2 Hz, 1H), 8.35 (s, 1H), 8.04 (d, J=8.9 Hz, 1H), 7.84 (d, J=8.9 Hz, 1H), 7.46 (s, 1H), 7.37 (d, J=4.9 Hz, 1H), 4.12-4.05 (m, 2H), 3.89-3.82 (m, 2H), 1.91-1.83 (m, 2H), 1.32-1.21 (m, 2H), 0.79 (t, J=7.3 Hz, 3H).

Example 89

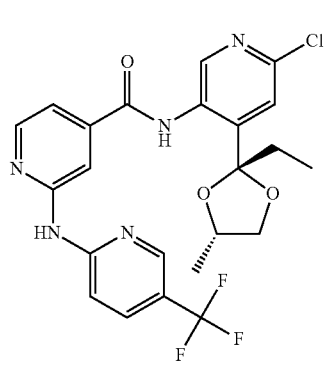 [SMILES: CC[C@@]1(c2cc(Cl)ncc2NC(=O)c2ccnc(Nc3ccc(C(F)(F)F)cn3)c2)OC[C@H](C)O1]

N-(6-Chloro-4-((2R,4S)-2-ethyl-4-methyl-1,3-dioxolan-2-yl)pyridin-3-yl)-2-((5-(trifluoromethyl)pyridin-2-yl)amino)isonicotinamide MS (ESI) (m/z) 508 (M+H)$^+$; $^1$H NMR (500 MHz, DMSO-d$_6$) δ 10.62 (s, 1H), 10.10 (d, J=10.4 Hz, 1H), 9.09 (s, 1H), 8.60 (br. s., 1H), 8.54 (d, J=5.2 Hz, 1H), 8.35 (s, 1H), 8.06 (d, J=7.0 Hz, 1H), 7.87 (d, J=8.9 Hz, 1H), 7.49 (s, 1H), 7.36 (d, J=5.2 Hz, 1H), 4.43-4.27 (m, 2H), 1.96-1.84 (m, 3H), 1.16 (d, J=5.8 Hz, 3H), 0.82 (t, J=7.3 Hz, 3H).

Example 90

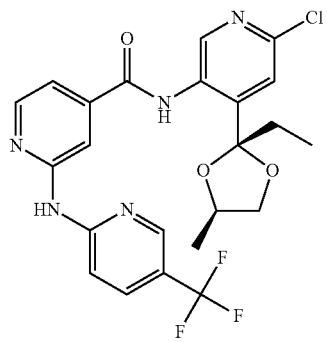 [SMILES: CC[C@@]1(c2cc(Cl)ncc2NC(=O)c2ccnc(Nc3ccc(C(F)(F)F)cn3)c2)OC[C@@H](C)O1]

N-(6-Chloro-4-((2R,4R)-2-ethyl-4-methyl-1,3-dioxolan-2-yl)pyridin-3-yl)-2-((5-(trifluoromethyl)pyridin-2-yl)amino)isonicotinamide MS (ESI) (m/z) 508 (M+H)$^+$; $^1$H NMR (500 MHz, DMSO-d$_6$) δ 10.59 (s, 1H), 10.07 (br. s., 1H), 9.04 (s, 1H), 8.61 (br. s., 1H), 8.53 (d, J=5.2 Hz, 1H), 8.39 (s, 1H), 8.09-8.01 (m, J=9.2 Hz, 1H), 7.83 (d, J=8.5 Hz, 1H), 7.48 (s, 1H), 7.37 (d, J=5.2 Hz, 1H), 4.24-4.14 (m, 1H), 4.02 (t, J=7.0 Hz, 1H), 3.57 (t, J=7.2 Hz, 1H), 1.95-1.83 (m, 2H), 1.26 (d, J=5.8 Hz, 3H), 0.84 (t, J=7.3 Hz, 3H).

Example 92

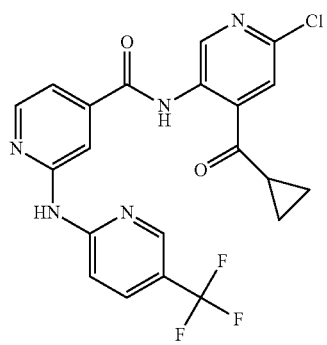

N-(6-Chloro-4-(cyclopropanecarbonyl)pyridin-3-yl)-2-((5-(trifluoromethyl)pyridin-2-yl)amino)isonicotinamide MS (ESI) (m/z) 462 (M+H)$^+$; $^1$H NMR (500 MHz, DMSO-d$_6$) δ 11.27 (br. s., 1H), 10.56 (br. s., 1H), 9.01 (d, J=3.7 Hz, 1H), 8.63 (br. s., 1H), 8.54-8.49 (m, J=4.3 Hz, 1H), 8.35 (br. s., 1H), 8.08-8.02 (m, J=8.2 Hz, 1H), 7.99-7.95 (m, J=3.7 Hz, 1H), 7.89-7.84 (m, J=8.5 Hz, 1H), 7.45-7.40 (m, 1H), 2.77-2.70 (m, J=3.7 Hz, 1H), 1.17-1.08 (m, J=3.4 Hz, 4H).

Example 93

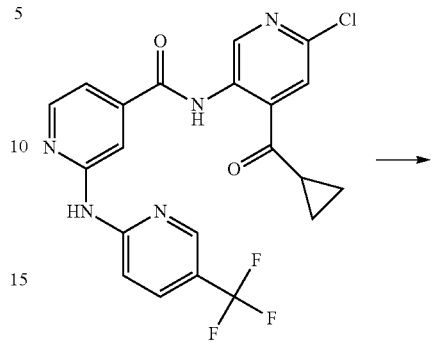

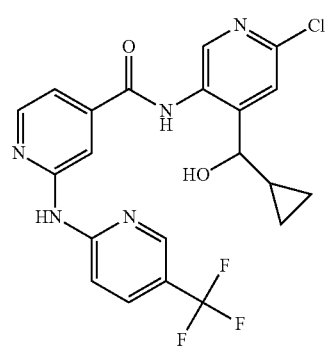 [SMILES: O=C(Nc1cnc(Cl)cc1C(=O)C1CC1)c1ccnc(Nc2ccc(C(F)(F)F)cn2)c1]

N-(6-Chloro-4-(cyclopropyl(hydroxy)methyl)pyridin-3-yl)-2-((5-(trifluoromethyl)pyridin-2-yl)amino)isonicotinamide MS (ESI) (m/z) 464 (M+H)$^+$; $^1$H NMR (500 MHz, DMSO-d$_6$) δ 10.56 (s, 1H), 8.90 (s, 1H), 8.64 (s, 1H), 8.52 (d, J=4.6 Hz, 1H), 8.41 (s, 1H), 8.05 (d, J=9.2 Hz, 1H), 7.85 (d, J=8.9 Hz, 1H), 7.58 (s, 1H), 7.41 (d, J=4.6 Hz, 1H), 4.40 (d, J=7.3 Hz, 1H), 1.17 (d, J=6.4 Hz, 1H), 0.52-0.32 (m, 4H).

Example 98

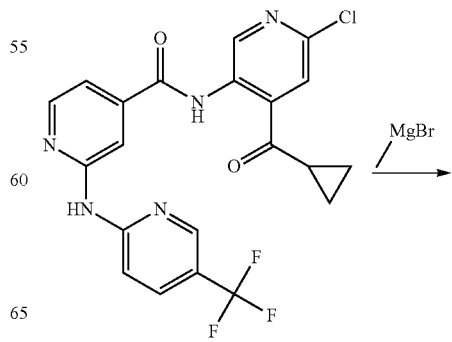

-continued

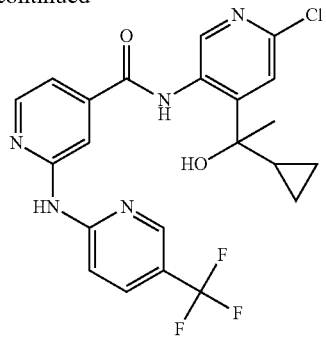

N-(6-Chloro-4-(1-cyclopropyl-1-hydroxyethyl)pyridin-3-yl)-2-((5-(trifluoromethyl)pyridin-2-yl)amino)isonicotinamide Methylmagnesium bromide (0.1 mL, 0.300 mmol) was added to the THF (1 mL) solution of N-(6-chloro-4-(cyclopropanecarbonyl)pyridin-3-yl)-2-((5-(trifluoromethyl)pyridin-2-yl)amino)isonicotinamide (1.8 mg, 3.90 μmol) at room temperature. The reaction was stirred at rt for 1 hour before quenched with MeOH. The solvent was removed via vacuum and the crude was partitioned between ethyl acetate and water. The ethyl acetate layer was separated, dried (Na$_2$SO$_4$), filtered and concentrated. The product was submitted to SCP for further purification (obtained 1.3 mg, 70% yield).

MS(ES+) m/e 478 [M+H]$^+$; $^1$H NMR (500 MHz, DMSO-d$_6$) δ 10.57 (br. s., 1H), 9.33 (s, 1H), 8.64 (s, 1H), 8.50 (d, J=4.9 Hz, 1H), 8.43 (s, 1H), 8.06 (d, J=8.5 Hz, 1H), 7.86 (d, J=8.9 Hz, 1H), 7.56 (s, 1H), 7.37 (d, J=5.2 Hz, 1H), 1.51 (s, 3H), 1.39 (d, J=5.8 Hz, 1H), 0.55-0.38 (m, 4H).

Example 99

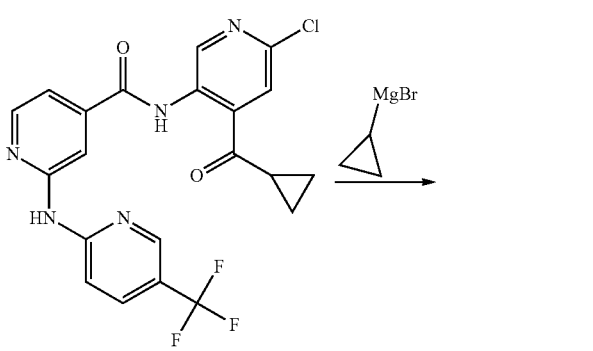

N-(6-Chloro-4-(dicyclopropyl(hydroxy)methyl)pyridin-3-yl)-2-((5-(trifluoromethyl)pyridin-2-yl)amino)isonicotinamide MS (ESI) (m/z) 504 (M+H)$^+$; $^1$H NMR (500 MHz, DMSO-d$_6$) δ 11.52 (br. s., 1H), 10.57 (s, 1H), 9.34 (s, 1H), 8.64 (s, 1H), 8.52 (d, J=5.2 Hz, 1H), 8.42 (s, 1H), 8.10-8.03 (m, 1H), 7.88 (d, J=8.9 Hz, 1H), 7.67 (s, 1H), 7.36 (dd, J=5.2, 1.2 Hz, 1H), 6.35 (s, 1H), 1.42-1.32 (m, 2H), 0.67-0.58 (m, 2H), 0.49 (dt, J=7.5, 3.9 Hz, 2H), 0.44-0.33 (m, 4H).

Example 101

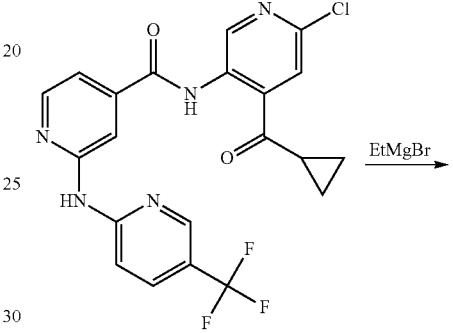

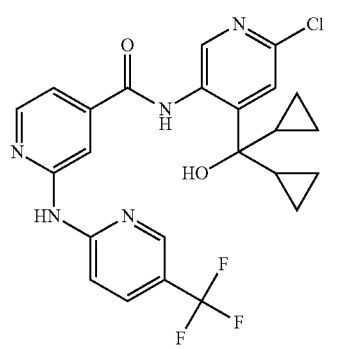

N-(6-Chloro-4-(1-cyclopropyl-1-hydroxypropyl)pyridin-3-yl)-2-((5-(trifluoromethyl)pyridin-2-yl)amino)isonicotinamide MS (ESI) (m/z) 492 (M+H)$^+$; $^1$H NMR (500 MHz, DMSO-d$_6$) δ 10.30 (s, 1H), 9.07 (s, 1H), 8.38 (s, 1H), 8.26 (d, J=5.2 Hz, 1H), 8.17 (s, 1H), 7.81 (dd, J=8.9, 2.1 Hz, 1H), 7.60 (d, J=8.9 Hz, 1H), 7.34 (s, 1H), 7.11-7.06 (m, 1H), 1.84-1.73 (m, 1H), 1.67-1.56 (m, 1H), 1.30-1.20 (m, 1H), 0.55 (t, J=7.3 Hz, 3H), 0.38-0.31 (m, 1H), 0.21 (dd, J=9.0, 5.3 Hz, 1H), 0.17-0.04 (m, 2H).

Example 102

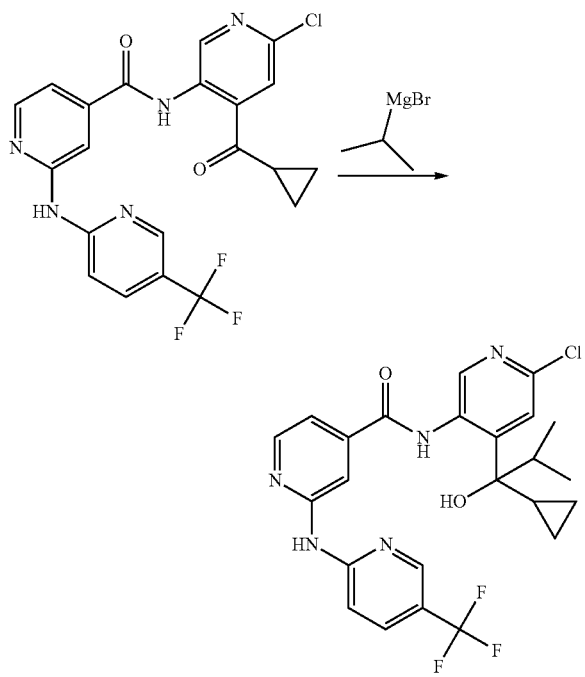

N-(6-Chloro-4-(1-cyclopropyl-1-hydroxy-2-methyl-propyl)pyridin-3-yl)-2-((5-(trifluoromethyl)pyridin-2-yl)amino)isonicotinamide MS (ESI) (m/z) 506 (M+H)$^+$; $^1$H NMR (500 MHz, DMSO-d$_6$) δ 10.33 (s, 1H), 9.14 (s, 1H), 8.44 (s, 1H), 8.30 (d, J=5.2 Hz, 1H), 8.21 (s, 1H), 7.86 (dd, J=9.0, 2.3 Hz, 1H), 7.68 (d, J=8.9 Hz, 1H), 7.39 (s, 1H), 7.17 (dd, J=5.2, 1.2 Hz, 1H), 2.13-2.05 (m, 1H), 1.37 (br. s., 1H), 0.71 (d, J=1.0 Hz, 3H), 0.70 (d, J=2.7 Hz, 3H), 0.56 (dd, J=9.3, 4.4 Hz, 1H), 0.34 (d, J=5.2 Hz, 1H), 0.20-0.12 (m, 1H), 0.01 (dd, J=9.2, 4.0 Hz, 1H).

Example 113

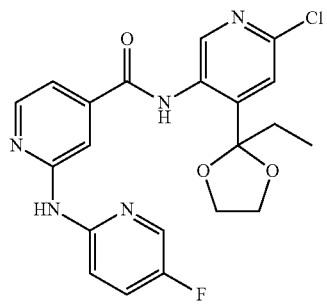 [SMILES: CCC1(c2cc(Cl)ncc2NC(=O)c2ccnc(Nc3ccc(F)cn3)c2)OCCO1]

N-(6-Chloro-4-(2-ethyl-1,3-dioxolan-2-yl)pyridin-3-yl)-2-((5-fluoropyridin-2-yl)amino)isonicotinamide MS (ESI) (m/z) 444 (M+H)$^+$; $^1$H NMR (500 MHz, DMSO-d$_6$) δ 10.14 (s, 1H), 10.08 (br. s., 1H), 9.06 (s, 1H), 8.45 (d, J=5.2 Hz, 1H), 8.27-8.21 (m, 2H), 7.80-7.65 (m, 2H), 7.47 (s, 1H), 7.27 (d, J=4.9 Hz, 1H), 4.15-4.07 (m, 2H), 3.94-3.85 (m, 2H), 1.91 (q, J=7.0 Hz, 2H), 0.82 (t, J=7.2 Hz, 3H).

Example 114

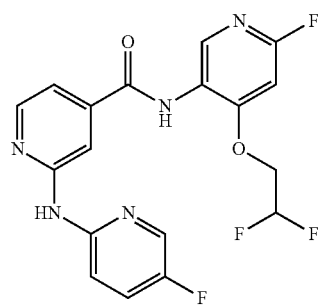 [SMILES: O=C(Nc1cnc(F)cc1OCC(F)F)c1ccnc(Nc2ccc(F)cn2)c1]

N-(4-(2,2-Difluoroethoxy)-6-fluoropyridin-3-yl)-2-((5-fluoropyridin-2-yl)amino)isonicotinamide MS (ESI) (m/z) 408 (M+H)$^+$; $^1$H NMR (500 MHz, DMSO-d$_6$) δ 10.02 (s, 1H), 8.40 (d, J=5.2 Hz, 1H), 8.28 (s, 1H), 8.24 (d, J=2.7 Hz, 1H), 8.06 (s, 1H), 7.84 (dd, J=9.2, 3.7 Hz, 1H), 7.68 (td, J=8.7, 3.1 Hz, 1H), 7.31 (d, J=4.3 Hz, 1H), 7.14 (s, 1H), 6.54-6.27 (m, 1H), 4.62-4.51 (m, 2H).

Example 95

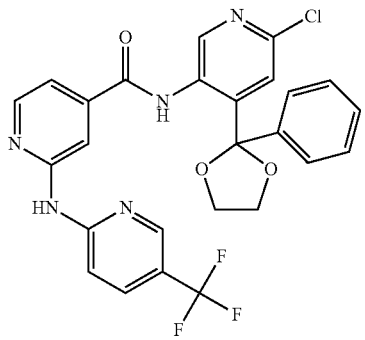 [SMILES: O=C(Nc1cnc(Cl)cc1C1(c2ccccc2)OCCO1)c1ccnc(Nc2ccc(C(F)(F)F)cn2)c1]

N-(6-Chloro-4-(2-phenyl-1,3-dioxolan-2-yl)pyridin-3-yl)-2-((5-(trifluoromethyl)pyridin-2-yl)amino)isonicotinamide MS (ESI) (m/z) 542 (M+H)$^+$; $^1$H NMR (500 MHz, DMSO-d$_6$) δ 10.59 (s, 1H), 10.02-9.55 (m, 1H), 8.94 (s, 1H), 8.58 (s, 1H), 8.49 (d, J=4.9 Hz, 1H), 8.23 (s, 1H), 8.06 (d, J=8.5 Hz, 1H), 7.87 (d, J=8.9 Hz, 1H), 7.78 (s, 1H), 7.43-7.36 (m, 2H), 7.32-7.20 (m, 4H), 4.26-4.09 (m, 4H).

Example 108

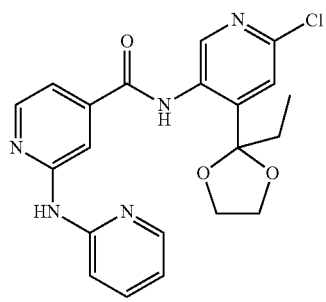 [SMILES: CCC1(c2cc(Cl)ncc2NC(=O)c2ccnc(Nc3ccccn3)c2)OCCO1]

N-(6-Chloro-4-(2-ethyl-1,3-dioxolan-2-yl)pyridin-3-yl)-2-(pyridin-2-ylamino)isonicotinamide MS (ESI) (m/z) 426 (M+H)$^+$; $^1$H NMR (500 MHz, DMSO-d$_6$) δ 10.05 (s, 1H), 9.09 (s, 1H), 8.46 (d, J=5.2 Hz, 1H), 8.43 (s, 1H), 8.28 (d, J=3.7 Hz, 1H), 7.73-7.67 (m, 1H), 7.62 (d, J=8.5 Hz, 1H), 7.47 (s, 1H), 7.28 (d, J=5.2 Hz, 1H), 6.96-6.91 (m, 1H), 4.15-4.08 (m, 2H), 3.90 (br. s., 2H), 1.97-1.88 (m, 2H), 0.83 (t, J=7.3 Hz, 3H).

Example 109

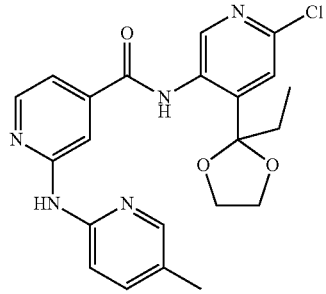 [SMILES: CCC1(c2cc(Cl)ncc2NC(=O)c2ccnc(Nc3ccc(C)cn3)c2)OCCO1]

N-(6-Chloro-4-(2-ethyl-1,3-dioxolan-2-yl)pyridin-3-yl)-2-((5-methylpyridin-2-yl)amino)isonicotinamide MS (ESI) (m/z) 440 (M+H)$^+$; $^1$H NMR (500 MHz, DMSO-d$_6$) δ 10.08 (br. s., 1H), 9.95 (s, 1H), 9.09 (s, 1H), 8.44 (d, J=4.9 Hz, 1H), 8.32 (s, 1H), 8.11 (s, 1H), 7.62-7.52 (m, 2H), 7.48 (s, 1H), 7.24 (d, J=5.2 Hz, 1H), 4.16-4.05 (m, 2H), 3.90 (t, J=6.9 Hz, 2H), 2.25 (s, 3H), 1.93 (q, J=7.1 Hz, 2H), 0.84 (t, J=7.3 Hz, 3H).

Example 96

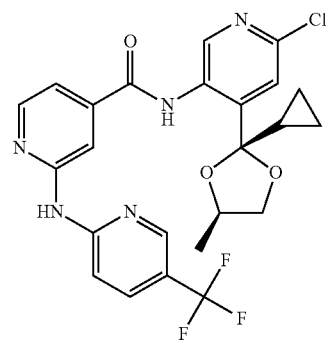 [SMILES: C[C@@H]1CO[C@](c2cc(Cl)ncc2NC(=O)c2ccnc(Nc3ccc(C(F)(F)F)cn3)c2)(C2CC2)O1]

N-(6-Chloro-4-((2R,4R)-2-cyclopropyl-4-methyl-1,3-dioxolan-2-yl)pyridin-3-yl)-2-((5-(trifluoromethyl)pyridin-2-yl)amino)isonicotinamide MS (ESI) (m/z) 520 (M+H)$^+$.

Example 97

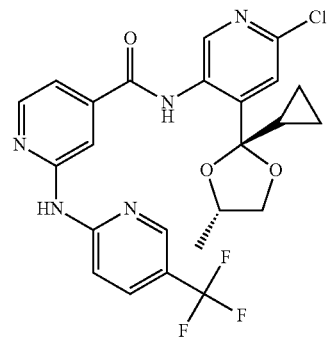 [SMILES: C[C@H]1CO[C@](c2cc(Cl)ncc2NC(=O)c2ccnc(Nc3ccc(C(F)(F)F)cn3)c2)(C2CC2)O1]

N-(6-Chloro-4-((2R,4S)-2-cyclopropyl-4-methyl-1,3-dioxolan-2-yl)pyridin-3-yl)-2-((5-(trifluoromethyl)pyridin-2-yl)amino)isonicotinamide MS (ESI) (m/z) 520 (M+H)$^+$; $^1$H NMR (500 MHz, DMSO-d$_6$) δ 10.62 (s, 1H), 10.21 (br. s., 1H), 9.11 (s, 1H), 8.64 (s, 1H), 8.55 (d, J=5.2 Hz, 1H), 8.47 (s, 1H), 8.07 (dd, J=8.9, 2.1 Hz, 1H), 7.82 (d, J=8.9 Hz, 1H), 7.45 (s, 1H), 7.42 (dd, J=5.2, 1.5 Hz, 1H), 4.22-4.14 (m, 1H), 4.02 (t, J=7.2 Hz, 1H), 3.54 (t, J=7.3 Hz, 1H), 1.53-1.44 (m, 1H), 1.24 (d, J=6.1 Hz, 3H), 0.60-0.53 (m, 1H), 0.52-0.43 (m, 3H).

93
Intermediate for Example 100

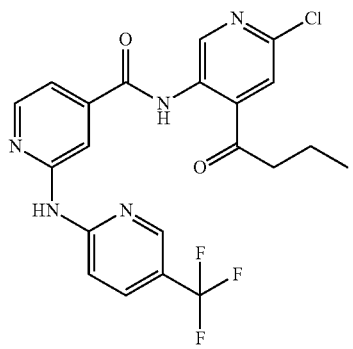 [SMILES: CCCC(=O)c1cc(Cl)ncc1NC(=O)c1ccnc(Nc2ccc(C(F)(F)F)cn2)c1]

N-(4-Butyryl-6-chloropyridin-3-yl)-2-((5-(trifluoromethyl)pyridin-2-yl)amino)isonicotinamide Followed synthesis of Example 4. MS(ES+) m/e 464 [M+H]+.

Example 100

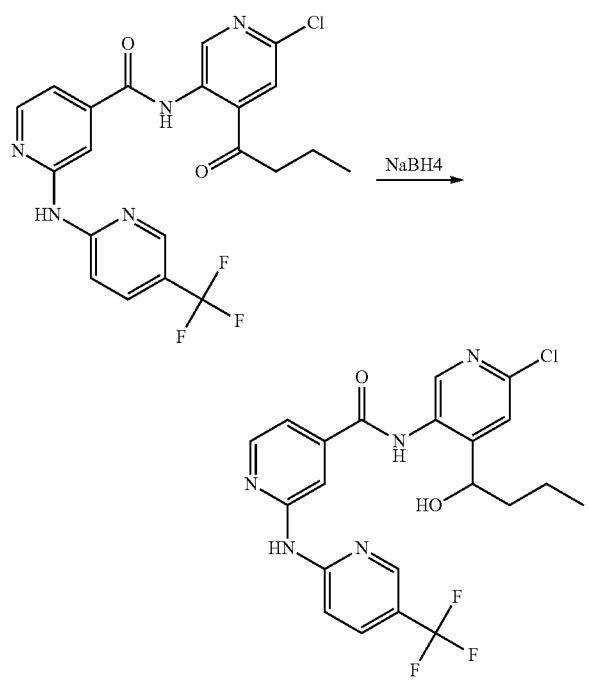

N-(6-Chloro-4-(1-hydroxybutyl)pyridin-3-yl)-2-((5-(trifluoromethyl)pyridin-2-yl)amino)isonicotinamide MS (ESI) (m/z) 466 (M+H)+; $^1$H NMR (500 MHz, DMSO-d$_6$) δ 10.56 (s, 1H), 8.68 (s, 1H), 8.63 (s, 1H), 8.52 (d, J=5.2 Hz, 1H), 8.36 (s, 1H), 8.06 (dd, J=9.0, 2.3 Hz, 1H), 7.87 (d, J=8.9 Hz, 1H), 7.57 (s, 1H), 7.43 (d, J=4.9 Hz, 1H), 4.88 (dd, J=7.5, 5.0 Hz, 1H), 1.64-1.54 (m, 2H), 1.36 (td, J=15.3, 7.5 Hz, 2H), 0.83 (t, J=7.3 Hz, 3H).

94
Intermediate for Example 103

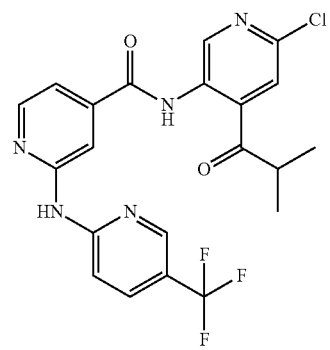 [SMILES: CC(C)C(=O)c1cc(Cl)ncc1NC(=O)c1ccnc(Nc2ccc(C(F)(F)F)cn2)c1]

N-(6-Chloro-4-isobutyrylpyridin-3-yl)-2-((5-(trifluoromethyl)pyridin-2-yl)amino)isonicotinamide Followed synthesis of Example 4. MS(ES+) m/e 464 [M+H]+; $^1$H NMR (400 MHz, CHLOROFORM-d) δ 12.20 (s, 1H), 10.09 (s, 1H), 8.71-8.68 (m, 1H), 8.54-8.49 (m, 2H), 7.86 (dd, J=8.8, 2.3 Hz, 1H), 7.83-7.80 (m, 2H), 7.59-7.52 (m, 2H), 3.67 (dt, J=13.6, 6.8 Hz, 1H), 1.34 (s, 3H), 1.32 (s, 3H).

Example 103

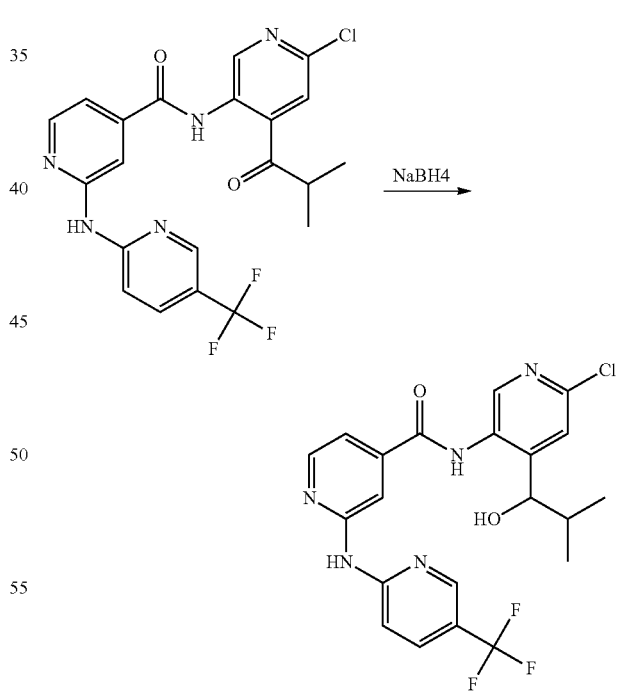

N-(6-Chloro-4-(1-hydroxy-2-methylpropyl)pyridin-3-yl)-2-((5-(trifluoromethyl)pyridin-2-yl)amino) isonicotinamide MS (ESI) (m/z) 466 (M+H)+; $^1$H NMR (500 MHz, DMSO-d$_6$) δ 10.55 (s, 1H), 8.80 (s, 1H), 8.63 (s, 1H), 8.52

(d, J=5.2 Hz, 1H), 8.38 (s, 1H), 8.05 (dd, J=9.2, 2.4 Hz, 1H), 7.84 (d, J=8.9 Hz, 1H), 7.53 (s, 1H), 7.40 (dd, J=5.2, 1.2 Hz, 1H), 4.71 (d, J=5.2 Hz, 1H), 1.90 (dd, J=12.2, 6.7 Hz, 1H), 0.85 (d, J=7.0 Hz, 3H), 0.82 (d, J=6.7 Hz, 3H).

Intermediate for Example 104

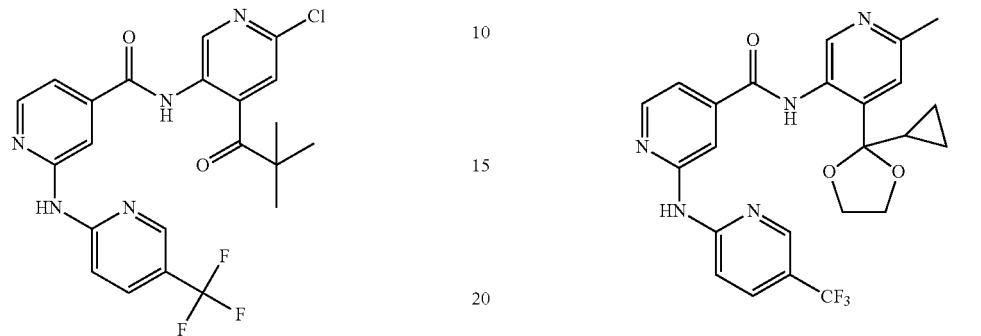

N-(6-Chloro-4-(1-hydroxy-2,2-dimethylpropyl)pyridin-3-yl)-2-((5-(trifluoromethyl)pyridin-2-yl)amino)isonicotinamide Followed synthesis of Example 4. MS (ESI) (m/z) 478 (M+H)$^+$.

Example 104

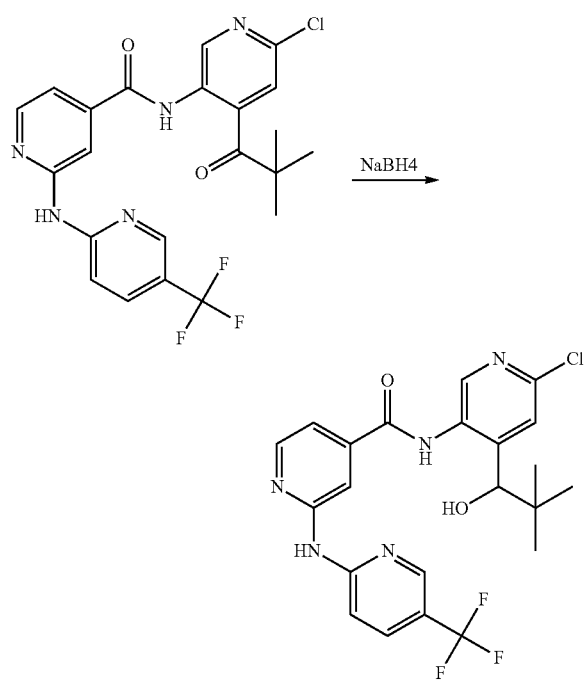

N-(6-Chloro-4-(1-hydroxy-2,2-dimethylpropyl)pyridin-3-yl)-2-((5-(trifluoromethyl)pyridin-2-yl)amino)isonicotinamide MS (ESI) (m/z) 480 (M+H)$^+$; $^1$H NMR (500 MHz, DMSO-d$_6$) δ 10.54 (s, 1H), 8.97 (s, 1H), 8.63 (s, 1H), 8.51 (d, J=5.2 Hz, 1H), 8.46 (s, 1H), 8.04 (dd, J=8.9, 2.4 Hz, 1H), 7.77 (d, J=8.9 Hz, 1H), 7.46 (s, 1H), 7.39 (dd, J=5.2, 1.2 Hz, 1H), 4.67 (s, 1H), 0.86 (s, 9H).

Example 105

N-(4-(2-Cyclopropyl-1,3-dioxolan-2-yl)-6-methylpyridin-3-yl)-2-((5-(trifluoromethyl)pyridin-2-yl)amino)isonicotinamide Followed synthesis of example 4. MS (ESI) (m/z): 486 (M+H)$^+$. $^1$H NMR (400 MHz, CHLOROFORM-d) δ 10.07 (s, 1H), 9.61 (s, 1H), 8.59 (s, 1H), 8.50 (d, J=5.1 Hz, 1H), 8.29 (s, 1H), 8.00-7.79 (m, 2H), 7.68 (d, J=8.8 Hz, 1H), 7.44 (dd, J=5.1, 1.5 Hz, 1H), 7.23 (s, 1H), 4.28-4.03 (m, 2H), 4.00-3.76 (m, 2H), 2.59 (s, 3H), 1.44-1.38 (m, 1H), 0.66-0.40 (m, 4H).

Example 106

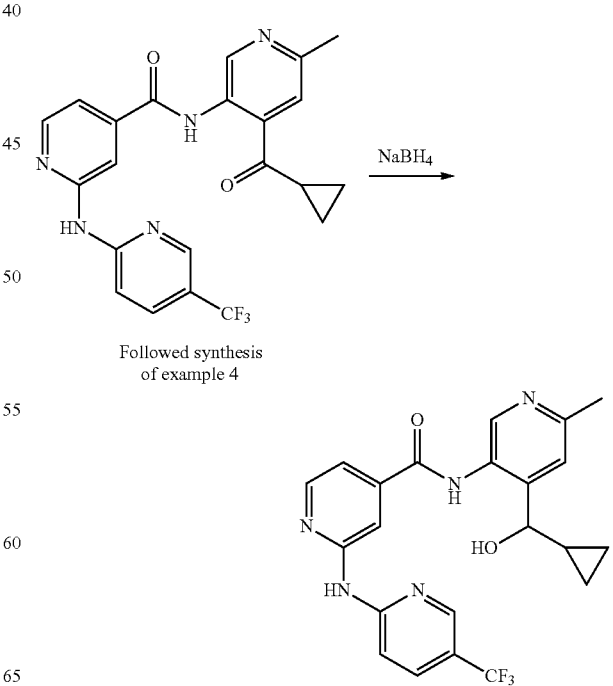

Followed synthesis of example 4

N-(4-(Cyclopropyl(hydroxy)methyl)-6-methylpyridin-3-yl)-2-((5-(trifluoromethyl)pyridin-2-yl)amino)isonicotinamide MS (ESI) (m/z): 444 (M+H)+. $^1$H NMR (500 MHz, DMSO-$d_6$) δ 10.55 (br. s., 2H), 8.88 (s, 1H), 8.65 (s, 1H), 8.51 (d, J=5.2 Hz, 1H), 8.40 (s, 1H), 8.06 (d, J=8.9 Hz, 1H), 7.87 (d, J=8.9 Hz, 1H), 7.42 (d, J=4.6 Hz, 1H), 7.33 (s, 1H), 6.10 (br. s., 1H), 4.33 (d, J=7.0 Hz, 1H), 1.20-1.10 (m, 1H), 0.50-0.29 (m, 4H).

Example 107

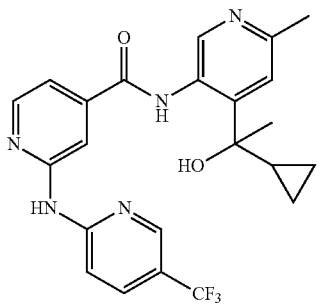 [SMILES: Cc1cc(C(C)(O)C2CC2)c(NC(=O)c2ccnc(Nc3ccc(C(F)(F)F)cn3)c2)cn1]

N-(4-(1-Cyclopropyl-1-hydroxyethyl)-6-methylpyridin-3-yl)-2-((5-(trifluoromethyl)pyridin-2-yl)amino)isonicotinamide Followed synthesis of example 4. MS (ESI) (m/z): 458 (M+H)+; $^1$H NMR (500 MHz, DMSO-$d_6$) δ 11.36 (br. s., 1H), 10.55 (s, 1H), 9.33 (s, 1H), 8.64 (s, 1H), 8.51 (d, J=5.5 Hz, 1H), 8.43 (s, 1H), 8.05 (dd, J=8.7, 2.3 Hz, 1H), 7.84 (d, J=8.9 Hz, 1H), 7.38-7.33 (m, 2H), 2.48 (s, 3H), 1.49 (s, 3H), 1.42-1.27 (m, 1H), 0.51-0.35 (m, 4H).

General Synthesis of Amine A

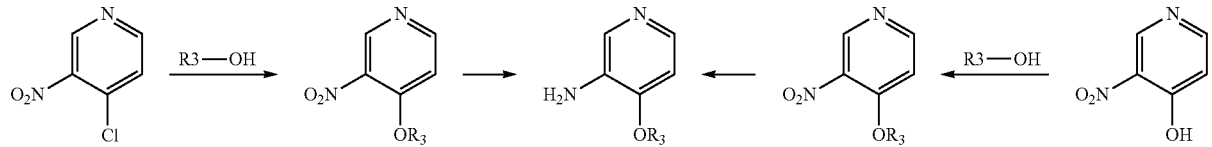

Formula IV 4-(Cyclopropylmethoxy)-3-nitropyridine

In a small round bottom flask was added 4-chloro-3-nitropyridine (191.4 mg, 1.21 mmol) and K$_2$CO$_3$ (334 mg, 2.41 mmol) in dimethylformamide (1.2 mL) to give a tan suspension. Cyclopropylmethanol (0.382 mL, 4.83 mmol) was added, and the mixture was stirred at 65° C. After 18 h, the mixture was diluted with water and ethyl acetate. The layers were separated. The aqueous layer was extracted again with ethyl acetate. The combined organic layers were washed with brine, dried, and concentrated. Purification by flash column chromatography on silica gel using 60% ethyl acetate/hexane afforded the desired product (95.3 mg, 41%) as an off-white solid: $^1$H NMR (400 MHz, CDCl3) δ 8.94 (s, 1H), 8.56 (d, J=5.9 Hz, 1H), 6.99 (d, J=5.9 Hz, 1H), 4.05 (d, J=6.9 Hz, 2H), 1.36-1.24 (m, 1H), 0.71-0.64 (m, 2H), 0.44-0.37 (m, 2H).

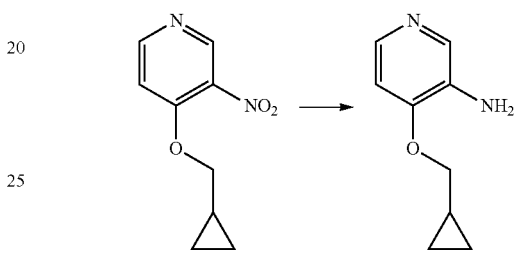

4-(Cyclopropylmethoxy)pyridin-3-amine

In a 100 mL round-bottom flask was dissolved 4-(cyclopropylmethoxy)-3-nitropyridine (95.3 mg, 0.491 mmol) in methanol (4 mL) to give a yellow solution. Pd/C (104 mg, 0.098 mmol) was carefully added, and the mixture was stirred under hydrogen (1 atm) for 3 h. The mixture was filtered, washed, and concentrated to a give tan solid (78 mg, 97%): $^1$H NMR (400 MHz, CDCl3) δ 7.94 (s, 1H), 7.87 (d, J=5.4 Hz, 1H), 6.58 (d, J=5.4 Hz, 1H), 3.86 (s, 2H), 3.81 (d, J=7.0 Hz, 2H), 1.32-1.17 (m, 1H), 0.64-0.55 (m, 2H), 0.35-0.27 (m, 2H).

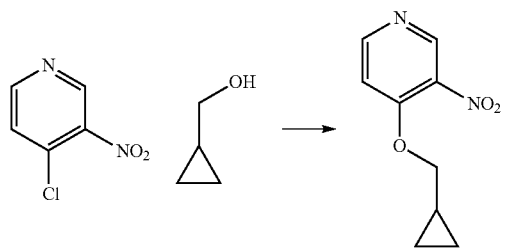

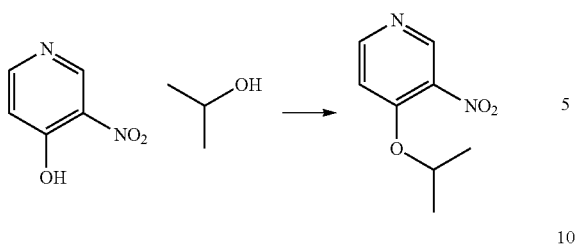

4-Isopropoxy-3-nitropyridine

In a 100 mL round-bottom flask was dissolved 3-nitropyridin-4-ol (0.985 g, 7.03 mmol), Ph₃P (2.77 g, 10.5 mmol), and 2-propanol (0.81 mL, 10.5 mmol) in tetrahydrofuran (20 mL) to give a yellow solution. DIAD (2.05 mL, 10.5 mmol) was added dropwise at rt. The mixture was stirred at rt. After 5 h, the mixture was concentrated to a tan oil and directly purified by flash column chromatography on silica, eluting with 8% methanol/methylene chloride. However the desired product could not be separated from triphenylphosphine oxide. The mixture was directly carried on to the next reaction.

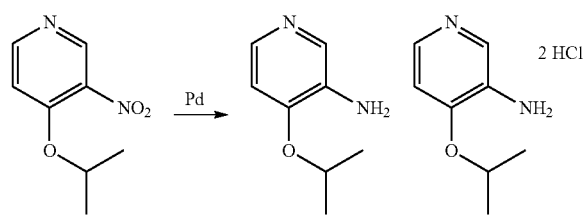

4-Isopropoxypyridin-3-amine

In a 100 mL round-bottom flask was dissolved 4-isopropoxy-3-nitropyridine (crude product from previous step, ca. 7.03 mmol) in methanol (40 mL) to give a yellow solution. Pd/C (748 mg, 0.703 mmol) was carefully added, and the mixture was stirred under hydrogen (1 atm) overnight. The mixture was filtered, washed, and concentrated. The residue was purified by flash column chromatography on silica gel, eluting 10% methanol/methylene chloride, to afford the desired product contaminated with triphenylphosphine oxide. The pure fractions were pooled and concentrated to a colorless oil (94 mg, 9%): ¹H NMR (400 MHz, CDCl3) δ 7.93 (s, 1H), 7.86 (d, J=5.5 Hz, 1H), 6.61 (d, J=5.5 Hz, 1H), 4.58 (dt, J=12.1, 6.1 Hz, 1H), 3.70 (s, 2H), 1.32 (d, J=6.1 Hz, 6H). The impure fractions were pooled, concentrated, and dissolved in ether/methylene chloride. HCl in ether were slowly added to precipitate out the desired product. After standing for 3 days, the organic solution was decanted and the solid was washed with ether and dried as a white solid (1.08 g, 68%). The total yield for the two-step reaction was 77%.

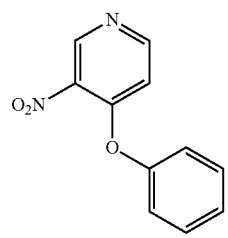 [SMILES: O=[N+]([O-])c1cnccc1Oc1ccccc1]

3-Nitro-4-phenoxypyridine

LCMS: M+H=217.03; ¹H NMR (400 MHz, CDCl3) δ 9.14 (s, 1H), 8.55 (d, J=5.9 Hz, 1H), 7.51 (dd, J=10.7, 5.3 Hz, 2H), 7.36 (dd, J=10.8, 4.2 Hz, 1H), 7.18 (dd, J=5.4, 3.3 Hz, 2H), 6.79 (d, J=5.9 Hz, 1H).

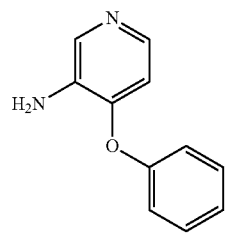

4-Phenoxypyridin-3-amine

¹H NMR (400 MHz, CDCl3) δ 8.16 (s, 1H), 7.90 (d, J=5.4 Hz, 1H), 7.42 (ddt, J=9.8, 7.6, 2.2 Hz, 2H), 7.27-7.19 (m, 1H), 7.11 (q, J=1.7 Hz, 1H), 7.09 (dd, J=2.0, 0.9 Hz, 1H), 6.58 (d, J=5.4 Hz, 1H), 3.93 (s, 2H).

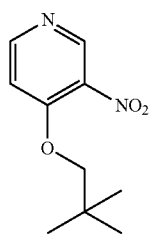

4-(Neopentyloxy)-3-nitropyridine

¹H NMR (400 MHz, CDCl3) δ 9.03 (s, 1H), 8.61 (d, J=5.8 Hz, 1H), 7.01 (d, J=5.9 Hz, 1H), 3.82 (s, 2H), 1.10 (s, 9H).

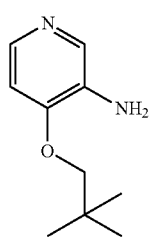

4-(Neopentyloxy)pyridin-3-amine $^1$H NMR (400 MHz, CDCl3) δ 7.92 (s, 1H), 7.86 (d, J=5.4 Hz, 1H), 6.59 (d, J=5.4 Hz, 1H), 3.84 (s, 2H), 3.59 (s, 2H), 0.99 (s, 9H).

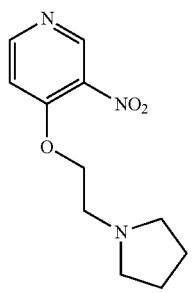 [SMILES: O=[N+]([O-])c1cnccc1OCCN1CCCC1]

3-Nitro-4-(2-(pyrrolidin-1-yl)ethoxy)pyridine

MS (ESI) (m/z): 238 (M+H)$^+$; $^1$H NMR (400 MHz, Chloroform-d) δ 9.01 (s, 1H), 8.62 (d, J=5.9 Hz, 1H), 7.04 (d, J=5.9 Hz, 1H), 4.33 (t, J=5.8 Hz, 2H), 3.01 (t, J=5.8 Hz, 2H), 2.71-2.60 (m, 4H), 1.87-1.76 (m, 4H).

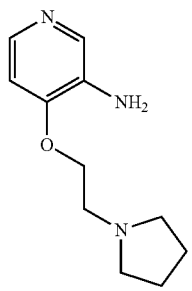 [SMILES: Nc1cnccc1OCCN1CCCC1]

4-(2-(Pyrrolidin-1-yl)ethoxy)pyridin-3-amine

MS (ESI) (m/z): 208 (M+H)$^+$.

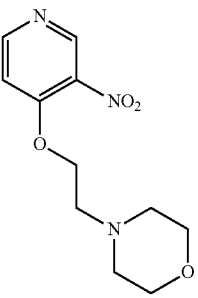

4-(2-((3-Nitropyridin-4-yl)oxy)ethyl)morpholine

MS (ESI) (m/z): 254 (M+H)$^+$; $^1$H NMR (400 MHz, Chloroform-d) δ 8.93 (d, J=1.5 Hz, 1H), 8.56 (dd, J=5.9, 1.3 Hz, 1H), 7.00 (d, J=5.9 Hz, 1H), 4.28 (t, J=5.4 Hz, 2H), 3.73-3.58 (m, 4H), 2.83 (td, J=5.5, 1.2 Hz, 2H), 2.61-2.49 (m, 4H).

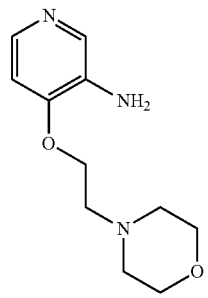 [SMILES: Nc1cnccc1OCCN1CCOCC1]

4-(2-Morpholinoethoxy)pyridin-3-amine

MS (ESI) (m/z): 224 (M+H)$^+$.

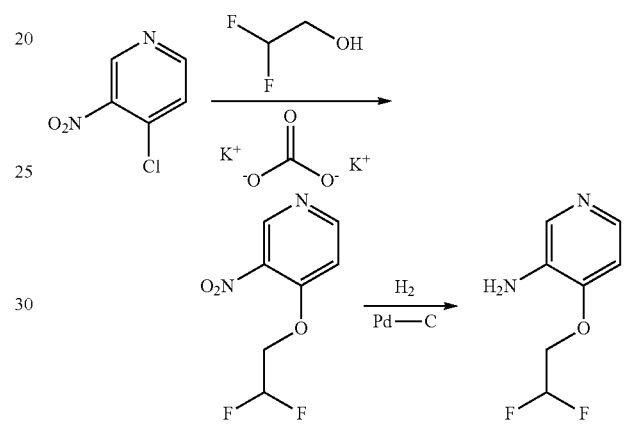

4-(2,2-Difluoroethoxy)pyridin-3-amine

A stirred suspension of 4-chloro-3-nitropyridine (1.5106 g, 9.53 mmol), potassium carbonate (2.63 g, 19.1 mmol) and 2,2-difluoroethanol (3.0 ml, 48 mmol) in 1,2,-dichloroethane (10 mL) was heated at reflux overnight. The mixture was diluted with ethyl acetate and washed with water (2x) and brine, dried over magnesium sulfate and evaporated to give the nitropyridine ether a light-yellow oil. A solution of crude 4-(2,2-difluoroethoxy)-3-nitropyridine (1.84 g, 9.01 mmol) in ethanol (40 mL) was degassed for 10 minutes with nitrogen and then 10% palladium on carbon (0.16 g) was carefully added. The mixture was stirred under 1 atm. of hydrogen overnight. The mixture was then degassed with nitrogen, and carefully filtered through celite. The filtrated was concentrated in vacuo, and the light-brown oil flushed with methylene chloride. The crude amine was used without further purification. MS (ESI) (m/z): 175.1 (M+H)$^+$.

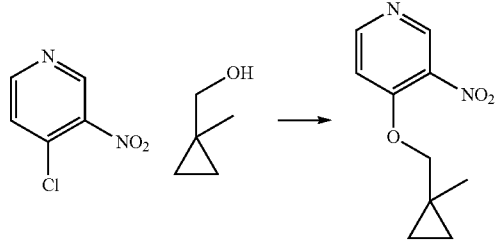

4-((1-Methylcyclopropyl)methoxy)-3-nitropyridine

To 4-chloro-3-nitropyridine (0.5 g, 3.15 mmol) and (1-methylcyclopropyl)methanol (0.543 g, 6.31 mmol) in THF (5 mL) at 0° C. was added NaH (0.139 g, 3.47 mmol). The reaction mixture was allowed to warm to rt overnight. LCMS did not show desired M+H, s/m was still present. DMF (2 mL) was added and the reaction was stirred at rt overnight. Ethyl acetate and water was added. The org layer was washed with water, brine and dried over sodium sulfate. The crude product was dissolved in a small amount of dichloromethane and charged to a 40 g silica gel cartridge which was eluted with 0-50% ethyl acetate/hexanes over a period of 40 mins. The desired fractions were combined and dried under vacuo to give 4-((1-methylcyclopropyl)methoxy)-3-nitropyridine (0.36 g, 1.729 mmol, 54.8% yield) as orange solid. $^1$H NMR (400 MHz, CHLOROFORM-d) δ ppm 9.03 (s, 1H) 8.61 (d, J=5.62 Hz, 1H) 6.96 (d, J=5.62 Hz, 1H) 3.97 (s, 2H) 1.29 (s, 3H) 0.59-0.65 (m, 2H) 0.49-0.56 (m, 2H).

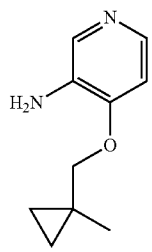

4-((1-Methylcyclopropyl)methoxy)pyridin-3-amine

To 4-((1-methylcyclopropyl)methoxy)-3-nitropyridine (0.36 g, 1.729 mmol) and Pd/C (0.1 g, 0.094 mmol) under N2 was added EtOH (20 mL). The reaction mixture was degassed and flushed with N2 (3×). Then H2 balloon (1.729 mmol) was introduced, mixture was degassed and flushed with H2 (3×). The reaction mixture was stirred under H2 overnight. The catalyst was carefully filtered over celite and washed with ethanol. The filtrate was concentrated and dried under vacuo to give 4-((1-methylcyclopropyl)methoxy)pyridin-3-amine (0.315 g, 1.767 mmol, 102% yield). $^1$H NMR (400 MHz, DMSO-$d_6$) δ ppm 7.87 (s, 1H) 7.69 (d, J=5.38 Hz, 1H) 6.74 (d, J=5.38 Hz, 1H) 4.73 (s, 2H) 3.81 (s, 2H) 1.21 (s, 3H) 0.51-0.58 (m, 2H) 0.37-0.43 (m, 2H).

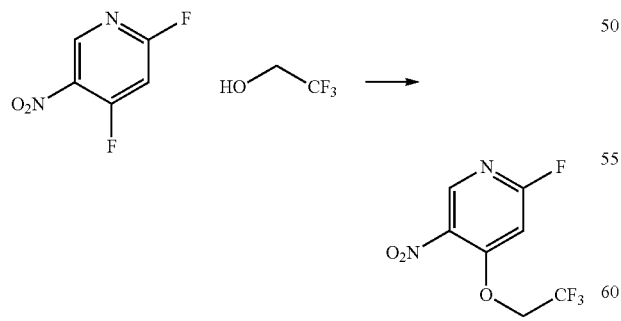

2-Fluoro-5-nitro-4-(2,2,2-trifluoroethoxy)pyridine

A solution of 2,4-difluoro-5-nitropyridine (0.1523 g, 0.951 mmol) in tetrahydrofuran (2 mL) was cooled to 0° C. 2,2,2-Trifluoroethanol (0.082 mL, 1.142 mmol) was added to the mixture. After 5 min, triethylamine (0.265 mL, 1.903 mmol) was added. The reaction was stirred at 0° C. for 1 h, and then allowed to warm to rt. The reaction was stirred at rt for 4.5 h. The solvent was removed in vacuo and the crude product carried on without further purification.

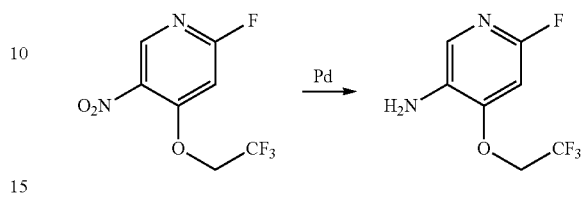

6-Fluoro-4-(2,2,2-trifluoroethoxy)pyridin-3-amine

A mixture of Pd/C (14.6 mg, 0.014 mmol) and 2-fluoro-5-nitro-4-(2,2,2-trifluoroethoxy)pyridine (228 mg, 0.951 mmol) in ethanol (4 mL) was stirred under hydrogen (1 atm) at room temperature overnight. The mixture was degassed before filtration through celite. The filtrate was concentrated and the product was purified by via flash chromatography on silica gel, eluting with methanol in methylene chloride from 0 to 10% to give the product as a tan solid (134 mg, 66%). $^1$H NMR (400 MHz, CHLOROFORM-d) δ 7.62 (d, J=1.5 Hz, 1H), 6.34 (d, J=1.5 Hz, 1H), 4.45 (q, J=7.8 Hz, 2H), 3.70 (br. s., 2H); $^{19}$F NMR (376 MHz, CHLOROFORM-d) δ −72.90--73.97 (m, 3F), −75.77 (s, 1F).

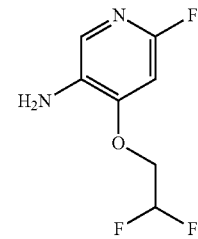 [SMILES: Nc1cnc(F)cc1OCC(F)F]

4-(2,2-Difluoroethoxy)-6-fluoropyridin-3-amine $^1$H NMR (400 MHz, CHLOROFORM-d) δ 7.53 (d, J=1.3 Hz, 1H), 6.31 (d, J=1.5 Hz, 1H), 6.28-5.98 (m, 1H), 4.25 (td, J=12.9, 4.0 Hz, 2H), 3.69 (d, J=6.8 Hz, 2H); MS(ES+) m/e 193 [M+H]$^+$.

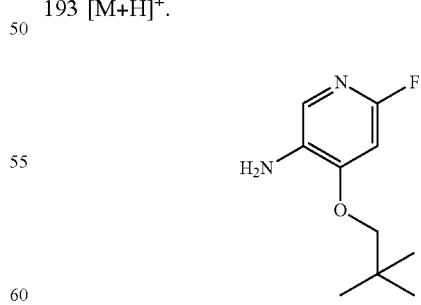

6-Fluoro-4-(neopentyloxy)pyridin-3-amine $^1$H NMR (400 MHz, CHLOROFORM-d) δ 7.51 (d, J=1.3 Hz, 1H), 6.31 (d, J=1.0 Hz, 1H), 3.68 (s, 2H), 1.07 (s, 9H); MS(ES+) m/e 199 [M+H]$^+$.

General Synthesis of Amine B

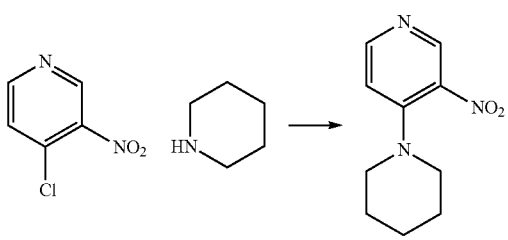 [SMILES: O=[N+]([O-])c1cnccc1Cl ; C1CCNCC1 ; O=[N+]([O-])c1cnccc1N1CCCCC1]

3-Nitro-4-(piperidin-1-yl)pyridine

In a 15 mL vial was dissolved 4-chloro-3-nitropyridine (300 mg, 1.892 mmol) in tetrahydrofuran (5 mL) to give a tan solution. Piperidine (0.281 mL, 2.84 mmol) and Et$_3$N (0.791 mL, 5.68 mmol) were added. The cloudy yellow mixture was stirred at rt overnight. After 18 h, the mixture was partitioned between water and ethyl acetate. The layers were separated. The organic layer was washed with brine, dried and concentrated. The residue was purified by flash column chromatography using 80% ethyl acetate/hexane to afford the desired product (297.3 mg, 76%) as a yellow solid: $^1$H NMR (400 MHz, CDCl$_3$) δ 8.81 (d, J=0.9 Hz, 1H), 8.32 (dd, J=6.0, 0.8 Hz, 1H), 6.86 (d, J=6.1 Hz, 1H), 3.21 (d, J=5.3 Hz, 4H), 1.72 (d, J=7.2 Hz, 6H).

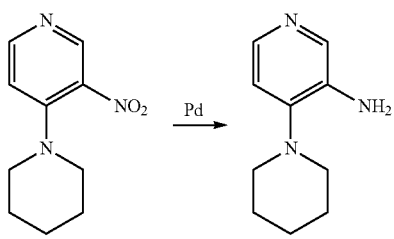

4-(Piperidin-1-yl)pyridin-3-amine

In a 250 mL round-bottom flask was dissolved 3-nitro-4-(piperidin-1-yl)pyridine (297.3 mg, 1.435 mmol) in methanol (12 mL) to give a yellow solution. Pd/C (153 mg, 0.143 mmol) was added, and the mixture was stirred under hydrogen (1 atm) overnight. After 16 h, the mixture was filtered, washed, and concentrated to give an off-white solid (254 mg, 100%): $^1$H NMR (500 MHz, MeOD) δ 7.90 (s, 1H), 7.81 (d, J=5.4 Hz, 1H), 6.94 (d, J=5.5 Hz, 1H), 3.03 (d, J=4.1 Hz, 4H), 1.74 (d, J=4.5 Hz, 4H), 1.65 (d, J=3.9 Hz, 2H).

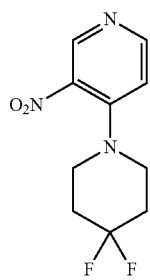 [SMILES: O=[N+]([O-])c1cnccc1N1CCC(F)(F)CC1]

4-(4,4-Difluoropiperidin-1-yl)-3-nitropyridine $^1$H NMR (400 MHz, CDCl3) δ 8.79 (s, 1H), 8.35 (d, J=5.9 Hz, 1H), 6.86 (d, J=5.9 Hz, 1H), 3.37-3.19 (m, 4H), 2.10 (ddd, J=19.4, 13.5, 5.8 Hz, 4H); $^{19}$F NMR (376 MHz, CDCl3) δ −98.19 (s).

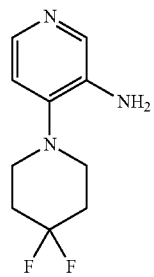 [SMILES: Nc1cnccc1N1CCC(F)(F)CC1]

4-(4,4-Difluoropiperidin-1-yl)pyridin-3-amine $^1$H NMR (500 MHz, MeOD) δ 7.94 (d, J=4.2 Hz, 1H), 7.80 (s, 1H), 6.90 (s, 1H), 3.12 (s, 4H), 2.15 (s, 4H); $^{19}$F NMR (470 MHz, MeOD) δ −98.65 (s).

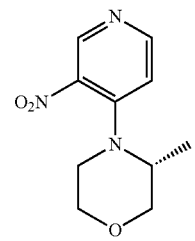 [SMILES: C[C@@H]1COCCN1c1ccncc1[N+](=O)[O-]]

(R)-3-Methyl-4-(3-nitropyridin-4-yl)morpholine $^1$H NMR (400 MHz, CDCl3) δ 8.72 (s, 1H), 8.31 (d, J=6.0 Hz, 1H), 6.82 (d, J=6.0 Hz, 1H), 3.89-3.82 (m, 1H), 3.81-3.74 (m, 1H), 3.69-3.58 (m, 2H), 3.58-3.50 (m, 1H), 3.46 (ddd, J=12.8, 11.4, 3.5 Hz, 1H), 2.81 (d, J=12.9 Hz, 1H), 1.28-1.19 (m, 3H).

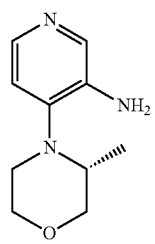

(R)-4-(3-Methylmorpholino)pyridin-3-amine $^1$H NMR (400 MHz, CDCl3) δ 8.12 (s, 1H), 7.94 (d, J=5.3 Hz, 1H), 6.87 (d, J=5.3 Hz, 1H), 4.42 (br, 2H), 3.84 (dt, J=7.0, 5.7 Hz, 2H), 3.75 (ddd, J=11.4, 9.0, 2.7 Hz, 1H), 3.45-3.29 (m, 2H), 3.08 (d, J=12.1 Hz, 1H), 2.65 (ddd, J=12.1, 8.9, 3.2 Hz, 1H), 0.85 (d, J=6.0 Hz, 3H).

107

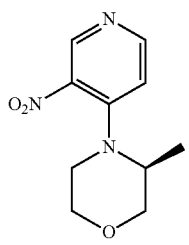 [SMILES: C[C@H]1COCCN1c1ccncc1[N+](=O)[O-]]

(S)-3-Methyl-4-(3-nitropyridin-4-yl)morpholine

¹H NMR (400 MHz, CDCl3) δ 8.78 (s, 1H), 8.37 (d, J=6.0 Hz, 1H), 6.86 (d, J=6.0 Hz, 1H), 3.94-3.87 (m, 1H), 3.87-3.80 (m, 1H), 3.68 (ddd, J=13.4, 11.1, 1.9 Hz, 2H), 3.62-3.55 (m, 1H), 3.51 (ddd, J=12.8, 11.4, 3.5 Hz, 1H), 2.86 (dd, J=10.2, 2.7 Hz, 1H), 1.34-1.22 (m, 3H).

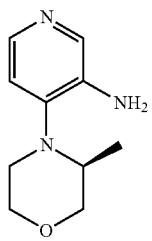

(S)-4-(3-Methylmorpholino)pyridin-3-amine

¹H NMR (400 MHz, CDCl3) δ 8.18 (s, 1H), 7.87 (d, J=5.5 Hz, 1H), 6.85 (d, J=5.5 Hz, 1H), 5.66 (br, 2H), 3.82 (d, J=8.4 Hz, 1H), 3.80-3.68 (m, 2H), 3.46-3.31 (m, 2H), 3.16-3.06 (m, 1H), 2.68-2.56 (m, 1H), 0.83 (d, J=6.0 Hz, 3H).

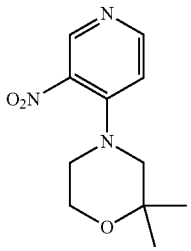 [SMILES: CC1(C)CN(c2ccncc2[N+](=O)[O-])CCO1]

2,2-Dimethyl-4-(3-nitropyridin-4-yl)morpholine

¹H NMR (400 MHz, CDCl3) δ 8.62 (s, 1H), 8.20 (d, J=6.0 Hz, 1H), 6.74 (d, J=6.0 Hz, 1H), 3.80-3.60 (m, 2H), 3.01-2.95 (m, 2H), 2.92 (s, 2H), 1.14 (s, 6H).

108

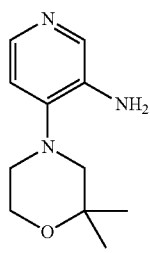

4-(2,2-Dimethylmorpholino)pyridin-3-amine

¹H NMR (400 MHz, CDCl3) δ 8.07 (s, 1H), 8.00 (d, J=5.3 Hz, 1H), 6.80 (d, J=5.3 Hz, 1H), 3.96-3.89 (m, 2H), 3.50 (s, 2H), 2.98 (dd, J=5.6, 4.0 Hz, 2H), 2.81 (s, 2H), 1.38 (s, 6H).

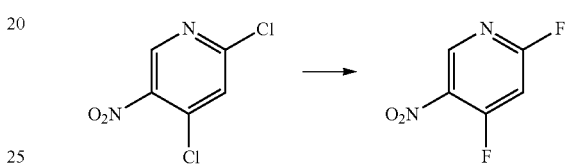

2,4-Difluoro-5-nitropyridine

In a 250 mL round-bottom flask was added 2,4-dichloro-5-nitropyridine (0.73 g, 3.8 mmol), potassium fluoride (0.659 g, 11.3 mmol), and 18-crown-6 (0.160 g, 0.605 mmol) in N-methylpyrrolidinone (3 mL) to give a tan suspension. The mixture was heated at 100° C. under nitrogen for 3 h. The mixture was then partitioned between water and ether/hexane. The organic layer was washed with water, brine, dried and concentrated to give a tan solid (0.515 g, 85%): 1H NMR (400 MHz, CDCl3) δ 9.07 (d, J=9.7 Hz, 1H), 6.96 (dd, J=9.5, 2.5 Hz, 1H); 19F NMR (376 MHz, CDCl3) δ -52.20 (d, J=29.3 Hz), -98.13 (d, J=28.9 Hz).

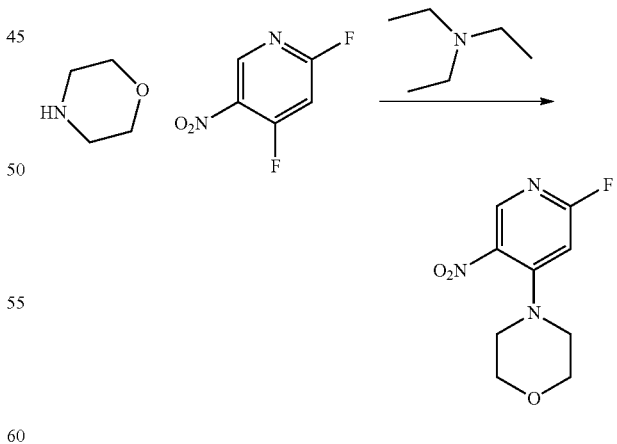

4-(2-Fluoro-5-nitropyridin-4-yl)morpholine

In a 50 mL round-bottom flask vial was dissolved 2,4-difluoro-5-nitropyridine (175.7 mg, 1.098 mmol) in tetrahydrofuran (5 mL) to give a tan solution. After cooling to -40° C., morpholine (0.080 mL, 0.918 mmol) was added, followed by Et₃N (0.256 mL, 1.83 mmol). The cloudy yellow mixture was stirred at −40° C.-0° C. for 3 h. The mixture was concentrated to give a yellow solid. The solid was purified by flash column chromatography on silica gel, eluting with 60% ethyl acetate/hexane, to afford the desired product (209 mg, 100%) as a yellow solid: $^1$H NMR (400 MHz, Chloroform-d) δ 8.60 (s, 1H), 6.42 (s, 1H), 3.96-3.81 (m, 4H), 3.33-3.18 (m, 4H); $^{19}$F NMR (376 MHz, Chloroform-d) δ −61.42.

4-(4,4-Difluoropiperidin-1-yl)-6-fluoropyridin-3-amine $^1$H NMR (500 MHz, CDCl₃) δ 7.92 (s, 1H), 7.55 (d, J=0.9 Hz, 1H), 6.39 (d, J=1.2 Hz, 1H), 3.15-3.04 (m, 4H), 2.16-2.10 (m, 4H).

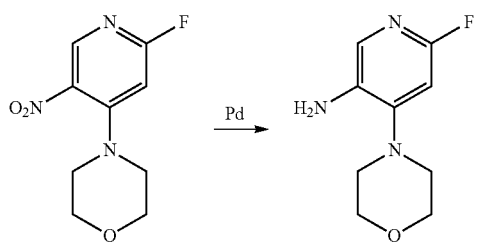

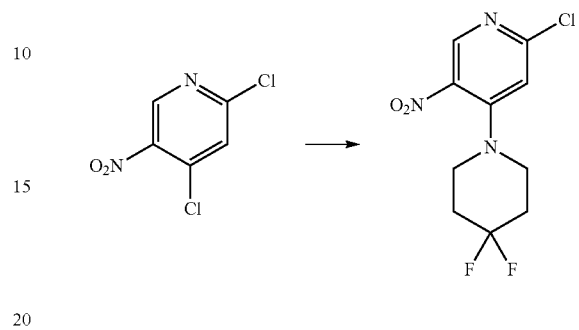

6-Fluoro-4-morpholinopyridin-3-amine

2-Chloro-4-(4,4-difluoropiperidin-1-yl)-5-nitropyridine

In a 100 mL round-bottom flask was dissolved 4-(2-fluoro-5-nitropyridin-4-yl)morpholine (209 mg, 0.920 mmol) in methanol (6 mL) to give a yellow solution. Pd/C (98.0 mg, 0.092 mmol) was added, and the mixture was stirred under hydrogen (1 atm) for 17 h. The mixture was filtered and the filtrate evaporated to afford the desired product (171 mg, 94%) as a tan solid: $^1$H NMR (400 MHz, Chloroform-d) δ 7.51 (d, J=1.1 Hz, 1H), 6.37 (d, J=1.3 Hz, 1H), 3.90-3.74 (m, 4H), 3.66 (s, 2H), 3.06-2.90 (m, 4H); $^{19}$F NMR (376 MHz, Chloroform-d) δ −78.22.

In a 50 mL round-bottom flask vial was added 2,4-dichloro-5-nitropyridine (314 mg, 1.627 mmol) in tetrahydrofuran (8 mL) to give a tan solution. 4,4-Difluoropiperidine hydrochloride (256 mg, 1.63 mmol) was added in one portion, followed by Et₃N (0.454 mL, 3.25 mmol). The cloudy yellow mixture was stirred at rt for 18 h. The mixture was partitioned between water and ethyl acetate. The layers were separated. The organic layer was washed with brine, dried and concentrated. The residue was purified by flash column chromatography on silica gel, eluting with 80% ethyl acetate/hexane, to afford the desired product (430 mg, 95%) as a crystalline yellow solid: $^1$H NMR (400 MHz, CDCl₃) δ 8.72 (s, 1H), 6.93 (s, 1H), 3.45-3.29 (m, 4H), 2.21 (ddd, J=19.3, 13.4, 5.9 Hz, 4H); $^{19}$F NMR (376 MHz, CDCl₃) δ −98.47 (s).

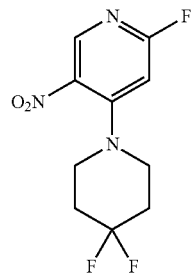

4-(4,4-Difluoropiperidin-1-yl)-2-fluoro-5-nitropyridine $^1$H NMR (400 MHz, CDCl₃) δ 8.63 (s, 1H), 6.46 (s, 1H), 3.40-3.30 (m, 4H), 2.22 (dd, J=13.4, 6.0 Hz, 4H).

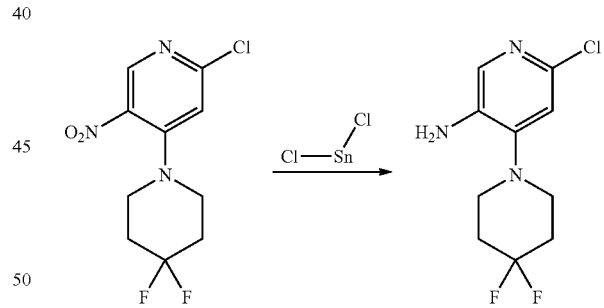

6-Chloro-4-(4,4-difluoropiperidin-1-yl)pyridin-3-amine

In a 20 mL round-bottom flask was dissolved 2-chloro-4-(4,4-difluoropiperidin-1-yl)-5-nitropyridine (181 mg, 0.652 mmol) in ethanol (4 ml) to give a yellow solution. Tin (II) chloride (618 mg, 3.26 mmol) was added, and the mixture was heated at 70° C. under nitrogen for 2 h. The reaction was cooled to rt and diluted with ethyl acetate. Aqueous NaHCO₃ was added to adjust pH to 7-8. The suspension was carefully filtered and washed with ethyl acetate. The organic layer was washed with brine, dried with Na₂SO₄, and concentrated to give the desired product (158 mg, 98%) as an off white solid: $^1$H NMR (400 MHz, CDCl₃)

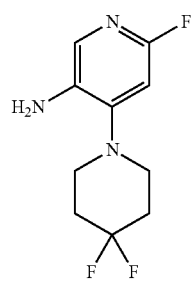 [SMILES: O=[N+]([O-])c1cnc(F)cc1N1CCC(F)(F)CC1]

δ 7.81 (s, 1H), 6.82 (s, 1H), 3.74 (s, 2H), 3.24-2.97 (m, 4H), 2.15 (ddd, J=19.1, 13.2, 5.7 Hz, 4H); ¹⁹F NMR (376 MHz, CDCl₃) δ −98.04 (s).

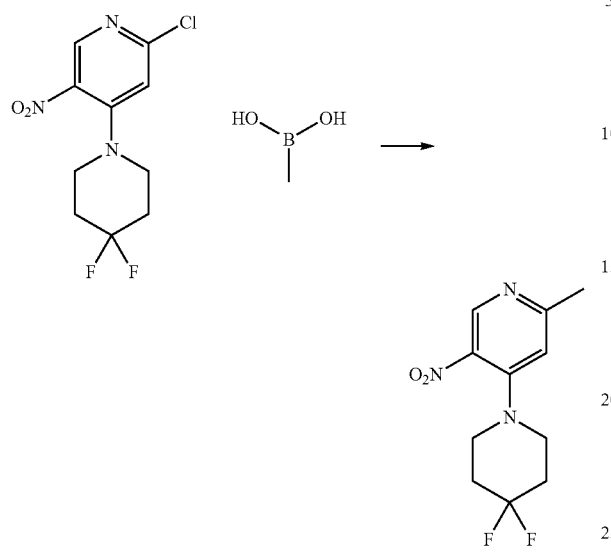

4-(4,4-Difluoropiperidin-1-yl)-2-methyl-5-nitropyridine

In a 5 mL vial was dissolved 2-chloro-4-(4,4-difluoropiperidin-1-yl)-5-nitropyridine (105 mg, 0.378 mmol), methylboronic acid (113 mg, 1.891 mmol), and potassium carbonate (105 mg, 0.756 mmol) in dioxane (1.6 mL) (degassed) and water (0.16 mL) to give a yellow solution under nitrogen. Pd(Ph₃P)₄ (21.85 mg, 0.019 mmol) was added, and the vial was sealed under nitrogen. The mixture was stirred at 120° C. for 21 h. The mixture was partitioned between water and ethyl acetate. The layers were separated. The organic layer was washed with brine, dried and concentrated. The residue was purified by flash column chromatography on silica gel, eluting with 60% ethyl acetate/hexane, to afford the desired product (69 mg, 71%) as a yellow solid: ¹H NMR (400 MHz, Chloroform-d) δ 8.84 (s, 1H), 6.75 (s, 1H), 3.37-3.26 (m, 4H), 2.54 (s, 3H), 2.23-2.15 (m, 4H); ¹⁹F NMR (376 MHz, Chloroform-d) δ −98.28.

Pd/C (28.5 mg, 0.027 mmol) was added, and the mixture was stirred under hydrogen (1 atm) for 16 h. The mixture was filtered and the filtrate concentrated to give the desired product (41 mg, 67%) as a tan solid: ¹H NMR (500 MHz, Chloroform-d) δ 8.01 (s, 1H), 6.69 (s, 1H), 3.84 (s, 2H), 3.12 (t, J=5.7 Hz, 4H), 2.45 (s, 3H), 2.15 (dt, J=13.6, 5.7 Hz, 4H); ¹⁹F NMR (470 MHz, Chloroform-d) δ −97.92.

General Synthesis of Amine C

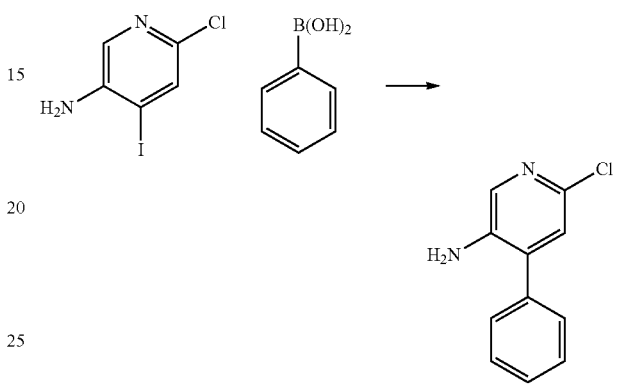

6-Chloro-4-phenylpyridin-3-amine

In a 15 mL vial was dissolved 6-chloro-4-iodopyridin-3-amine (186 mg, 0.731 mmol), phenylboronic acid (143 mg, 1.170 mmol), and Na₂CO₃ (1.096 mL, 2.193 mmol) in dioxane (4 mL) to give a slightly tan solution under nitrogen. 1,1'-Bis(diphenylphosphino)ferrocenepalladium(II) dichloride, toluene (30.1 mg, 0.037 mmol) was added under nitrogen. The vial was sealed and heated at 100° C. (oil bath) for 1 h. The mixture was partitioned between water and ethyl acetate. The layers were separated. The organic layer was washed with brine, dried and concentrated. The residue was purified by flash column chromatography on silica gel, eluting with 60% ethyl acetate/hexane, to afford the desired product (145 mg, 97%) as a wax solid/oil: ¹H NMR (400 MHz, CDCl3) δ 7.91 (s, 1H), 7.55-7.48 (m, 2H), 7.47-7.42 (m, 3H), 7.08 (s, 1H), 3.89 (s, 2H).

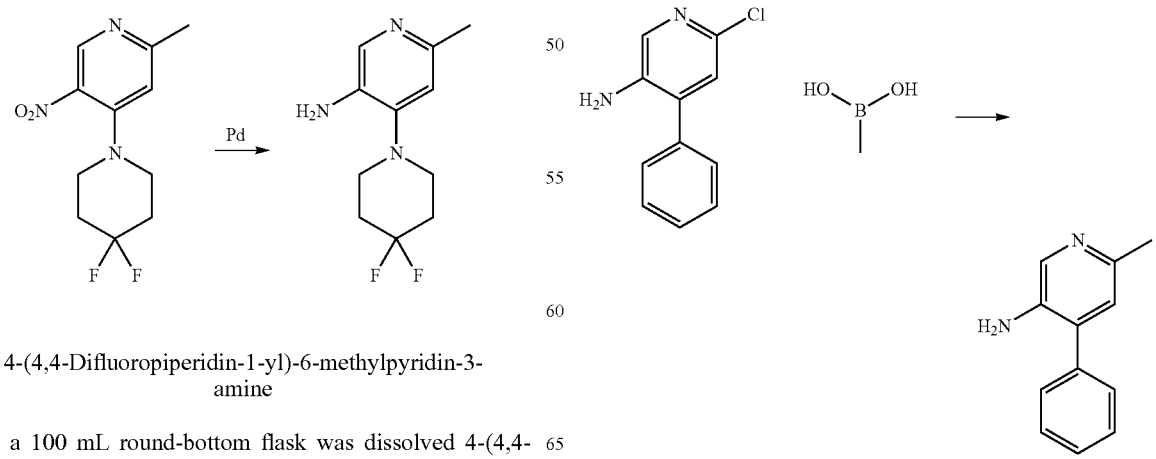

4-(4,4-Difluoropiperidin-1-yl)-6-methylpyridin-3-amine

In a 100 mL round-bottom flask was dissolved 4-(4,4-difluoropiperidin-1-yl)-2-methyl-5-nitropyridine (69 mg, 0.268 mmol) in methanol (2 mL) to give a yellow solution.

6-Methyl-4-phenylpyridin-3-amine

In a 2 mL vial was dissolved 6-chloro-4-phenylpyridin-3-amine (44.2 mg, 0.216 mmol), methylboronic acid (64.6 mg, 1.080 mmol), and potassium carbonate (59.7 mg, 0.432 mmol) in dioxane (1 mL) (degassed) and water (0.1 mL) to give a tan solution. Pd(Ph$_3$P)$_4$ (12.48 mg, 10.80 μmol) was added. The mixture was stirred at 120° C. for 16 h. The mixture was diluted with ethyl acetate and water. The layers were separated. The organic layer was washed with brine, dried and concentrated. The residue was purified by flash column chromatography on silica gel, eluting with 10% methanol/methylene chloride, to afford the desired product as a tan oil (7.5 mg, 19%): $^1$H NMR (400 MHz, CDCl3) δ 8.09 (s, 1H), 7.53-7.45 (m, 4H), 7.45-7.39 (m, 1H), 6.94 (s, 1H), 3.68 (s, 2H), 2.49 (s, 3H).

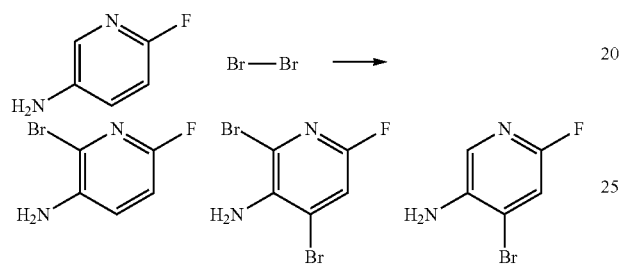

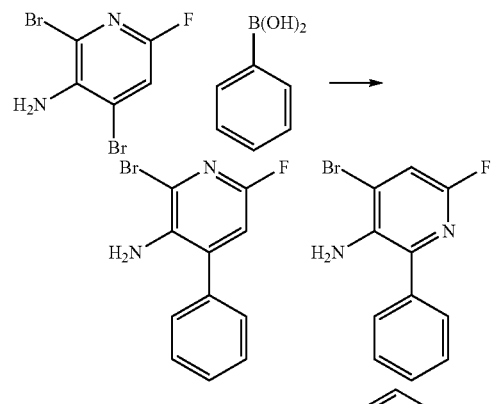

In a 50 mL round-bottom flask was dissolved 6-fluoro-pyridin-3-amine (332 mg, 2.96 mmol) in acetic acid (6 mL) to give a tan solution. At 70° C., bromine (0.168 mL, 3.26 mmol) was added. After 30 min, the mixture was diluted with ethyl acetate and water. The layers were separated. The organic layer was washed with 1N NaOH, saturated NaHCO$_3$, and brine, dried and concentrated. The dark oil was purified by flash column chromatography on silica gel, eluting with 60% ethyl acetate/hexane, to afford several components. The first (M+H=270.9) was the dibrominated product (118 mg, 15%), which was used in the next step.

In a 50 mL flask was dissolved 2,4-dibromo-6-fluoropyridin-3-amine (118 mg, 0.437 mmol), phenylboronic acid (64.0 mg, 0.525 mmol), and Na$_2$CO$_3$ (0.656 mL, 1.31 mmol) in dioxane (3 mL) to give a slightly tan solution under nitrogen. 1,1'-bis(diphenylphosphino)ferrocenepalladium (II) dichloride, toluene (18.0 mg, 0.022 mmol) was added under nitrogen. The vial was sealed and heated at 100° C. for 1.5 h. The mixture was partitioned between water and ethyl acetate. The layers were separated. The organic layer was washed with brine, dried and concentrated. The residue was directly carried on to next reaction without further purification and characterization.

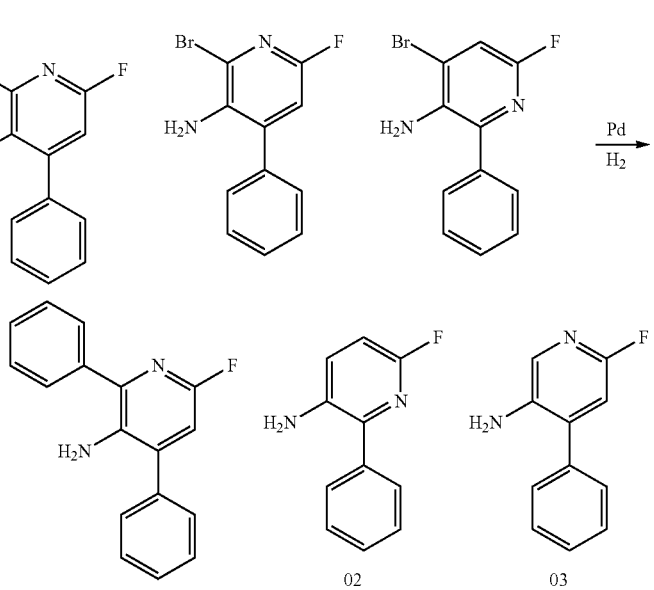

In a 100 mL round-bottom flask was added the crude mixture from the previous step (117 mg, 0.437 mmol) in methanol (4 mL) to give a tan solution. Pd/C (93 mg, 0.087 mmol) was carefully added, and the mixture was stirred under hydrogen (1 atm) for 18 h. The mixture was filtered and the filtrate concentrated in vacuo. The residue was purified by flash column chromatography on silica gel, 70% ethyl acetate/hexane, to afford three components: the first was the bis-phenyl component; the second and the third were identified by $^1$H NMR. 02 (4.8 mg, 5.8%): $^1$H NMR (400 MHz, CDCl$_3$) δ 7.73 (t, J=1.7 Hz, 1H), 7.71 (q, J=1.6 Hz, 1H), 7.54-7.47 (m, 2H), 7.46-7.39 (m, 1H), 7.20 (dd, J=8.5, 6.9 Hz, 1H), 6.76 (dd, J=8.5, 3.7 Hz, 1H), 3.81 (s, 2H); $^{19}$F NMR (376 MHz, CDCl3) δ −79.87 (s). 03 (7.5 mg, 9.1%): $^1$H NMR (400 MHz, CDCl3) δ 7.72 (d, J=1.3 Hz, 1H), 7.58-7.43 (m, 5H), 6.75 (d, J=2.6 Hz, 1H), 3.71 (s, 2H); $^{19}$F NMR (376 MHz, CDCl3) δ −81.64 (s).

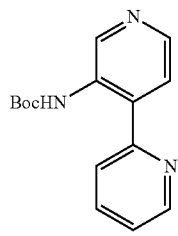 [SMILES: CC(C)(C)OC(=O)Nc1cnccc1-c1ccccn1]

tert-Butyl [2,4'-bipyridin]-3'-ylcarbamate

To a pressure vessel was added tert-butyl (4-iodopyridin-3-yl)carbamate (0.25 g, 0.781 mmol), 2-(4,4,5,5-tetramethyl-1,3,2-dioxaborolan-2-yl)pyridine (0.176 g, 0.859 mmol) and PdCl2(dppf)-CH2Cl2Adduct (0.032 g, 0.039 mmol). The reaction mixture was degassed and flushed with N2 (3×). Then Dioxane (5) was added and the system was degassed and flushed with N2 (3×). SODIUM CARBONATE (0.781 ml, 1.562 mmol) was added and the system was degassed and flushed with N2 (3×). The reaction mixture was heated to 85° C. for 3 h. The reaction was diluted with ethyl acetate and satd ammonium chloride. The org layer was washed with water, brine and dried over sodium sulfate. The crude product was dissolved in a small amount of dichloromethane and charged to 110 g silica gel cartridge which was eluted with 0-100% ethyl acetate/hexanes over a period of 60 mins. The desired fractions were combined and dried under vacuo to give tert-butyl [2,4'-bipyridin]-3'-ylcarbamate (0.02 g, 0.074 mmol, 9.44% yield). MS (ESI) (m/z): 272.1 (M+H)$^+$.

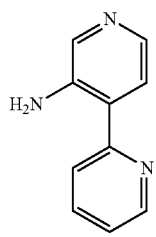

2,4'-Bipyridin]-3'-amine

To tert-butyl [2,4'-bipyridin]-3'-ylcarbamate (0.02 g, 0.074 mmol) was added HCl, 4 M dioxane (0.5 ml, 2.000 mmol). The reaction mixture was stirred overnight at rt. The solvent was removed and the residue was neutralized with satd sodium bicarbonate and extracted with ethyl acetate (3×). The org extracts were combined and dried over sodium sulfate. The solvent was removed, dried under vacuo to give [2,4'-bipyridin]-3'-amine (15 mg, 0.088 mmol. MS (ESI) (m/z): 172.4 (M+H)$^+$.

General Synthesis of Amine D

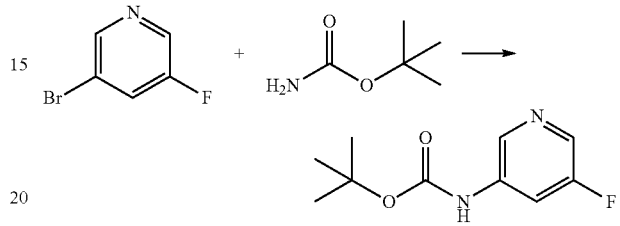

tert-Butyl (5-fluoropyridin-3-yl)carbamate

In a 250 mL round-bottom flask was added 3-bromo-5-fluoropyridine (2.84 g, 16.1 mmol), tert-butyl carbamate (2.080 g, 17.75 mmol), and Cs$_2$CO$_3$ (10.52 g, 32.3 mmol) in dioxane (40 mL) (degassed) to give a colorless suspension under nitrogen. Pd$_2$(dba)$_3$ (0.443 g, 0.484 mmol) and XANTPHOS (0.374 g, 0.646 mmol) were added. The flasked was heated at 100° C. under nitrogen overnight for 20 h. The mixture was diluted with water and extracted twice with ethyl acetate. The combined organic layers were washed with water, brine, dried and concentrated. The residue was purified by flash column chromatography on silica gel, eluting with 30% ethyl acetate/hexane, to afford the desired product (2.93 g, 86%) as an off-white solid: $^1$H NMR (400 MHz, Chloroform-d) δ 8.22-8.18 (m, 1H), 8.16 (d, J=2.6 Hz, 1H), 7.98 (d, J=10.8 Hz, 1H), 6.88 (s, 1H), 1.55 (s, 9H); $^{19}$F NMR (376 MHz, Chloroform-d) δ −125.88.

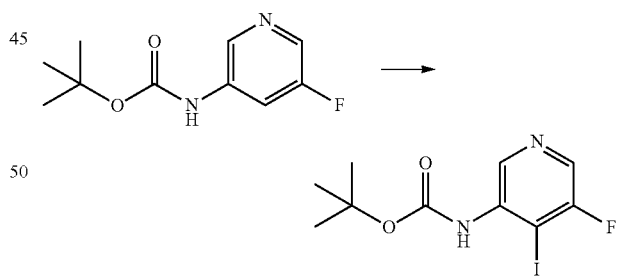

tert-Butyl (5-fluoro-4-iodopyridin-3-yl)carbamate

In a 500 mL round-bottom flask was dissolved tert-butyl (5-fluoropyridin-3-yl)carbamate (1.802 g, 8.49 mmol) and N,N,N',N'-tetramethylethylenediamine (3.84 mL, 25.5 mmol) in ethyl ether (40 mL) to give a light yellow solution. After cooling to −78° C., n-BuLi (9.69 mL, 25.5 mmol) was slowly added via syringe (to maintain the temperature below −60° C.). Upon addition, the mixture was allowed to warm to −20° C. and was stirred for 90 min. The mixture was cooled to −78° C. and a solution of iodine in THF (12 mL)

was added dropwise over 10 min. The reaction mixture was allowed to gradually warm to rt and stirred overnight. The mixture was poured onto 1M HCl (20 mL) and crushed ice. The aqueous phase was extracted twice with ether. The combined organic layers were washed with water, NaHCO₃ solution, sodium thiosulfate solution, and brine, dried and concentrated. Purification by flash column chromatography on silica gel, eluting with 30% ethyl acetate/hexane, afforded the desired product (1.79 g, 62%) as a light yellow solid: ¹H NMR (400 MHz, Chloroform-d) δ 9.03 (s, 1H), 8.07 (d, J=0.9 Hz, 1H), 6.77 (s, 1H), 1.58 (s, 9H); ¹⁹F NMR (376 MHz, Chloroform-d) δ −105.13.

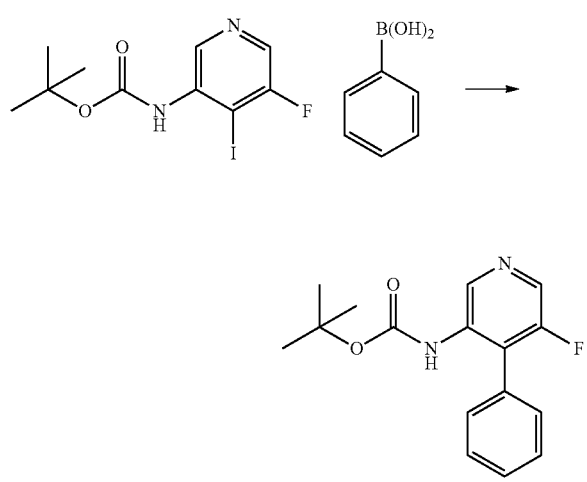

tert-Butyl (5-fluoro-4-phenylpyridin-3-yl)carbamate

In a 15 mL vial was dissolved tert-butyl (5-fluoro-4-iodopyridin-3-yl)carbamate (188.3 mg, 0.557 mmol), phenylboronic acid (109 mg, 0.891 mmol), and Na₂CO₃ (0.835 mL, 1.67 mmol) in dioxane (3 mL) to give a slightly yellow solution under nitrogen. 1,1′-Bis(diphenylphosphino)ferrocenepalladium (II) dichloride, toluene (22.91 mg, 0.028 mmol) was added under nitrogen. The vial was sealed and heated at 80° C. for 20 h. The mixture was partitioned between water and ethyl acetate. The layers were separated. The organic layer was washed with brine, dried and concentrated. The residue was purified by flash column chromatography on silica gel, eluting with 30% ethyl acetate/hexane, to afford the desired product (144 mg, 90%) as a white solid: ¹H NMR (400 MHz, Chloroform-d) δ 9.22 (s, 1H), 8.26 (s, 1H), 7.60-7.46 (m, 3H), 7.40-7.30 (m, 2H), 6.41 (s, 1H), 1.46 (s, 9H); ¹⁹F NMR (376 MHz, Chloroform-d) δ −130.69.

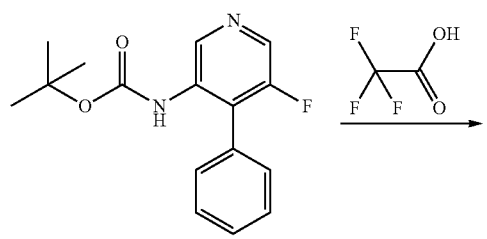

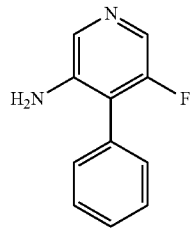

5-Fluoro-4-phenylpyridin-3-amine

In a 100 mL round-bottom flask was dissolved tert-butyl (5-fluoro-4-phenylpyridin-3-yl)carbamate (143.3 mg, 0.497 mmol) in methylene chloride (2 mL) to give a colorless solution. TFA (1.0 mL, 13 mmol) was added, and the mixture was stirred at rt for 1 h. The mixture was evaporated and the residue diluted with ethyl acetate. The solution was washed with 10 ml 1N NaOH, water, saturated NaHCO₃ solution, and brine, dried and concentrated to give the desired product (94 mg, 100%) as a white solid: ¹H NMR (400 MHz, Chloroform-d) δ 7.98 (s, 1H), 7.94 (s, 1H), 7.55-7.47 (m, 2H), 7.47-7.36 (m, 3H), 3.96 (s, 2H); ¹⁹F NMR (376 MHz, Chloroform-d) δ −132.65.

General Synthesis of Amine E

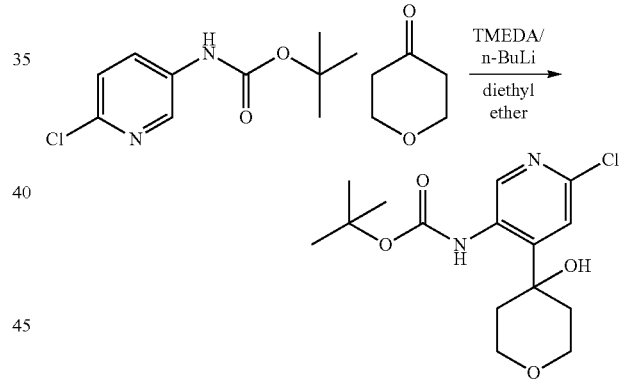

tert-Butyl (6-chloro-4-(4-hydroxytetrahydro-2H-pyran-4-yl)pyridin-3-yl)carbamate BuLi (2.166 mL, 5.70 mmol) was added to the diethyl ether (17 mL) solution of TMEDA (0.706 mL, 4.68 mmol) and tert-butyl (6-chloropyridin-3-yl)carbamate (0.4653 g, 2.035 mmol) at −78° C. The reaction was stirred at this temperature for 1 hour. Dihydro-2H-pyran-4(3H)-one (0.230 mL, 2.442 mmol) was added to the reaction mixture (at this moment, the bath temperature was −75° C.). The reaction was stirred for 2.5 hours before quenched with NH₄Cl (sat.). The reaction was diluted with ethyl acetate and washed with water three times. The organic layer was separated, dried (Na₂SO₄), filtered and concentrated. Flash column eluted with ethyl acetate in hexane from 0 to 25% to 50% gave the desired product (0.3600 g, 45% yield, 83% pure). MS(ES+) m/e 329 [M+H]+.

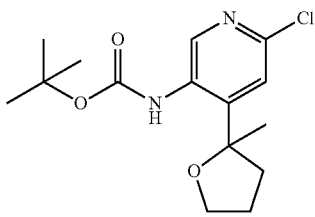 [SMILES: CC(C)(C)OC(=O)Nc1cnc(Cl)cc1C1(C)CCCO1]

tert-Butyl (6-chloro-4-(2-methyltetrahydrofuran-2-yl)pyridin-3-yl)carbamate

BuLi (2.224 mL, 5.85 mmol) was added to the diethyl ether (20 mL) solution of TMEDA (0.802 mL, 5.32 mmol) and tert-butyl (6-chloropyridin-3-yl)carbamate (0.6079 g, 2.66 mmol) at −78° C. The reaction was stirred at this temperature for 1 hour. 5-chloropentan-2-one (0.366 mL, 3.19 mmol) was added to the reaction mixture (at this moment, the bath temperature was −70° C.). The reaction was stirred for 1 hour before it was quenched by adding water. The reaction was diluted with ethyl acetate and washed with water three times. The organic layer was separated, dried (Na$_2$SO$_4$), filtered and concentrated. Flash column eluted with ethyl acetate in hexane from 0 to 25% to 50% gave the desired product (67.33 mg, 7% yield). MS(ES+) m/e 313 [M+H]+.

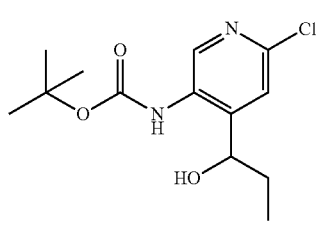

tert-Butyl (6-chloro-4-(1-hydroxypropyl)pyridin-3-yl)carbamate

BuLi (2.90 mL, 4.65 mmol) was added to the diethyl ether (10 mL) solution of TMEDA (0.638 mL, 4.22 mmol) and tert-butyl (6-chloropyridin-3-yl)carbamate (0.483 g, 2.112 mmol) at −78° C. The reaction was stirred at this temperature for 0.5 hour. propionaldehyde (0.349 mL, 4.65 mmol) was added to the reaction mixture (at this moment, the bath temperature was −78° C.). The reaction was stirred for 1 hour before it was quenched by adding water. The reaction was diluted with ethyl acetate and washed with water three times. The ethyl acetate layer was separated, dried (Na2SO4), filtered and concentrated. Flash column eluted with ethyl acetate in hexane from 0 to 50% gave the desired product (obtained 306.6 mg, 40% yield). MS(ES+) m/e 309 [M+Na]$^+$.

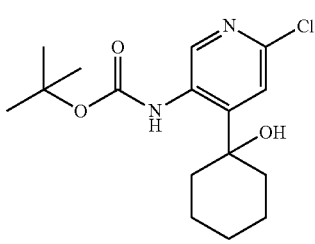 [SMILES: CC(C)(C)OC(=O)Nc1cnc(Cl)cc1C1(O)CCCCC1]

tert-Butyl (6-chloro-4-(1-hydroxycyclohexyl)pyridin-3-yl)carbamate

BuLi (1.432 mL, 3.77 mmol) was added to the diethyl ether (10 mL) solution of TMEDA (0.467 mL, 3.09 mmol) and tert-butyl (6-chloropyridin-3-yl)carbamate (0.3075 g, 1.345 mmol) at −78° C. The reaction was stirred at this temperature for 1 hour. cyclohexanone (0.167 mL, 1.614 mmol) was added to the reaction mixture (at this moment, the bath temperature was −78° C.). The reaction was stirred for overnight while it was slowly warmed up to the room temperature. The reaction was diluted with ethyl acetate and washed with water three times. The organic layer was separated, dried (Na$_2$SO$_4$), filtered and concentrated. Flash column eluted with ethyl acetate in hexane from 0 to 25% to 50% gave the desired product with contamination of the starting material. (0.312 g, 24% yield, 34% pure). MS(ES+) m/e 327 [M+H]+.

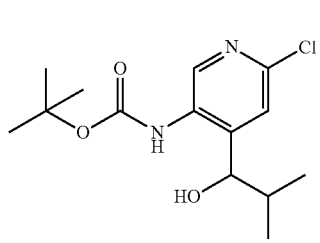 [SMILES: CC(C)C(O)c1cc(Cl)ncc1NC(=O)OC(C)(C)C]

tert-Butyl (6-chloro-4-(1-hydroxy-2-methylpropyl)pyridin-3-yl)carbamate

React with isobutylaldehyde. 1H NMR (400 MHz, CHLOROFORM-d) δ 8.86 (br. s., 1H), 8.29 (br. s., 1H), 6.95 (s, 1H), 4.58 (d, J=3.3 Hz, 1H), 4.34 (dd, J=7.8, 3.8 Hz, 1H), 1.49 (s, 9H), 1.04 (d, J=6.5 Hz, 3H), 0.78 (d, J=6.8 Hz, 3H).

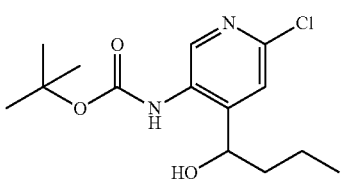 [SMILES: CCCC(O)c1cc(Cl)ncc1NC(=O)OC(C)(C)C]

tert-Butyl (6-chloro-4-(1-hydroxybutyl)pyridin-3-yl) carbamate

React with butylaldehyde. MS(ES+) m/e 301 [M+H]+.

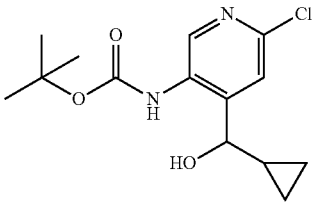 [SMILES: CC(C)(C)OC(=O)Nc1cnc(Cl)cc1C(O)C1CC1]

tert-Butyl (6-chloro-4-(cyclopropyl(hydroxy)methyl) pyridin-3-yl)carbamate

React with cyclopropanecarbaldehyde. MS(ES+) m/e 299 [M+H]+. $^1$H NMR (400 MHz, CHLOROFORM-d) δ 8.97 (br. s., 1H), 8.13 (br. s., 1H), 7.19 (s, 1H), 3.93 (dd, J=8.9, 3.1 Hz, 1H), 3.43 (d, J=3.3 Hz, 1H), 1.52 (s, 9H), 1.39-1.32 (m, 1H), 0.84-0.65 (m, 2H), 0.54 (dq, J=9.7, 4.9 Hz, 1H), 0.38-0.31 (m, 1H).

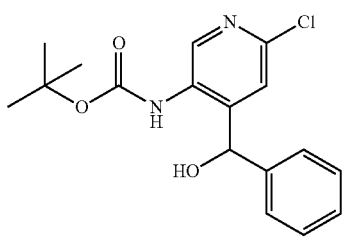 [SMILES: CC(C)(C)OC(=O)Nc1cnc(Cl)cc1C(O)c1ccccc1]

tert-butyl (6-chloro-4-(hydroxy(phenyl)methyl)pyridin-3-yl)carbamate

React with benzaldehyde. MS(ES+) m/e 335 [M+H]+. $^1$H NMR (400 MHz, CHLOROFORM-d) δ 8.72 (s, 1H), 7.64 (br. s., 1H), 7.43-7.30 (m, 5H), 7.04 (s, 1H), 5.83 (d, J=3.5 Hz, 1H), 4.37 (d, J=3.0 Hz, 1H), 1.46 (s, 9H).

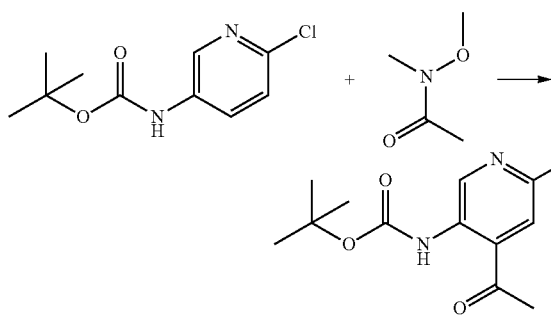

tert-Butyl (4-acetyl-6-chloropyridin-3-yl)carbamate $^1$H NMR (400 MHz, CHLOROFORM-d) δ 10.19 (br. s., 1H), 9.57 (s, 1H), 7.63 (s, 1H), 2.67 (s, 3H), 1.53 (s, 9H).

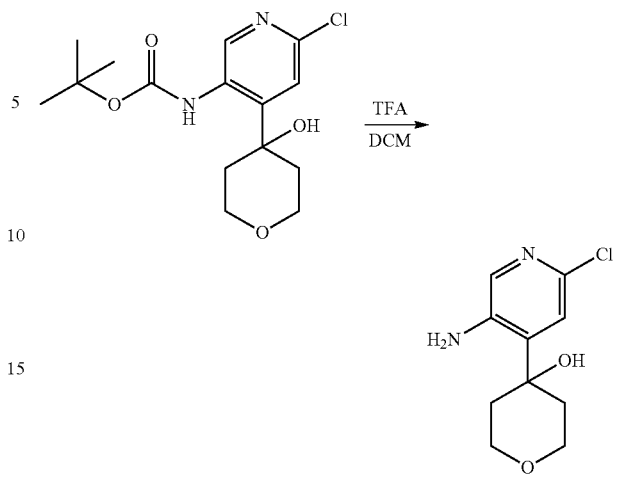

4-(5-Amino-2-chloropyridin-4-yl)tetrahydro-2H-pyran-4-ol

The solution of tert-butyl (6-chloro-4-(4-hydroxytetrahydro-2H-pyran-4-yl)pyridin-3-yl)carbamate (0.1572 g, 0.478 mmol) in CH$_2$Cl$_2$ (3 mL) and TFA (2 mL) was stirred at room temperature for 30 min. LCMS showed completely conversion to the desired product. The solvent was removed via vacuum and the crude was partitioned between ethyl acetate and NaOH (1N). The organic layer was separated and washed two more times by water before dried (Na$_2$SO$_4$), filtered and concentrated. The crude was purified by flash column eluted with ethyl acetate in hexane from 0 to 45% to 85% to give the product as a white solid (82.3 mg. 75% yield). MS(ES+) m/e 229 [M+H]+. $^1$H NMR (400 MHz, CHLOROFORM-d) δ 7.76 (s, 1H), 7.00 (s, 1H), 4.67 (br. s., 2H), 4.00-3.86 (m, 5H), 2.14-2.06 (m, 3H), 2.04-2.01 (m, 1H).

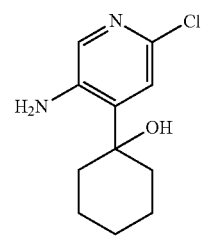 [SMILES: Nc1cnc(Cl)cc1C1(O)CCCCC1]

1-(5-Amino-2-chloropyridin-4-yl)cyclohexanol

The mixture of TFA (2 mL, 26.0 mmol) and tert-butyl (6-chloro-4-(1-hydroxycyclohexyl)pyridin-3-yl)carbamate (0.312 g, 0.325 mmol) in CH2Cl2 (5 mL) was stirred at room temperature for over night. The solvent was removed via vacuum and the crude was partitioned between ethyl acetate and NaOH (1N). The organic layer was separated and washed with water two more times before dried (Na2SO4), filtered and concentrated. Flash column eluted by ethyl acetate in hexane from 0 to 50% gave the desired product (26.4 mg, 36% yield). $^1$H NMR (400 MHz, CHLOROFORM-d) δ 7.63 (s, 1H), 6.98 (s, 1H), 4.73 (br. s., 2H), 2.11 (d, J=12.0 Hz, 2H), 1.81-1.61 (m, 7H), 1.30-1.21 (m, 2H). MS(ES+) m/e 227 [M+H]+.

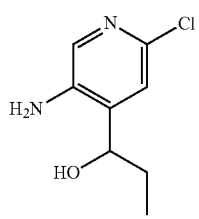

1-(5-Amino-2-chloropyridin-4-yl)propan-1-ol

¹H NMR (400 MHz, CHLOROFORM-d) δ 7.76 (s, 1H), 6.97 (s, 1H), 4.58 (t, J=6.9 Hz, 1H), 4.27 (br. s., 2H), 2.47 (br. s., 1H), 1.93-1.84 (m, 2H), 0.99 (t, J=7.4 Hz, 3H). MS(ES+) m/e 187 [M+H]⁺.

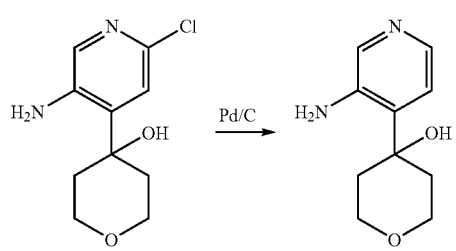 [SMILES: Nc1cnc(Cl)cc1C1(O)CCOCC1 ; Nc1cnccc1C1(O)CCOCC1]

1-(3-Aminopyridin-4-yl)cyclohexanol

The mixture of Pd/C (15 mg, 0.014 mmol) and 1-(5-amino-2-chloropyridin-4-yl)cyclohexanol (26.4 mg, 0.116 mmol) in EtOH (4 mL) was hydrogenated via H2 balloon at room temperature for 5 hours. The reaction was filtered through celite cartridge and washed with DCM. The filtrate was concentrated to give the crude product (22 mg, 100% yield). MS(ES+) m/e 193 [M+H]⁺. ¹H NMR (400 MHz, METHANOL-d4) δ 7.98 (d, J=0.8 Hz, 1H), 7.88 (dd, J=5.9, 0.9 Hz, 1H), 7.60 (d, J=6.0 Hz, 1H), 2.14 (d, J=11.5 Hz, 2H), 1.96-1.82 (m, 2H), 1.80-1.60 (m, 5H), 1.41-1.28 (m, 1H).

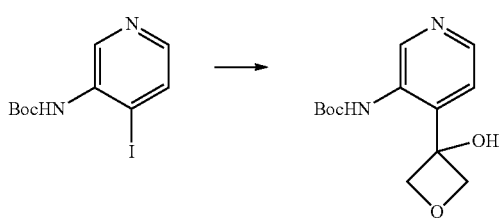 [SMILES: CC(C)(C)OC(=O)Nc1cnccc1I ; CC(C)(C)OC(=O)Nc1cnccc1C1(O)COC1]

tert-Butyl (4-(3-hydroxyoxetan-3-yl)pyridin-3-yl)carbamate

To tert-butyl (4-iodopyridin-3-yl)carbamate (1.0 g, 3.12 mmol) in THF (8 ml) was added ISOPROPYLMAGNESIUM CHLORIDE, 2.9 M (3.23 ml, 9.37 mmol) dropwise at –40° C. The reaction mixture was stirred at this temp for 1.5 h then cooled to –78° C. before being cannulated to a solution of oxetan-3-one (0.405 g, 5.62 mmol) in THF (8 ml) at –78° C. After addition, the reaction mixture was stirred at –78° C. for 10 mins, then at 0° C. for 2 hrs and then at rt for 30 mins. Satd ammonium chloride was added then solvent was removed. Ethyl acetate and water was added to the residue. The layers were separated and the org layer was washed with brine and dried over sodium sulfate. The crude product was dissolved in a small amount of dichloromethane and charged to a 24 g silica gel cartridge which was eluted with 0-100% ethyl acetate/hexanes over a period of 50 mins. The desired fractions were combined and dried under vacuo to give the tert-butyl (4-(3-hydroxyoxetan-3-yl)pyridin-3-yl)carbamate (0.4 g, 1.502 mmol, 48.1% yield). ¹H NMR (400 MHz, DMSO-d₆) δ ppm 8.81 (s, 1H) 8.37 (d, J=4.89 Hz, 1H) 8.30 (br. s., 1H) 7.47 (d, J=5.14 Hz, 1H)) 6.93 (br. s., 1H) 4.87 (d, J=7.58 Hz, 2H) 4.73 (d, J=7.58 Hz, 2H) 1.46 (s, 9H). ¹H NMR (400 MHz, DMSO-d₆) ppm 8.81 (s, 1H) 8.37 (d, J=5.14 Hz, 1H) 8.29 (br. s., 1H) 7.47 (d, J=4.89 Hz, 1H) 6.91 (s, 1H) 4.87 (d, J=7.09 Hz, 2H) 4.73 (d, J=7.09 Hz, 2H) 1.47 (s, 9H).

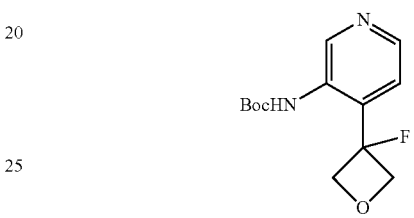

tert-Butyl (4-(3-fluorooxetan-3-yl)pyridin-3-yl)carbamate

To tert-butyl (4-(3-hydroxyoxetan-3-yl)pyridin-3-yl)carbamate (0.11 g, 0.413 mmol) in CH2Cl2 (2.5 mL) at –78° C. was added DAST (0.055 mL, 0.413 mmol). The reaction mixture was stirred for 1 hr at –78° C. then quenched with water. The reaction mixture was warmed to rt then extracted with DCM. The org extracts were combined and dried over sodium sulfate, filtered and concentrated. The crude product was dissolved in a small amount of dichloromethane and charged to a 24 g silica gel cartridge which was eluted with 0-80% ethyl acetate/hexanes over a period of 50 mins. The desired fractions were combined and dried under vacuo to give tert-butyl (4-(3-fluorooxetan-3-yl)pyridin-3-yl)carbamate (0.052 g, 0.194 mmol, 46.9% yield). MS (ESI) (m/z): 269.0 (M+H)⁺.

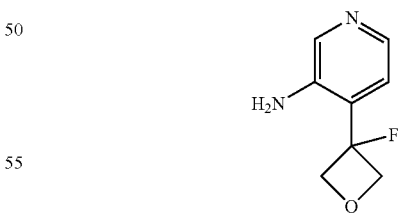

4-(3-Fluorooxetan-3-yl)pyridin-3-amine

To tert-butyl (4-(3-fluorooxetan-3-yl)pyridin-3-yl)carbamate (0.052 g, 0.194 mmol) in CH2Cl2 (3 mL) at 0° C. was added TFA (0.03 ml, 0.389 mmol). The reaction mixture was stirred at rt for 24 hrs. The reaction was concentrated and dried under vacuo to give the desired prod. Taken as is to the next step. MS (ESI) (m/z): 169.0 (M+H)⁺.

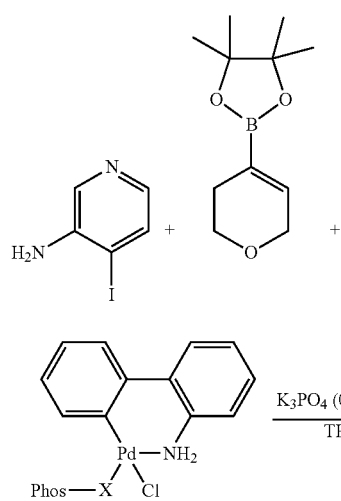

4-(3,6-Dihydro-2H-pyran-4-yl)pyridin-3-amine

The mixture of 4-iodopyridin-3-amine (0.316 g, 1.437 mmol), 2-(3,6-dihydro-2H-pyran-4-yl)-4,4,5,5-tetramethyl-1,3,2-dioxaborolane (0.3019 g, 1.437 mmol), XPhos precatalyst (0.045 g, 0.057 mmol) and Phosphoric acid, potassium salt (0.5 M aq) (5.75 mL, 2.87 mmol) in dioxane (3.0 mL) was heat at 80° C. for 2.5 hours. The reaction was cooled to room temperature and diluted with ethyl acetate. The organic layer was washed with water three times before dried (Na2SO4), filtered and concentrated. The product was purified by flash column eluted with ethyl acetate in hexane from 0 to 100% and eluted with 100% of ethyl acetate until the purple fraction (desired product) was eluted out (0.020 g, 8% yield). $^1$H NMR (400 MHz, CHLOROFORM-d) δ 8.10 (s, 1H), 8.00 (d, J=5.0 Hz, 1H), 6.90 (d, J=5.0 Hz, 1H), 5.97 (dt, J=3.0, 1.3 Hz, 1H), 4.32 (q, J=2.8 Hz, 2H), 3.95 (t, J=5.4 Hz, 2H), 3.83 (br. s., 2H), 2.45-2.38 (m, 2H). MS(ES+) m/e 177 [M+H]$^+$.

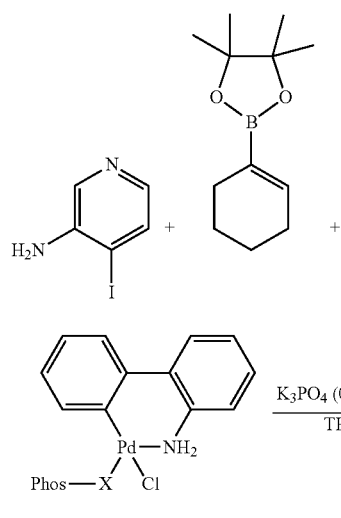

4-(Cyclohex-1-en-1-yl)pyridin-3-amine

The mixture of 4-iodopyridin-3-amine (0.161 g, 0.734 mmol), cyclohex-1-en-1-ylboronic acid (0.0924 g, 0.734 mmol), XPhos precatalyst (0.023 g, 0.029 mmol), Phosphoric acid, potassium salt (2M aq) (0.550 mL, 1.100 mmol) in THF (3.0 mL) was stirred at room temperature for 24 hours. The reaction was diluted with ethyl acetate and washed with water three times. The ethyl acetate layer was separated, dried (Na$_2$SO$_4$), filtered and concentrated. Flash column eluted with ethyl acetate in hexane from 0 to 100% gave the desired product (33 mg, 25% yield). MS(ES+) m/e 175 MS[M+H]$^+$; $^1$H NMR (400 MHz, CHLOROFORM-d) δ 8.06 (s, 1H), 7.95 (d, J=5.0 Hz, 1H), 6.89-6.85 (m, 1H), 5.86 (dt, J=3.8, 1.9 Hz, 1H), 3.80 (br. s., 2H), 2.26-2.15 (m, 4H), 1.81-1.74 (m, 2H), 1.73-1.64 (m, 2H).

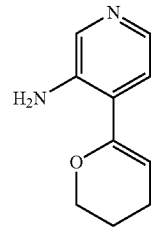

4-(3,4-Dihydro-2H-pyran-6-yl)pyridin-3-amine $^1$H NMR (400 MHz, CHLOROFORM-d) δ 8.02 (s, 1H), 7.91 (d, J=5.0 Hz, 1H), 7.05 (d, J=5.0 Hz, 1H), 5.18 (t, J=4.0 Hz, 1H), 4.34 (br. s., 2H), 4.19-4.13 (m, 2H), 2.24-2.17 (m, J=6.3, 6.3, 4.1 Hz, 2H), 1.96-1.88 (m, 2H); MS(MS+) m/e 177 [M+H]$^+$.

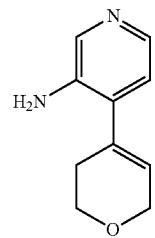 [SMILES: Nc1cnccc1C1=CCOCC1]

4-(3,6-Dihydro-2H-pyran-4-yl)pyridin-3-amine $^1$H NMR (400 MHz, CDCl$_3$) δ 8.11 (s, 1H), 8.02 (d, J=4.8 Hz, 1H), 6.92 (d, J=4.8 Hz, 1H), 5.98 (tt, J=2.9, 1.5 Hz, 1H), 4.33 (q, J=2.8 Hz, 2H), 3.96 (t, J=5.5 Hz, 2H), 3.83 (br. s., 2H), 2.46-2.38 (m, 2H); MS(MS+) m/e 177 [M+H]$^+$.

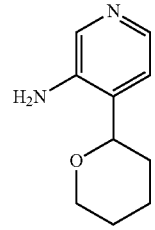 [SMILES: Nc1cnccc1C1CCCCO1]

4-(Tetrahydro-2H-pyran-2-yl)pyridin-3-amine

The mixture of Pd/C (0.015 g, 0.014 mmol) and 4-(3,4-dihydro-2H-pyran-6-yl)pyridin-3-amine (0.080 g, 0.454 mmol) in MeOH (0.3 mL) and Ethyl acetate (0.3 mL) was hydrogenated by H$_2$ balloon overnight at room temperature. The reaction was filtered through celite plug and washed with ethyl acetate. The filtrate was concentrated and the crude was used as it is. MS(MS+) m/e 179 [M+H]$^+$.

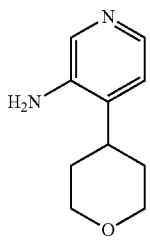 [SMILES: Nc1cnccc1C1CCOCC1]

4-(Tetrahydro-2H-pyran-4-yl)pyridin-3-amine

MS(MS+) m/e 179 [M+H]$^+$.

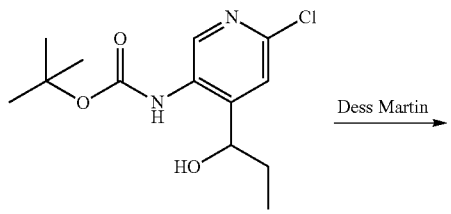

tert-Butyl (6-chloro-4-propionylpyridin-3-yl)carbamate

Dess-MartinPeriodinane (0.458 g, 1.080 mmol) was added to the CH2Cl2 (8 mL) solution of tert-butyl (6-chloro-4-(1-hydroxypropyl)pyridin-3-yl)carbamate (0.258 g, 0.900 mmol) at room temperature. The reaction was stirred at room temperature for 1 hour and the reaction mixture was directly loaded onto the column, which was eluted with ethyl acetate in hexane from 0 to 25%. The product was obtained as a white solid (0.1319 g, 52% yield). $^1$H NMR (400 MHz, CHLOROFORM-d) δ 10.21 (br. s., 1H), 9.57 (s, 1H), 7.65 (s, 1H), 3.04 (q, J=7.1 Hz, 2H), 1.53 (s, 9H), 1.23 (t, J=7.2 Hz, 3H).

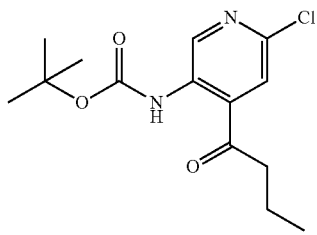 [SMILES: CCCC(=O)c1cc(Cl)ncc1NC(=O)OC(C)(C)C]

tert-Butyl (4-butyryl-6-chloropyridin-3-yl)carbamate

MS(ES+) m/e 299 [M+H]$^+$; $^1$H NMR (400 MHz, CHLOROFORM-d) δ 10.21 (br. s., 1H), 9.58 (s, 1H), 7.65 (s, 1H), 2.98 (t, J=7.2 Hz, 2H), 1.83-1.72 (m, 2H), 1.54 (s, 9H), 1.03 (t, J=7.5 Hz, 3H).

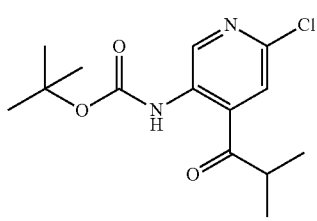 [SMILES: CC(C)C(=O)c1cc(Cl)ncc1NC(=O)OC(C)(C)C]

tert-Butyl (6-chloro-4-isobutyrylpyridin-3-yl)carbamate $^1$H NMR (400 MHz, CHLOROFORM-d) δ 10.17 (br. s., 1H), 9.60 (s, 1H), 7.66 (s, 1H), 3.55 (spt, J=6.8 Hz, 1H), 1.54 (s, 9H), 1.25 (d, J=6.8 Hz, 6H).

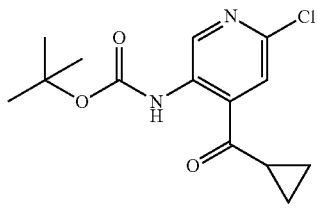 [SMILES: CC(C)(C)OC(=O)Nc1cnc(Cl)cc1C(=O)C1CC1]

tert-Butyl (6-chloro-4-(cyclopropanecarbonyl)pyridin-3-yl)carbamate

MS(ES+) m/e 297 [M+H]$^+$; $^1$H NMR (400 MHz, CHLOROFORM-d) δ 9.95 (s, 1H), 9.51 (s, 1H), 7.83 (s, 1H), 2.61 (tt, J=7.7, 4.5 Hz, 1H), 1.51 (s, 9H), 1.36-1.30 (m, 2H), 1.23-1.17 (m, 2H).

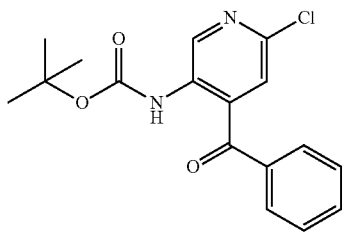 [SMILES: CC(C)(C)OC(=O)Nc1cnc(Cl)cc1C(=O)c1ccccc1]

tert-Butyl (4-benzoyl-6-chloropyridin-3-yl)carbamate

¹H NMR (400 MHz, CHLOROFORM-d) δ 9.42 (s, 1H), 8.90 (s, 1H), 7.77 (dd, J=8.3, 1.3 Hz, 2H), 7.72-7.65 (m, 1H), 7.59-7.51 (m, 2H), 7.34 (d, J=0.5 Hz, 1H), 1.51 (s, 9H); MS(ES+) m/e 333 [M+H]⁺.

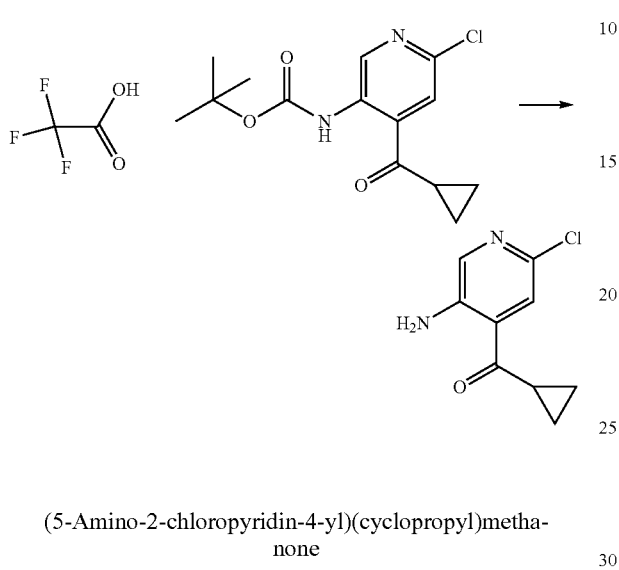

(5-Amino-2-chloropyridin-4-yl)(cyclopropyl)methanone

The mixture of TFA (0.5 mL, 6.49 mmol) and tert-butyl (6-chloro-4-(cyclopropanecarbonyl)pyridin-3-yl)carbamate (0.1912 g, 0.644 mmol) in DCM (4 mL) was stirred at room temperature for 6 hours. The solvent was removed via vacuum. The crude was diluted with ethyl acetate and washed with NaOH (1N). The ethyl acetate layer was separated, dried (Na₂SO₄), filtered and concentrated to give the crude product (0.118 g, 93% yield) as a yellow solid: MS(ES+) m/e 197 [M+H]⁺.

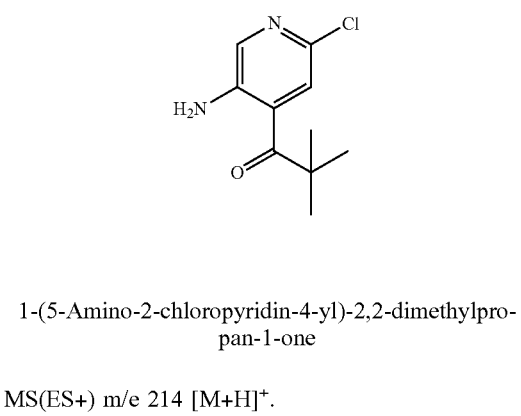

1-(5-Amino-2-chloropyridin-4-yl)-2,2-dimethylpropan-1-one

MS(ES+) m/e 214 [M+H]⁺.

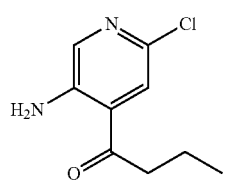

1-(5-Amino-2-chloropyridin-4-yl)butan-1-one

MS(ES+) m/e 199 [M+H]⁺.

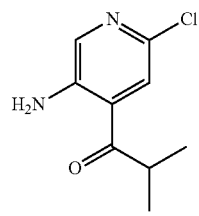

1-(5-Amino-2-chloropyridin-4-yl)-2-methylpropan-1-one

MS(ES+) m/e 199 [M+H]⁺.

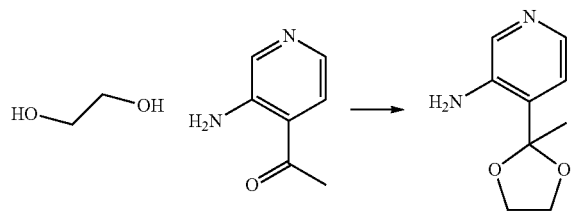

4-(2-Methyl-1,3-dioxolan-2-yl)pyridin-3-amine

The mixture of P-TOLUENESULFONIC ACID MONOHYDRATE (0.065 g, 0.340 mmol), ETHYLENE GLYCOL (0.379 mL, 6.80 mmol) and 1-(3-aminopyridin-4-yl)ethanone (0.4631 g, 3.40 mmol) in Toluene (5 mL) was heat to reflux for over night. The reaction was diluted with ethyl acetate and washed with water three times. The ethyl acetate layer was separated, dried (Na2SO4), filtered and concentrated. Flash column eluted with ethyl acetate in hexane from 0 to 25% to 50% gave the desired product (59.8 mg obtained, 8% yield) as a wax. MS(ES+) m/e 181 [M+H]⁺; ¹H NMR (400 MHz, CHLOROFORM-d) δ 8.01 (s, 1H), 7.95 (d, J=5.0 Hz, 1H), 7.18 (d, J=4.8 Hz, 1H), 4.46 (br. s., 2H), 4.09-4.04 (m, 2H), 3.82-3.77 (m, 2H), 1.66 (s, 3H).

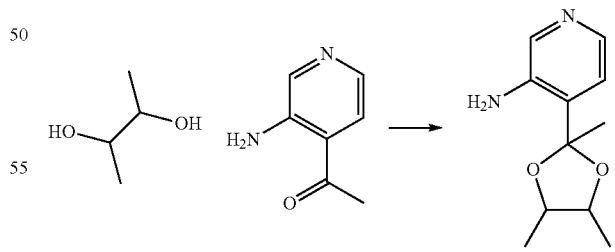

6-Chloro-4-(2,4,5-trimethyl-1,3-dioxolan-2-yl)pyridin-3-amine

The mixture of p-toluenesulfonic acid monohydrate (0.034 g, 0.179 mmol), butane-2,3-diol (0.5 mL, 0.060 mmol) and 1-(5-amino-2-chloropyridin-4-yl)ethanone (0.0102 g, 0.060 mmol) in Toluene (4 mL) was heat to reflux for 3 hours. The reaction was diluted with ethyl acetate and washed with water three times. The ethyl acetate layer was separated, dried (Na2SO4), filtered and concentrated. Flash column eluted with ethyl acetate in hexane from 0 to 25% to 50% gave the desired product (15.6 mg obtained, 66% yield) as a wax. MS(ES+) m/e 243 [M+H]$^+$.

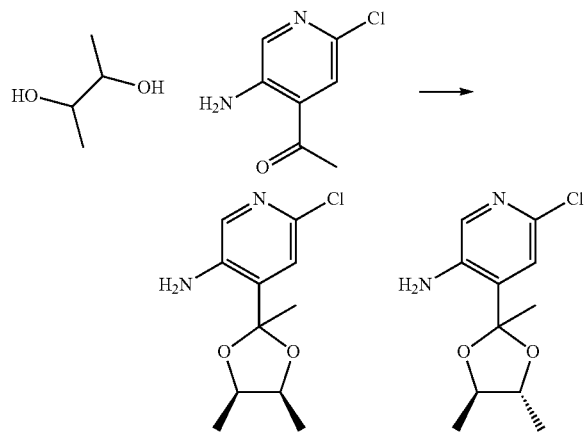

The mixture of p-toluenesulfonic acid monohydrate (0.557 g, 2.93 mmol), butane-2,3-diol (0.5 mL, 0.975 mmol) and 1-(5-amino-2-chloropyridin-4-yl)ethanone (0.1664 g, 0.975 mmol) in Toluene (4 mL) was heat to reflux for 3 hours. The reaction was diluted with ethyl acetate and washed with water three times. The ethyl acetate layer was separated, dried (Na2SO4), filtered and concentrated. Flash column eluted with ethyl acetate in hexane from 0 to 25% to 50% gave the desired product. 6-Chloro-4-((4S,5R)-2,4,5-trimethyl-1,3-dioxolan-2-yl)pyridin-3-amine. (0.0923 g, 39%); 6-Chloro-4-((4R,5R)-2,4,5-trimethyl-1,3-dioxolan-2-yl)pyridin-3-amine. (0.0490 g, 21%). MS(ES+) m/e 243 [M+H]$^+$. (Structure assignment is arbitrary).

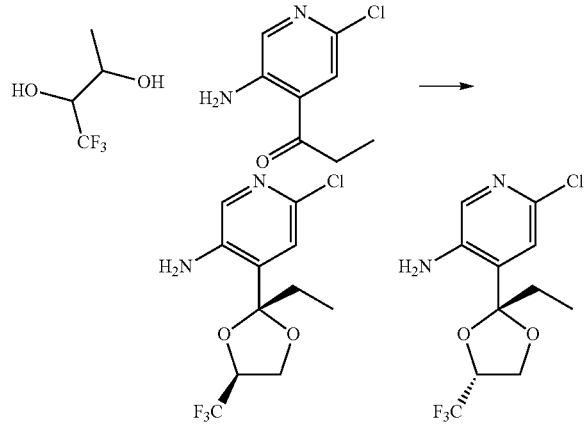

The mixture of p-toluenesulfonic acid monohydrate (0.035 g, 0.182 mmol), 3,3,3-trifluoropropane-1,2-diol (0.05 mL, 0.182 mmol) and tert-butyl (6-chloro-4-propionylpyridin-3-yl)carbamate (0.0517 g, 0.182 mmol) in Toluene (0.4 mL) was heated to reflux for 18 hours. The reaction was diluted with ethyl acetate and washed with water three times. The ethyl acetate layer was separated, dried (Na$_2$SO$_4$), filtered and concentrated. Flash column eluted with ethyl acetate in hexane from 0 to 25% to 45% gave the desired product.

6-Chloro-4-((2R,4S)-2-ethyl-4-(trifluoromethyl)-1,3-dioxolan-2-yl)pyridin-3-amine (0.0104 g, 19%): $^1$H NMR (400 MHz, CHLOROFORM-d) δ 7.81 (s, 1H), 7.18 (s, 1H), 4.58-4.48 (m, 1H), 4.41 (dd, J=8.9, 6.9 Hz, 1H), 4.37-4.27 (m, 2H), 3.96 (dd, J=9.0, 7.5 Hz, 1H), 2.06-1.95 (m, 2H), 0.92 (t, J=7.4 Hz, 3H); $^{19}$F NMR (376 MHz, CHLOROFORM-d) S δ -76.52 (s, 3F). MS(ES+) m/e 297 [M+H]$^+$. (Structure assignment is arbitrary).

6-Chloro-4-((2R,4R)-2-ethyl-4-(trifluoromethyl)-1,3-dioxolan-2-yl)pyridin-3-amine (0.0132 g, 24%). $^1$H NMR (400 MHz, CHLOROFORM-d) δ 7.82 (s, 1H), 7.19 (s, 1H), 4.45-4.34 (m, 3H), 4.28 (dd, J=9.5, 3.3 Hz, 1H), 3.94 (td, J=8.5, 0.8 Hz, 1H), 2.12-2.02 (m, 2H), 0.95 (t, J=7.5 Hz, 3H); $^{19}$F NMR (376 MHz, CHLOROFORM-d) δ -78.09 (s, 3F); MS(ES+) m/e 297 [M+H]$^+$. (Structure assignment is arbitrary).

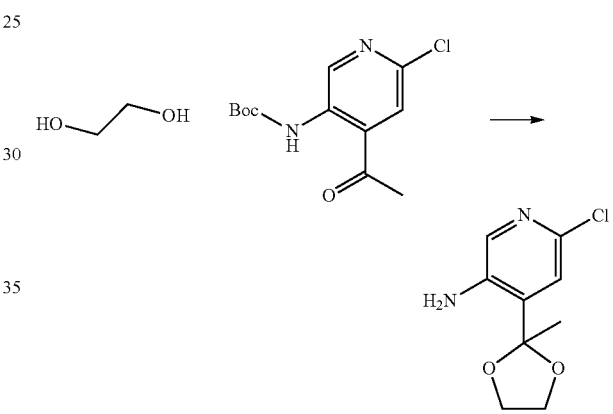

6-Chloro-4-(2-methyl-1,3-dioxolan-2-yl)pyridin-3-amine

The mixture of p-toluenesulfonic acid monohydrate (7.59 mg, 0.040 mmol), ethylene glycol (0.111 mL, 1.995 mmol) and tert-butyl (4-acetyl-6-chloropyridin-3-yl)carbamate (0.108 g, 0.399 mmol) in Toluene (5 mL) was heat to reflux for over night. The reaction was diluted with ethyl acetate and washed with water three times. The ethyl acetate layer was separated, dried (Na2SO4), filtered and concentrated. Flash column eluted with ethyl acetate in hexane from 0 to 25% to 50% gave the desired product (43.3 mg obtained, 51% yield) as a wax. MS(ES+) m/e 215 [M+H]$^+$; $^1$H NMR (400 MHz, CHLOROFORM-d) δ 7.78 (s, 1H), 7.24 (s, 1H), 4.46 (br. s., 2H), 4.12-4.06 (m, 2H), 3.85-3.79 (m, 2H), 1.66 (s, 3H).

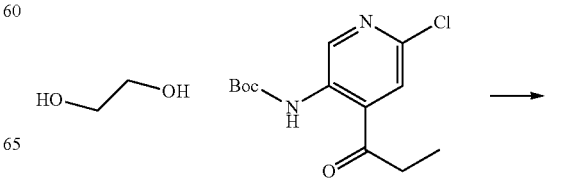

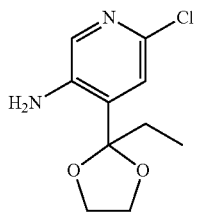

6-Chloro-4-(2-ethyl-1,3-dioxolan-2-yl)pyridin-3-amine

The mixture of p-toluenesulfonic acid monohydrate (5.01 mg, 0.026 mmol), ethylene glycol (0.2 mL, 3.59 mmol) and tert-butyl (6-chloro-4-propionylpyridin-3-yl)carbamate (0.025 g, 0.088 mmol) in Toluene (2 mL) was heat to reflux for 2 hours. The reaction was diluted with ethyl acetate and washed with water three times. The ethyl acetate layer was separated, dried ($Na_2SO_4$), filtered and concentrated. Flash column eluted with ethyl acetate in hexane from 0 to 25% to 45% gave the desired product (9.3 mg obtained, 46% yield) as a wax. MS(ES+) m/e 229 [M+H]$^+$; $^1$H NMR (400 MHz, CHLOROFORM-d) δ 7.78 (s, 1H), 7.21 (s, 1H), 4.44 (br. s., 2H), 4.10-4.05 (m, 2H), 3.87-3.82 (m, 2H), 1.97 (q, J=7.4 Hz, 2H), 0.91 (t, J=7.4 Hz, 3H).

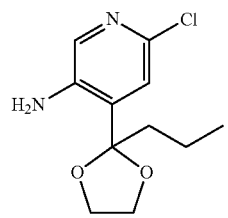 [SMILES: CCCC1(c2cc(Cl)ncc2N)OCCO1]

6-Chloro-4-(2-propyl-1,3-dioxolan-2-yl)pyridin-3-amine

MS(ES+) m/e 243 [M+H]$^+$; $^1$H NMR (400 MHz, CHLOROFORM-d) δ 7.77 (s, 1H), 7.20 (s, 1H), 4.45 (br. s., 2H), 4.08-4.02 (m, 2H), 3.85-3.79 (m, 2H), 1.95-1.88 (m, 2H), 1.45-1.32 (m, 2H), 0.90 (t, J=7.4 Hz, 3H).

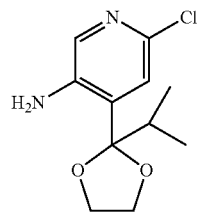 [SMILES: CC(C)C1(c2cc(Cl)ncc2N)OCCO1]

6-Chloro-4-(2-isopropyl-1,3-dioxolan-2-yl)pyridin-3-amine

MS(ES+) m/e 243 [M+H]$^+$; $^1$H NMR (400 MHz, CHLOROFORM-d) δ 7.77 (s, 1H), 7.17 (s, 1H), 4.46 (br. s., 2H), 4.09-3.98 (m, 2H), 3.88-3.77 (m, 2H), 2.35 (dt, J=13.7, 6.8 Hz, 1H), 0.92 (d, J=6.8 Hz, 6H).

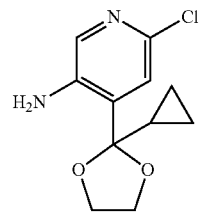 [SMILES: Nc1cnc(Cl)cc1C1(C2CC2)OCCO1]

6-Chloro-4-(2-cyclopropyl-1,3-dioxolan-2-yl)pyridin-3-amine

MS(ES+) m/e 241 [M+H]$^+$; $^1$H NMR (400 MHz, CHLOROFORM-d) δ 7.79 (s, 1H), 7.16 (s, 1H), 4.52 (br. s., 2H), 4.08-4.02 (m, 2H), 3.85-3.79 (m, 2H), 1.55-1.46 (m, 1H), 0.59-0.47 (m, 4H).

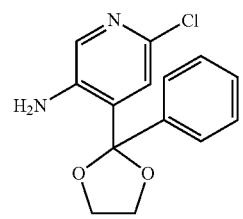 [SMILES: Nc1cnc(Cl)cc1C1(c2ccccc2)OCCO1]

6-Chloro-4-(2-phenyl-1,3-dioxolan-2-yl)pyridin-3-amine $^1$H NMR (400 MHz, CHLOROFORM-d) δ 7.77 (s, 1H), 7.51-7.43 (m, 3H), 7.40-7.32 (m, 3H), 4.32 (br. s., 2H), 4.24-4.16 (m, 2H), 4.09-4.00 (m, 2H); MS(ES+) m/e 277 [M+H]$^+$.

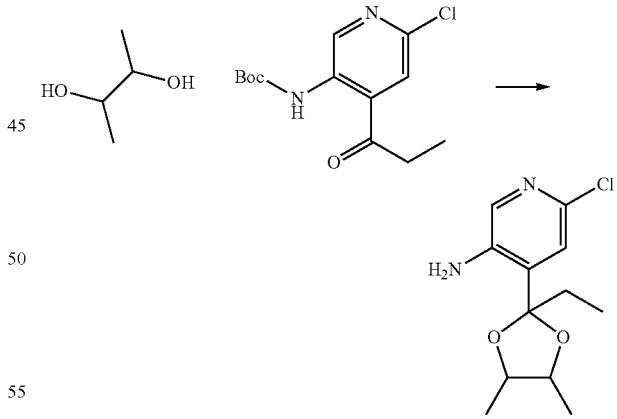

6-Chloro-4-(2-ethyl-4,5-dimethyl-1,3-dioxolan-2-yl)pyridin-3-amine

The mixture of p-toluenesulfonic acid monohydrate (3.95 mg, 0.021 mmol), butane-2,3-diol (0.2 mL, 0.069 mmol) and tert-butyl (6-chloro-4-propionylpyridin-3-yl)carbamate (0.0197 g, 0.069 mmol) in Toluene (1 mL) was heat to reflux for 2 hours. The reaction was diluted with ethyl acetate and washed with water three times. The ethyl acetate layer was separated, dried (Na₂SO₄), filtered and concentrated. Flash column eluted with ethyl acetate in hexane from 0 to 25% to 45% gave the desired product (11.3 mg obtained, 59% yield) as a green wax. MS(ES+) m/e 257 [M+H]⁺.

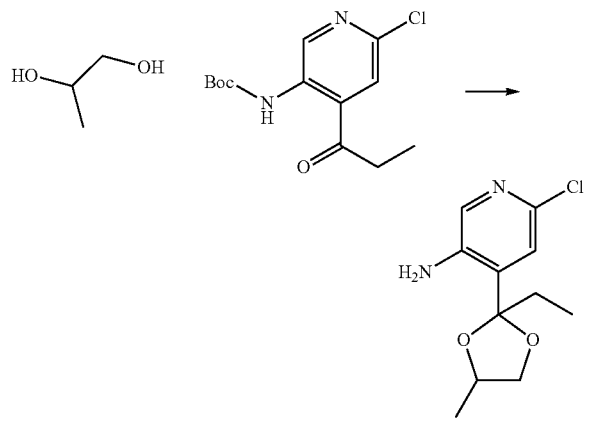

6-Chloro-4-(2-ethyl-4-methyl-1,3-dioxolan-2-yl)pyridin-3-amine

The mixture of p-toluenesulfonic acid monohydrate (0.030 g, 0.158 mmol), propane-1,2-diol (0.05 mL, 0.158 mmol) and tert-butyl (6-chloro-4-propionylpyridin-3-yl)carbamate (0.045 g, 0.158 mmol) in Toluene (0.5 mL) was heated to reflux for 2 hours. The reaction was diluted with ethyl acetate and washed with NaOH (1N) one time and water two times. The ethyl acetate layer was separated, dried (Na₂SO₄), filtered and concentrated. Flash column eluted with ethyl acetate in hexane from 0 to 25% to 45% gave the desired product (33 mg obtained, 86% yield) as a wax. MS(ES+) m/e 243 [M+H]⁺; NMR showed that the product is a mixture with ratio about 2:1.

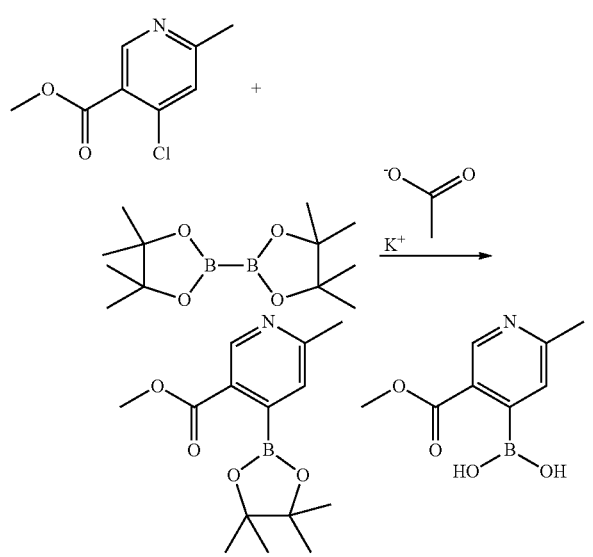

Methyl 6-methyl-4-(4,4,5,5-tetramethyl-1,3,2-dioxaborolan-2-yl)nicotinate

To a solution of methyl 4-chloro-6-methylnicotinate (0.371 g, 2 mmol) in dioxane (3 ml) were added 4,4,4',4', 5,5,5',5'-octamethyl-2,2'-bi(1,3,2-dioxaborolane) (0.762 g, 3.00 mmol), potassium acetate (0.589 g, 6.00 mmol) and PdCl₂(dppf)-CH₂Cl₂Adduct (0.114 g, 0.140 mmol). The reaction mixture was flushed with Argon for 5 min and then heated to 90° C. for ~96 h. At the end, the mixture was filtered through celite and the filtrate was evaporated in vacuo. The residual crude product was used as is for the reaction with the cyclopropanecarbonyl chloride.

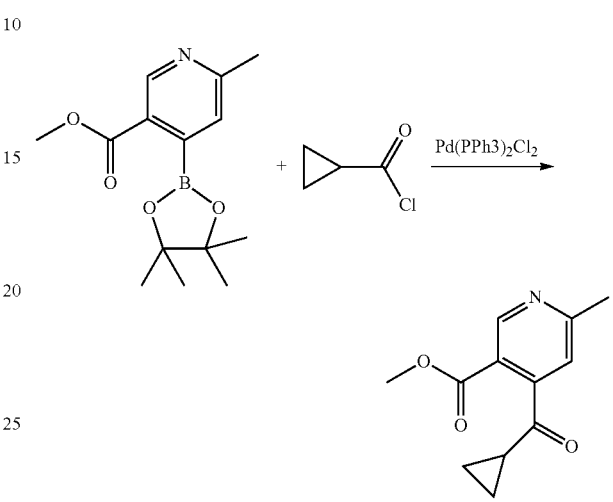

Methyl 4-(cyclopropanecarbonyl)-6-methylnicotinate

To a suspension of crude boronate ester (554 mg, 2 mmol) with bis(triphenylphosphine)palladium(II) dichloride (23.44 mg, 0.033 mmol), potassium phosphate tribasic (532 mg, 2.505 mmol) and water (0.068 mL, 3.76 mmol) in toluene (8.35 mL) was added cyclopropanecarbonyl chloride (0.156 mL, 1.67 mmol). The reaction mixture was heated to 80° C. for ~18 h. Another portion of bis(triphenylphosphine)palladium(II) dichloride (23.44 mg, 0.033 mmol), potassium phosphate tribasic (426 mg, 2 mmol) and cyclopropanecarbonyl chloride (0.125 mL, 1.34 mmol) was added and continued heating for another ~18 h. At the end, the reaction mixture was diluted with toluene (20 mL), sat. NaHCO₃ (20 mL) and filtered through celite. From the filtrate layers were separated and the organic layer was dried (Na₂SO₄) and evaporated in vacuo. The residue was purified by silica gel chromatography Biotage (EtOAc:Hexane=1:3) to give the required product (83 mg, 20%) as light yellow oil: MS (ESI) (m/z): 220 (M+H)⁺; ¹H NMR (400 MHz, CHLOROFORM-d) δ 9.05 (s, 1H), 7.11 (s, 1H), 3.92 (d, J=0.7 Hz, 3H), 2.65 (s, 3H), 2.22-2.07 (m, 1H), 1.38-1.29 (m, 2H), 1.19-1.08 (m, 2H).

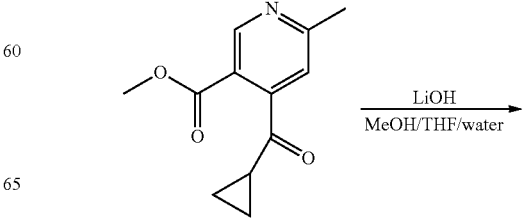

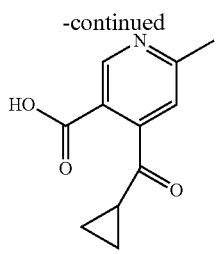

4-(Cyclopropanecarbonyl)-6-methylnicotinic acid

To a solution of Methyl 4-(cyclopropanecarbonyl)-6-methylnicotinate (50 mg, 0.228 mmol) in mixed solvents THF/MeOH/Water (1 mL:0.5 mL:0.5 mL) was added lithium hydroxide (27.3 mg, 1.140 mmol). The reaction mixture was stirred at ambient temperature for ~18 h. At the end, all volatiles were evaporated in vacuo and the residue was dissolved in MeOH (2 mL) and purified by Prep-HPLC. The fractions with required product were combined and added Hunig's base (80 µL, 0.456 mmol, 2 equivalent). All volatiles were removed under vacuo and white Hunig's base salt was obtained (69 mg, 90%). The sample was directly used for next step. MS (ESI) (m/z): 206 (M+H)$^+$.

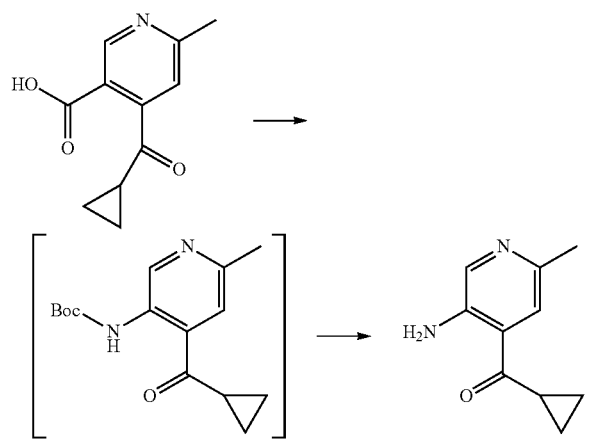

5-Amino-2-methylpyridin-4-yl)(cyclopropyl)methanone

To a solution of 4-(cyclopropanecarbonyl)-6-methylnicotinic acid (69 mg, 0.206 mmol) in tert-butanol (1 mL) was added TEA (0.086 mL, 0.619 mmol) followed by Diphenylphosphoryl azide (0.133 mL, 0.619 mmol) under nitrogen. The reaction mixture was heated at 80° C. for ~18 h. At the end volatiles were evaporated in vacuo. The residue taken in EtOAc (100 mL) was washed with water, brine and dried (Na$_2$SO$_4$). The solution was filtered and evaporated and the residue was purified by silica gel chromatography (EtOAc:Hexane=1:2) to give desired intermediate as white solid (23.4 mg, 40%): MS (ESI) (m/z): 277 (M+H)$^+$; $^1$H NMR (400 MHz, CHLOROFORM-d) δ 9.88 (br. s., 1H), 9.59 (s, 1H), 7.65 (s, 1H), 2.71-2.63 (m, 1H), 2.61 (s, 3H), 1.53 (s, 9H), 1.33-1.29 (m, 2H), 1.20-1.01 (m, 2H). The intermediate (23.4 mg) obtained above was dissolved in TFA/Dichloromethane (10%, 2 mL) and stirred at ambient temperature for 4 h. The TFA/Dichloromethane were evaporated and the residue was coevaporated with heptane twice and dried under vacuum. The crude was directly used without further purification: MS (ESI) (m/z): 177 (M+H)$^+$.

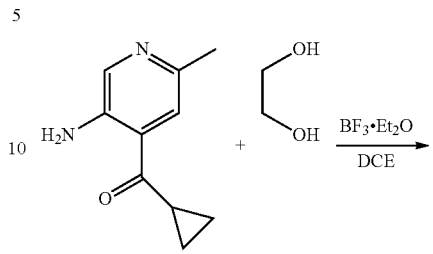

4-(2-Cyclopropyl-1,3-dioxolan-2-yl)-6-methylpyridin-3-amine

This compound was prepared according to a described procedure (Fieser, L. F. and Stevenson, R. in JACS 1954, 76, 1728-1733) except that dichloroethane was used as solvent instead of acetic acid (8.5 mg, purity >98%): MS (ESI) (m/z): 221 (M+H)$^+$; $^1$H NMR (400 MHz, CHLOROFORM-d) δ 7.94 (s, 1H), 6.99 (s, 1H), 4.37 (br. s., 2H), 4.14-3.95 (m, 2H), 3.88-3.69 (m, 2H), 2.43 (s, 3H), 1.60-1.44 (m, 1H), 0.63-0.38 (m, 4H).

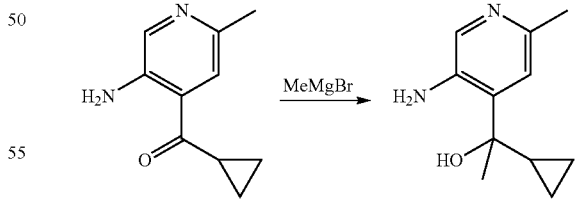

41-(5-Amino-2-methylpyridin-4-yl)-1-cyclopropylethanol

MS (ESI) (m/z): 193 (M+H)$^+$; $^1$H NMR (400 MHz, CHLOROFORM-d) δ 7.87 (s, 1H), 7.05 (s, 1H), 4.49 (br. s., 2H), 2.43 (s, 3H), 1.44 (s, 3H), 1.55-1.34 (m, 1H), 0.72-0.42 (m, 4H).

General Synthesis of Formula IV

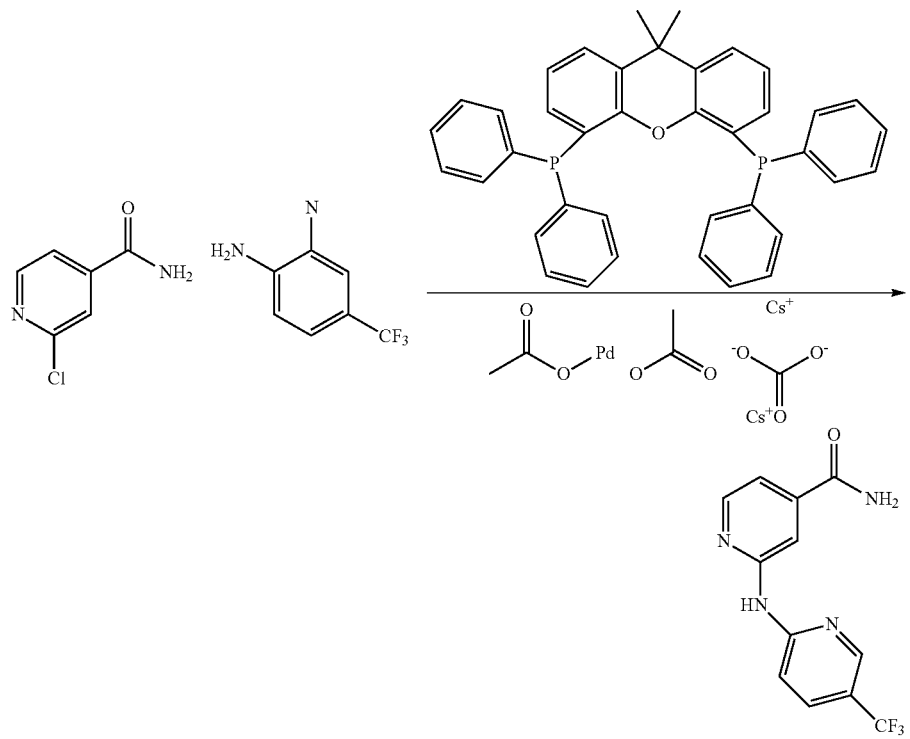

2-((5-(Trifluoromethyl)pyridin-2-yl)amino)isonicotinamide

The mixture of XANTPHOS (0.087 g, 0.151 mmol), cesium carbonate (0.817 g, 2.509 mmol), palladium acetate (0.023 g, 0.100 mmol), 2-chloroisonicotinamide (0.3928 g, 2.509 mmol) and 5-(trifluoromethyl)pyridin-2-amine (0.488 g, 3.01 mmol) in Dioxane (15 mL) was heat at 110° C. for over night under $N_2$. The reaction was partitioned between ethyl acetate and water. The ethyl acetate layer was separated and washed with water two more times. The ethyl acetate layer was separated, dried ($Na_2SO_4$), filtered and concentrated to give the crude product as a yellow solid. The product was purified via flash column eluted with ethyl acetate in hexane from 0 to 100% and gave the desired product as a white solid (0.1937 g, 27% yield). MS[ES+] m/e 283 [M+H]$^+$; $^1$H NMR (500 MHz, DMSO-d$_6$) δ 9.96 (s, 1H), 8.90 (d, J=2.1 Hz, 1H), 8.51 (d, J=8.9 Hz, 1H), 8.35 (d, J=5.2 Hz, 1H), 8.19 (br. s., 1H), 7.79 (d, J=8.5 Hz, 1H), 7.67 (br. s., 1H), 7.33 (s, 1H), 7.27 (d, J=5.5 Hz, 1H).

General Synthesis of Formula V

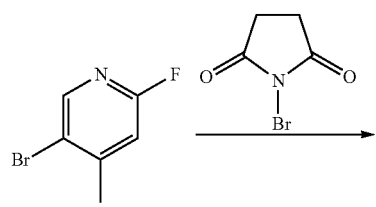

5-Bromo-4-(dibromomethyl)-2-fluoropyridine and 5-bromo-4-(bromomethyl)-2-fluoropyridine BENZOYL PEROXIDE (0.434 g, 1.792 mmol) was added to the CCl$_4$ (25 mL) mixture of NBS (3.83 g, 21.51 mmol) and 5-bromo-2-fluoro-4-methylpyridine (3.4059 g, 17.92 mmol) at room temperature. The reaction was heated to reflux overnight. The solid was filtered off and the filtrate was passed through a silica plug, which was washed by DCM. The filtrate was concentrated. The product was purified by flash column eluted with ethyl acetate in hexane from 0 to 25%. The product obtained is the mixture of mono, bis bromides as well as the unreacted starting material. The crude was used as it is.

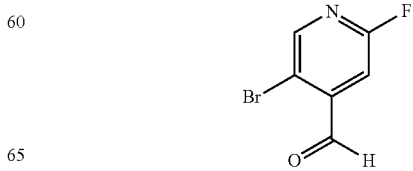

5-Bromo-2-fluoroisonicotinaldehyde

The suspension of 5-bromo-4-(bromomethyl)-2-fluoropyridine compound with 5-bromo-4-(dibromomethyl)-2-fluoropyridine (1:1) (5.6 g, 9.08 mmol) and Calcium carbonate (4.54 g, 45.4 mmol) in DMSO (12 mL) was stirred at 145° C. for 3 hours. The reaction was filtered and the solid was washed with ethyl acetate. The filtrate was diluted more with ethyl acetate and washed with water three times. The ethyl acetate layer was separated, dried (Na$_2$SO$_4$), filtered and concentrated. The product was purified via flash column eluted with ethyl acetate in hexane from 0 to 45% (0.843 g, 45% yield). MS(ES+) m/e 208 MS[M+H]$^+$; $^1$H NMR (400 MHz, CHLOROFORM-d) δ 10.31 (d, J=2.5 Hz, 1H), 8.53-8.50 (m, 1H), 7.37 (d, J=2.8 Hz, 1H).

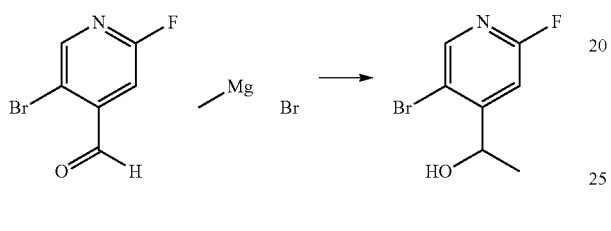

1-(5-Bromo-2-fluoropyridin-4-yl)ethanol methylmagnesium bromide (0.4058 g, 3.40 mmol) was added to the Tetrahydrofuran (5 mL) solution of 5-bromo-2-fluoroisonicotinaldehyde (1.134 mL, 3.40 mmol) at 0° C. The reaction was stirred for 3 hours before quenched by water. The reaction was diluted with ethyl acetate and washed with water three times. The aqueous layer was extract one time with ethyl acetate. The ethyl acetate was combined, dried (Na$_2$SO$_4$), filtered and concentrated. The product (0.2370 g, 32% yield) was purified via flash column, which was eluted with ethyl acetate in hexane from 0 to 25% to 40%. $^1$H NMR (400 MHz, CHLOROFORM-d) δ 8.26 (s, 1H), 7.25 (d, J=2.0 Hz, 1H), 5.15 (qd, J=6.4, 3.8 Hz, 1H), 2.09 (dd, J=3.6, 1.1 Hz, 1H), 1.51 (d, J=6.5 Hz, 3H). 19F NMR (376 MHz, CHLOROFORM-d) Shift −69.60 (s, 1F).

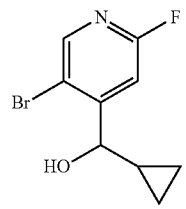

(5-Bromo-2-fluoropyridin-4-yl)(cyclopropyl)methanol

Grignard reagent: cyclopropylmagnesium bromide. MS(ES+) m/e 248 [M+2H]$^+$; $^1$H NMR (400 MHz, CHLOROFORM-d) δ 8.28 (s, 1H), 7.21 (d, J=2.3 Hz, 1H), 4.67 (dd, J=6.9, 3.1 Hz, 1H), 2.28 (d, J=3.5 Hz, 1H), 1.31-1.19 (m, 1H), 0.72-0.46 (m, 4H); $^{19}$F NMR (376 MHz, CHLOROFORM-d) Shift −70.09 (s, 1F).

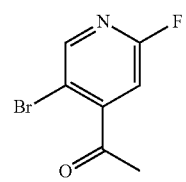

1-(5-Bromo-2-fluoropyridin-4-yl)ethanone

Dess-Martin oxidation of corresponding alcohol as previously described for similar alcohols. $^1$H NMR (400 MHz, CHLOROFORM-d) δ 8.42 (s, 1H), 6.98 (d, J=3.0 Hz, 1H), 2.65 (s, 3H); $^{19}$F NMR (470 MHz, CHLOROFORM-d) δ −68.45 (br. s., 1F).

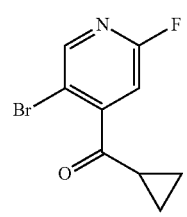 [SMILES: O=C(c1cc(F)ncc1Br)C1CC1]

(5-Bromo-2-fluoropyridin-4-yl)(cyclopropyl)methanone $^1$H NMR (400 MHz, CHLOROFORM-d) δ 8.40 (d, J=0.5 Hz, 1H), 7.02-6.94 (m, 1H), 2.36 (tt, J=7.8, 4.5 Hz, 1H), 1.43-1.35 (m, 2H), 1.28-1.18 (m, 2H); $^{19}$F NMR (376 MHz, CHLOROFORM-d) δ −68.81 (s, 1F).

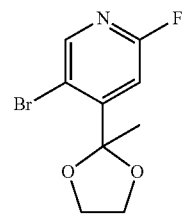

5-Bromo-2-fluoro-4-(2-methyl-1,3-dioxolan-2-yl)pyridine

MS(ES+) m/e 262 [M+H]$^+$; $^1$H NMR (400 MHz, CHLOROFORM-d) δ 8.34 (s, 1H), 7.24 (d, J=2.3 Hz, 1H), 4.16-4.05 (m, 2H), 3.85-3.75 (m, 2H), 1.78 (s, 3H); $^{19}$F NMR (376 MHz, CHLOROFORM-d) δ −70.45 (s, 1F).

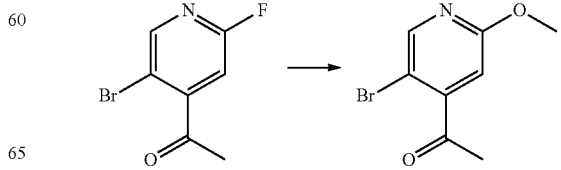

1-(5-Bromo-2-methoxypyridin-4-yl)ethanone

The mixture of 1-(5-bromo-2-fluoropyridin-4-yl)ethanone (0.1055 g, 0.484 mmol) and sodium methanolate (1.161 ml, 0.581 mmol) was heated at rt for 2 hours. LCMS showed the desired product. The solvent was removed via vacuum and the crude was purified via flash column eluted with ethyl acetate in hexane from 0 to 25% to give the desired product as a clear oil (obtained 67 mg, 51% yield). MS(ES+) m/e 232 [M+H]+.

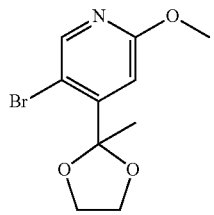

5-Bromo-2-methoxy-4-(2-methyl-1,3-dioxolan-2-yl)pyridine

Starting material is 1-(5-bromo-2-methoxypyridin-4-yl)ethanone. MS(ES+) m/e 276 [M+H]$^+$.

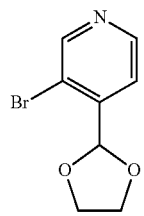

3-Bromo-4-(1,3-dioxolan-2-yl)pyridine

Starting material is 3-bromoisonicotinaldehyde. $^1$H NMR (400 MHz, CHLOROFORM-d) δ 8.74 (s, 1H), 8.56 (d, J=5.0 Hz, 1H), 7.50 (d, J=5.0 Hz, 1H), 6.04 (s, 1H), 4.19-4.07 (m, 4H); MS (ES+) m/e 232 (M+H)$^+$.

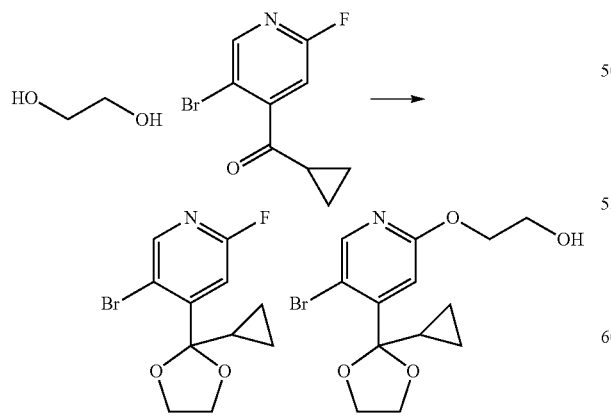

The mixture of p-toluenesulfonic acid monohydrate (0.168 g, 0.885 mmol), ethane-1,2-diol (0.110 g, 1.770 mmol) and (5-bromo-2-fluoropyridin-4-yl)(cyclopropyl) methanone (0.108 g, 0.443 mmol) in benzene (3 mL) was heat to reflux for 5 hours. The reaction was diluted with ethyl acetate and washed with water three times. The ethyl acetate layer was separated, dried (Na$_2$SO$_4$), filtered and concentrated. Flash column eluted with ethyl acetate in hexane from 0 to 25% to 50% gave the desired products.

5-Bromo-4-(2-cyclopropyl-1,3-dioxolan-2-yl)-2-fluoropyridine (21% yield, 81% pure). $^1$H NMR (400 MHz, CHLOROFORM-d) δ 8.35 (s, 1H), 7.13 (d, J=2.3 Hz, 1H), 4.08-4.02 (m, 2H), 3.84-3.77 (m, 2H), 1.77 (tt, J=8.3, 5.2 Hz, 1H), 0.66-0.60 (m, 2H), 0.55-0.48 (m, 2H); $^{19}$F NMR (376 MHz, CHLOROFORM-d) Shift −68.78 (s, 1F), −70.83 (s, 1F) (main peak); MS(ES+) m/e 290 [M+2H]$^+$.

2-((5-Bromo-4-(2-methyl-1,3-dioxolan-2-yl)pyridin-2-yl)oxy)ethanol (33% yield). MS(ES+) m/e 305 [M+H]$^+$; $^1$H NMR (400 MHz, CHLOROFORM-d) δ 8.23 (s, 1H), 7.10 (s, 1H), 4.46-4.43 (m, 2H), 4.11-4.06 (m, 2H), 3.96 (m, 2H), 3.81-3.77 (m, 2H), 1.77 (s, 3H).

General Synthesis of Formula I

Example 91

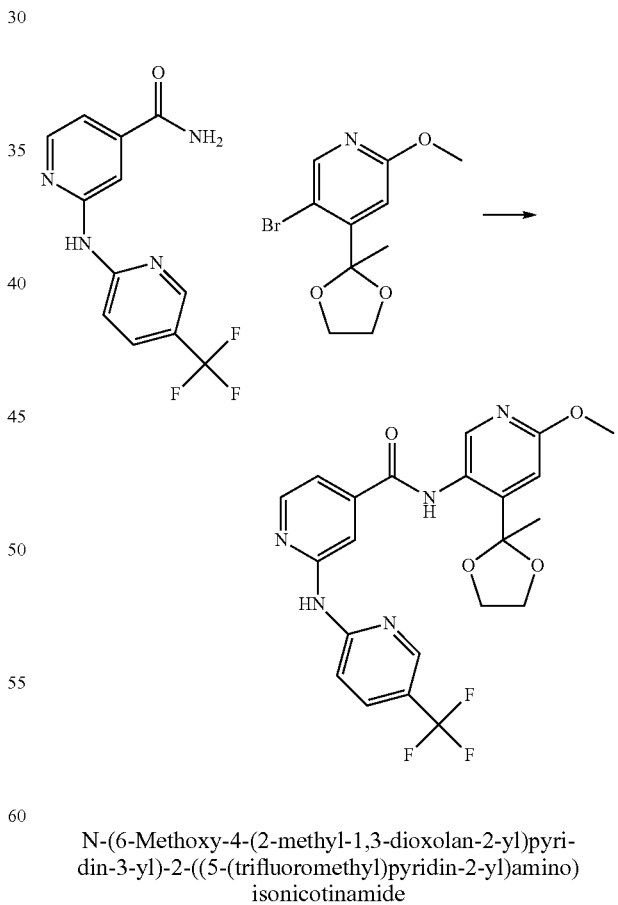

N-(6-Methoxy-4-(2-methyl-1,3-dioxolan-2-yl)pyridin-3-yl)-2-((5-(trifluoromethyl)pyridin-2-yl)amino)isonicotinamide The mixture of XANTPHOS (5.09 mg, 8.80 µmol) cesium carbonate (0.048 g, 0.147 mmol), palladium acetate (1.317 mg, 5.87 µmol), 2-((5-(trifluoromethyl)pyridin-2-yl)

amino)isonicotinamide (0.041 g, 0.147 mmol) and 5-bromo-2-methoxy-4-(2-methyl-1,3-dioxolan-2-yl)pyridine (0.060 g, 0.147 mmol) in Dioxane (1.5 mL) was heated at 110° C. for 5 hours under $N_2$. The reaction was partitioned between ethyl acetate and water. The ethyl acetate layer was separated and washed two more times with water. The ethyl acetate layer was dried ($Na_2SO_4$), filtered and concentrated. The crude was purified via flash column eluted with ethyl acetate in hexane from 0 to 45% to 80% (obtained 8.0 mg, 11% yield). MS(ES+) m/e 476 [M+H]$^+$; $^1$H NMR (400 MHz, CHLOROFORM-d) δ 9.67 (s, 1H), 9.13 (s, 1H), 8.76 (d, J=2.5 Hz, 1H), 8.47 (d, J=5.3 Hz, 1H), 8.36 (dd, J=8.5, 2.5 Hz, 1H), 7.64 (d, J=8.5 Hz, 1H), 7.49 (s, 1H), 7.25-7.21 (m, 2H), 6.95 (s, 1H), 4.22-4.17 (m, 2H), 3.96 (s, 3H), 3.96-3.90 (m, 2H), 1.68 (s, 3H); $^{19}$F NMR (376 MHz, CHLOROFORM-d) δ −67.06 (s, 3F).

Example 40

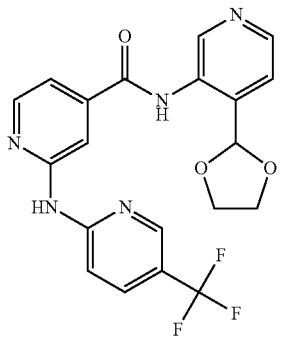 [SMILES: O=C(Nc1cnccc1C1OCCO1)c1ccnc(Nc2ccc(C(F)(F)F)cn2)c1]

N-(4-(1,3-Dioxolan-2-yl)pyridin-3-yl)-2-((5-(trifluoromethyl)pyridin-2-yl)amino)isonicotinamide MS (ESI) (m/z) 432 (M+H)$^+$; $^1$H NMR (500 MHz, DMSO-d$_6$) δ 10.39 (br. s., 1H), 10.08 (s, 1H), 8.94 (d, J=1.8 Hz, 1H), 8.71 (s, 1H), 8.58-8.51 (m, 2H), 8.46 (d, J=5.2 Hz, 1H), 7.82 (d, J=8.9 Hz, 1H), 7.55 (d, J=4.9 Hz, 1H), 7.43 (s, 1H), 7.39 (d, J=5.5 Hz, 1H), 6.05 (s, 1H), 4.05-3.93 (m, 4H).

Example 84

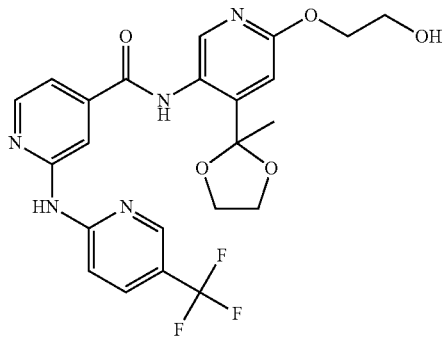 [SMILES: CC1(c2cc(OCCO)ncc2NC(=O)c2ccnc(Nc3ccc(C(F)(F)F)cn3)c2)OCCO1]

N-(6-(2-Hydroxyethoxy)-4-(2-methyl-1,3-dioxolan-2-yl)pyridin-3-yl)-2-((5-(trifluoromethyl)pyridin-2-yl)amino)isonicotinamide MS (ESI) (m/z) 506 (M+H)$^+$; $^1$H NMR (500 MHz, DMSO-d$_6$) δ 10.10 (br. s., 1H), 9.83 (br. s., 1H), 8.94 (br. s., 1H), 8.59-8.38 (m, 3H), 7.82 (d, J=8.5 Hz, 1H), 7.46-7.31 (m, 2H), 6.88 (br. s., 1H), 4.87 (br. s., 1H), 4.29 (br. s., 2H), 4.04 (br. s., 2H), 3.82-3.67 (m, 4H), 1.58 (br. s., 3H).

Example 82

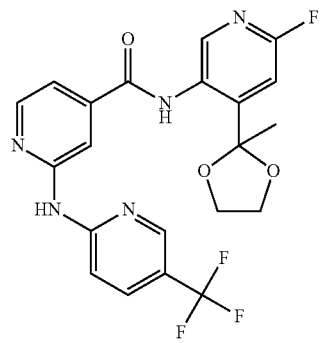 [SMILES: CC1(c2cc(F)ncc2NC(=O)c2ccnc(Nc3ccc(C(F)(F)F)cn3)c2)OCCO1]

N-(6-Fluoro-4-(2-methyl-1,3-dioxolan-2-yl)pyridin-3-yl)-2-((5-(trifluoromethyl)pyridin-2-yl)amino)isonicotinamide MS (ESI) (m/z) 464 (M+H)$^+$; $^1$H NMR (500 MHz, DMSO-d$_6$) δ 10.10 (br. s., 1H), 10.02 (br. s., 1H), 8.94 (br. s., 1H), 8.66-8.44 (m, 3H), 7.82 (d, J=8.2 Hz, 1H), 7.47-7.20 (m, 3H), 4.07 (br. s., 2H), 3.81 (br. s., 2H), 1.61 (br. s., 3H).

Example 94

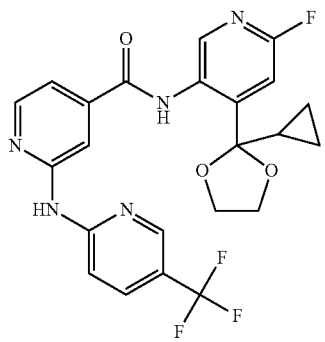 [SMILES: O=C(Nc1cnc(F)cc1C1(C2CC2)OCCO1)c1ccnc(Nc2ccc(C(F)(F)F)cn2)c1]

N-(4-(2-Cyclopropyl-1,3-dioxolan-2-yl)-6-fluoropyridin-3-yl)-2-((5-(trifluoromethyl)pyridin-2-yl)amino)isonicotinamide MS (ESI) (m/z) 490 (M+H)$^+$; $^1$H NMR (500 MHz, DMSO-d$_6$) δ 10.59 (s, 1H), 10.09 (br. s., 1H), 8.79 (s, 1H), 8.62 (br. s., 1H), 8.53 (d, J=5.2 Hz, 1H), 8.38 (s, 1H), 8.06 (d, J=8.5 Hz, 1H), 7.87 (d, J=8.9 Hz, 1H), 7.42 (d, J=4.9 Hz, 1H), 7.16 (s, 1H), 4.10-4.00 (m, 2H), 3.91-3.81 (m, 2H), 1.45 (d, J=5.2 Hz, 1H), 0.53-0.39 (m, 4H).

Synthesis of Intermediate Bromide

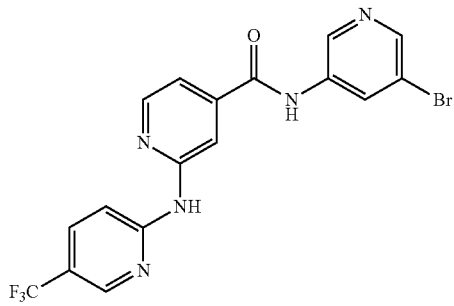 [SMILES: O=C(Nc1cncc(Br)c1)c1ccnc(Nc2ccc(C(F)(F)F)cn2)c1]

N-(5-Bromopyridin-3-yl)-2-((5-(trifluoromethyl)pyridin-2-yl)amino)isonicotinamide To 5-bromopyridin-3-amine (0.096 g, 0.556 mmol) and 2-((5-(trifluoromethyl)pyridin-2-yl)amino)isonicotinic acid (0.15 g, 0.530 mmol) in DMF (10 mL) was added DIEA (0.463 mL, 2.65 mmol) followed by 1-Propanephosphonic acid cyclic anhydride (1.546 mL, 2.65 mmol) dropwise. The reaction was stirred at rt overnight. The reaction was diluted with ethyl acetate and water. The org extracts was washed with brine and dried over sodium sulfate and evaporated. The crude product was dissolved in a small amount of dichloromethane and charged to a 80 g silica gel cartridge which was eluted with 0-80% ethyl acetate/hexanes over a period of 40 mins. The desired frns were combined, evaporated and dried to give N-(5-bromopyridin-3-yl)-2-((5-(trifluoromethyl)pyridin-2-yl)amino)isonicotinamide (0.21 g, 0.479 mmol, 90% yield). MS (ESI) (m/z): 439.8 (M+H)$^+$.

Example 118

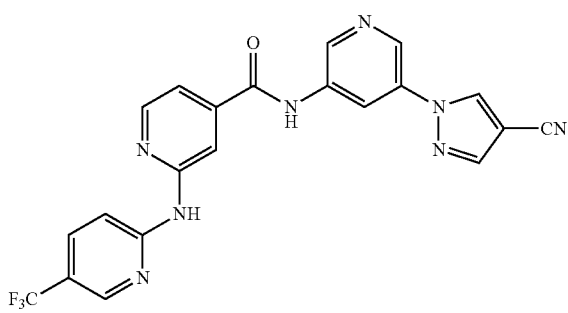 [SMILES: N#Cc1cnn(-c2cncc(NC(=O)c3ccnc(Nc4ccc(C(F)(F)F)cn4)c3)c2)c1]

N-(5-(4-Cyano-1H-pyrazol-1-yl)pyridin-3-yl)-2-((5-(trifluoromethyl)pyridin-2-yl)amino)isonicotinamide To an oven dried vial with a stir bar, N-(5-bromopyridin-3-yl)-2-((5-(trifluoromethyl)pyridin-2-yl)amino)isonicotinamide (0.02 g, 0.046 mmol), RockPhos (0.428 mg, 0.913 µmol), Pd2(dba)3 (0.042 g, 0.046 mmol), 1H-pyrazole-4-carbonitrile (4.25 mg, 0.046 mmol) and K3PO4 (9.69 mg, 0.046 mmol) were added. The solid mixture was purged with N2 (degassed and flushed) (3×). Then tBuOH (1 mL) was added. The vial was degassed and flushed with N2 (3×) and the vessel was capped and placed in a preheated oil bath at 120° C. for 5 hrs. The reaction mixture was diluted with ethyl acetate and washed with ammonium chloride. The org layer was dried over sodium sulfate, filtered and then concentrated. The residue was purified by prep LCMS to give desired prod. $^1$H NMR (500 MHz, DMSO-d$_6$) δ ppm 11.02 (br. s., 1H) 10.55 (s, 1H) 9.48 (s, 1H) 8.98 (d, J=1.83 Hz, 1H) 8.90 (d, J=2.14 Hz, 1H) 8.84 (t, J=2.29 Hz, 1H) 8.65 (s, 1H) 8.52 (d, J=5.19 Hz, 1H) 8.48 (s, 1H) 8.28 (s, 1H) 8.07 (dd, J=8.85, 2.44 Hz, 1H) 7.90-7.98 (m, 1H) 7.51 (dd, J=5.19, 1.22 Hz, 1H). MS (ESI) (m/z): 451.1 (M+H)$^+$.

Example 119

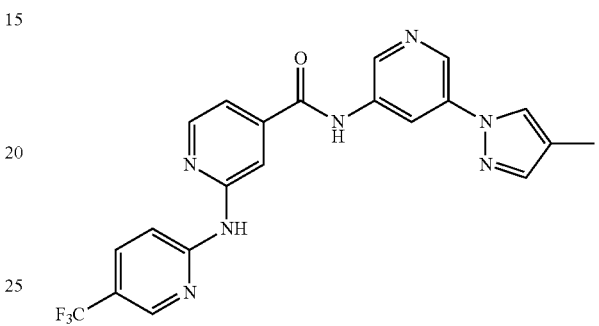

N-(5-(4-Methyl-1H-pyrazol-1-yl)pyridin-3-yl)-2-((5-(trifluoromethyl)pyridin-2-yl)amino)isonicotinamide $^1$H NMR (500 MHz, DMSO-d$_6$) δ ppm 10.87 (s, 1H) 10.53 (s, 1H) 8.85 (d, J=1.83 Hz, 1H) 8.83 (d, J=2.44 Hz, 1H) 8.74 (t, J=2.14 Hz, 1H) 8.65 (s, 1H) 8.52 (d, J=5.19 Hz, 1H) 8.39 (s, 1H) 8.27 (s, 1H) 8.07 (dd, J=9.00, 2.59 Hz, 1H) 7.93 (d, J=8.55 Hz, 1H) 7.68 (s, 1H) 7.50 (d, J=5.19 Hz, 1H) 2.14 (s, 3H). MS (ESI) (m/z): 440.3 (M+H)$^+$.

Example 120

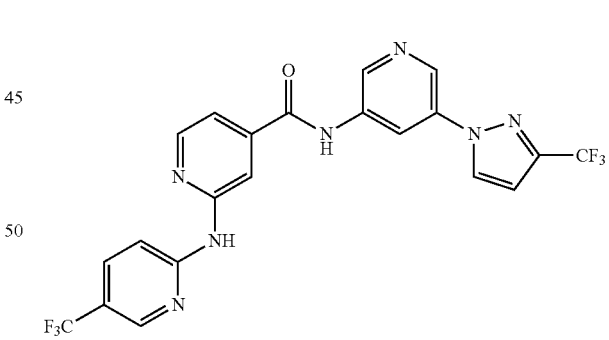

N-(5-(3-(Trifluoromethyl)-1H-pyrazol-1-yl)pyridin-3-yl)-2-((5-(trifluoromethyl)pyridin-2-yl)amino)isonicotinamide To an oven dried microwave vial was added N-(5-bromopyridin-3-yl)-2-((5-(trifluoromethyl)pyridin-2-yl)amino)isonicotinamide (0.02 g, 0.046 mmol), 3-(trifluoromethyl)-1H-pyrazole (7.45 mg, 0.055 mmol), POTASSIUM CARBONATE (0.013 g, 0.091 mmol) and COPPER(I) IODIDE (4.87 mg, 0.026 mmol). The vial was capped with a septum and the system was degassed and flushed with nitrogen (3×). Then 2,2,6,6-tetramethylheptane-3,5-dione (0.013 mL, 0.064 mmol) and DMF (1 mL) was added and then the reaction mixture was degassed and flushed with nitrogen (3×). The vial was sealed and place on a pre-heated oil bath at 110° C. The reaction mixture was stirred at 110° C. for 20 hrs, then at rt for 48 hrs. The reaction was diluted with ethyl acetate and satd ammonium chloride. The org layer was washed with water, brine and dried over sodium sulfate. The solvent was evaporated and the residue was purified by prep LCMS to give desired prod. MS (ESI) (m/z): 494.2 (M+H)+.

Example 121

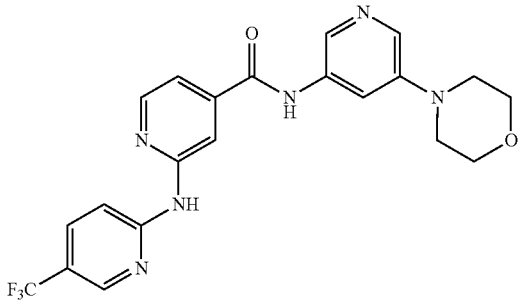 [SMILES: O=C(Nc1cncc(N2CCOCC2)c1)c1ccnc(Nc2ccc(C(F)(F)F)cn2)c1]

N-(5-Morpholinopyridin-3-yl)-2-((5-(trifluoromethyl)pyridin-2-yl)amino)isonicotinamide To an oven dried microwave vial was added N-(5-bromopyridin-3-yl)-2-((5-(trifluoromethyl)pyridin-2-yl)amino)isonicotinamide (0.025 g, 0.057 mmol), XPhos (2.176 mg, 4.56 μmol) and Pd2(dba)3 (2.090 mg, 2.282 μmol). The solid mixture was degassed and flushed with N2 (3×). Then LiHMDS, 1 M THF (0.228 mL, 0.228 mmol), morpholine (0.00753 mL, 0.086 mmol) and THF (1 mL) was added and the reaction mixture was degassed and flushed with N2 (3×). The vial was capped, reaction placed on a preheated oil bath at 65° C. and stirred overnight. The reaction mixture was diluted with ethylacetate, washed with sat'd ammonium chloride, water and dried over sodium sulfate. The solvent was evaporated and the residue was purified by prep LCMS to give desired prod. MS (ESI) (m/z): 445.2 (M+H)+.

Example 127

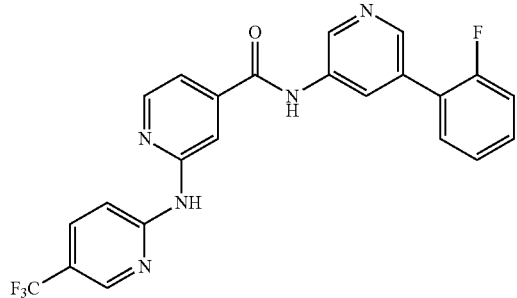 [SMILES: O=C(Nc1cncc(-c2ccccc2F)c1)c1ccnc(Nc2ccc(C(F)(F)F)cn2)c1]

N-(5-(2-Fluorophenyl)pyridin-3-yl)-2-((5-(trifluoromethyl)pyridin-2-yl)amino)isonicotinamide 1H NMR (500 MHz, DMSO-d6) δ ppm 10.86 (s, 1H), 10.54 (s, 1H), 9.00 (d, J=2.3 Hz, 1H), 8.65 (s, 1H), 8.56 (s, 1H), 8.52 (d, J=5.2 Hz, 1H), 8.45 (s, 1H), 8.26 (s, 1H), 8.06 (dd, J=8.9, 2.5 Hz, 1H), 7.93 (d, J=8.9 Hz, 1H), 7.65 (td, J=7.9, 1.6 Hz, 1H), 7.58-7.48 (m, 2H), 7.45-7.37 (m, 2H); MS (ESI) (m/z): 454 (M+H)+.

Example 128

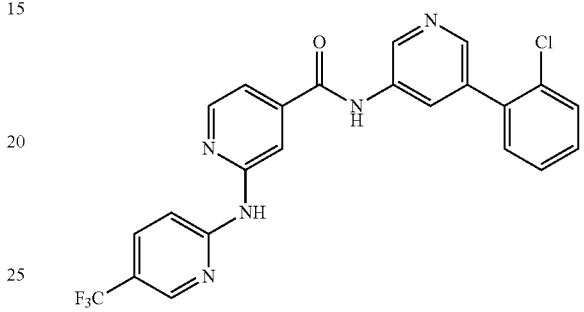

N-(5-(2-Chlorophenyl)pyridin-3-yl)-2-((5-(trifluoromethyl)pyridin-2-yl)amino)isonicotinamide 1H NMR (500 MHz, DMSO-d6) δ ppm 10.86 (s, 1H), 10.53 (s, 1H), 9.00 (d, J=2.3 Hz, 1H), 8.64 (s, 1H), 8.51 (d, J=5.2 Hz, 1H), 8.43 (d, J=1.9 Hz, 1H), 8.35 (t, J=2.1 Hz, 1H), 8.25 (s, 1H), 8.06 (dd, J=8.9, 2.5 Hz, 1H), 7.93 (d, J=8.9 Hz, 1H), 7.66 (dd, J=5.8, 3.3 Hz, 1H), 7.59-7.44 (m, 4H); MS (ESI) (m/z): 470 (M+H)+.

Example 129

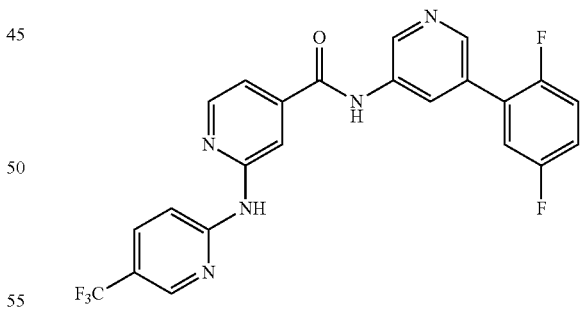

N-(5-(2,5-Difluorophenyl)pyridin-3-yl)-2-((5-(trifluoromethyl)pyridin-2-yl)amino)isonicotinamide 1H NMR (400 MHz, DMSO-d6) δ ppm 10.90 (br. s., 1H) 10.56 (s, 1H) 9.02 (s, 1H) 8.65 (br. s., 1H) 8.58 (s, 1H) 8.52 (d, J=5.19 Hz, 1H) 8.47 (br. s., 1H) 8.28 (s, 1H) 8.07 (d, J=8.54 Hz, 1H) 7.94 (d, J=8.85 Hz, 1H) 7.57 (br. s., 1H) 7.44-7.52 (m, 2H) 7.39 (d, J=8.24 Hz, 1H). MS (ESI) (m/z): 472.3 (M+H)+.

Example 130

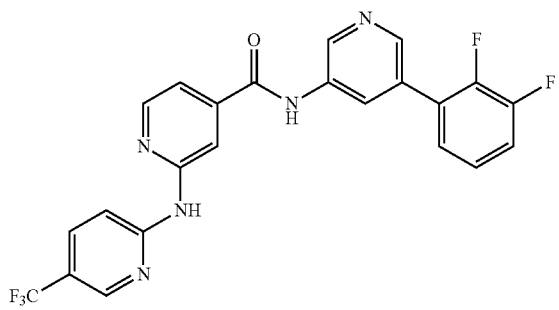 [SMILES: O=C(Nc1cncc(-c2cccc(F)c2F)c1)c1ccnc(Nc2ccc(C(F)(F)F)cn2)c1]

N-(5-(2,3-Difluorophenyl)pyridin-3-yl)-2-((5-(trifluoromethyl)pyridin-2-yl)amino)isonicotinamide $^1$H NMR (500 MHz, DMSO-d$_6$) δ ppm 10.87 (s, 1H) 10.54 (s, 1H) 9.02 (br. s., 1H) 8.65 (s, 1H) 8.59 (br. s., 1H) 8.52 (d, J=5.19 Hz, 1H) 8.47 (br. s., 1H) 8.27 (s, 1H) 8.07 (d, J=7.02 Hz, 1H) 7.93 (d, J=8.85 Hz, 1H) 7.53-7.61 (m, 1H) 7.45-7.51 (m, 2H) 7.36-7.43 (m, 1H). MS (ESI) (m/z): 472.3 (M+H)$^+$.

Synthesis of Intermediate Bromide

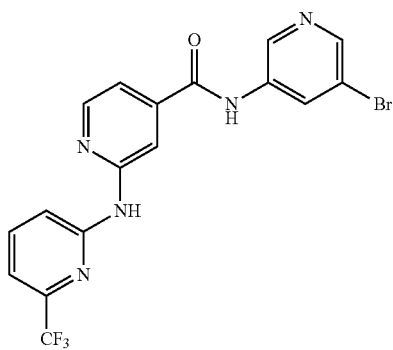 [SMILES: O=C(Nc1cncc(Br)c1)c1ccnc(Nc2cccc(C(F)(F)F)n2)c1]

N-(5-Bromopyridin-3-yl)-2-((6-(trifluoromethyl)pyridin-2-yl)amino)isonicotinamide To 5-bromopyridin-3-amine (0.128 g, 0.742 mmol) and 2-((6-(trifluoromethyl)pyridin-2-yl)amino)isonicotinic acid (0.2 g, 0.706 mmol) in DMF (2 mL) was added DIEA (0.617 mL, 3.53 mmol) followed by 1-Propanephosphonic acid cyclic anhydride (0.825 mL, 1.412 mmol) dropwise. The reaction was stirred at rt overnight. The reaction was diluted with ethyl acetate and water. The org extracts was washed with satd sodium bicarbonate brine, and dried over sodium sulfate and evaporated. The crude product triturated in dichloromethane, filtered to obtain white solid. The solid was collected and dried under vacuo to give N-(5-bromopyridin-3-yl)-2-((6-(trifluoromethyl)pyridin-2-yl)amino) isonicotinamide (0.3 g, 0.685 mmol, 97% yield). $^1$H NMR (400 MHz, DMSO-d$_6$) δ ppm 10.85 (s, 1H) 10.48 (s, 1H) 8.89 (d, J=1.96 Hz, 1H) 8.53 (t, J=2.08 Hz, 1H) 8.46-8.51 (m, 2H) 8.17 (s, 1H) 8.11 (d, J=8.56 Hz, 1H) 7.97 (t, J=7.95 Hz, 1H) 7.43 (dd, J=5.14, 1.47 Hz, 1H) 7.39 (d, J=7.09 Hz, 1H). $^{19}$F NMR (376 MHz, DMSO-d$_6$) d ppm −66.80 (s, 3F). MS (ESI) (m/z): 440.0 (M+H)$^+$.

Example 122

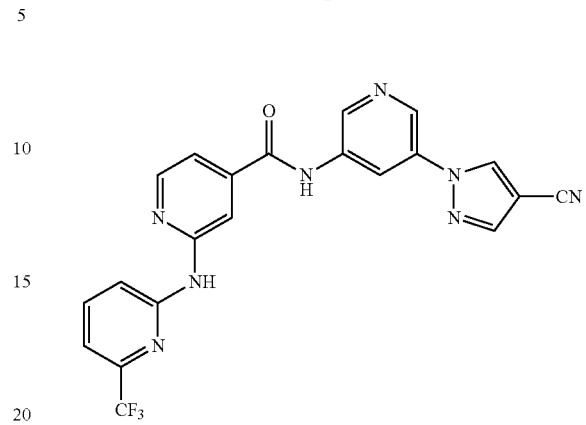

N-(5-(4-Cyano-1H-pyrazol-1-yl)pyridin-3-yl)-2-((6-(trifluoromethyl)pyridin-2-yl)amino)isonicotinamide $^1$H NMR (500 MHz, DMSO-d$_6$) δ ppm 11.05 (br. s., 1H) 10.48 (s, 1H) 9.48 (s, 1H) 8.95 (d, J=1.83 Hz, 1H) 8.88 (d, J=2.14 Hz, 1H) 8.83-8.86 (m, 1H) 8.49 (d, J=5.19 Hz, 1H) 8.47 (s, 1H) 8.20 (s, 1H) 8.14 (d, J=8.54 Hz, 1H) 7.95-8.01 (m, 1H) 7.49 (d, J=5.19 Hz, 1H) 7.40 (d, J=7.32 Hz, 1H). MS(ESI) (m/z): 451.4 (M+H)$^+$.

Example 123

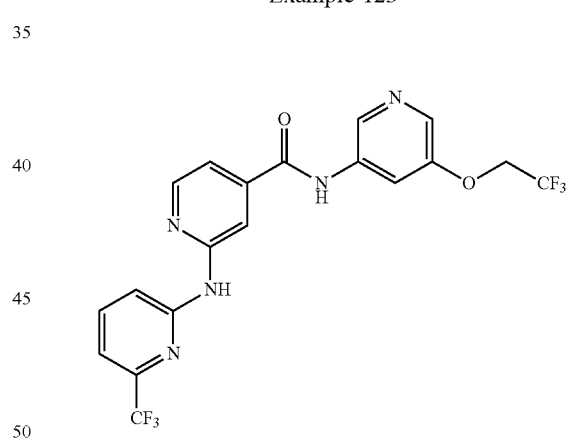

N-(5-(2,2,2-Trifluoroethoxy)pyridin-3-yl)-2-((6-(trifluoromethyl)pyridin-2-yl)amino)isonicotinamide To an oven dried vial with a stir bar, N-(5-bromopyridin-3-yl)-2-((6-(trifluoromethyl)pyridin-2-yl)amino)isonicotinamide-01 (0.02 g, 0.046 mmol), RockPhos (0.428 mg, 0.913 μmol), Pd2(dba)3 (0.418 mg, 0.456 μmol), 2,2,2-trifluoroethanol (4.57 mg, 0.046 mmol) and K3PO4 (0.015 g, 0.068 mmol) were added. The solid mixture was purged with N2 (degassed and flushed) (3×). Then tBuOH (1 mL) was added. The vial was degassed and flushed with N2 (3×) and the vessel was capped and placed in a preheated oil bath at 120° C. for 5 hrs. The solvent was evaporated and the residue was purified with prep LCMS to give desired prod. $^1$H NMR (500 MHz, METHANOL-d$_4$) δ ppm 8.58 (s, 1H)

8.43 (d, J=5.19 Hz, 1H) 8.30 (s, 1H) 8.17 (d, J=2.14 Hz, 1H) 8.12 (d, J=2.14 Hz, 1H) 7.83-7.95 (m, 2H) 7.33-7.39 (m, 1H) 7.30 (d, J=7.02 Hz, 1H) 4.72 (q, J=8.34 Hz, 2H). MS(ESI) (m/z): 458.2 (M+H)⁺.

Example 124

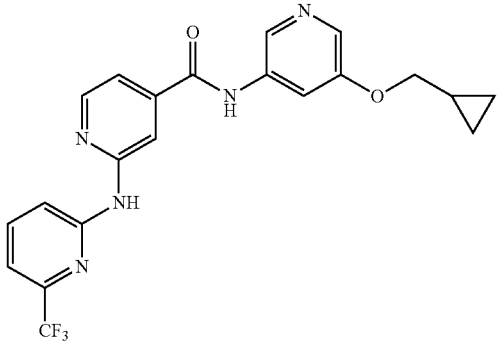 [SMILES: O=C(Nc1cncc(OCC2CC2)c1)c1ccnc(Nc2cccc(C(F)(F)F)n2)c1]

N-(5-(Cyclopropylmethoxy)pyridin-3-yl)-2-((6-(trifluoromethyl)pyridin-2-yl)amino)isonicotinamide To an oven dried vial with a stir bar, N-(5-bromopyridin-3-yl)-2-((6-(trifluoromethyl)pyridin-2-yl)amino)isonicotinamide (0.04 g, 0.091 mmol), RockPhos (0.856 mg, 1.826 µmol), Pd2(dba)3 (0.836 mg, 0.913 µmol), cyclopropylmethanol (6.58 mg, 0.091 mmol) and K3PO4 (0.029 g, 0.137 mmol) were added. The solid mixture was purged with N2 (degassed and flushed) (3×). Then tBuOH (1 mL) was added. The vial was degassed and flushed with N2 (3×) and the vessel was capped and placed in a preheated oil bath at 120° C. for 5 hrs, then at rt for 48 hrs. The reaction mixture was diluted with ethyl acetate and washed with ammonium chloride. The org layer was dried over sodium sulfate, filtered and then concentrated. The residue was purified by prep LCMS to give desired prod. ¹H NMR (500 MHz, DMSO-d₆) δ ppm 10.67 (s, 1H) 10.47 (s, 1H) 8.54 (d, J=1.53 Hz, 1H) 8.48 (d, J=5.19 Hz, 1H) 8.07-8.15 (m, 3H) 7.98 (t, J=7.93 Hz, 1H) 7.87 (s, 1H) 7.34-7.46 (m, 2H) 3.92 (d, J=7.02 Hz, 2H) 1.22-1.33 (m, 2H) 0.54-0.67 (m, 2H) 0.33-0.42 (m, 2H). MS (ESI) (m/z): 430.5 (M+H)⁺.

Example 125

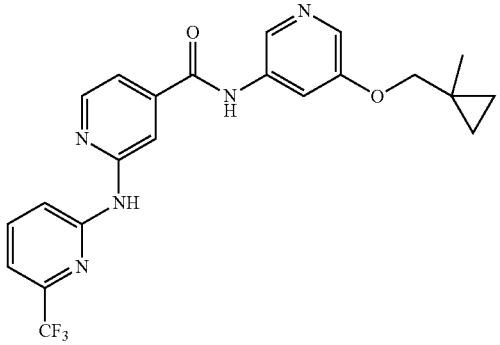 [SMILES: CC1(COc2cncc(NC(=O)c3ccnc(Nc4cccc(C(F)(F)F)n4)c3)c2)CC1]

N-(5-((1-Methylcyclopropyl)methoxy)pyridin-3-yl)-2-((6-(trifluoromethyl)pyridin-2-yl)amino)isonicotinamide ¹H NMR (500 MHz, DMSO-d₆) δ ppm 8.47 (d, J=1.83 Hz, 1H) 8.43 (d, J=5.19 Hz, 1H) 8.28 (s, 1H) 8.05 (d, J=2.44 Hz, 1H) 7.96 (t, J=2.29 Hz, 1H) 7.83-7.94 (m, 2H) 7.36 (dd, J=5.19, 1.53 Hz, 1H) 7.30 (d, J=7.32 Hz, 1H) 3.89 (s, 2H) 1.27 (s, 3H) 0.59-0.65 (m, 2H) 0.44-0.50 (m, 2H). MS(ESI) (m/z): 444.2 (M+H)⁺.

Example 126

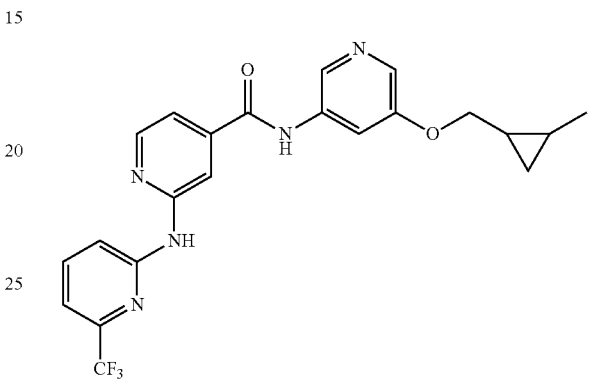

N-(5-((2-Methylcyclopropyl)methoxy)pyridin-3-yl)-2-((6-(trifluoromethyl)pyridin-2-yl)amino)isonicotinamide ¹H NMR (500 MHz, DMSO-d₆) δ ppm 8.47 (d, J=1.53 Hz, 1H) 8.42 (d, J=5.19 Hz, 1H) 8.29 (s, 1H) 8.04 (d, J=2.44 Hz, 1H) 7.95 (t, J=2.14 Hz, 1H) 7.83-7.94 (m, 2H) 7.35 (dd, J=5.19, 1.53 Hz, 1H) 7.30 (d, J=7.32 Hz, 1H) 3.89-4.03 (m, 2H) 1.12 (d, J=6.10 Hz, 3H) 0.97-1.06 (m, 1H) 0.79-0.87 (m, 1H) 0.55-0.62 (m, 1H) 0.37-0.45 (m, 1H). MS(ESI) (m/z): 444.5 (M+H)⁺.

Example 144

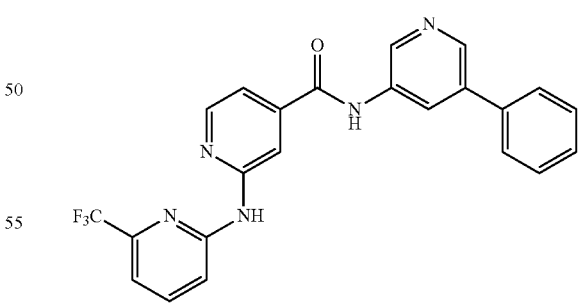

N-(5-Phenylpyridin-3-yl)-2-((6-(trifluoromethyl)pyridin-2-yl)amino)isonicotinamide To a microwave vial was added N-(5-bromopyridin-3-yl)-2-((6-(trifluoromethyl)pyridin-2-yl)amino)isonicotinamide (0.02 g, 0.046 mmol), phenylboronic acid (5.57 mg, 0.046 mmol) and PdCl2(dppf)-CH2Cl2Adduct (3.73 mg, 4.56

μmol). The reaction mixture was degassed and flushed with N2 (3×). Then DMF (1.0 mL) was added and the system was degassed and flushed with N2 (3×). SODIUM CARBONATE (0.046 mL, 0.091 mmol) was added and the system was degassed and flushed with N2 (3×). The reaction mixture was heated to 85° C. for 3 h. The reaction was diluted with ethyl acetate and satd ammonium chloride. The org layer was washed with water, brine and dried over sodium sulfate. The solvent was evaporated and the residue was purified with prep LCMS to give desired prod. $^1$H NMR (500 MHz, DMSO-d$_6$) δ ppm 10.79 (s, 1H) 10.49 (s, 1H) 8.95 (d, J=2.14 Hz, 1H) 8.69 (d, J=2.14 Hz, 1H) 8.47-8.53 (m, 2H) 8.18 (s, 1H) 8.14 (d, J=8.54 Hz, 1H) 7.98 (t, J=7.93 Hz, 1H) 7.74 (d, J=7.32 Hz, 2H) 7.56 (t, J=7.63 Hz, 2H) 7.44-7.51 (m, 2H) 7.40 (d, J=7.32 Hz, 1H). MS (ESI) (m/z): 436.1 (M+H)$^+$.

Example 145

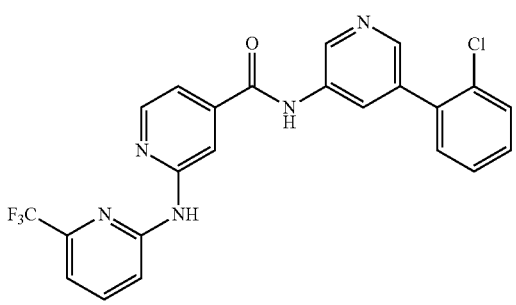 [SMILES: O=C(Nc1cncc(-c2ccccc2Cl)c1)c1ccnc(Nc2cccc(C(F)(F)F)n2)c1]

N-(5-(2-Chlorophenyl)pyridin-3-yl)-2-((6-(trifluoromethyl)pyridin-2-yl)amino)isonicotinamide $^1$H NMR (500 MHz, DMSO-d$_6$) δ ppm 10.83 (s, 1H) 10.48 (s, 1H) 8.99 (d, J=2.14 Hz, 1H) 8.49 (d, J=5.19 Hz, 1H) 8.43 (d, J=1.83 Hz, 1H) 8.34 (s, 1H) 8.17 (s, 1H) 8.13 (d, J=8.54 Hz, 1H) 7.98 (t, J=7.93 Hz, 1H) 7.63-7.69 (m, 1H) 7.48-7.56 (m, 3H) 7.46 (d, J=4.88 Hz, 1H) 7.40 (d, J=7.63 Hz, 1H). MS (ESI) (m/z): 470.1 (M+H)$^+$.

Example 146

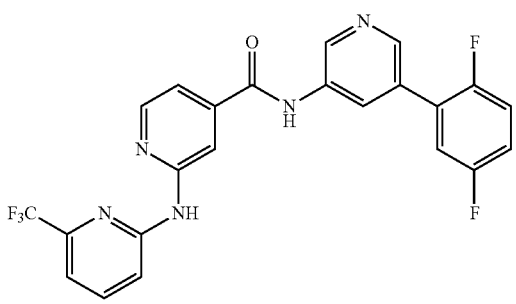 [SMILES: O=C(Nc1cncc(-c2cc(F)ccc2F)c1)c1ccnc(Nc2cccc(C(F)(F)F)n2)c1]

N-(5-(2,5-Difluorophenyl)pyridin-3-yl)-2-((6-(trifluoromethyl)pyridin-2-yl)amino)isonicotinamide $^1$H NMR (500 MHz, DMSO-d$_6$) δ ppm 10.84 (br. s., 1H) 10.49 (s, 1H) 9.00 (d, J=2.14 Hz, 1H) 8.58 (s, 1H) 8.50 (d, J=5.19 Hz, 1H) 8.46 (s, 1H) 8.18 (s, 1H) 8.13 (d, J=8.54 Hz, 1H) 7.98 (t, J=7.93 Hz, 1H) 7.57 (ddd, J=9.00, 5.95, 3.36 Hz, 1H) 7.43-7.52 (m, 2H) 7.35-7.42 (m, 2H). MS (ESI) (m/z): 472.2 (M+H)$^+$.

Example 147

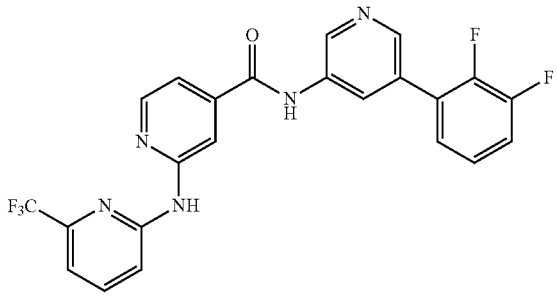 [SMILES: O=C(Nc1cncc(-c2cccc(F)c2F)c1)c1ccnc(Nc2cccc(C(F)(F)F)n2)c1]

N-(5-(2,3-Difluorophenyl)pyridin-3-yl)-2-((6-(trifluoromethyl)pyridin-2-yl)amino)isonicotinamide MS (ESI) (m/z): 472.2 (M+H)$^+$.

Synthesis of Amine F

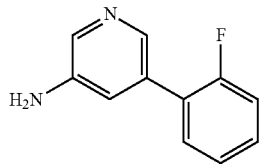 [SMILES: Nc1cncc(-c2ccccc2F)c1]

5-(2-Fluorophenyl)pyridin-3-amine

A mixture of Phosphoric acid, potassium salt (1.043 g, 4.91 mmol), PCy3 (0.019 g, 0.069 mmol), Pd2(dba)3 (0.026 g, 0.029 mmol), 5-bromopyridin-3-amine (0.5 g, 2.89 mmol) and (2-fluorophenyl)boronic acid (0.607 g, 4.33 mmol) in DMF (5 mL) and water (0.5 mL) was heated at 100° C. under N2 overnight. The reaction was filtered through a silica plug and washed with ethyl acetate. The filtrate was concentrated and the product was purified via flash column eluted with ethyl acetate in hexane from 0 to 100% to give 5-(2-fluorophenyl)pyridin-3-amine (0.5 g, 2.66 mmol, 92% yield). $^1$H NMR (400 MHz, CHLOROFORM-d) δ ppm 8.22 (t, J=1.59 Hz, 1H) 8.12 (d, J=2.69 Hz, 1H) 7.45 (td, J=7.70, 1.71 Hz, 1H) 7.34-7.41 (m, 1H) 7.15-7.28 (m, 3H) 3.78 (br. s., 2H). MS (ESI) (m/z): 189.1 (M+H)$^+$.

Example 164

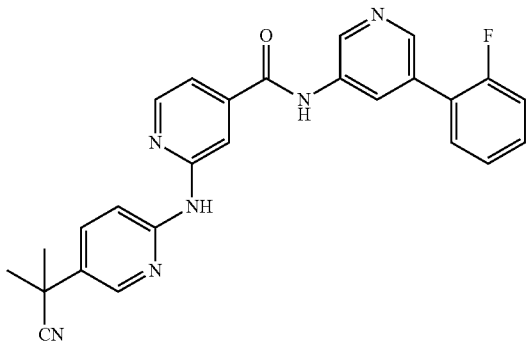 [SMILES: CC(C)(C#N)c1ccc(Nc2cc(C(=O)Nc3cncc(-c4ccccc4F)c3)ccn2)nc1]

2-((5-(2-Cyanopropan-2-yl)pyridin-2-yl)amino)-N-(5-(2-fluorophenyl)pyridin-3-yl)isonicotinamide To 5-(2-fluorophenyl)pyridin-3-amine (0.035 g, 0.186 mmol) and 2-((5-(2-cyanopropan-2-yl)pyridin-2-yl)amino) isonicotinic acid (0.05 g, 0.177 mmol) in 2 was added DIEA (0.155 mL, 0.886 mmol) followed by 1-Propanephosphonic acid cyclic anhydride, 50% in EtOAc (0.207 mL, 0.354 mmol) dropwise. The reaction was stirred at rt overnight. The reaction was diluted with ethyl acetate and satd sodium bicarbonate and water and dried over sodium sulfate. The solvent was evaporated and the residue was purified with prep LCMS to give desired prod. $^1$H NMR (500 MHz, DMSO-$d_6$) δ ppm 10.80 (s, 1H) 10.14 (s, 1H) 9.00 (d, J=2.14 Hz, 1H) 8.56 (s, 1H) 8.36-8.48 (m, 3H) 8.23 (s, 1H) 7.88 (dd, J=8.85, 2.75 Hz, 1H) 7.79 (d, J=8.85 Hz, 1H) 7.65 (td, J=7.78, 1.83 Hz, 1H) 7.48-7.58 (m, 1H) 7.35-7.45 (m, 3H) 1.72 (s, 6H). MS(ESI) (m/z): 453.5 (M+H)$^+$.

Synthesis of Intermediate Chloride

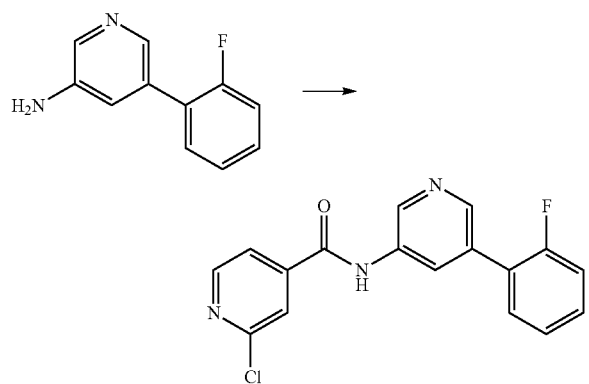

2-Chloro-N-(5-(2-fluorophenyl)pyridin-3-yl)isonicotinamide

To 5-(2-fluorophenyl)pyridin-3-amine (0.5 g, 2.66 mmol) and 2-chloroisonicotinic acid (0.440 g, 2.79 mmol) in DMF (10 mL) was added DIEA (2.320 mL, 13.28 mmol) followed by T3P, 50% in DMF (4.65 mL, 7.97 mmol). The reaction was stirred at rt overnight. It was diluted with EtOAc and washed with water, brine and dried over sodium sulfate. The crude product was dissolved in a small amount of dichloromethane and charged to a 120 g silica gel cartridge which was eluted with 0-15% dichloromethane/methanol over a period of 40 mins. The desired fractions were combined and dried under vacuo to give 2-chloro-N-(5-(2-fluorophenyl)pyridin-3-yl)isonicotinamide (0.5 g, 1.526 mmol, 57.4% yield). $^1$H NMR (400 MHz, CHLOROFORM-d) δ ppm 11.77 (s, 1H) 10.00 (d, J=1.96 Hz, 1H) 9.85 (s, 1H) 8.69 (d, J=5.87 Hz, 1H) 8.62 (s, 1H) 8.28 (br. s., 1H) 8.04 (s, 1H) 7.56-7.65 (m, 2H) 7.31-7.46 (m, 2H). MS (ESI) (m/z): 328.0 (M+H)$^+$. $^{19}$F NMR (376 MHz, CHLOROFORM-d) d ppm −116.96 (s, 1F).

Example 131

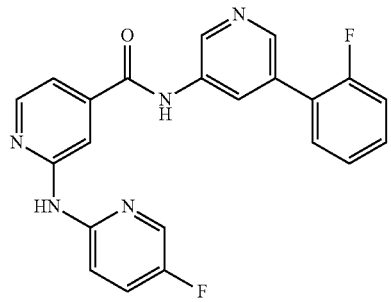 [SMILES: O=C(Nc1cncc(-c2ccccc2F)c1)c1ccnc(Nc2ccc(F)cn2)c1]

N-(5-(2-Fluorophenyl)pyridin-3-yl)-2-((5-fluoropyridin-2-yl)amino)isonicotinamide To an oven dried vial with a stir bar, brettphos precatalyst (0.731 mg, 0.915 brett phos (0.482 mg, 0.915 μmol), 5-fluoropyridin-2-amine (10.26 mg, 0.092 mmol), 2-chloro-N-(5-(2-fluorophenyl)pyridin-3-yl)isonicotinamide (0.03 g, 0.092 mmol) and K2CO3 (0.019 g, 0.137 mmol) were added. The solid mixture was purged with N2 (degassed and flushed) (3×). Then tBuOH (1 mL) was added. The vial was degassed and flushed with N2 (3×) and the vessel was capped and placed in a preheated oil bath at 110° C. for 3 hrs. The reaction was diluted with ethyl acetate and satd ammonium chloride. The org layer was washed with water, brine and dried over sodium sulfate. The solvent was evaporated and the residue was dissolved in methanol/DMF, filtered and purified by prep LCMS to give desired prod. $^1$H NMR (500 MHz, DMSO-$d_6$) δ ppm 10.80 (s, 1H) 10.07 (s, 1H) 9.00 (d, J=2.14 Hz, 1H) 8.56 (s, 1H) 8.40-8.46 (m, 2H) 8.28 (d, J=3.05 Hz, 1H) 8.12 (s, 1H) 7.85 (dd, J=9.16, 3.97 Hz, 1H) 7.61-7.75 (m, 2H) 7.47-7.57 (m, 1H) 7.35-7.45 (m, 3H). MS (ESI) (m/z): 404.1 (M+H)$^+$.

Example 132

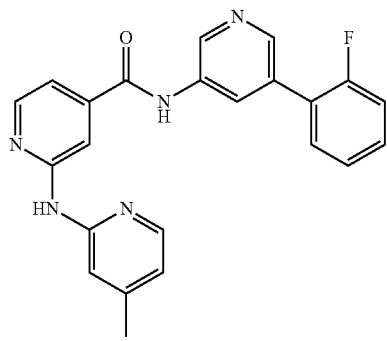 [SMILES: Cc1ccnc(Nc2cc(C(=O)Nc3cncc(-c4ccccc4F)c3)ccn2)c1]

N-(5-(2-Fluorophenyl)pyridin-3-yl)-2-((4-methyl-pyridin-2-yl)amino)isonicotinamide $^1$H NMR (500 MHz, DMSO-d$_6$) δ ppm 10.82 (br. s., 1H) 9.89 (s, 1H) 8.99 (d, J=2.44 Hz, 1H) 8.55 (s, 1H) 8.43 (d, J=5.49 Hz, 2H) 8.28 (s, 1H) 8.14 (d, J=4.88 Hz, 1H) 7.65 (t, J=7.78 Hz, 1H) 7.50-7.57 (m, 2H) 7.35-7.46 (m, 3H) 6.78 (d, J=4.88 Hz, 1H) 2.30 (s, 3H). MS (ESI) (m/z): 400.2 (M+H)$^+$.

Example 133

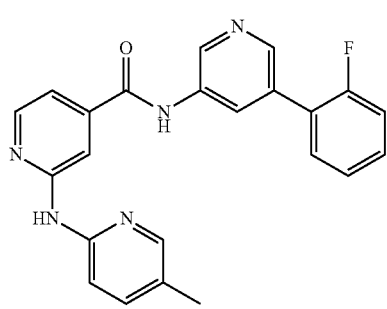 [SMILES: Cc1ccc(Nc2cc(C(=O)Nc3cncc(-c4ccccc4F)c3)ccn2)nc1]

N-(5-(2-Fluorophenyl)pyridin-3-yl)-2-((5-methyl-pyridin-2-yl)amino)isonicotinamide $^1$H NMR (500 MHz, DMSO-d$_6$) δ ppm 10.82 (br. s., 1H) 9.86 (s, 1H) 9.00 (d, J=2.14 Hz, 1H) 8.55 (s, 1H) 8.44 (br. s., 1H) 8.41 (d, J=5.19 Hz, 1H) 8.19 (s, 1H) 8.11 (s, 1H) 7.61-7.70 (m, 2H) 7.50-7.57 (m, 2H) 7.37-7.45 (m, 2H) 7.34 (dd, J=5.19, 1.22 Hz, 1H) 2.24 (s, 3H). MS (ESI) (m/z): 400.1 (M+H)$^+$.

Example 134

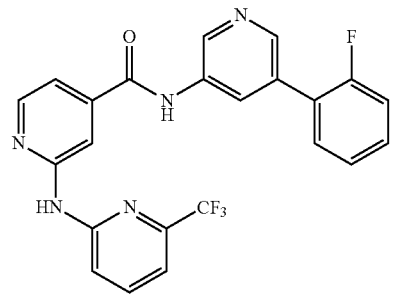 [SMILES: O=C(Nc1cncc(-c2ccccc2F)c1)c1ccnc(Nc2cccc(C(F)(F)F)n2)c1]

N-(5-(2-Fluorophenyl)pyridin-3-yl)-2-((6-(trifluoromethyl)pyridin-2-yl)amino)isonicotinamide $^1$H NMR (500 MHz, DMSO-d$_6$) δ ppm 10.83 (br. s., 1H) 10.48 (s, 1H) 8.98 (d, J=2.14 Hz, 1H) 8.56 (s, 1H) 8.50 (d, J=5.19 Hz, 1H) 8.44 (s, 1H) 8.18 (s, 1H) 8.14 (d, J=8.54 Hz, 1H) 7.98 (t, J=7.93 Hz, 1H) 7.65 (td, J=7.86, 1.68 Hz, 1H) 7.50-7.57 (m, 1H) 7.47 (dd, J=5.19, 1.53 Hz, 1H) 7.35-7.44 (m, 3H). MS (ESI) (m/z): 454.1 (M+H)$^+$.

Example 135

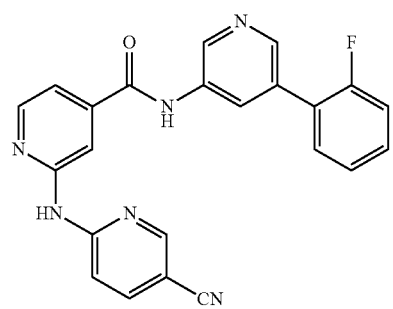 [SMILES: N#Cc1ccc(Nc2cc(C(=O)Nc3cncc(-c4ccccc4F)c3)ccn2)nc1]

2-((5-Cyanopyridin-2-yl)amino)-N-(5-(2-fluorophenyl)pyridin-3-yl)isonicotinamide $^1$H NMR (500 MHz, DMSO-d$_6$) δ ppm 10.86 (br. s., 1H) 10.66 (br. s., 1H) 9.00 (d, J=2.44 Hz, 1H) 8.73 (d, J=2.14 Hz, 1H) 8.56 (s, 1H) 8.53 (d, J=5.19 Hz, 1H) 8.45 (s, 1H) 8.27 (s, 1H) 8.11 (dd, J=8.85, 2.14 Hz, 1H) 7.88 (d, J=8.85 Hz, 1H) 7.65 (t, J=7.78 Hz, 1H) 7.48-7.57 (m, 2H) 7.32-7.45 (m, 2H). MS (ESI) (m/z): 411.1 (M+H)$^+$.

Example 136

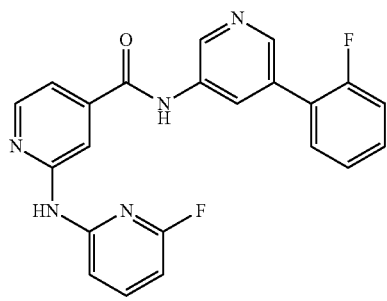 [SMILES: O=C(Nc1cncc(-c2ccccc2F)c1)c1ccnc(Nc2cccc(F)n2)c1]

N-(5-(2-Fluorophenyl)pyridin-3-yl)-2-((6-fluoropyridin-2-yl)amino)isonicotinamide ¹H NMR (500 MHz, DMSO-d₆) δ ppm 10.81 (s, 1H) 10.26 (s, 1H) 8.99 (d, J=2.14 Hz, 1H) 8.56 (s, 1H) 8.49 (d, J=5.19 Hz, 1H) 8.44 (s, 1H) 8.04 (s, 1H) 7.88 (q, J=8.24 Hz, 1H) 7.78 (dd, J=8.09, 2.29 Hz, 1H) 7.61-7.69 (m, 1H) 7.49-7.57 (m, 1H) 7.43-7.46 (m, 1H) 7.37-7.42 (m, 2H) 6.64 (dd, J=7.93, 2.14 Hz, 1H). MS (ESI) (m/z): 404.1 (M+H)⁺.

Example 137

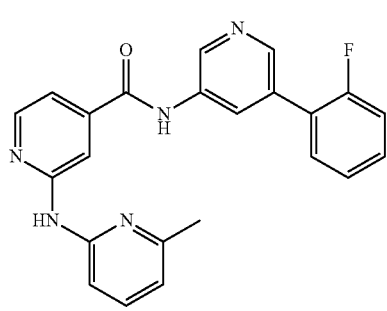

N-(5-(2-Fluorophenyl)pyridin-3-yl)-2-((6-methylpyridin-2-yl)amino)isonicotinamide ¹H NMR (500 MHz, DMSO-d₆) δ ppm 10.80 (s, 1H) 9.93 (s, 1H) 8.99 (d, J=2.44 Hz, 1H) 8.55 (s, 1H) 8.45 (d, J=1.22 Hz, 1H) 8.42 (d, J=5.19 Hz, 1H) 8.20 (s, 1H) 7.57-7.68 (m, 3H) 7.49-7.57 (m, 1H) 7.37-7.45 (m, 2H) 7.35 (dd, J=5.19, 1.53 Hz, 1H) 6.80 (d, J=7.02 Hz, 1H) 2.42 (s, 3H). MS (ESI) (m/z): 400.1 (M+H)⁺.

Example 138

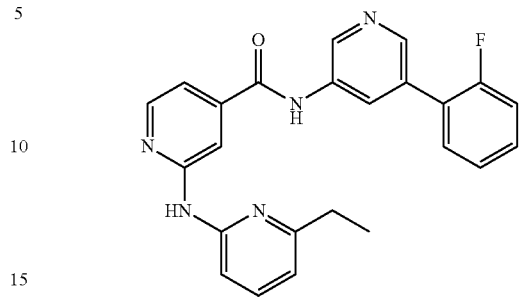

N-(5-(2-Fluorophenyl)pyridin-3-yl)-2-((6-ethylpyridin-2-yl)amino)isonicotinamide ¹H NMR (500 MHz, DMSO-d₆) δ ppm 10.79 (s, 1H) 9.92 (s, 1H) 8.99 (d, J=2.44 Hz, 1H) 8.55 (t, J=1.68 Hz, 1H) 8.36-8.47 (m, 3H) 7.58-7.70 (m, 2H) 7.49-7.57 (m, 2H) 7.37-7.44 (m, 2H) 7.33-7.36 (m, 1H) 6.80 (d, J=7.32 Hz, 1H) 2.71 (q, J=7.63 Hz, 2H) 1.28 (t, J=7.63 Hz, 3H). MS (ESI) (m/z): 414.2 (M+H)⁺.

Example 139

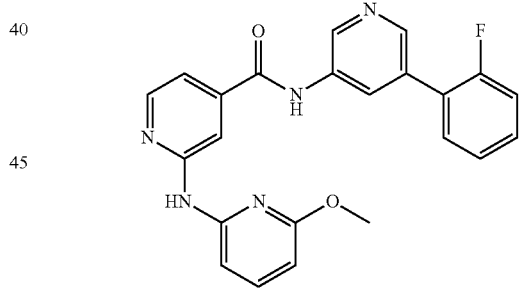

N-(5-(2-Fluorophenyl)pyridin-3-yl)-2-((6-methoxylpyridin-2-yl)amino)isonicotinamide ¹H NMR (500 MHz, DMSO-d₆) δ ppm 10.81 (br. s., 1H) 9.95 (s, 1H) 9.00 (d, J=2.14 Hz, 1H) 8.60 (s, 1H) 8.55 (s, 1H) 8.38-8.46 (m, 2H) 7.58-7.69 (m, 2H) 7.49-7.56 (m, 1H) 7.33-7.45 (m, 3H) 7.09 (d, J=7.63 Hz, 1H) 6.33 (d, J=7.93 Hz, 1H) 3.92 (s, 3H). MS (ESI) (m/z): 416.1 (M+H)⁺.

Example 140

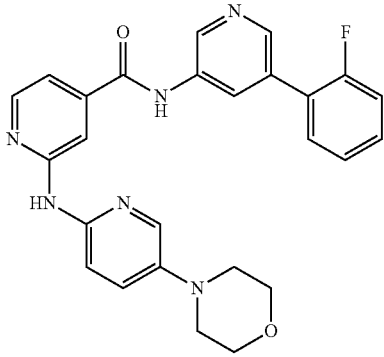 [SMILES: O=C(Nc1cncc(-c2ccccc2F)c1)c1ccnc(Nc2ccc(N3CCOCC3)cn2)c1]

N-(5-(2-Fluorophenyl)pyridin-3-yl)-2-((5-morpholinopyridin-2-yl)amino)isonicotinamide MS (ESI) (m/z): 471.2 (M+H)⁺.

Example 141

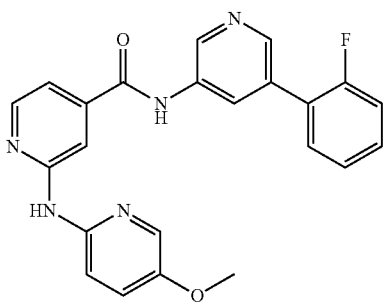 [SMILES: COc1ccc(Nc2cc(C(=O)Nc3cncc(-c4ccccc4F)c3)ccn2)nc1]

N-(5-(2-Fluorophenyl)pyridin-3-yl)-2-((5-methoxylpyridin-2-yl)amino)isonicotinamide $^1$H NMR (500 MHz, DMSO-d$_6$) δ ppm 10.80 (br. s., 1H) 9.80 (s, 1H) 9.00 (d, J=2.14 Hz, 1H) 8.55 (s, 1H) 8.44 (s, 1H) 8.39 (d, J=5.19 Hz, 1H) 8.10 (s, 1H) 8.02 (d, J=3.05 Hz, 1H) 7.75 (d, J=8.85 Hz, 1H) 7.65 (td, J=7.78, 1.53 Hz, 1H) 7.49-7.57 (m, 1H) 7.35-7.45 (m, 3H) 7.31 (dd, J=5.19, 1.22 Hz, 1H) 3.81 (s, 3H). MS (ESI) (m/z): 416.2 (M+H)⁺.

Example 142

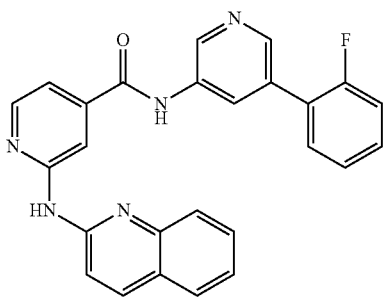

N-(5-(2-Fluorophenyl)pyridin-3-yl)-2-(quinolin-2-ylamino)isonicotinamide $^1$H NMR (500 MHz, DMSO-d$_6$) δ ppm 10.91 (br. s., 1H) 10.38 (s, 1H) 8.93-9.09 (m, 2H) 8.54-8.60 (m, 1H) 8.51 (d, J=5.19 Hz, 1H) 8.49 (d, J=1.22 Hz, 1H) 8.21 (d, J=9.16 Hz, 1H) 7.82 (d, J=7.32 Hz, 1H) 7.78 (d, J=8.54 Hz, 1H) 7.66 (qd, J=7.58, 1.37 Hz, 2H) 7.62 (d, J=8.85 Hz, 1H) 7.51-7.58 (m, 1H) 7.49 (dd, J=5.04, 1.37 Hz, 1H) 7.35-7.45 (m, 3H). MS (ESI) (m/z): 436.2 (M+H)⁺.

Example 143

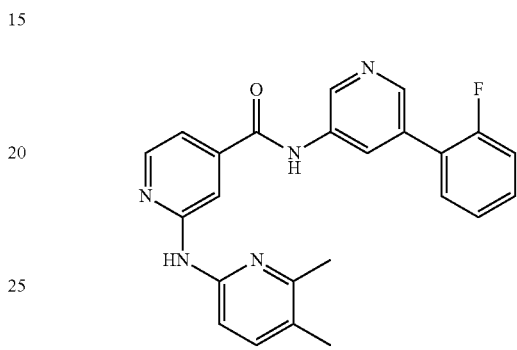

2-((5,6-Dimethylpyridin-2-yl)amino)-N-(5-(2-fluorophenyl)pyridin-3-yl)isonicotinamide $^1$H NMR (500 MHz, DMSO-d$_6$) δ ppm 10.80 (s, 1H) 9.80 (s, 1H) 8.99 (d, J=2.44 Hz, 1H) 8.55 (t, J=1.53 Hz, 1H) 8.45 (d, J=1.53 Hz, 1H) 8.40 (d, J=5.19 Hz, 1H) 8.15 (s, 1H) 7.59-7.69 (m, 2H) 7.49-7.56 (m, 1H) 7.36-7.47 (m, 3H) 7.31 (dd, J=5.19, 1.53 Hz, 1H) 2.39 (s, 3H) 2.20 (s, 3H). MS (ESI) (m/z): 414.2 (M+H)⁺.

Example 148

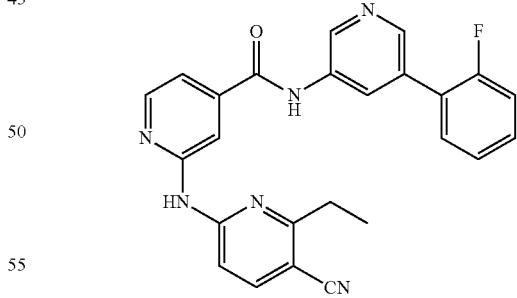

2-((5-Cyano-6-ethylpyridin-2-yl)amino)-N-(5-(2-fluorophenyl)pyridin-3-yl)isonicotinamide $^1$H NMR (500 MHz, DMSO-d$_6$) δ ppm 10.85 (br. s., 1H) 10.61 (s, 1H) 8.99 (d, J=2.14 Hz, 1H) 8.38-8.61 (m, 4H) 8.04 (d, J=8.54 Hz, 1H) 7.59-7.67 (m, 2H) 7.48-7.57 (m, 2H) 7.33-7.45 (m, 2H) 2.92 (q, J=7.43 Hz, 2H) 1.34 (t, J=7.63 Hz, 3H). MS (ESI) (m/z): 439.2 (M+H)⁺.

Example 149

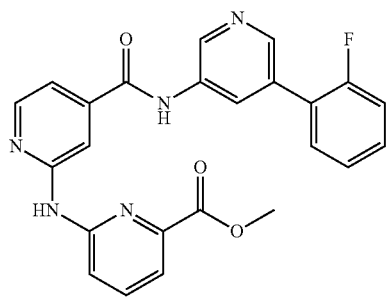 [SMILES: COC(=O)c1cccc(Nc2cc(C(=O)Nc3cncc(-c4ccccc4F)c3)ccn2)n1]

Methyl 6-((4-((5-(2-fluorophenyl)pyridin-3-yl)carbamoyl)pyridin-2-yl)amino)picolinate ¹H NMR (500 MHz, DMSO-d₆) δ ppm 10.85 (br. s., 1H) 10.39 (s, 1H) 9.02 (d, J=2.14 Hz, 1H) 8.56 (s, 1H) 8.43-8.49 (m, 2H) 8.39 (s, 1H) 8.08 (d, J=8.24 Hz, 1H) 7.90 (t, J=7.78 Hz, 1H) 7.60-7.70 (m, 2H) 7.47-7.57 (m, 1H) 7.34-7.44 (m, 3H) 3.85 (s, 3H). MS (ESI) (m/z): 444.2 (M+H)⁺.

Example 150

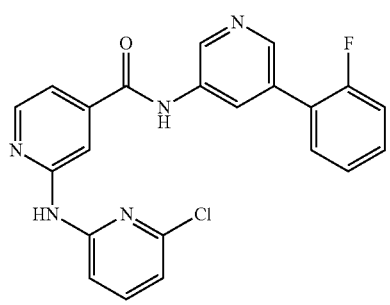

2-((5-Cyano-6-ethylpyridin-2-yl)amino)-N-(5-(2-fluorophenyl)pyridin-3-yl)isonicotinamide ¹H NMR (500 MHz, DMSO-d₆) δ ppm 10.84 (br. s., 1H) 10.35 (s, 1H) 8.99 (d, J=2.44 Hz, 1H) 8.56 (s, 1H) 8.48 (d, J=5.19 Hz, 1H) 8.44 (s, 1H) 7.99 (s, 1H) 7.93 (d, J=8.24 Hz, 1H) 7.77 (t, J=7.93 Hz, 1H) 7.65 (td, J=7.78, 1.83 Hz, 1H) 7.49-7.57 (m, 1H) 7.33-7.47 (m, 3H) 7.01 (d, J=7.63 Hz, 1H). MS (ESI) (m/z): 420.1 (M+H)⁺.

Example 151

2-((5,6-Dimethoxypyridin-2-yl)amino)-N-(5-(2-fluorophenyl)pyridin-3-yl)isonicotinamide ¹H NMR (500 MHz, DMSO-d₆) δ ppm 10.77 (s, 1H) 9.66 (s, 1H) 8.99 (d, J=2.14 Hz, 1H) 8.54 (s, 1H) 8.42 (s, 1H) 8.39 (d, J=5.19 Hz, 1H) 8.35 (s, 1H) 7.61-7.68 (m, 1H) 7.49-7.57 (m, 1H) 7.36-7.44 (m, 2H) 7.34 (d, J=8.55 Hz, 1H) 7.31 (d, J=5.19 Hz, 1H) 7.14 (d, J=8.55 Hz, 1H) 3.94 (s, 3H) 3.75 (s, 3H). MS (ESI) (m/z): 446.2 (M+H)⁺.

Example 152

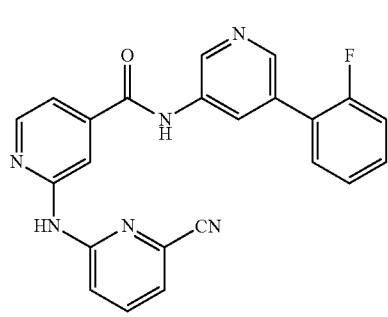

2-((6-Cyanopyridin-2-yl)amino)-N-(5-(2-fluorophenyl)pyridin-3-yl)isonicotinamide ¹H NMR (500 MHz, DMSO-d₆) δ ppm 10.84 (br. s., 1H) 10.50 (s, 1H) 8.99 (d, J=2.14 Hz, 1H) 8.56 (s, 1H) 8.50 (d, J=4.88 Hz, 1H) 8.45 (s, 1H) 8.15 (d, J=8.54 Hz, 1H) 8.11 (s, 1H) 7.94 (t, J=7.93 Hz, 1H) 7.65 (t, J=7.93 Hz, 1H) 7.47-7.58 (m, 3H) 7.34-7.46 (m, 2H). MS(ESI) (m/z): 411.0 (M+H)⁺.

Example 153

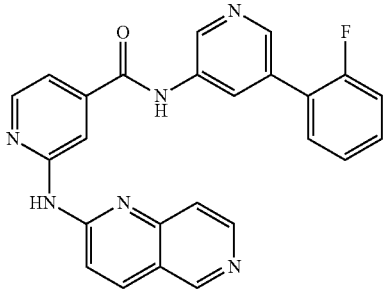 [SMILES: O=C(Nc1cncc(-c2ccccc2F)c1)c1ccnc(Nc2ccc3cnccc3n2)c1]

2-((1,6-Naphthyridin-2-yl)amino)-N-(5-(2-fluorophenyl)pyridin-3-yl)isonicotinamide $^1$H NMR (500 MHz, DMSO-d$_6$) δ ppm 10.92 (br. s., 1H) 10.72 (s, 1H) 9.10 (s, 1H) 9.00-9.07 (m, 2H) 8.57 (t, J=6.10 Hz, 3H) 8.49 (s, 1H) 8.35 (d, J=9.16 Hz, 1H) 7.64-7.72 (m, 2H) 7.62 (d, J=5.80 Hz, 1H) 7.51-7.59 (m, 2H) 7.36-7.45 (m, 2H). MS(ESI) (m/z): 437.2 (M+H)$^+$.

Example 154

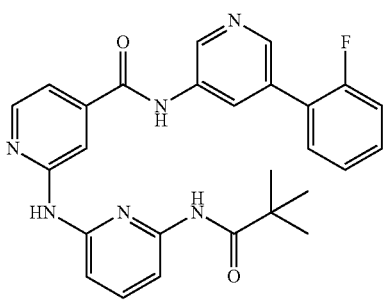 [SMILES: CC(C)(C)C(=O)Nc1cccc(Nc2cc(C(=O)Nc3cncc(-c4ccccc4F)c3)ccn2)n1]

N-(5-(2-Fluorophenyl)pyridin-3-yl)-2-((6-pivalamidopyridin-2-yl)amino)isonicotinamide $^1$H NMR (500 MHz, DMSO-d$_6$) δ ppm 10.92 (s, 1H) 9.95 (s, 1H) 9.17 (s, 1H) 9.10 (d, J=2.14 Hz, 1H) 8.69 (s, 1H) 8.55 (s, 1H) 8.38-8.48 (m, 2H) 7.59-7.72 (m, 2H) 7.48-7.57 (m, 2H) 7.37-7.45 (m, 2H) 7.35 (d, J=4.88 Hz, 1H) 7.19 (d, J=8.24 Hz, 1H) 1.14 (s, 9H). MS(ESI) (m/z): 485.2 (M+H)$^+$.

Example 155

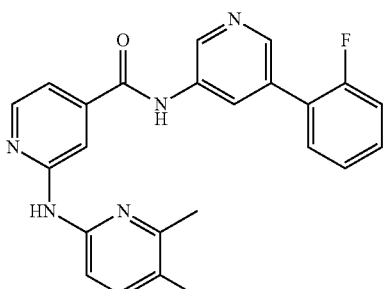

2-((5-Cyano-6-methylpyridin-2-yl)amino)-N-(5-(2-fluorophenyl)pyridin-3-yl)isonicotinamide $^1$H NMR (500 MHz, DMSO-d$_6$) δ ppm 10.87 (br. s., 1H) 10.63 (s, 1H) 8.99 (d, J=2.14 Hz, 1H) 8.56 (s, 1H) 8.52 (d, J=5.19 Hz, 1H) 8.45 (s, 1H) 8.24 (s, 1H) 8.05 (d, J=8.85 Hz, 1H) 7.83 (d, J=8.85 Hz, 1H) 7.60-7.68 (m, 1H) 7.49-7.56 (m, 2H) 7.35-7.46 (m, 2H) 2.61 (s, 3H); MS(ESI) (m/z): 425.1 (M+H)$^+$.

Example 156

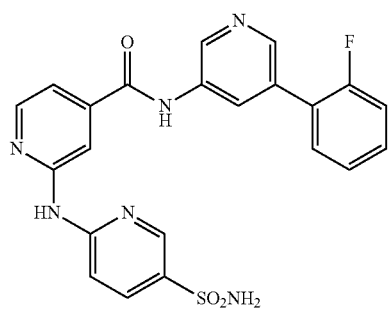 [SMILES: NS(=O)(=O)c1ccc(Nc2cc(C(=O)Nc3cncc(-c4ccccc4F)c3)ccn2)nc1]

N-(5-(2-Fluorophenyl)pyridin-3-yl)-2-((5-sulfamoylpyridin-2-yl)amino)isonicotinamide MS (ESI) (m/z): 465.0 (M+H)$^+$.

Example 157

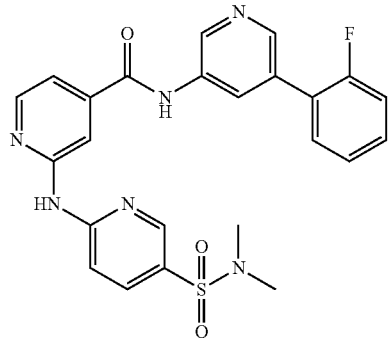 [SMILES: CN(C)S(=O)(=O)c1ccc(Nc2cc(C(=O)Nc3cncc(-c4ccccc4F)c3)ccn2)nc1]

2-((5-(N,N-Dimethylsulfamoyl)pyridin-2-yl)amino)-N-(5-(2-fluorophenyl)pyridin-3-yl)isonicotinamide $^1$H NMR (500 MHz, DMSO-d$_6$) δ ppm 10.85 (s, 1H) 10.66 (s, 1H) 9.00 (d, J=2.14 Hz, 1H) 8.60 (d, J=2.44 Hz, 1H) 8.56 (s, 1H) 8.53 (d, J=5.19 Hz, 1H) 8.45 (s, 1H) 8.28 (s, 1H) 8.02-8.07 (m, 1H) 7.96 (d, J=8.85 Hz, 1H) 7.65 (t, J=7.93 Hz, 1H) 7.52 (d, J=6.10 Hz, 2H) 7.36-7.45 (m, 2H) 2.65 (s, 6H). MS(ESI) (m/z): 493.3 (M+H)$^+$.

Example 158

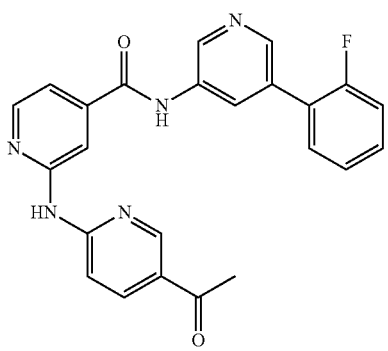 [SMILES: CC(=O)c1ccc(Nc2cc(C(=O)Nc3cncc(-c4ccccc4F)c3)ccn2)nc1]

2-((5-Acetylpyridin-2-yl)amino)-N-(5-(2-fluorophenyl)pyridin-3-yl)isonicotinamide $^1$H NMR (500 MHz, DMSO-d$_6$) δ ppm 10.85 (s, 1H) 10.56 (s, 1H) 9.00 (d, J=2.14 Hz, 1H) 8.93 (d, J=2.44 Hz, 1H) 8.56 (s, 1H) 8.52 (d, J=5.19 Hz, 1H) 8.45 (s, 1H) 8.36 (s, 1H) 8.19 (dd, J=8.70, 2.29 Hz, 1H) 7.81 (d, J=9.16 Hz, 1H) 7.65 (t, J=7.78 Hz, 1H) 7.46-7.56 (m, 2H) 7.36-7.45 (m, 2H) 2.56 (s, 3H). MS(ESI) (m/z): 428.5 (M+H)$^+$.

Example 159

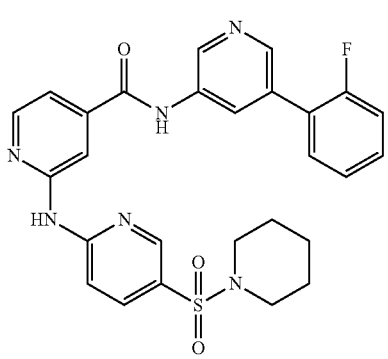 [SMILES: O=C(Nc1cncc(-c2ccccc2F)c1)c1ccnc(Nc2ccc(S(=O)(=O)N3CCCCC3)cn2)c1]

N-(5-(2-Fluorophenyl)pyridin-3-yl)-2-((5-(piperidin-1-ylsulfonyl)pyridin-2-yl)amino)isonicotinamide $^1$H NMR (500 MHz, DMSO-d$_6$) δ ppm 10.86 (s, 1H) 10.67 (s, 1H) 9.00 (d, J=2.14 Hz, 1H) 8.55-8.59 (m, 1H) 8.53 (d, J=5.19 Hz, 1H) 8.45 (s, 1H) 8.28 (s, 1H) 7.99-8.04 (m, 1H) 7.93-7.98 (m, 2H) 7.65 (t, J=7.78 Hz, 1H) 7.50-7.56 (m, 2H) 7.37-7.46 (m, 2H) 2.93 (t, J=5.19 Hz, 4H) 1.54-1.60 (m, 4H) 1.40 (d, J=4.58 Hz, 2H). MS(ESI) (m/z): 533.3 (M+H)$^+$.

Example 160

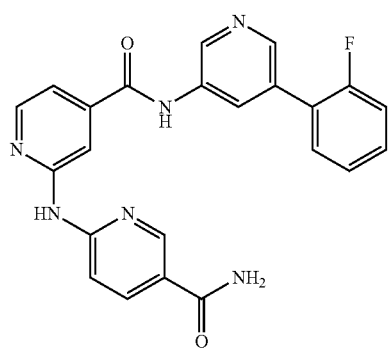 [SMILES: NC(=O)c1ccc(Nc2cc(C(=O)Nc3cncc(-c4ccccc4F)c3)ccn2)nc1]

6-((4-((5-(2-Fluorophenyl)pyridin-3-yl)carbamoyl)pyridin-2-yl)amino)nicotinamide MS (ESI) (m/z): 429.5 (M+H)$^+$.

Example 161

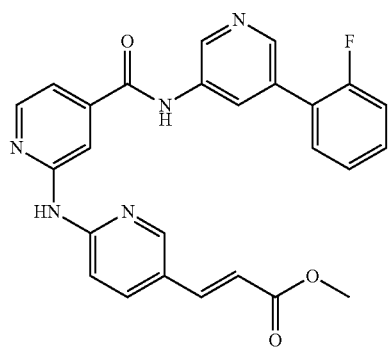 [SMILES: COC(=O)/C=C/c1ccc(Nc2cc(C(=O)Nc3cncc(-c4ccccc4F)c3)ccn2)nc1]

(E)-Eethyl 3-(6-((4-((5-(2-fluorophenyl)pyridin-3-yl)carbamoyl)pyridin-2-yl)amino)pyridin-3-yl)acrylate MS (ESI) (m/z): 470.3 (M+H)$^+$.

Synthesis of Amine F

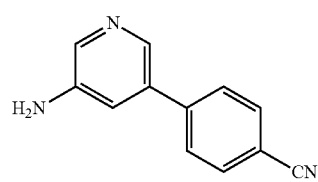 [SMILES: N#Cc1ccc(-c2cncc(N)c2)cc1]

4-(5-Aminopyridin-3-yl)benzonitrile

To a pressure vessel was added 5-bromopyridin-3-amine (0.3 g, 1.734 mmol), (4-cyanophenyl)boronic acid (0.255 g, 1.734 mmol) and PdCl2(dppf)-CH2Cl2Adduct (0.283 g, 0.347 mmol). The reaction mixture was degassed and flushed with N2 (3×). Then DMF (5 mL) was added and the system was degassed and flushed with N2 (3×). SODIUM CARBONATE (1.734 mL, 3.47 mmol) was added and the system was degassed and flushed with N2 (3×). The reaction mixture was heated to 85° C. for 3 h. LCMS showed desired prod. The reaction was diluted with ethyl acetate and satd ammonium chloride. The org layer was washed with water, brine and dried over sodium sulfate. The crude product was dissolved in a small amount of dichloromethane and charged to a 120 g silica gel cartridge which was eluted with 0-100% ethyl acetate/hexanes over a period of 60 mins. The desired fractions were combined and dried under vacuo to give 4-(5-aminopyridin-3-yl)benzonitrile (0.28 g, 1.434 mmol, 83% yield). $^1$H NMR (400 MHz, DMSO-$d_6$) δ ppm 8.10 (d, J=1.96 Hz, 1H) 8.01 (d, J=2.45 Hz, 1H) 7.90-7.96 (m, 2H) 7.78-7.84 (m, 2H) 7.21 (t, J=2.20 Hz, 1H) 5.46 (s, 2H). MS (ESI) (m/z): 196.1 (M+H)$^+$.

Example 162

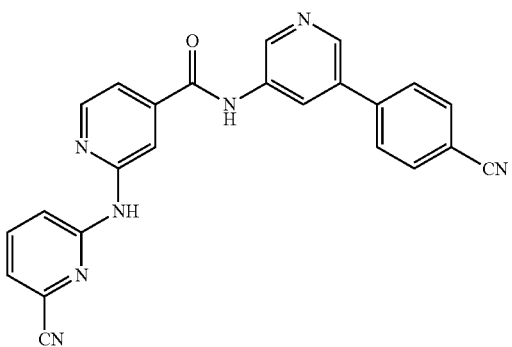 [SMILES: N#Cc1ccc(-c2cncc(NC(=O)c3ccnc(Nc4cccc(C#N)n4)c3)c2)cc1]

N-(5-(4-Cyanophenyl)pyridin-3-yl)-2-((6-cyanopyridin-2-yl)amino)isonicotinamide

To 2-((6-cyanopyridin-2-yl)amino)isonicotinic acid (0.05 g, 0.208 mmol) and 4-(5-aminopyridin-3-yl)benzonitrile (0.041 g, 0.208 mmol) in Ethyl acetate (2 mL) was added DIEA (0.182 mL, 1.041 mmol) followed by 1-Propanephosphonic acid cyclic anhydride, 50% in EtOAc (0.243 mL, 0.416 mmol) dropwise. The reaction was stirred at rt overnight. LCMS showed product. The reaction was diluted with ethyl acetate and satd sodium bicarbonate and water. Solid was formed between layers which was filtered, collected and washed with dichloromethane. The solid was triturated in dichloromethane, filtered and dried under vacuo to obtain white solid. Water and ethyl acetate was added and the org layer was dried over sodium sulfate. The crude material was purified by prep LCMS to give desired product. MS (ESI) (m/z): 418.3 (M+H)$^+$.

Synthesis of Intermediate

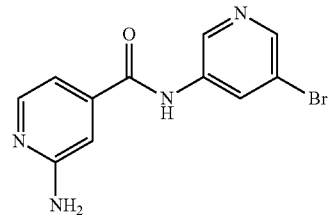 [SMILES: Nc1cc(C(=O)Nc2cncc(Br)c2)ccn1]

2-Amino-N-(5-bromopyridin-3-yl)isonicotinamide

To 5-bromopyridin-3-amine (0.406 g, 2.348 mmol) and 2-(cyclopentanecarboxamido)isonicotinic acid (0.5 g, 2.134 mmol) in DMF (2 mL) was added DIEA (1.864 mL, 10.67 mmol) followed by HATU (1.623 g, 4.27 mmol). The reaction was stirred at rt overnight. The reaction was diluted with ethyl acetate and water. The org extracts was washed with brine and dried over sodium sulfate and evaporated. The crude product was dissolved in a small amount of dichloromethane and charged to a 24 g silica gel cartridge which was eluted with 0-80% ethyl acetate/hexanes over a period of 40 mins. The desired frns were combined, evaporated and dried to give 2-amino-N-(5-bromopyridin-3-yl)isonicotinamide (0.19 g, 0.648 mmol, 30.4% yield) and N-(5-bromopyridin-3-yl)-2-(cyclopentanecarboxamido)isonicotinamide (0.03 g, 0.077 mmol, 3.61% yield). MS (ESI) (m/z): 295.0 (M+H)$^+$.

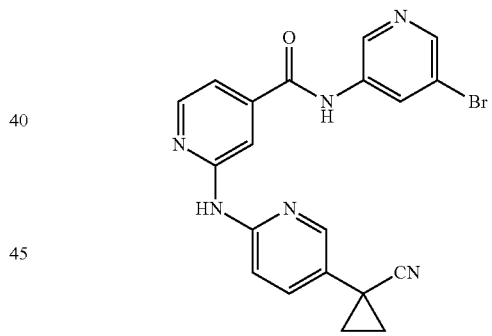

N-(5-Bromopyridin-3-yl)-2-((5-(1-cyanocyclopropyl)pyridin-2-yl)amino)isonicotinamide To an oven dried vial with a stir bar, brettphos precatalyst (2.73 mg, 3.41 µmol), brett phos (1.797 mg, 3.41 µmol), 1-(6-chloropyridin-3-yl)cyclopropanecarbonitrile (0.061 g, 0.341 mmol), 2-amino-N-(5-bromopyridin-3-yl)isonicotinamide (0.1 g, 0.341 mmol) and K2CO3 (0.071 g, 0.512 mmol) were added. The solid mixture was purged with N2 (degassed and flushed) (3×). Then tBuOH (1 mL) was added. The vial was degassed and flushed with N2 (3×) and the vessel was capped and placed in a preheated oil bath at 110° C. for 3 hrs. LCMS—showed a bit of prod with both s/m still present. The reaction was heated for 10 more hrs at 110° C. LCMS showed no improvement. The reaction mixture was cooled, diluted with ethyl acetate and satd ammonium chloride. The org layer was washed with brine and dried over sodium sulfate. The crude product was dissolved in a small amount of dichloromethane and charged to a 24 g silica gel cartridge which was eluted with 0-15% dichloromethane/methanol over a period of 40 mins. The desired fractions were combined and dried under vacuo to give N-(5-bromopyridin-3-yl)-2-((5-(1-cyanocyclopropyl)pyridin-2-yl)amino)isonicotinamide (10 mg, 0.023 mmol, 6.73% yield). MS (ESI) (m/z): 434.9 (M+H)⁺.

Example 163

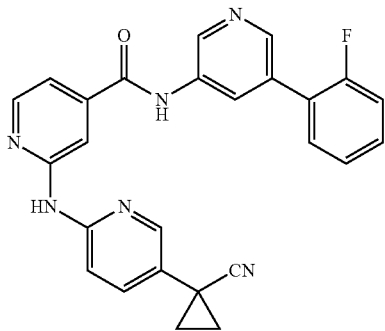 [SMILES: N#CC1(c2ccc(Nc3cc(C(=O)Nc4cncc(-c5ccccc5F)c4)ccn3)nc2)CC1]

2-((5-(1-Cyanocyclopropyl)pyridin-2-yl)amino)-N-(5-(2-fluorophenyl)pyridin-3-yl)isonicotinamide To a pressure vessel was added N-(5-bromopyridin-3-yl)-2-((5-(1-cyanocyclopropyl)pyridin-2-yl)amino)isonicotinamide (10 mg, 0.023 mmol), (2-fluorophenyl)boronic acid (3.21 mg, 0.023 mmol) and PdCl2(dppf)-CH2Cl2Adduct (3.75 mg, 4.59 μmol). The reaction mixture was degassed and flushed with N2 (3×). Then DMF (1) was added and the system was degassed and flushed with N2 (3×). SODIUM CARBONATE (0.02297 mL, 0.046 mmol) was added and the system was degassed and flushed with N2 (3×). The reaction mixture was heated to 85° C. for 3 h. LCMS showed desired product. The reaction was diluted with ethyl acetate and satd ammonium chloride. The org layer was dried over sodium sulfate. The crude material was purified by prep LCMS to give desired prod. ¹H NMR (500 MHz, DMSO-d₆) δ ppm 10.80 (br. s., 1H) 10.13 (s, 1H) 8.99 (d, J=2.44 Hz, 1H) 8.56 (s, 1H) 8.40-8.48 (m, 2H) 8.30 (d, J=2.44 Hz, 1H) 8.20 (s, 1H) 7.74-7.80 (m, 1H) 7.70 (dd, J=8.70, 2.59 Hz, 1H) 7.65 (td, J=7.78, 1.83 Hz, 1H) 7.51-7.57 (m, 1H) 7.36-7.45 (m, 3H) 1.70-1.75 (m, 2H) 1.49-1.54 (m, 2H). MS (ESI) (m/z): 451.3 (M+H)⁺.

Synthesis of Intermediate Bromide

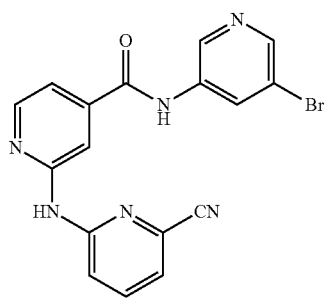 [SMILES: N#Cc1cccc(Nc2cc(C(=O)Nc3cncc(Br)c3)ccn2)n1]

N-(5-Bromopyridin-3-yl)-2-((6-cyanopyridin-2-yl)amino)isonicotinamide

To 2-((6-cyanopyridin-2-yl)amino)isonicotinic acid (0.1 g, 0.416 mmol) and 5-bromopyridin-3-amine (0.076 g, 0.437 mmol) in Ethyl acetate (2 mL) 2 was added DIEA (0.364 mL, 2.081 mmol) followed by 1-Propanephosphonic acid cyclic anhydride, 50% in EtOAc (0.486 mL, 0.833 mmol) dropwise. The reaction was stirred at rt overnight. The reaction was diluted with ethyl acetate and satd sodium bicarbonate and water and dried over sodium sulfate. The solvent was removed and the residue was dried under vacuo to give N-(5-bromopyridin-3-yl)-2-((6-cyanopyridin-2-yl)amino)isonicotinamide (0.15 g, 0.380 mmol, 91% yield). MS (ESI) (m/z): 396.8 (M+H)⁺.

Example 165

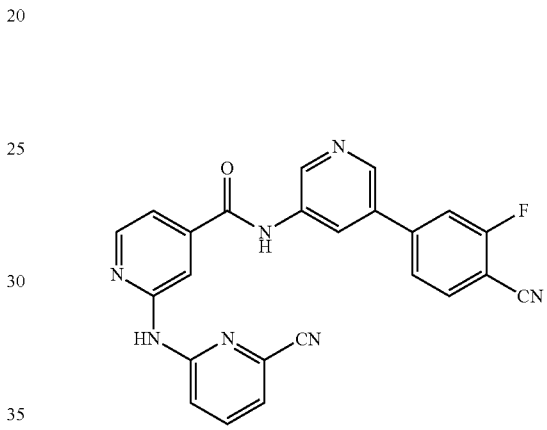

N-(5-(4-Cyano-3-fluorophenyl)pyridin-3-yl)-2-((6-cyanopyridin-2-yl)amino)isonicotinamide To a microwave vial was added N-(5-bromopyridin-3-yl)-2-(6-cyanopyridin-2-yl)amino)isonicotinamide (0.03 g, 0.076 mmol), (4-cyano-3-fluorophenyl)boronic acid (0.013 g, 0.076 mmol) and PdCl2(dppf)-CH2Cl2Adduct (0.012 g, 0.015 mmol). The reaction mixture was degassed and flushed with N2 (3×). Then DMF (1 mL) was added and the system was degassed and flushed with N2 (3×). SODIUM CARBONATE (0.076 mL, 0.152 mmol) was added and the system was degassed and flushed with N2 (3×). The reaction mixture was heated to 85° C. for 3 hrs. LCMS showed desired prod. The reaction was diluted with ethyl acetate and satd ammonium chloride. The org layer was washed with water, brine and dried over sodium sulfate. The solvent was evaporated and the residue purified by prep LCMS to give N-(5-(4-cyano-3-fluorophenyl)pyridin-3-yl)-2-((6-cyanopyridin-2-yl)amino)isonicotinamide. ¹H NMR (500 MHz, DMSO-d₆) δ ppm 10.88 (s, 1H) 10.52 (s, 1H) 9.01 (d, J=2.14 Hz, 1H) 8.81 (d, J=2.14 Hz, 1H) 8.60 (t, J=2.14 Hz, 1H) 8.52 (d, J=5.19 Hz, 1H) 8.07-8.17 (m, 3H) 8.00 (dd, J=10.68, 1.53 Hz, 1H) 7.91-7.98 (m, 1H) 7.82 (dd, J=7.93, 1.53 Hz, 1H) 7.56 (d, J=7.02 Hz, 1H) 7.50 (dd, J=5.19, 1.53 Hz, 1H). MS (ESI) (m/z): 436.2 (M+H)⁺.

Example 166

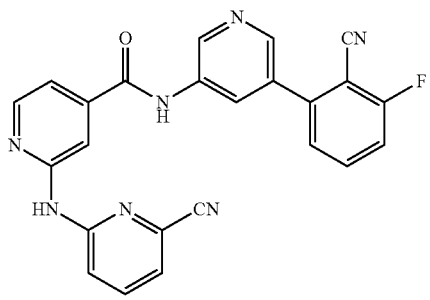 [SMILES: N#Cc1cccc(Nc2cc(C(=O)Nc3cncc(-c4cccc(F)c4C#N)c3)ccn2)n1]

N-(5-(2-Cyano-3-fluorophenyl)pyridin-3-yl)-2-((6-cyanopyridin-2-yl)amino)isonicotinamide To a microwave vial was added N-(5-bromopyridin-3-yl)-2-((6-cyanopyridin-2-yl)amino)isonicotinamide (0.03 g, 0.076 mmol), (2-cyano-3-fluorophenyl)boronic acid (0.013 g, 0.076 mmol) and PdCl2(dppf)-CH2Cl2Adduct (0.012 g, 0.015 mmol). The reaction mixture was degassed and flushed with N2 (3×). Then DMF (3 mL) was added and the system was degassed and flushed with N2 (3×). SODIUM CARBONATE (0.076 mL, 0.152 mmol) was added and the system was degassed and flushed with N2 (3×). The reaction mixture was heated to 85° C. for 3 hrs. The reaction was diluted with ethyl acetate and satd ammonium chloride. The org layer was washed with water, brine and dried over sodium sulfate. The solvent was evaporated and the residue was purified by prep LCMS to give desired prod. MS (ESI) (m/z): 436.5 (M+H)$^+$.

Synthesis of Intermediate for Example 166-167

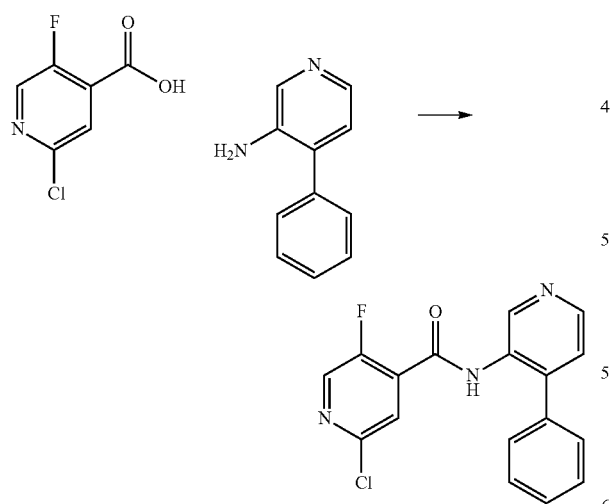

2-Chloro-5-fluoro-N-(4-phenylpyridin-3-yl)isonicotinamide 2 2,4,6-Tripropyl-1,3,5,2,4,6-trioxatriphosphinane 2,4,6-trioxide (1.61 mL, 2.71 mmol) was added to a solution of triethylamine (0.378 mL, 2.71 mmol), 4-phenylpyridin-3-amine (0.1539 g, 0.904 mmol) and 2-chloro-5-fluoroisonicotinic acid (0.159 g, 0.904 mmol) in DMF (2.5 mL) at rt. The mixture was stirred overnight at rt. The reaction was diluted with ethyl acetate and washed with water (3×). The organic layer was separated, dried (Na2SO4), filtered and concentrated to give the crude product as a tan solid (145 mg, 49%): LCMS: M+H=328.0.

Example 167

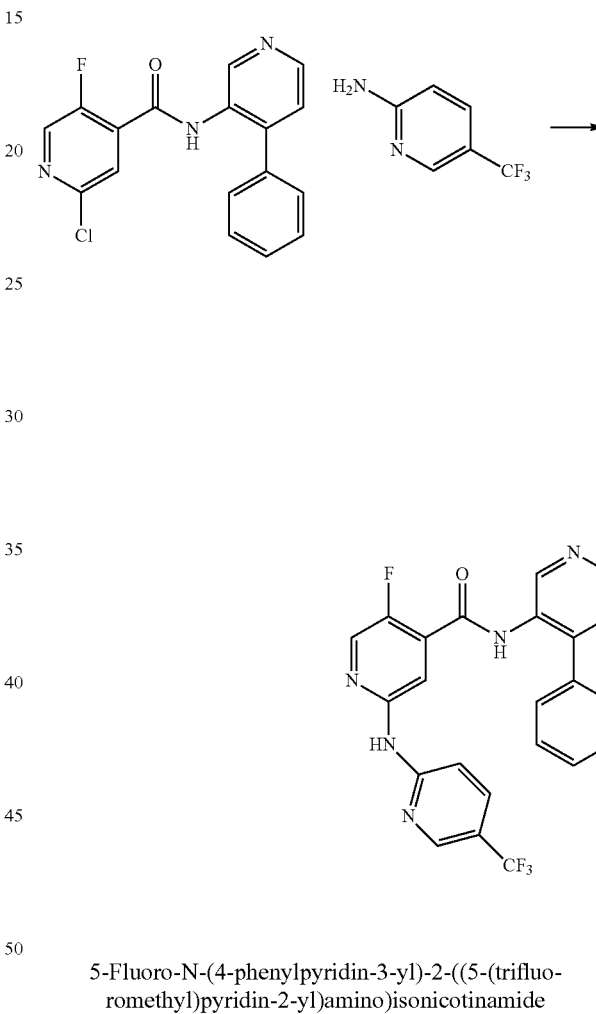

5-Fluoro-N-(4-phenylpyridin-3-yl)-2-((5-(trifluoromethyl)pyridin-2-yl)amino)isonicotinamide A mixture of potassium carbonate (7.84 mg, 0.057 mmol), 2-chloro-5-fluoro-N-(4-phenylpyridin-3-yl)isonicotinamide (12.4 mg, 0.038 mmol), 5-(trifluoromethyl)pyridin-2-amine (12.27 mg, 0.076 mmol), dicyclohexyl(2',4',6'-triisopropyl-3,6-dimethoxy-[1,1'-biphenyl]-2-yl)phosphine (0.203 mg, 0.378 μmol), Brettphos precatalyst (0.302 mg, 0.378 μmol) in t-butanol (0.7 mL) (degassed) was heated at 110° C. for 18 h. The reaction was filtered through a small silica pad and washed with methanol. The filtrate was purified by prep-HPLC (6.0 mg, 35%): $^1$H NMR (500 MHz, DMSO-d$_6$) δ 10.51 (s, 1H), 10.45 (br. s., 1H), 8.72 (s, 1H), 8.63-8.54 (m, 2H), 8.42 (s, 1H), 8.09-8.01 (m, 2H), 7.71 (d, J=8.9 Hz, 1H), 7.59-7.41 (m, 6H).

Example 168

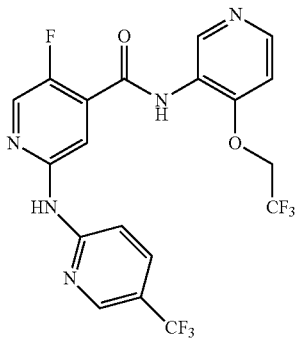 [SMILES: O=C(Nc1cnccc1OCC(F)(F)F)c1cc(Nc2ccc(C(F)(F)F)cn2)ncc1F]

5-Fluoro-N-(4-(2,2,2-trifluoroethoxy)pyridin-3-yl)-
2-((5-(trifluoromethyl)pyridin-2-yl)amino)isonicoti-
namide $^1$H NMR (500 MHz, DMSO-$d_6$) δ 10.52 (br. s., 1H), 8.83 (br. s., 1H), 8.60 (s, 1H), 8.45 (s, 1H), 8.37 (d, J=5.5 Hz, 1H), 8.22 (d, J=4.6 Hz, 1H), 8.04 (dd, J=9.0, 2.3 Hz, 1H), 7.74 (d, J=8.9 Hz, 1H), 7.28 (d, J=5.5 Hz, 1H), 5.00 (q, J=8.9 Hz, 2H).

Example 169

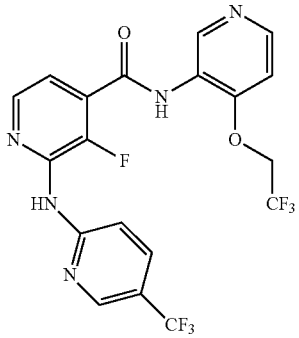 [SMILES: O=C(Nc1cnccc1OCC(F)(F)F)c1ccnc(Nc2ccc(C(F)(F)F)cn2)c1F]

3-Fluoro-N-(4-(2,2,2-trifluoroethoxy)pyridin-3-yl)-
2-((5-(trifluoromethyl)pyridin-2-yl)amino)isonicoti-
namide $^1$H NMR (500 MHz, DMSO-$d_6$) δ 10.22 (br. s., 1H), 10.08 (br. s., 1H), 8.76 (s, 1H), 8.61 (s, 1H), 8.44 (d, J=5.5 Hz, 1H), 8.30 (d, J=4.9 Hz, 1H), 8.09 (dd, J=8.9, 2.4 Hz, 1H), 7.98 (d, J=8.9 Hz, 1H), 7.37-7.26 (m, 2H), 4.99 (q, J=8.5 Hz, 2H).

General Synthesis of Amine G

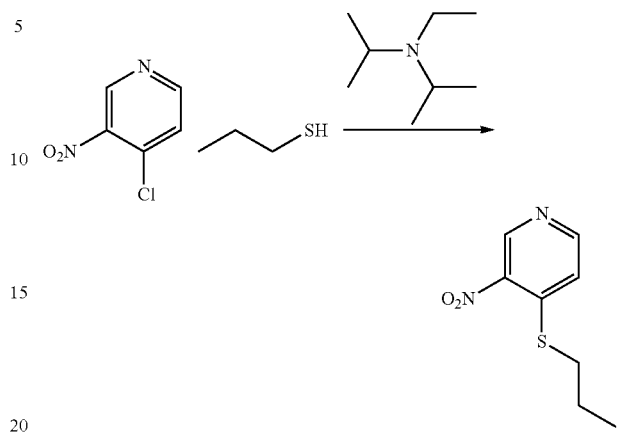

3-Nitro-4-(propylthio)pyridine

In a 20 mL vial was propane-1-thiol (150 mg, 1.968 mmol) in Tetrahydrofuran (3 mL) to give a colorless solution. 4-chloro-3-nitropyridine (260 mg, 1.640 mmol) and Hunig's Base (0.372 mL, 2.132 mmol) were added. The mixture was stirred at rt overnight. TLC (3/1 hexane/EtOAc) indicated a major more polar spot with a little SM left. Another equivalent of thiol was added and the mixture was stirred over the weekend. TLC showed complete conversion. It was concentrated to a tan solid. Purification by FCC up to 50% EtOAc/hexane afforded the desired product (280 mg, 86%) as a yellow solid: $^1$H NMR (500 MHz, Chloroform-d) δ 9.32 (s, 1H), 8.57 (d, J=5.6 Hz, 1H), 7.32 (d, J=5.6 Hz, 1H), 2.98 (t, J=7.4 Hz, 2H), 1.83 (h, J=7.4 Hz, 2H), 1.14 (t, J=7.4 Hz, 3H).

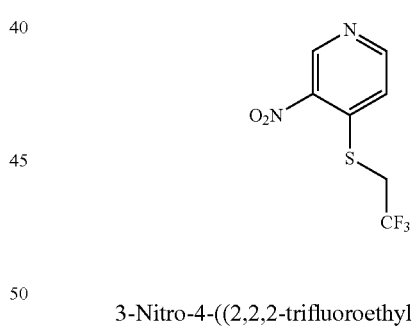

3-Nitro-4-((2,2,2-trifluoroethyl)thio)pyridine $^1$H NMR (500 MHz, Chloroform-d) δ 9.37 (s, 1H), 8.68 (d, J=5.6 Hz, 1H), 7.40 (d, J=5.6 Hz, 1H), 3.70 (q, J=9.3 Hz, 2H).

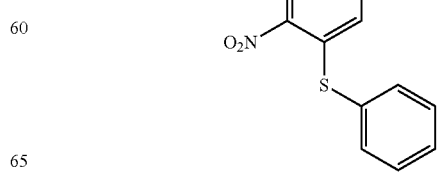

3-Nitro-4-(phenylthio)pyridine $^1$H NMR (500 MHz, Chloroform-d) δ 9.30 (s, 1H), 8.34 (d, J=5.6 Hz, 1H), 7.63-7.50 (m, 5H), 6.69 (d, J=5.6 Hz, 1H).

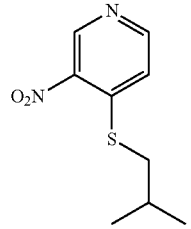

3-Nitro-4-(isobutylthio)pyridine $^1$H NMR (400 MHz, Chloroform-d) δ 9.34 (d, J=1.3 Hz, 1H), 8.57 (dd, J=5.6, 1.0 Hz, 1H), 7.31 (d, J=5.6 Hz, 1H), 2.87 (d, J=6.8 Hz, 2H), 2.15-2.00 (m, 1H), 1.16 (d, J=6.6 Hz, 6H).

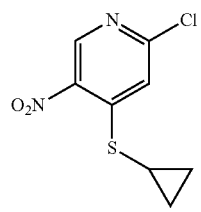 [SMILES: O=[N+]([O-])c1cnc(Cl)cc1SC1CC1]

2-Chloro-4-(cyclopropylthio)-5-nitropyridine $^1$H NMR (400 MHz, Chloroform-d) δ 9.16 (s, 1H), 7.82 (s, 1H), 2.13 (tt, J=7.4, 4.5 Hz, 1H), 1.39-1.29 (m, 2H), 0.96-0.82 (m, 2H).

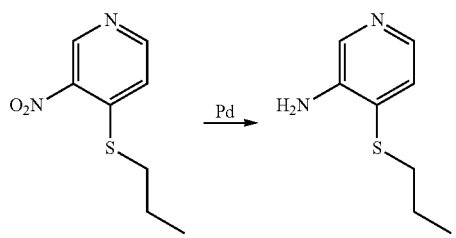

4-(Propylthio)pyridin-3-amine

In a 100 mL round-bottomed flask was 3-nitro-4-(propylthio)pyridine (131 mg, 0.661 mmol) and Pd/C (141 mg, 0.132 mmol) in MeOH (3 mL) to give a black suspension. The mixture was stirred under hydrogen (balloon) for 24 h. LCMS showed slow reaction to completion. It was filtered and washed with MeOH. The elute was concentrated to the desired product (101 mg, 91%) as a tan oil: $^1$H NMR (400 MHz, Chloroform-d) δ 7.99 (s, 1H), 7.90 (d, J=5.1 Hz, 1H), 7.07 (d, J=5.1 Hz, 1H), 4.12 (s, 2H), 2.89-2.85 (m, 2H), 1.71-1.64 (m, 2H), 1.03-0.99 (m, 3H).

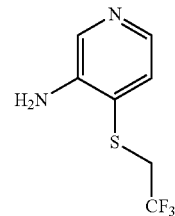

4-((2,2,2-Trifluoroethyl)thio)pyridin-3-amine

MS (ESI) (m/z): 209 (M+H)$^+$.

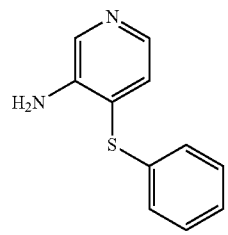

4-(Phenylthio)pyridin-3-amine

MS (ESI) (m/z): 203 (M+H)+.

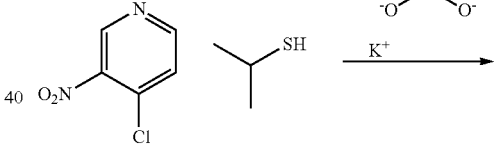

3-Nitro-4-(isopropylthio)pyridine

In a 20 mL vial was 4-chloro-3-nitropyridine (323 mg, 2.037 mmol) in DMF (4 mL) to give a tan solution. Potassium carbonate (563 mg, 4.07 mmol) and propane-2-thiol (0.388 mL, 4.07 mmol) were added. The vial was tightly capped and the mixture was stirred at 100° C. overnight for 18 h. TLC (3/1 hexane/EtOAc) showed good conversion. It was diluted with water and EtOAc. The layers were separated. The organic layer was washed with water, brine, dried and concentrated to a tan oil. FCC up to 50% EtOAc/hexane afforded the desired product (149 mg, 37%) as a tan solid: $^1$H NMR (400 MHz, Chloroform-d) δ 9.33 (s, 1H), 8.59 (d, J=5.7 Hz, 1H), 7.37 (d, J=5.6 Hz, 1H), 3.63 (hept, J=6.7 Hz, 1H), 1.49 (d, J=6.5 Hz, 6H).

181

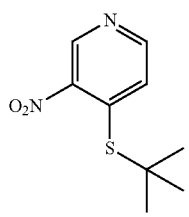

3-Nitro-4-(tert-butylthio)pyridine $^1$H NMR (400 MHz, Chloroform-d) δ 9.18-9.10 (m, 1H), 8.60 (dt, J=5.4, 1.0 Hz, 1H), 7.66 (d, J=5.5 Hz, 1H), 1.58 (s, 9H).

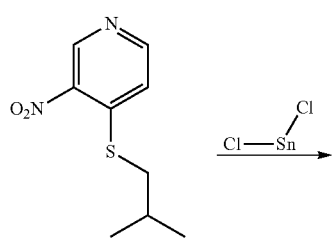 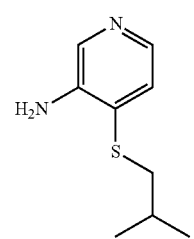

4-(Isobutylthio)pyridin-3-amine

In a 20 mL vial was 4-(isobutylthio)-3-nitropyridine (433 mg, 2.040 mmol) in EtOH (6 ml) to give a yellow solution. SnCl$_2$ (967 mg, 5.10 mmol) was added, and the mixture was heated at 70° C. under nitrogen. 2 h: LCMS indicated good conversion to the desired product along with likely hydroxylamine product (M+16) as major. The heating was continued for another 18 h. LCMS showed mainly the desired products. Cooled to r.t. Aqueous NaHCO3 was added to adjust pH around 7-8 (till no solids were forming). Some celite and Na2SO4 were added and stirring continued for 30 min. The suspension was then carefully filtered (through a plug of celite) and washed with EtOAc. The filtrated solution was concentrated to remove EtOH. The remainder was partitioned between water and EtOAc. The layers were separated. The organic layer was washed with brine, dried with Na2SO4, and concentrated to the desired product (150 mg, 40%) as a tan oil. MS (ESI) (m/z): 209 (M+H)$^+$.

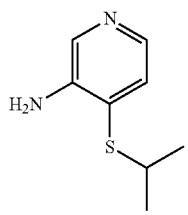

182

4-(Isoropylthio)pyridin-3-amine

MS (ESI) (m/z): 169 (M+H)$^+$.

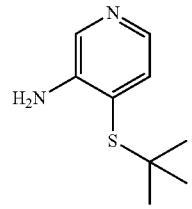

4-(tert-Butylthio)pyridin-3-amine

MS (ESI) (m/z): 183 (M+H)$^+$.

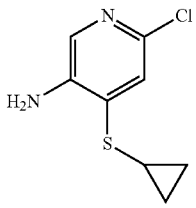

6-Chloro-4-(cyclopropylthio)pyridin-3-amine

MS (ESI) (m/z): 201 (M+H)$^+$. $^1$H NMR (400 MHz, Chloroform-d) δ 7.71 (s, 1H), 7.30 (s, 1H), 3.66 (s, 2H), 2.15 (tt, J=7.4, 4.4 Hz, 1H), 1.23-1.13 (m, 2H), 0.78-0.70 (m, 2H).

Example 170

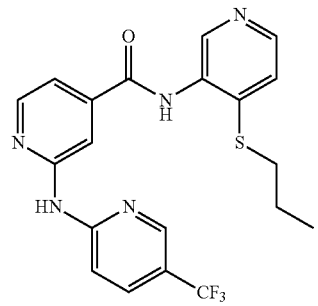

N-(4-(Propylthio)pyridin-3-yl)-2-((5-(trifluoromethyl)pyridin-2-yl)amino)isonicotinamide Followed synthesis of example 4. MS (ESI) (m/z): 434 (M+H)$^+$; $^1$H NMR (400 MHz, Methanol-d4) δ 8.58 (s, 1H), 8.52 (s, 1H), 8.45 (d, J=5.2 Hz, 1H), 8.33 (s, 1H), 8.31 (s, 1H), 7.94-7.84 (m, 1H), 7.80-7.70 (m, 1H), 7.42 (dd, J=8.9, 5.3 Hz, 2H), 3.06 (t, J=7.3 Hz, 2H), 1.79 (q, J=7.3 Hz, 2H), 1.10 (t, J=7.4 Hz, 3H).

Example 171

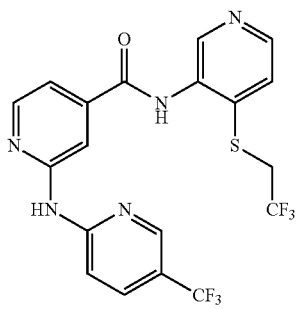 [SMILES: O=C(Nc1cnccc1SCC(F)(F)F)c1ccnc(Nc2ccc(C(F)(F)F)cn2)c1]

N-(4-((2,2,2-Trifluoroethyl)thio)pyridin-3-yl)-2-((5-(trifluoromethyl)pyridin-2-yl)amino)isonicotinamide Followed synthesis of example 4. MS (ESI) (m/z): 474 (M+H)$^+$; $^1$H NMR (500 MHz, DMSO-d6) δ 10.57 (s, 1H), 10.51 (s, 1H), 8.61 (s, 1H), 8.50 (d, J=5.2 Hz, 1H), 8.47-8.40 (m, 2H), 8.28 (s, 1H), 8.05 (dd, J=9.0, 2.6 Hz, 1H), 7.92 (d, J=8.9 Hz, 1H), 7.70 (d, J=5.4 Hz, 1H), 7.48 (d, J=5.1 Hz, 1H), 4.23 (q, J=10.1 Hz, 2H).

Example 173

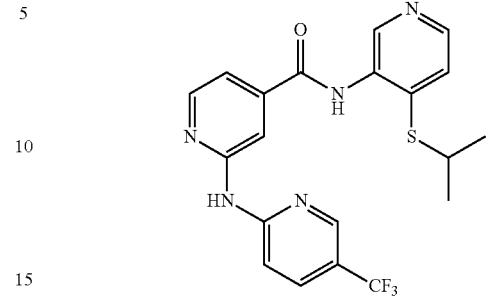

N-(4-(Isopropylthio)pyridin-3-yl)-2-((5-(trifluoromethyl)pyridin-2-yl)amino)isonicotinamide Followed synthesis of example 4. MS (ESI) (m/z): 434 (M+H)$^+$; $^1$H NMR (500 MHz, DMSO-d6) δ 10.50 (s, 1H), 10.29 (s, 1H), 8.61 (s, 1H), 8.49 (d, J=5.2 Hz, 1H), 8.41 (s, 1H), 8.39 (d, J=5.3 Hz, 1H), 8.26 (s, 1H), 8.05 (dd, J=9.1, 2.6 Hz, 1H), 7.92 (d, J=8.9 Hz, 1H), 7.56-7.40 (m, 2H), 3.75 (p, J=6.7 Hz, 1H), 1.32 (d, J=6.7 Hz, 6H).

Example 172

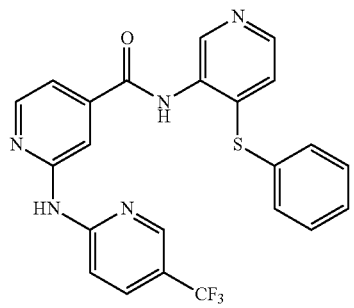 [SMILES: O=C(Nc1cnccc1Sc1ccccc1)c1ccnc(Nc2ccc(C(F)(F)F)cn2)c1]

N-(4-(Phenylthio)pyridin-3-yl)-2-((5-(trifluoromethyl)pyridin-2-yl)amino)isonicotinamide Followed synthesis of example 4. MS (ESI) (m/z): 468 (M+H)$^+$; $^1$H NMR (500 MHz, DMSO-d6) δ 10.57 (s, 1H), 10.51 (s, 1H), 8.61 (s, 1H), 8.54-8.41 (m, 2H), 8.37-8.24 (m, 2H), 8.05 (d, J=8.9 Hz, 1H), 7.95 (d, J=9.0 Hz, 1H), 7.68-7.41 (m, 6H), 6.76 (d, J=5.3 Hz, 1H).

Example 174

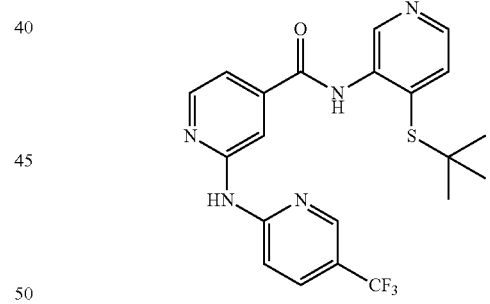

N-(4-(tert-Butylthio)pyridin-3-yl)-2-((5-(trifluoromethyl)pyridin-2-yl)amino)isonicotinamide Followed synthesis of example 4. MS (ESI) (m/z): 448 (M+H)$^+$; $^1$H NMR (500 MHz, DMSO-d6) δ 10.56 (s, 1H), 10.23 (s, 1H), 8.91 (s, 1H), 8.60 (s, 1H), 8.51 (d, J=5.2 Hz, 1H), 8.45 (d, J=5.6 Hz, 1H), 8.31 (d, J=7.5 Hz, 1H), 8.05 (d, J=8.2 Hz, 1H), 7.89 (d, J=8.9 Hz, 1H), 7.64 (d, J=5.0 Hz, 1H), 7.45 (d, J=5.3 Hz, 1H), 1.32 (s, 9H).

Example 175

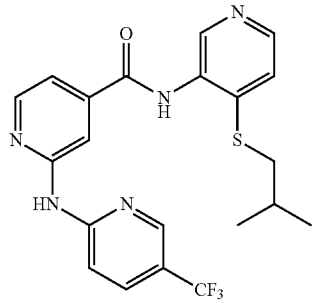

N-(4-(Isobutylthio)pyridin-3-yl)-2-((5-(trifluoromethyl)pyridin-2-yl)amino)isonicotinamide Followed synthesis of example 4. MS (ESI) (m/z): 448 (M+H)$^+$; $^1$H NMR (500 MHz, DMSO-d6) δ 10.49 (s, 1H), 10.33 (s, 1H), 8.60 (s, 1H), 8.49 (d, J=5.2 Hz, 1H), 8.37 (d, J=4.8 Hz, 2H), 8.26 (s, 1H), 8.12-8.00 (m, 1H), 7.91 (d, J=8.9 Hz, 1H), 7.53-7.35 (m, 2H), 2.94 (d, J=6.9 Hz, 2H), 1.86 (p, J=6.7 Hz, 1H), 1.01 (d, J=6.7 Hz, 6H).

Example 176

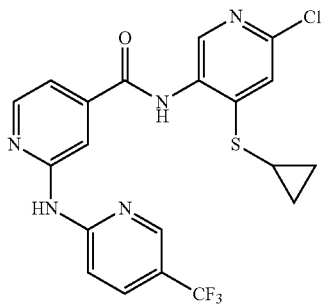 [SMILES: O=C(Nc1cnc(Cl)cc1SC1CC1)c1ccnc(Nc2ccc(C(F)(F)F)cn2)c1]

N-(6-Chloro-4-(cyclopropylthio)pyridin-3-yl)-2-((5-(trifluoromethyl)pyridin-2-yl)amino)isonicotinamide Followed synthesis of example 4. MS (ESI) (m/z): 466 (M+H)$^+$; $^1$H NMR (500 MHz, DMSO-d6) δ 10.48 (s, 1H), 8.60 (s, 1H), 8.47 (d, J=5.2 Hz, 1H), 8.27 (s, 1H), 8.23 (s, 1H), 8.05 (dd, J=9.1, 2.6 Hz, 1H), 7.94 (t, J=9.8 Hz, 1H), 7.66 (s, 1H), 7.44 (d, J=5.2 Hz, 1H), 2.37 (tt, J=7.7, 4.5 Hz, 1H), 1.21 (td, J=7.1, 4.9 Hz, 2H), 0.64 (q, J=5.1, 3.8 Hz, 2H).

Examples 177 and 183

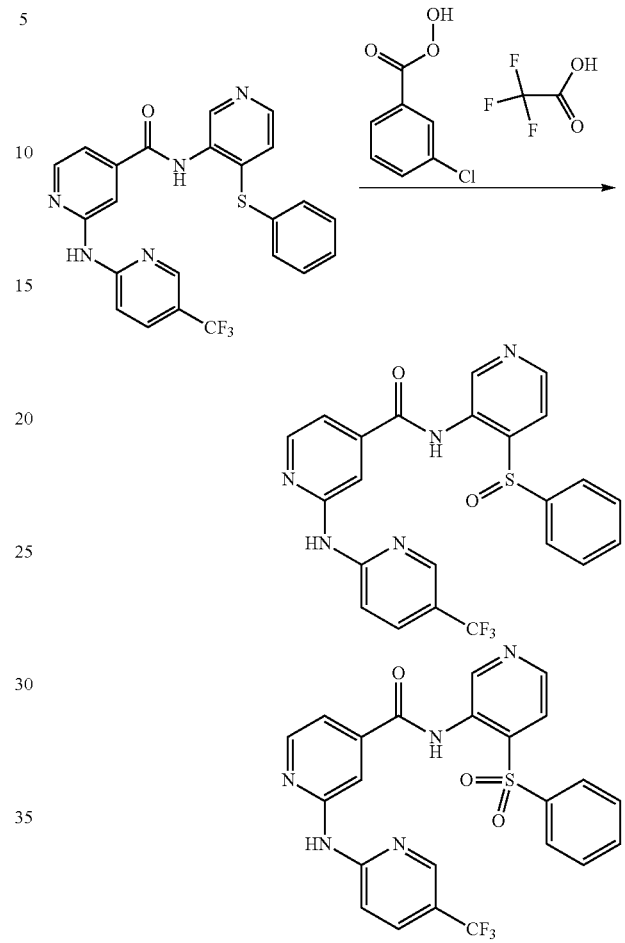

In a 100 mL round-bottomed flask was N-(4-(phenylthio)pyridin-3-yl)-2-((5-(trifluoromethyl)pyridin-2-yl)amino)isonicotinamide (108 mg, 0.231 mmol) in CH2Cl2 (3 mL) to give a white suspension. TFA (0.178 mL, 2.310 mmol) and mCPBA (88 mg, 0.393 mmol) were added. The mixture was stirred at rt for 1 h. LCMS showed the formation of the desired products. The products were purified by prep-HPLC.

N-(4-(Phenylsulfinyl)pyridin-3-yl)-2-((5-(trifluoromethyl)pyridin-2-yl)amino)isonicotinamide (177)

MS (ESI) (m/z): 484 (M+H)$^+$; $^1$H NMR (500 MHz, DMSO-d6) δ 10.92 (s, 1H), 10.54 (s, 1H), 8.74 (d, J=5.1 Hz, 1H), 8.71 (s, 1H), 8.60 (s, 1H), 8.51 (d, J=5.2 Hz, 1H), 8.25 (s, 1H), 8.09-8.01 (m, 1H), 7.92 (dd, J=10.4, 7.1 Hz, 2H), 7.63 (d, J=7.5 Hz, 2H), 7.49 (q, J=7.2, 5.9 Hz, 3H), 7.36 (d, J=5.2 Hz, 1H).

N-(4-(Phenylsulfonyl)pyridin-3-yl)-2-((5-(trifluoromethyl)pyridin-2-yl)amino)isonicotinamide (183)

MS (ESI) (m/z): 500 (M+H)$^+$; $^1$H NMR (500 MHz, DMSO-d6) δ 10.59 (s, 1H), 10.45 (s, 1H), 9.07 (s, 1H), 8.80 (d, J=5.3 Hz, 1H), 8.60 (s, 1H), 8.54 (d, J=5.3 Hz, 1H), 8.33 (s, 1H), 8.09 (d, J=5.2 Hz, 1H), 8.06 (d, J=8.9 Hz, 1H), 7.93

(d, J=7.9 Hz, 2H), 7.88 (d, J=9.1 Hz, 1H), 7.70 (t, J=7.6 Hz, 1H), 7.54 (t, J=7.8 Hz, 2H), 7.43 (d, J=5.2 Hz, 1H).

Example 178

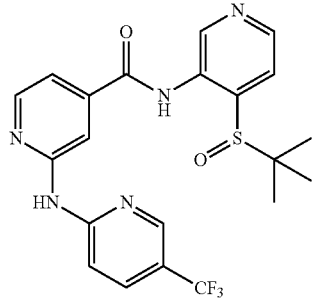 [SMILES: CC(C)(C)S(=O)c1ccncc1NC(=O)c1ccnc(Nc2ccc(C(F)(F)F)cn2)c1]

N-(4-(tert-Butylsulfinyl)pyridin-3-yl)-2-((5-(trifluoromethyl)pyridin-2-yl)amino)isonicotinamide MS (ESI) (m/z): 464 (M+H)⁺; ¹H NMR (500 MHz, DMSO-d6) δ 10.58 (s, 1H), 9.12 (s, 1H), 8.66 (d, J=5.1 Hz, 1H), 8.63-8.58 (m, 1H), 8.52 (d, J=5.2 Hz, 1H), 8.34 (s, 1H), 8.06 (dd, J=8.9, 2.5 Hz, 1H), 7.88 (d, J=8.9 Hz, 1H), 7.67 (d, J=5.0 Hz, 1H), 7.41 (d, J=5.2 Hz, 1H), 1.16 (s, 9H).

Example 187

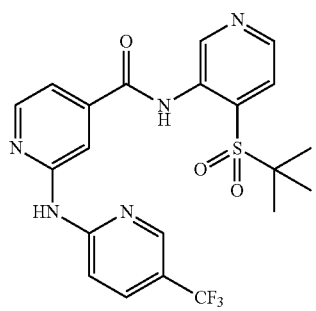 [SMILES: CC(C)(C)S(=O)(=O)c1ccncc1NC(=O)c1ccnc(Nc2ccc(C(F)(F)F)cn2)c1]

N-(4-(tert-butylsulfonyl)pyridin-3-yl)-2-((5-(trifluoromethyl)pyridin-2-yl)amino)isonicotinamide MS (ESI) (m/z): 480 (M+H)⁺; ¹H NMR (500 MHz, DMSO-d6) δ 10.63 (s, 1H), 10.55 (s, 1H), 9.61 (s, 1H), 8.73 (d, J=5.1 Hz, 1H), 8.62 (s, 1H), 8.55 (d, J=5.2 Hz, 1H), 8.47 (s, 1H), 8.06 (dd, J=8.8, 2.3 Hz, 1H), 7.84 (d, J=5.1 Hz, 1H), 7.80 (d, J=8.8 Hz, 1H), 7.42 (d, J=5.2 Hz, 1H), 1.29 (s, 9H).

Example 179

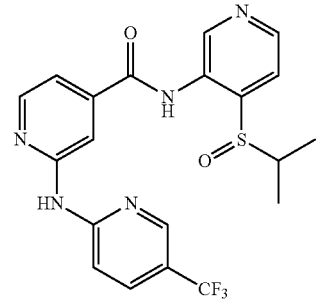 [SMILES: CC(C)S(=O)c1ccncc1NC(=O)c1ccnc(Nc2ccc(C(F)(F)F)cn2)c1]

N-(4-(isopropylsulfinyl)pyridin-3-yl)-2-((5-(trifluoromethyl)pyridin-2-yl)amino)isonicotinamide MS (ESI) (m/z): 450 (M+H)⁺; ¹H NMR (400 MHz, Methanol-d4) δ 9.35 (s, 1H), 8.62 (d, J=5.1 Hz, 1H), 8.58-8.55 (m, 1H), 8.47 (d, J=5.3 Hz, 1H), 8.44-8.40 (m, 1H), 7.92 (dd, J=8.8, 2.7 Hz, 1H), 7.74 (d, J=8.8 Hz, 1H), 7.67 (d, J=5.1 Hz, 1H), 7.44 (dd, J=5.2, 1.6 Hz, 1H), 3.31-3.24 (m, 1H), 1.35 (d, J=6.9 Hz, 3H), 1.23 (d, J=6.8 Hz, 3H).

Example 186

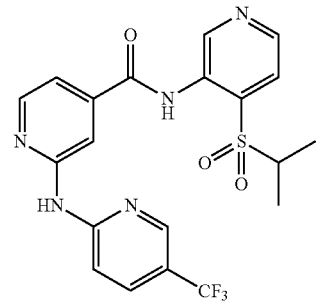 [SMILES: CC(C)S(=O)(=O)c1ccncc1NC(=O)c1ccnc(Nc2ccc(C(F)(F)F)cn2)c1]

N-(4-(Isopropylsulfonyl)pyridin-3-yl)-2-((5-(trifluoromethyl)pyridin-2-yl)amino)isonicotinamide MS (ESI) (m/z): 466 (M+H)⁺; ¹H NMR (500 MHz, DMSO-d6) δ 10.59 (s, 1H), 10.55 (s, 1H), 9.42 (s, 1H), 8.78 (d, J=5.1 Hz, 1H), 8.61 (d, J=2.3 Hz, 1H), 8.54 (d, J=5.2 Hz, 1H), 8.41 (s, 1H), 8.05 (dd, J=9.0, 2.6 Hz, 1H), 7.89 (d, J=5.1 Hz, 1H), 7.84 (d, J=9.0 Hz, 1H), 7.42 (dd, J=5.3, 1.7 Hz, 1H), 3.68 (p, J=6.7 Hz, 1H), 1.21 (d, J=6.8 Hz, 6H).

Example 180

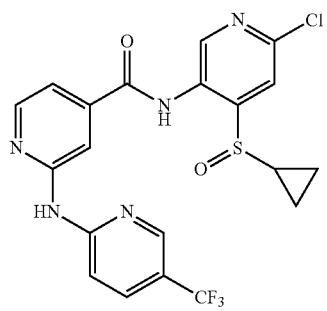 [SMILES: O=C(Nc1cnc(Cl)cc1S(=O)C1CC1)c1ccnc(Nc2ccc(C(F)(F)F)cn2)c1]

N-(6-Chloro-4-(cyclopropylsulfinyl)pyridin-3-yl)-2-((5-(trifluoromethyl)pyridin-2-yl)amino)isonicotinamide MS (ESI) (m/z): 482 (M+H)$^+$; $^1$H NMR (500 MHz, DMSO-d6) δ 11.06 (s, 1H), 10.55 (s, 1H), 8.76 (s, 1H), 8.62 (d, J=2.4 Hz, 1H), 8.52 (d, J=5.2 Hz, 1H), 8.31 (s, 1H), 8.06 (dd, J=8.9, 2.6 Hz, 1H), 7.91 (d, J=8.9 Hz, 1H), 7.82 (s, 1H), 7.45 (dd, J=5.2, 1.6 Hz, 1H), 2.77 (q, J=6.0, 5.3 Hz, 1H), 1.11 (q, J=6.9, 6.2 Hz, 1H), 1.04-0.95 (m, 1H), 0.92-0.84 (m, 2H).

Example 182

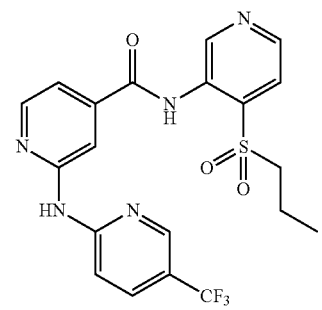

N-(4-(Propylsulfonyl)pyridin-3-yl)-2-((5-(trifluoromethyl)pyridin-2-yl)amino)isonicotinamide MS (ESI) (m/z): 466 (M+H)$^+$; $^1$H NMR (500 MHz, DMSO-d6) δ 10.57 (d, J=8.4 Hz, 2H), 9.34 (d, J=2.2 Hz, 1H), 8.78 (d, J=5.0 Hz, 1H), 8.62 (s, 1H), 8.53 (d, J=5.2 Hz, 1H), 8.39 (s, 1H), 8.06 (dd, J=8.8, 2.6 Hz, 1H), 7.91 (d, J=4.8 Hz, 1H), 7.86 (d, J=9.0 Hz, 1H), 7.50-7.37 (m, 1H), 3.63-3.49 (m, 2H), 1.61 (q, J=7.7 Hz, 2H), 0.92 (td, J=7.2, 2.2 Hz, 3H).

Example 184

Example 188

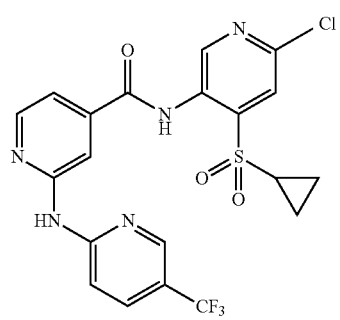 [SMILES: Cl ; Cc1cc(S(=O)(=O)C2CC2)c(NC(=O)c2ccnc(Nc3ccc(C(F)(F)F)cn3)c2)cn1]

N-(6-Chloro-4-(cyclopropylsulfonyl)pyridin-3-yl)-2-((5-(trifluoromethyl)pyridin-2-yl)amino)isonicotinamide MS (ESI) (m/z): 498 (M+H)$^+$; $^1$H NMR (500 MHz, DMSO-d6) δ 10.58 (s, 1H), 10.56 (s, 1H), 9.16 (s, 1H), 8.61 (d, J=2.2 Hz, 1H), 8.54 (d, J=5.2 Hz, 1H), 8.40 (s, 1H), 8.06 (dd, J=9.0, 2.5 Hz, 1H), 8.02 (s, 1H), 7.86 (d, J=8.9 Hz, 1H), 7.44 (dd, J=5.2, 1.6 Hz, 1H), 3.29 (dd, J=8.1, 4.7 Hz, 1H), 1.27 (p, J=4.8 Hz, 2H), 1.17 (dt, J=7.7, 3.7 Hz, 2H).

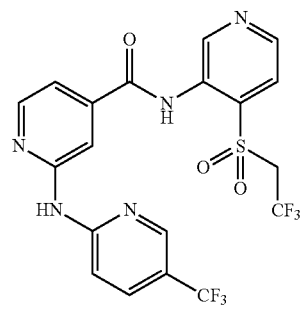 [SMILES: O=C(Nc1cnccc1S(=O)(=O)CC(F)(F)F)c1ccnc(Nc2ccc(C(F)(F)F)cn2)c1]

N-(4-((2,2,2-Trifluoroethyl)sulfonyl)pyridin-3-yl)-2-((5-(trifluoromethyl)pyridin-2-yl)amino)isonicotinamide MS (ESI) (m/z): 506 (M+H)$^+$; $^1$H NMR (500 MHz, DMSO-d6) δ 11.03 (s, 1H), 10.54 (s, 1H), 8.85 (d, J=5.0 Hz, 1H), 8.77 (d, J=2.9 Hz, 1H), 8.60 (s, 1H), 8.52 (d, J=5.1 Hz, 1H), 8.29 (s, 1H), 8.14-8.01 (m, 2H), 7.89 (d, J=9.0 Hz, 1H), 7.45 (d, J=5.2 Hz, 1H), 4.38 (dd, J=13.7, 9.8 Hz, 1H), 4.26-4.08 (m, 1H).

Example 185

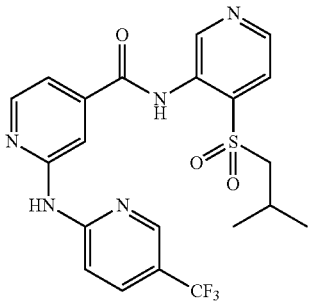 [SMILES: CC(C)CS(=O)(=O)c1ccncc1NC(=O)c1ccnc(Nc2ccc(C(F)(F)F)cn2)c1]

N-(4-(Isobutylsulfonyl)pyridin-3-yl)-2-((5-(trifluoromethyl)pyridin-2-yl)amino)isonicotinamide MS (ESI) (m/z): 480 (M+H)+; 1H NMR (500 MHz, DMSO-d6) δ 10.59 (s, 1H), 10.57 (s, 1H), 9.28 (s, 1H), 8.80 (d, J=5.2 Hz, 1H), 8.61 (s, 1H), 8.53 (d, J=5.3 Hz, 1H), 8.41 (s, 1H), 8.05 (d, J=8.9 Hz, 1H), 7.94 (d, J=5.3 Hz, 1H), 7.84 (d, J=8.6 Hz, 1H), 7.43 (d, J=5.5 Hz, 1H), 3.43 (d, J=6.5 Hz, 2H), 2.21-2.01 (m, 1H), 1.13-0.89 (m, 6H).

Example 181

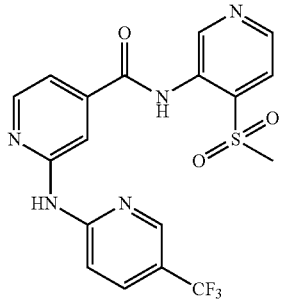

N-(4-(Methylsulfonyl)pyridin-3-yl)-2-((5-(trifluoromethyl)pyridin-2-yl)amino)isonicotinamide Followed synthesis of example 4. MS (ESI) (m/z): 438.1 (M+H)+; 1H NMR (500 MHz, DMSO-d6) δ 10.60 (d, J=4.2 Hz, 2H), 9.29 (s, 1H), 8.81 (d, J=5.2 Hz, 1H), 8.67-8.61 (m, 1H), 8.54 (d, J=5.2 Hz, 1H), 8.37 (s, 1H), 8.07 (dd, J=8.9, 2.5 Hz, 1H), 7.96 (d, J=5.0 Hz, 1H), 7.90 (d, J=8.8 Hz, 1H), 7.44 (dd, J=5.0, 1.4 Hz, 1H), 3.45 (s, 3H).

Example 189

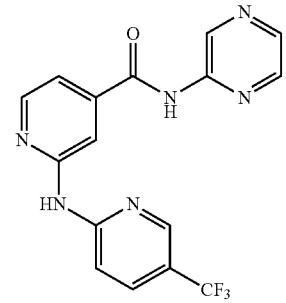 [SMILES: O=C(Nc1cnccn1)c1ccnc(Nc2ccc(C(F)(F)F)cn2)c1]

N-(Pyrazin-2-yl)-2-((5-(trifluoromethyl)pyridin-2-yl)amino)isonicotinamide

Followed synthesis of example 4. MS (ESI) (m/z): 361 (M+H)+; 1H NMR (500 MHz, DMSO) δ 11.40 (s, 1H), 10.51 (s, 1H), 9.44 (d, J=1.4 Hz, 1H), 8.64 (s, 1H), 8.56-8.50 (m, 1H), 8.50-8.41 (m, 2H), 8.26 (s, 1H), 8.06 (dd, J=8.9, 2.5 Hz, 1H), 7.94 (d, J=8.8 Hz, 1H), 7.53 (dd, J=5.2, 1.4 Hz, 1H).

Synthesis of Intermediate Amine H

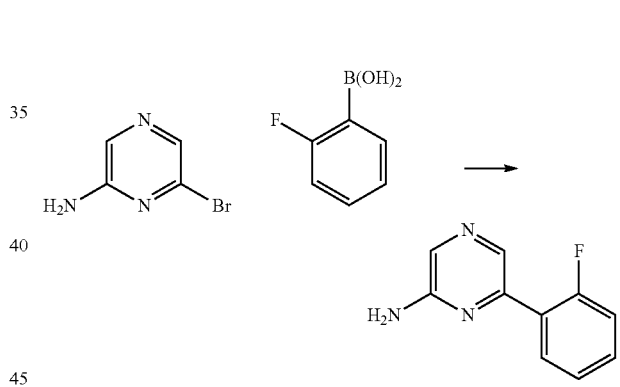

6-(2-fluorophenyl)pyrazin-2-amine

In a 15 mL vial was 6-bromopyrazin-2-amine, (2-fluorophenyl)boronic acid (280 mg, 2.005 mmol), and Na2CO3 (1.879 mL, 3.76 mmol) in Dioxane (6 mL) to give a slightly tan solution under nitrogen. 1,1'-Bis(diphenylphosphino)ferrocenepalladium(II) dichloride, Toluene (51.5 mg, 0.063 mmol) was added under nitrogen. The vial was sealed and heated at 135° C. for 2 h. LCMS showed the desired product (M+H=190) as the major peak. The mixture was partitioned between water and EtOAc. The layers were separated. The organic layer was washed with brine, dried and concentrated. The residue was purified by FCC up to 60% EtOAc/hexane to afford the desired product (211 mg, 89%) as an off-white solid: 1H NMR (400 MHz, CDCl3) δ 8.39 (d, J=2.7 Hz, 1H), 7.93 (s, 1H), 7.88 (td, J=7.8, 1.8 Hz, 1H), 7.43-7.33 (m, 1H), 7.24 (td, J=7.6, 1.0 Hz, 1H), 7.15 (ddd, J=11.1, 8.3, 0.8 Hz, 1H), 4.99 (s, 2H); 19F NMR (376 MHz, CDCl3) δ −114.88 (s).

Example 190

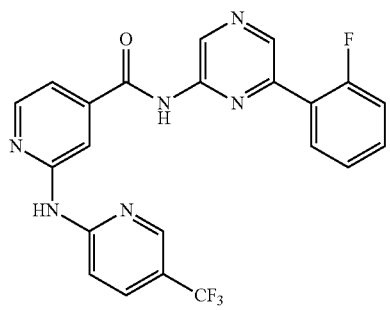 [SMILES: O=C(Nc1cncc(-c2ccccc2F)n1)c1ccnc(Nc2ccc(C(F)(F)F)cn2)c1]

N-(6-(2-Fluorophenyl)pyrazin-2-yl)-2-((5-(trifluoromethyl)pyridin-2-yl)amino)isonicotinamide Followed synthesis of example 4. MS (ESI) (m/z): 455 (M+H)[+]; $^1$H NMR (500 MHz, DMSO) δ 10.47 (s, 1H), 9.34 (s, 1H), 8.72 (s, 1H), 8.63 (s, 1H), 8.45 (d, J=5.2 Hz, 1H), 8.27 (s, 1H), 8.05 (dd, J=9.0, 2.5 Hz, 1H), 8.00 (dd, J=9.3, 3.5 Hz, 2H), 7.61-7.55 (m, 2H), 7.42 (dd, J=13.6, 5.4 Hz, 2H).

Example 191

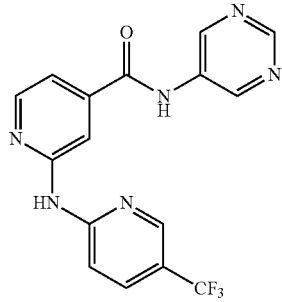 [SMILES: O=C(Nc1cncnc1)c1ccnc(Nc2ccc(C(F)(F)F)cn2)c1]

N-(Pyrimidin-5-yl)-2-((5-(trifluoromethyl)pyridin-2-yl)amino)isonicotinamide

Followed synthesis of example 4. MS (ESI) (m/z): 361 (M+H)[+]; $^1$H NMR (500 MHz, DMSO) δ 10.91 (s, 1H), 10.55 (s, 1H), 9.19 (s, 2H), 8.99 (s, 1H), 8.65 (s, 1H), 8.53 (d, J=5.2 Hz, 1H), 8.28 (s, 1H), 8.07 (dd, J=8.9, 2.4 Hz, 1H), 7.92 (d, J=8.9 Hz, 1H), 7.49 (dd, J=5.2, 1.3 Hz, 1H).

Example 192

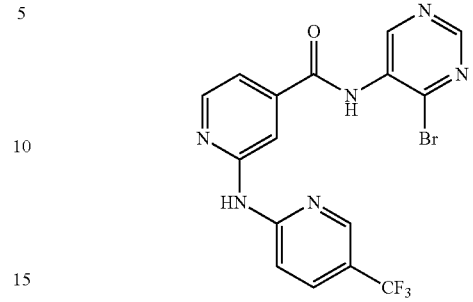

N-(4-Bromopyrimidin-5-yl)-2-((5-(trifluoromethyl)pyridin-2-yl)amino)isonicotinamide Followed synthesis of example 4. MS (ESI) (m/z): 439 (M+H)[+]; $^1$H NMR (500 MHz, DMSO) δ 10.74 (s, 1H), 10.56 (s, 1H), 8.98 (s, 1H), 8.93 (s, 1H), 8.64 (s, 1H), 8.53 (d, J=5.2 Hz, 1H), 8.31 (s, 1H), 8.07 (d, J=8.9 Hz, 1H), 7.93 (d, J=8.9 Hz, 1H), 7.50 (d, J=5.0 Hz, 1H).

General Synthesis of Amine I

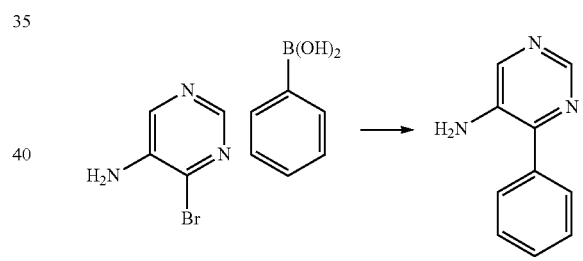

4-Phenylpyrimidin-5-amine

In a 50 mL flask was dissolved 4-bromopyrimidin-5-amine (279 mg, 1.60 mmol), phenylboronic acid (293 mg, 2.40 mmol), and Na$_2$CO$_3$ (2.4 mL, 4.8 mmol) in dioxane (5 mL) to give a tan solution under nitrogen. 1,1'-Bis(diphenylphosphino)ferrocenepalladium(II) dichloride, toluene (66.0 mg, 0.080 mmol) was added under nitrogen. The vial was sealed and heated in a microwave reactor at 100° C. for 2 h. The mixture was partitioned between water and ethyl acetate. The layers were separated. The organic layer was washed with brine, dried and concentrated. The residue was purified by flash column chromatography on silica gel, eluting with 80% ethyl acetate/hexane, to afford the desired product (47.6 mg, 17%) as a tan oil: $^1$H NMR (400 MHz, CDCl$_3$) δ 8.73 (s, 1H), 8.25 (s, 1H), 7.75 (s, 2H), 7.52 (s, 3H), 3.99 (s, 2H).

Example 193

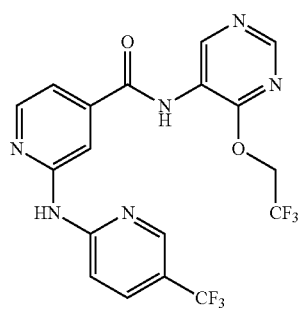

N-(4-Phenylpyrimidin-5-yl)-2-((5-(trifluoromethyl)pyridin-2-yl)amino)isonicotinamide Followed synthesis of example 4. MS (ESI) (m/z): 437 (M+H)+; $^1$H NMR (500 MHz, DMSO) δ 10.69 (s, 1H), 10.51 (s, 1H), 9.20 (s, 1H), 8.96 (s, 1H), 8.60 (s, 1H), 8.47 (d, J=5.1 Hz, 1H), 8.19 (s, 1H), 8.05 (dd, J=8.9, 2.3 Hz, 1H), 7.90 (d, J=8.8 Hz, 1H), 7.89-7.80 (m, 2H), 7.57-7.46 (m, 3H), 7.38 (d, J=5.2 Hz, 1H).

Synthesis of Amine J

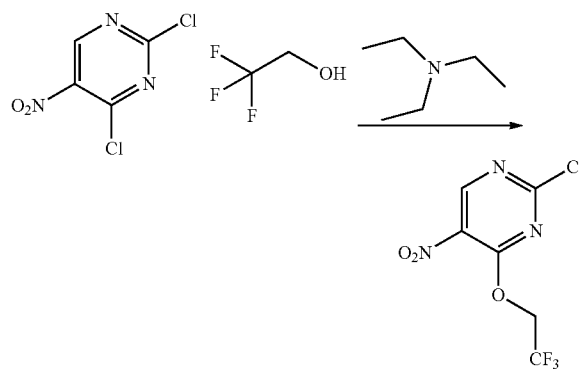

2-Chloro-5-nitro-4-(2,2,2-trifluoroethoxy)pyrimidine

MS (ESI) (m/z): 258 (M+H)+.

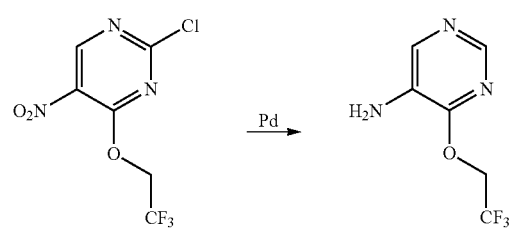

4-(2,2,2-Trifluoroethoxy)pyrimidin-5-amine $^1$H NMR (400 MHz, Chloroform-d) δ 8.25 (s, 1H), 8.02 (s, 1H), 4.85 (q, J=8.4 Hz, 2H), 3.89 (s, 2H); $^{19}$F NMR (376 MHz, Chloroform-d) δ −73.77.

Example 194

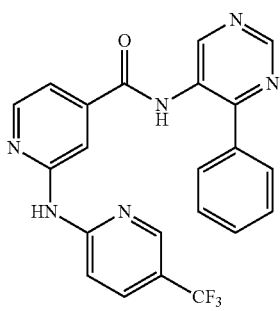 [SMILES: O=C(Nc1cncnc1-c1ccccc1)c1ccnc(Nc2ccc(C(F)(F)F)cn2)c1]

N-(4-(2,2,2-Trifluoroethoxy)pyrimidin-5-yl)-2-((5-(trifluoromethyl)pyridin-2-yl)amino)isonicotinamide Followed synthesis of example 4. MS (ESI) (m/z): 459 (M+H)+; $^1$H NMR (500 MHz, DMSO-d6) δ 10.54 (s, 1H), 10.41 (s, 1H), 8.89 (s, 1H), 8.79 (s, 1H), 8.62 (d, J=2.2 Hz, 1H), 8.51 (d, J=5.1 Hz, 1H), 8.27 (s, 1H), 8.06 (dd, J=9.0, 2.6 Hz, 1H), 7.90 (d, J=8.9 Hz, 1H), 7.43 (dd, J=5.0, 1.5 Hz, 1H), 5.19 (q, J=8.9 Hz, 2H).

Synthesis of Amine K

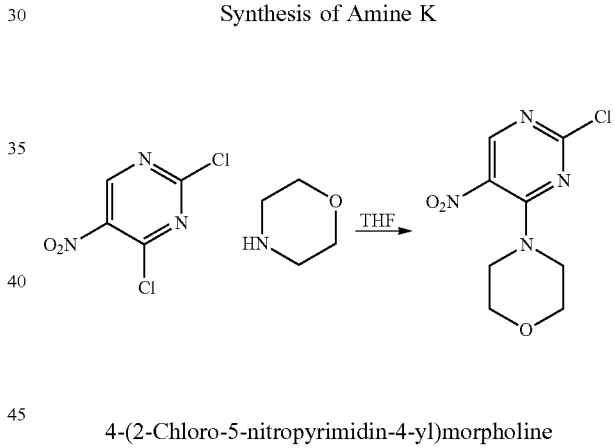

4-(2-Chloro-5-nitropyrimidin-4-yl)morpholine

MS (ESI) (m/z): 245 (M+H)+.

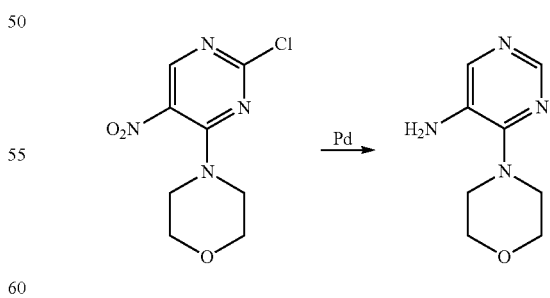

4-Morpholinopyrimidin-5-amine

MS (ESI) (m/z): 181 (M+H)+; $^1$H NMR (400 MHz, Chloroform-d) δ 8.37 (s, 1H), 7.94 (s, 1H), 3.90-3.81 (m, 4H), 3.54 (s, 2H), 3.41-3.33 (m, 4H).

Example 195

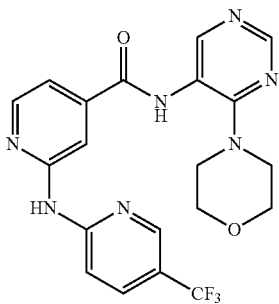 [SMILES: O=C(Nc1cncnc1N1CCOCC1)c1ccnc(Nc2ccc(C(F)(F)F)cn2)c1]

N-(4-Morpholinopyrimidin-5-yl)-2-((5-(trifluoromethyl)pyridin-2-yl)amino)isonicotinamide Followed synthesis of example 4. MS (ESI) (m/z): 446 (M+H)$^+$; $^1$H NMR (500 MHz, DMSO-d6) δ 10.52 (s, 1H), 10.38 (s, 1H), 8.62 (d, J=2.3 Hz, 1H), 8.55 (s, 1H), 8.49 (d, J=5.2 Hz, 1H), 8.25 (s, 1H), 8.21 (s, 1H), 8.07 (dd, J=8.9, 2.6 Hz, 1H), 7.96 (d, J=8.8 Hz, 1H), 7.45 (dd, J=5.2, 1.5 Hz, 1H), 3.66 (s, 8H).

Example 196

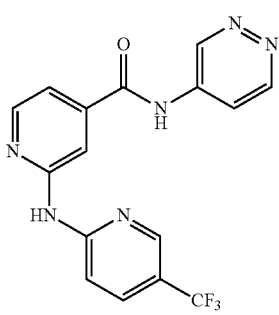 [SMILES: O=C(Nc1ccnnc1)c1ccnc(Nc2ccc(C(F)(F)F)cn2)c1]

N-(Pyridazin-4-yl)-2-((5-(trifluoromethyl)pyridin-2-yl)amino)isonicotinamide

Followed synthesis of example 4. MS (ESI) (m/z): 361 (M+H)$^+$; $^1$H NMR (500 MHz, DMSO) δ 11.09 (s, 1H), 10.57 (s, 1H), 9.53 (d, J=2.0 Hz, 1H), 9.14 (d, J=5.8 Hz, 1H), 8.65 (s, 1H), 8.54 (d, J=5.2 Hz, 1H), 8.26 (s, 1H), 8.12 (dd, J=5.9, 2.7 Hz, 1H), 8.07 (dd, J=8.9, 2.5 Hz, 1H), 7.92 (d, J=8.9 Hz, 1H), 7.48 (dd, J=5.2, 1.4 Hz, 1H).

Synthesis of Amine L

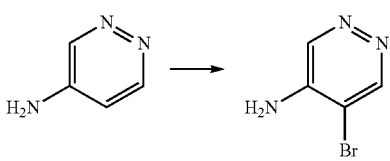 [SMILES: Nc1ccnnc1 ; Nc1cnncc1Br]

5-Bromopyridazin-4-amine

To a solution of pyridazin-4-amine (1.18 g, 12.41 mmol) in Acetic Acid (2.5 mL) was added dibromide (0.638 mL, 12.41 mmol) dropwise at rt in a water bath. After 1 h, 10 N NaOH was added and then extracted with dichloromethane (3×). The combined extracts were dried over sodium sulfate and concentrated in vacuo. The crude product was dissolved in a small amount of dichloromethane and charged to a 40 g silica gel cartridge which was eluted with 0-15% dichloromethane/methanol over a period of 40 mins. The desired fractions were combined and dried under vacuo to give 3-bromopyridazin-4-amine (0.1 g, 0.575 mmol, 4.63% yield)(first eluting) and 5-bromopyridazin-4-amine (0.12 g, 0.690 mmol, 5.56% yield)(second eluting). $^1$H NMR (400 MHz, DMSO-d$_6$) δ ppm 8.75 (s, 1H) 8.55 (s, 1H) 6.72-6.79 (m, 2H).

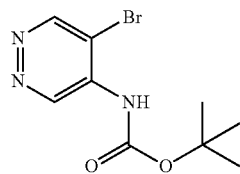

tert-Butyl (5-bromopyridazin-4-yl)carbamate

To 5-bromopyridazin-4-amine (0.1 g, 0.575 mmol) and TRIETHYLAMINE (0.104 mL, 0.747 mmol) in DCM (2 mL) at 0° C. The solution was stirred at rt for 10 mins then BOC2O (0.147 mL, 0.632 mmol) was added. The reaction was stirred at rt for 1 hr. The reaction was diluted with DCM and washed with brine, and dried over sodium sulfate. The crude product was dissolved in a small amount of dichloromethane and charged to a 24 g silica gel cartridge which was eluted with 0-10% dichloromethane/methanol over a period of 40 mins. The desired fractions were combined and dried under vacuo to give tert-butyl (5-bromopyridazin-4-yl)carbamate (0.12 g, 0.438 mmol, 76% yield). MS (ESI) (m/z): 276 (M+H)$^+$.

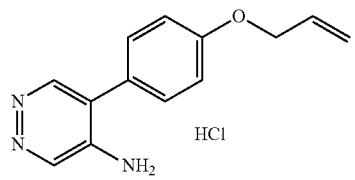

5-(4-(Allyloxy)phenyl)pyridazin-4-amine hydrochloride

A mixture of tert-butyl (5-bromopyridazin-4-yl)carbamate (0.05 g, 0.182 mmol), (4-(allyloxy)phenyl)boronic acid (0.032 g, 0.182 mmol), (PdCl2(dppf)-CH2Cl2Adduct (0.030 g, 0.036 mmol) in a microwave vial was flushed and degassed with N2. Na2CO3, 2M (0.182 ml, 0.365 mmol) followed by Dioxane (2 ml) was added and then microwave vial was flushed and degassed with N2. The resulting mixture was heated to 100° C. at reflux for 4 h.

Satd ammonium chloride and ethyl acetate was added. The org layer was separated and washed with water and brine and dried over sodium sulfate. The crude product was dissolved in a small amount of dichloromethane and charged to a 80 g silica gel cartridge which was eluted with 0-15% dichloromethane/methanol over a period of 50 mins. The desired fractions were combined and dried under vacuo to give desired prod intermediate. To the intermediate was added HCl, 4 M dioxane (1 ml, 4.00 mmol) and ethyl acetate (0.5 mL) and stirred overnight. After solvent was removed, the residue was dried under to give the desired prod. MS (ESI) (m/z): 228.1 (M+H)⁺.

Example 197

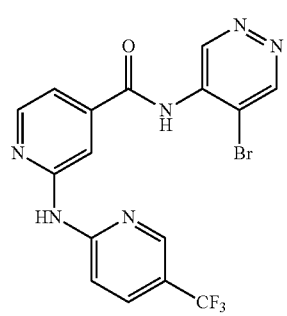 [SMILES: O=C(Nc1cnncc1Br)c1ccnc(Nc2ccc(C(F)(F)F)cn2)c1]

N-(5-Bromopyridazin-4-yl)-2-((5-(trifluoromethyl)pyridin-2-yl)amino)isonicotinamide Followed synthesis of example 4. MS (ESI) (m/z): 441 (M+H)⁺; $^1$H NMR (500 MHz, DMSO) δ 10.47 (s, 1H) 9.56 (s, 1H) 9.38 (s, 1H) 8.61 (s, 1H) 8.47 (d, J=5.19 Hz, 1H) 8.28 (s, 1H) 8.04 (d, J=8.54 Hz, 1H) 7.93 (d, J=9.16 Hz, 1H) 7.51 (d, J=5.49 Hz, 1H).

Example 199

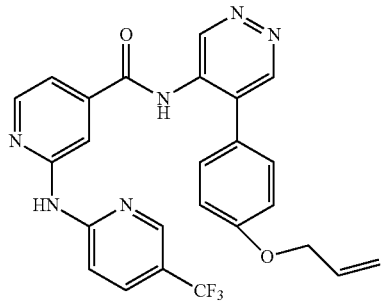 [SMILES: C=CCOc1ccc(-c2cnncc2NC(=O)c2ccnc(Nc3ccc(C(F)(F)F)cn3)c2)cc1]

N-(5-(4-(Allyloxy)phenyl)pyridazin-4-yl)-2-((5-(trifluoromethyl)pyridin-2-yl)amino)isonicotinamide Followed synthesis of example 4. MS (ESI) (m/z): 493.5 (M+H)⁺; $^1$H NMR (400 MHz, METHANOL-d$_4$) δ ppm 9.86 (s, 1H) 9.10 (s, 1H) 8.40-8.44 (m, 2H) 8.24 (s, 1H) 7.86 (dd, J=9.03, 2.26 Hz, 1H) 7.69 (s, 1H) 7.52-7.62 (m, 4H) 7.29 (dd, J=5.27, 1.51 Hz, 1H) 7.02-7.15 (m, 2H) 6.02 (ddt, J=17.32, 10.54, 5.27, 5.27 Hz, 1H) 5.33-5.45 (m, 1H) 5.26 (dq, J=10.54, 1.42 Hz, 1H) 4.57 (dt, J=5.27, 1.51 Hz, 2H).

Example 198

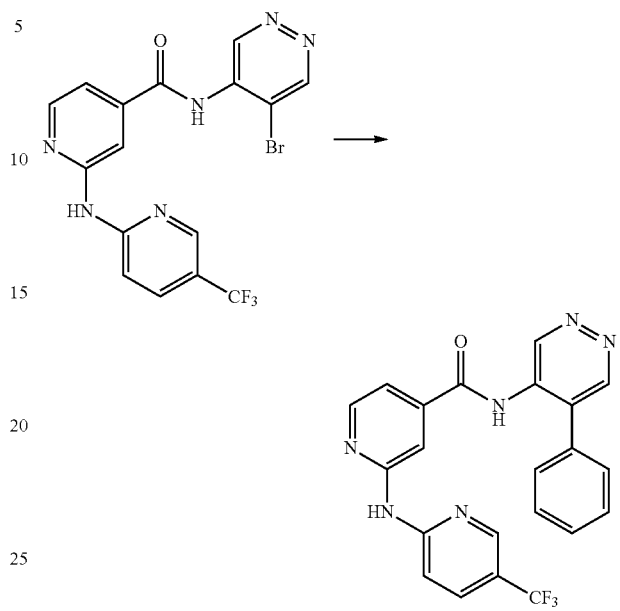

N-(5-Phenylpyridazin-4-yl)-2-((5-(trifluoromethyl)pyridin-2-yl)amino)isonicotinamide To N-(5-bromopyridazin-4-yl)-2-((5-(trifluoromethyl)pyridin-2-yl)amino)isonicotinamide (0.084 g, 0.191 mmol) and phenylboronic acid (0.026 g, 0.210 mmol) was added DMF (3 mL). The reaction was stirred at rt until solids are dissolved then PdCl2(dppf)-CH2Cl2Adduct (0.016 g, 0.019 mmol) was added. The flask was degassed and flushed with nitrogen and then Na2CO3, 2M (0.143 mL, 0.287 mmol) was added dropwise. The flask was degassed and flushed with nitrogen and then reaction vessel was sealed and then heated at 100° C. for 2.5 hrs. The reaction was diluted with ethyl acetate and satd ammonium chloride. The org layer was washed with water, brine and dried over sodium sulfate. The crude residue purified by prep LCMS to give desired product. $^1$H NMR (500 MHz, DMSO-d$_6$) δ ppm 10.61 (br. s., 1H) 10.48 (s, 1H) 9.53 (s, 1H) 9.25 (s, 1H) 8.58 (br. s., 1H) 8.45 (d, J=5.19 Hz, 1H) 8.16 (s, 1H) 8.04 (d, J=8.85 Hz, 1H) 7.86 (d, J=8.85 Hz, 1H) 7.65 (d, J=7.63 Hz, 2H) 7.43-7.58 (m, 3H) 7.32 (d, J=5.19 Hz, 1H). MS (ESI) (m/z): 437.3 (M+H)⁺.

Synthesis of Amine M

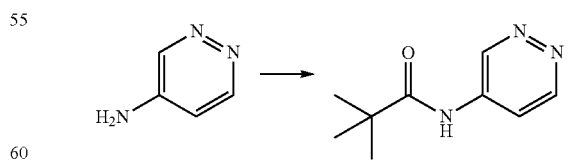

N-(Pyridazin-4-yl)pivalamide

This compound was prepared as reported in literature (Haider, N. and Schuller, H. J. Heterocyclic Chemistry 1995, 32, 841) and showed the reported spectral characteristics.

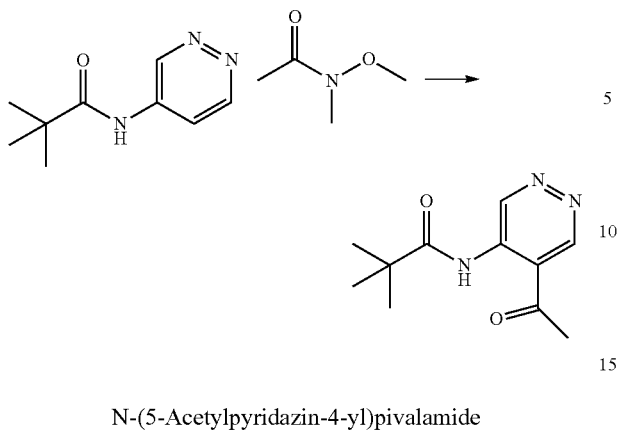

N-(5-Acetylpyridazin-4-yl)pivalamide

To 10 mL of anhydrous THF under argon at −40° C. (dry ice-MeCN bath) was added n-BuLi (1.6M, 3 mL). To this was added dropwise 2,2,6,6-Tetramethylpiperidine (0.682 g, 4.83 mmol) via a syringe with stirring. After addition the pale yellow solution was warmed up to 0° C. in about 10 min and then allowed to stir at this temperature for another 25 min. At the end, the yellow solution was cooled down in a dry ice-2-propanol bath. N-(Pyridazin-4-yl)pivalamide (214 mg, 1.194 mmol) was dissolved in 7 mL anhydrous THF and the solution was added dropwise via syringe to the LiTMP generated during 5 min. The dark solution was stirred at −77° C. for 2 h. At the end N-methoxy-N-methylacetamide (0.51 mL, 4.8 mmol) was added in a thin stream in 3 min to the reaction mixture and the reaction was continued at the same temperature. After 2 h a mixture of 4.8 mL of 1N HCl and 4.8 mL of ethanol were added to the reaction mixture and the pale brown suspension was stirred for 10 min at −77° C. and then stored at −22° C. for ~18 h. The reaction mixture was brought up to ambient temperature. Volatiles were evaporated in vacuo. The residue taken in 60 mL EtOAC was washed with satd. aq. NaHCO3 (40 mL) and then with water (2×50 mL). Organic layer was dried (Na2SO4) and evaporated in vacuo to give the crude product (206 mg, 87% pure, 78% yield). The crude product thus obtained was purified by prep HPLC (Waters XTERRA 30×200 mm, A=90% H$_2$O/10% MeOH, B=90% MeOH/10% H$_2$O, Modifier 0.1% TFA, 0.00 min=20% B, 15 min=100% B, 20.0 min=100% B, Flow rate=40 mL/min.). Fractions corresponding to the peak with $t_R$=9.5 min were combined and evaporated in vacuo to give the required product as the TFA salt (215 mg, 54%): MS (ESI) (m/z): 222 (M+H)$^+$; $^1$H NMR (400 MHz, METHANOL-d$_4$) δ 10.59 (s, 1H), 9.73 (s, 1H), 2.82 (s, 3H), 1.39 (s, 9H).

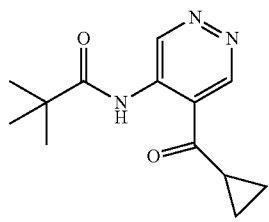 [SMILES: CC(C)(C)C(=O)Nc1cnncc1C(=O)C1CC1]

N-(5-(Cyclopropanecarbonyl)pyridazin-4-yl)pivalamide

This compound was prepared in 31% yield and isolated after purification as TFA salt from N-(Pyridazin-4-yl)pivalamide (214 mg, 1.194 mmol) following the same procedure used for the synthesis of N-(5-Acetylpyridazin-4-yl)pivalamide. LC-MS (Phenomenex C18 (3 um) 2×50 mm, A=90% H$_2$O/10% MeOH, B=90% MeOH/10% H$_2$O, Modifier 0.1% TFA, 0.00 min=0% B, 4.0 min=100% B, 5.0 min=100% B, Flow rate=0.8 mL/min) $t_R$=3.2 min, MS (ESI) (m/z): 248 (M+H)$^+$; $^1$H NMR (400 MHz, METHANOL-d$_4$) δ 10.59 (s, 1H), 9.97 (s, 1H), 3.08-2.90 (m, 1H), 1.40-1.31 (m, 13H).

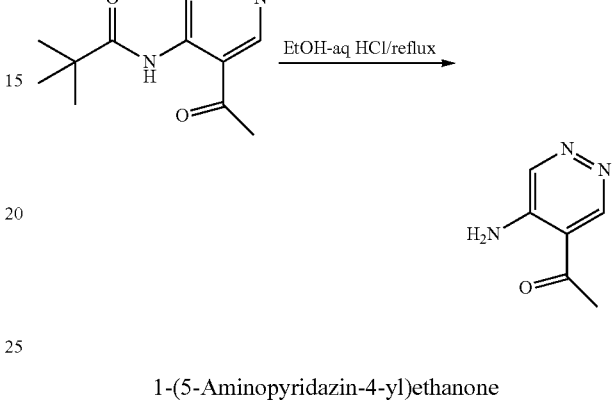

1-(5-Aminopyridazin-4-yl)ethanone

An amber colored solution of pivalamide (215 mg, 0.56 mmol) in a mixture of EtOH (1.5 mL) and water (0.62 mL) was combined with hydrochloric acid (0.93 mL, 11.2 mmol) and was refluxed for ~18 h. At the end, the ethanol was evaporated in vacuo and the remaining aq. solution was carefully basified with conc. NH4OH and then evaporated in vacuo. The residue was triturated with MeOH:DCM (1:9, 15 mL) and filtered. The filtrate was evaporated in vacuo. The residue was purified by silica gel chromatography on a biotage 12 g silica gel cartridge using a linear gradient of dichloromethane to 10% MeOH in dichloromethane. Fractions were pooled and evaporated in vacuo to give 56 mg (73% yield) of the aminopyridazine derivative: MS (ESI) (m/z): 138 (M+H)$^+$; $^1$H NMR (400 MHz, METHANOL-d$_4$) δ 9.00 (s, 1H), 8.72 (s, 1H), 2.62 (s, 3H).

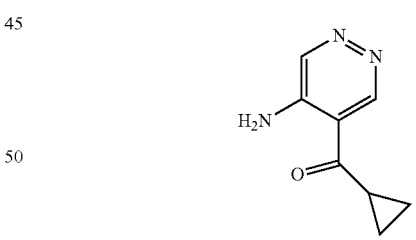

(5-Aminopyridazin-4-yl)(cyclopropyl)methanone tert-Butyl pyridazin-4-ylcarbamate (98 mg, 0.37 mmol) was dissolved in 20% TFA in DCM (7 mL) and stored at ambient temperature overnight. After ~19 h volatiles were evaporated, the residue coevaporated with DCM (15 mL) and then dried in vacuo. The crude product thus obtained was dissolved in 15 mL ethanol and stirred with BioRad AG-X2 resin (100-200 mesh, 2-2.5 m equiv/g) hydroxide form (2.4 g wet resin, ~30% water). After stirring for 10 min, the suspension was filtered, washed with 30 mL more ethanol. The solution of the free base thus obtained was evaporated in vacuo to dryness to give the desired product (71.3 mg, 83% purity, 97% yield). LC-MS (Phenomenex C18 2×50 mm (3 um) A=95% H₂O/5% ACN, B=95% ACN/5% H₂O, Modifier 10 mM NH₄OAc, 0.00 min=0% B, 4 min=100% B 5 min=100% B, Flow rate=0.8 mL/min) $t_R$=1.6 min, MS (ESI) (m/z): 164 (M+H)⁺.

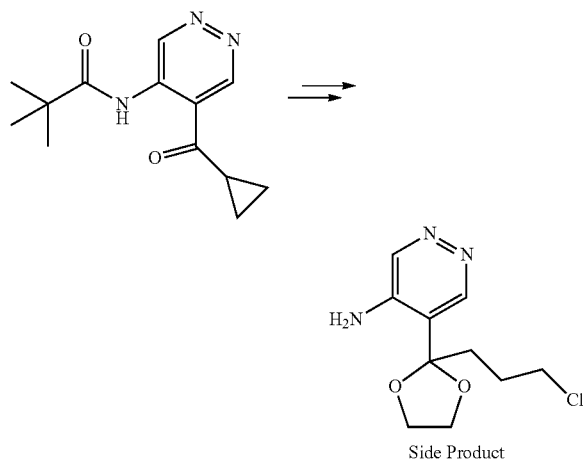

Side Product

5-(2-(3-Chloropropyl)-1,3-dioxolan-2-yl)pyridazin-4-amine

Hydrolysis of N-(5-(Cyclopropanecarbonyl)pyridazin-4-yl)pivalamide was carried out on 146 mg scale using conditions similar to the hydrolysis of N-(5-Acetylpyridazin-4-yl)pivalamide. The crude product was purified by silica gel chromatography on a biotage 12 g silica gel cartridge using a linear gradient of dichloromethane to 10% MeOH in dichloromethane. The major product isolated was: 1-(5-aminopyridazin-4-yl)-4-chlorobutan-1-one (85 mg, 87% pure, 41% yield). MS (ESI) (m/z): 200, 202 (Cl pattern) (M+H)⁺. ¹H NMR (400 MHz, METHANOL-d₄) δ 9.04 (s, 1H), 8.73 (s, 1H), 3.70 (t, J=6.6 Hz, 2H), 3.23 (t, J=7.0 Hz, 2H), 2.19 (m, 2H). This product was ketalized with ethylene glycol using the literature procedure (Fieser, L. F. and Stevenson, R. JACS 1954, 76, 1728-1733) with the exception that dichloroethane was used as solvent instead of acetic acid: MS (ESI) (m/z): 244 (M+H)⁺; ¹H NMR (400 MHz, METHANOL-d₄) δ 8.53 (s, 1H), 8.51 (s, 1H), 4.19-4.08 (m, 2H), 3.89-3.84 (m, 2H), 3.60 (t, J=6.6 Hz, 2H), 2.11-2.05 (m, 2H), 1.94-1.85 (m, 2H).

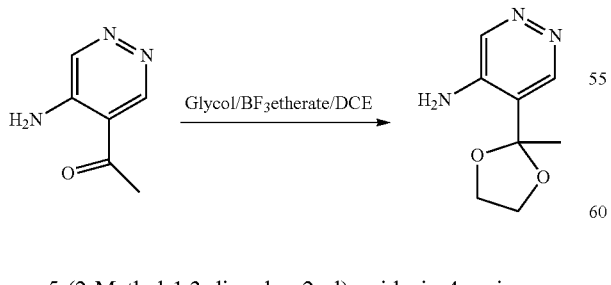

5-(2-Methyl-1,3-dioxolan-2-yl)pyridazin-4-amine

This compound was prepared in 64% yield on a 16 mg scale following the BF₃ etherate method for ketalization that was described before. MS (ESI) (m/z): 182 (M+H)⁺; ¹H NMR (400 MHz, METHANOL-d₄) δ 8.54 (s, 1H), 8.53 (s, 1H), 4.20-4.03 (m, 2H), 3.90-3.74 (m, 2H), 1.64 (s, 3H).

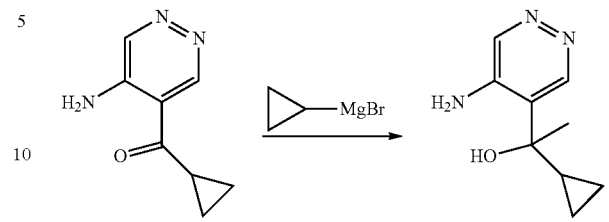

1-(5-Aminopyridazin-4-yl)-1-cyclopropylethanol

MS (ESI) (m/z): 180 (M+H)⁺; ¹H NMR (400 MHz, METHANOL-d₄) δ 8.69 (s, 1H), 8.48 (s, 1H), 1.51 (s, 3H), 1.42-1.33 (m, 1H), 0.70-0.40 (m, 4H).

Example 200

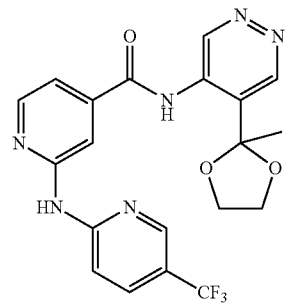 [SMILES: CC1(c2cnncc2NC(=O)c2ccnc(Nc3ccc(C(F)(F)F)cn3)c2)OCCO1]

N-(5-(2-Methyl-1,3-dioxolan-2-yl)pyridazin-4-yl)-2-((5-(trifluoromethyl)pyridin-2-yl)amino)isonicotinamide Followed synthesis of example 4. MS (ESI) (m/z): 447 (M+H)⁺; ¹H NMR (500 MHz, DMSO-d₆) δ 10.66 (s, 1H), 10.34 (s, 1H), 10.15 (s, 1H), 9.14 (s, 1H), 8.62 (s, 1H), 8.56 (d, J=5.2 Hz, 1H), 8.39 (s, 1H), 8.07 (d, J=8.9 Hz, 1H), 7.87 (d, J=8.9 Hz, 1H), 7.37 (d, J=5.2 Hz, 1H), 4.19-4.13 (m, 2H), 3.92-3.87 (m, 2H), 1.72 (s, 3H).

Example 201

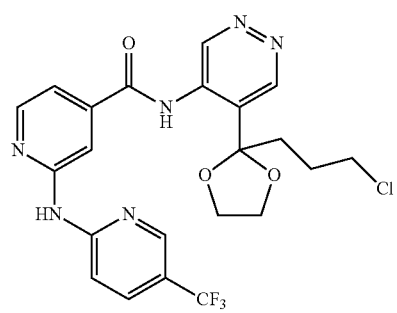 [SMILES: O=C(Nc1cnncc1C1(CCCCl)OCCO1)c1ccnc(Nc2ccc(C(F)(F)F)cn2)c1]

N-(5-(2-(3-Chloropropyl)-1,3-dioxolan-2-yl)
pyridazin-4-yl)-2-((5-(trifluoromethyl)pyridin-2-yl)
amino)isonicotinamide Followed synthesis of example 4. MS (ESI) (m/z): 509 (M+H)+; 1H NMR (500 MHz, DMSO-d6) δ 10.67 (s, 1H), 10.28 (br. s., 1H), 10.17 (s, 1H), 9.11 (s, 1H), 8.63 (s, 1H), 8.57 (d, J=5.1 Hz, 1H), 8.42 (s, 1H), 8.08 (dd, J=8.8, 2.3 Hz, 1H), 7.85 (d, J=8.8 Hz, 1H), 7.39 (dd, J=5.1, 1.5 Hz, 1H), 4.25-4.12 (m, 2H), 4.02-3.86 (m, 2H), 3.63 (t, J=6.6 Hz, 2H), 2.23-2.07 (m, 2H), 1.87-1.73 (m, 2H).

Example 202

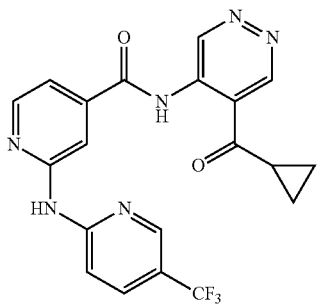 [SMILES: O=C(Nc1cnncc1C(=O)C1CC1)c1ccnc(Nc2ccc(C(F)(F)F)cn2)c1]

N-(5-(Cyclopropanecarbonyl)pyridazin-4-yl)-2-((5-(trifluoromethyl)pyridin-2-yl)amino)isonicotinamide Followed synthesis of example 4. LC-MS (Phenomenex C18 (3 um) 2×50 mm, A=90% H2O/10% MeOH, B=90% MeOH/10% H2O, Modifier 0.1% TFA, 0.00 min=0% B, 4.0 min=100% B, 5.0 min=100% B, Flow rate=0.8 mL/min.) $t_R$=3.3 min, MS (ESI) (m/z): 429 (M+H)+.

Example 203

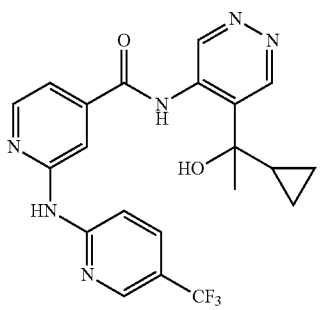 [SMILES: CC(O)(c1cnncc1NC(=O)c1ccnc(Nc2ccc(C(F)(F)F)cn2)c1)C1CC1]

N-(5-(1-Cyclopropyl-1-hydroxyethyl)pyridazin-4-yl)-2-((5-(trifluoromethyl)pyridin-2-yl)amino)isonicotinamide Followed synthesis of example 4. MS (ESI) (m/z): 445 (M+H)+; 1H NMR (500 MHz, DMSO-d6) δ 11.73 (br. s., 1H), 10.60 (s, 1H), 10.24 (s, 1H), 9.25 (s, 1H), 8.64 (s, 1H), 8.54 (d, J=5.2 Hz, 1H), 8.49 (s, 1H), 8.06 (dd, J=9.0, 2.3 Hz, 1H), 7.81 (d, J=9.2 Hz, 1H), 7.34 (dd, J=5.2, 1.2 Hz, 1H), 1.58 (s, 3H), 1.48-1.41 (m, 1H), 0.61-0.40 (m, 4H).

Synthesis of Amine N

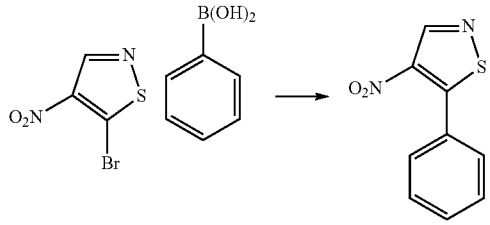

4-Nitro-5-phenylisothiazole

In a 15 mL vial was 5-bromo-4-nitroisothiazole (220 mg, 1.053 mmol), phenylboronic acid (205 mg, 1.684 mmol), and Na2CO3 (1.579 mL, 3.16 mmol) in Dioxane (3 mL) to give a slightly yellow solution under nitrogen. 1,1'-Bis (diphenylphosphino)ferrocenepalladium(II) dichloride, Toluene (43.3 mg, 0.053 mmol) was added under nitrogen. The vial was sealed and heated at 130° C. (microwave) for 2 h. LCMS showed a major new peak but no parent ion. TLC (3/1 hexane/EtOAc) showed the same spot as SM. The mixture was partitioned between water and EtOAc. The layers were separated. The organic layer was washed with brine, dried and concentrated. The residue was purified by FCC up to 30% EtOAc/hexane to afford the desired product (147 mg, 68%) as a light yellow solid: 1H NMR (400 MHz, Chloroform-d) δ 9.04 (s, 1H), 7.64-7.46 (m, 5H); 13C NMR (101 MHz, Chloroform-d) δ 166.95, 154.54, 141.23, 130.69, 128.83, 128.56, 126.10.

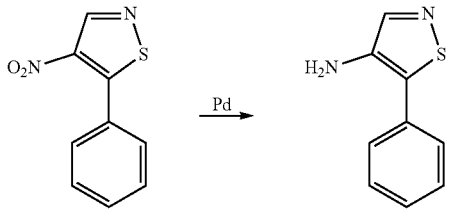

5-Phenylisothiazol-4-amine

In a 100 mL round-bottomed flask was 4-nitro-5-phenylisothiazole (147 mg, 0.713 mmol) (94149-042) in MeOH (4 mL) to give a light yellow solution. Pd/C (76 mg, 0.071 mmol) was added, and the mixture was stirred overnight under 1 atom hydrogen (balloon) (2:30 pm). After 18 h, LCMS showed complete conversion to the desired product (119 mg, 95%) as a tan solid: 1H NMR (400 MHz, Chloroform-d) δ 8.10 (s, 1H), 7.60-7.44 (m, 4H), 7.41-7.32 (m, 1H), 3.85 (s, 2H); 13C NMR (101 MHz, Chloroform-d) δ 150.87, 139.30, 138.42, 130.39, 129.01, 127.89, 127.13.

Example 204

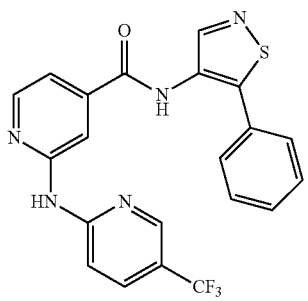 [SMILES: O=C(Nc1cnsc1-c1ccccc1)c1ccnc(Nc2ccc(C(F)(F)F)cn2)c1]

N-(5-Phenylisothiazol-4-yl)-2-((5-(trifluoromethyl)pyridin-2-yl)amino)isonicotinamide Followed synthesis of example 4. MS (ESI) (m/z): 442 (M+H)+; 1H NMR (500 MHz, DMSO-d6) δ 10.55 (s, 1H), 10.51 (s, 1H), 8.78 (s, 1H), 8.61 (d, J=2.3 Hz, 1H), 8.48 (d, J=5.2 Hz, 1H), 8.24 (s, 1H), 8.06 (dd, J=9.0, 2.6 Hz, 1H), 7.91 (d, J=8.9 Hz, 1H), 7.72-7.63 (m, 2H), 7.59-7.52 (m, 2H), 7.52-7.46 (m, 1H), 7.44 (dd, J=5.2, 1.5 Hz, 1H).

Example 205

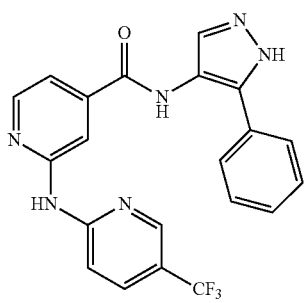

N-(5-Phenyl-1H-pyrazol-4-yl)-2-((5-(trifluoromethyl)pyridin-2-yl)amino)isonicotinamide Followed synthesis of example 4. MS (ESI) (m/z): 425.3 (M+H)+.

Synthesis of Amine P

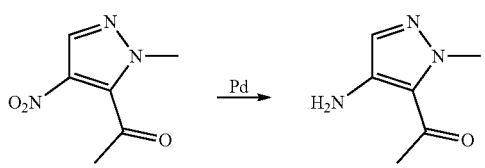

1-(4-Amino-1-methyl-1H-pyrazol-5-yl)ethanone

In a 250 mL round-bottomed flask was 1-(1-methyl-4-nitro-1H-pyrazol-5-yl)ethanone (77.8 mg, 0.460 mmol) and Pd/C (49.0 mg, 0.046 mmol) in MeOH (4 mL) to give a black suspension. The mixture was stirred under 1 atm hydrogen (balloon) for 1 h. LCMS showed good conversion to the desired product (M+H=140.1). It was filtered, washed with MeOH and concentrated to the desired product (63.1 mg, 99%) as a gray solid.

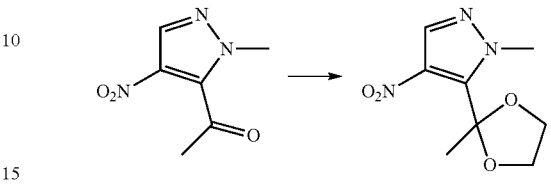

1-Methyl-5-(2-methyl-1,3-dioxolan-2-yl)-4-nitro-1H-pyrazole

In a 100 mL round-bottomed flask was 1-(1-methyl-4-nitro-1H-pyrazol-5-yl)ethanone (340 mg, 2.010 mmol), Ts-OH (191 mg, 1.005 mmol), and Glycol (500 µl, 8.97 mmol) in Toluene (10 mL) to give a colorless suspension. The mixture was heated at 110° C. for 2 h. TLC (1/1 EtOAc/hexane) showed around 1/3 conversion to a slightly more polar spot. The reaction continued for another 18 h. TLC showed a little SM left. It was concentrated in vacuo and the residue was purified by FCC up to 70% EtOAc/hexane to afford the desired product (339 mg, 79%) as a white solid: 1H NMR (400 MHz, Chloroform-d) δ 7.96 (s, 1H), 4.16-4.10 (m, 2H), 4.06 (s, 3H), 3.84-3.78 (m, 2H), 1.92 (s, 3H). 55 mg (16%) starting material was also recovered.

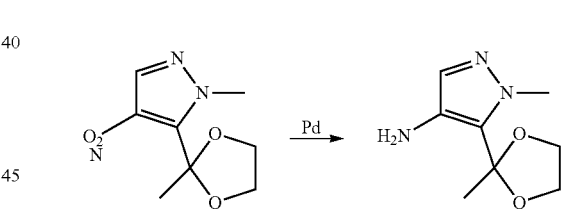

1-Methyl-5-(2-methyl-1,3-dioxolan-2-yl)-1H-pyrazol-4-amine

In a 250 mL round-bottomed flask was 1-methyl-5-(2-methyl-1,3-dioxolan-2-yl)-4-nitro-1H-pyrazole (226 mg, 1.060 mmol) and Pd/C (113 mg, 0.106 mmol) in MeOH (6 mL) to give a black suspension. The mixture was stirred under 1 atm hydrogen (balloon) for 2 h. LCMS showed complete conversion. It was filtered, washed with MeOH and concentrated to the desired product (194 mg, 100%) as a tan solid: 1H NMR (400 MHz, Chloroform-d) δ 6.92 (s, 1H), 4.01 (tt, J=5.9, 2.6 Hz, 2H), 3.80 (dd, J=5.8, 2.1 Hz, 2H), 3.77 (s, 3H), 3.37 (s, 2H), 1.62 (s, 3H).

Example 206

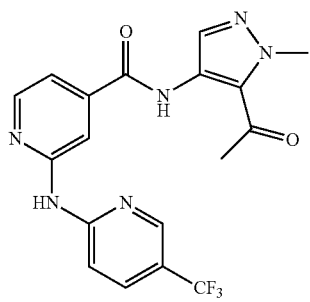 [SMILES: CC(=O)c1c(NC(=O)c2ccnc(Nc3ccc(C(F)(F)F)cn3)c2)cnn1C]

N-(5-Acetyl-1-methyl-1H-pyrazol-4-yl)-2-((5-(trifluoromethyl)pyridin-2-yl)amino)isonicotinamide Followed synthesis of example 4. MS (ESI) (m/z): 405 (M+H)$^+$; $^1$H NMR (500 MHz, DMSO-d6) δ 10.55 (s, 1H), 10.48 (s, 1H), 8.63 (s, 1H), 8.51 (d, J=5.1 Hz, 1H), 8.32 (s, 1H), 8.06 (d, J=9.1 Hz, 1H), 7.91 (d, J=8.9 Hz, 1H), 7.85 (d, J=2.4 Hz, 1H), 7.42 (d, J=5.2 Hz, 1H), 4.08 (s, 3H), 2.58 (s, 3H).

Example 207

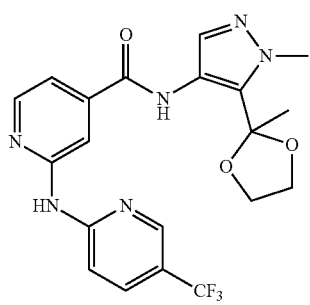 [SMILES: Cn1ncc(NC(=O)c2ccnc(Nc3ccc(C(F)(F)F)cn3)c2)c1C1(C)OCCO1]

N-(1-Methyl-5-(2-methyl-1,3-dioxolan-2-yl)-1H-pyrazol-4-yl)-2-((5-(trifluoromethyl)pyridin-2-yl)amino)isonicotinamide MS (ESI) (m/z): 449 (M+H)$^+$; $^1$H NMR (500 MHz, DMSO-d6) δ 10.54 (s, 1H), 9.52 (s, 1H), 8.64-8.56 (m, 1H), 8.47 (d, J=5.1 Hz, 1H), 8.23 (s, 1H), 8.04 (dd, J=8.9, 2.6 Hz, 1H), 7.92 (d, J=8.9 Hz, 1H), 7.78 (s, 1H), 7.33 (dd, J=5.2, 1.6 Hz, 1H), 4.14-4.04 (m, 2H), 3.88 (s, 3H), 3.85-3.78 (m, 2H), 1.73 (s, 3H).

Example 208

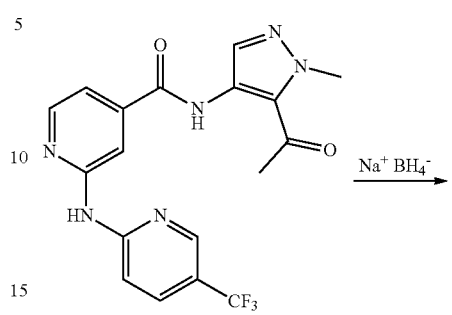

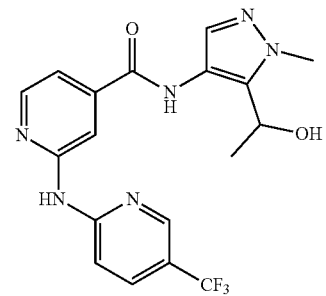

N-(5-(1-Hydroxyethyl)-1-methyl-1H-pyrazol-4-yl)-2-((5-(trifluoromethyl)pyridin-2-yl)amino)isonicotinamide In a 5 mL vial was N-(5-acetyl-1-methyl-1H-pyrazol-4-yl)-2-((5-(trifluoromethyl)pyridin-2-yl)amino)isonicotinamide (21.6 mg, 0.053 mmol) in MeOH (0.5 mL) to give a yellow suspension. NaBH4 (8.08 mg, 0.214 mmol) was added. The vial was sealed and the mixture was stirred at rt for 110 min. LCMS showed good conversion to the desired product. The suspension was dissolved in DMF and purified by prep-HPLC (10 mg, 45%): MS (ESI) (m/z): 407 (M+H)$^+$; $^1$H NMR (500 MHz, DMSO-d6) δ 10.50 (s, 1H), 9.89 (s, 1H), 8.63 (s, 1H), 8.46 (t, J=5.1 Hz, 1H), 8.24 (d, J=4.5 Hz, 1H), 8.10-8.02 (m, 1H), 7.96-7.86 (m, 1H), 7.64 (d, J=4.7 Hz, 1H), 7.37 (d, J=5.6 Hz, 1H), 5.72 (t, J=4.4 Hz, 1H), 5.07 (dd, J=7.4, 4.2 Hz, 1H), 3.87 (s, 3H), 1.46 (d, J=6.2 Hz, 3H).

Example 209

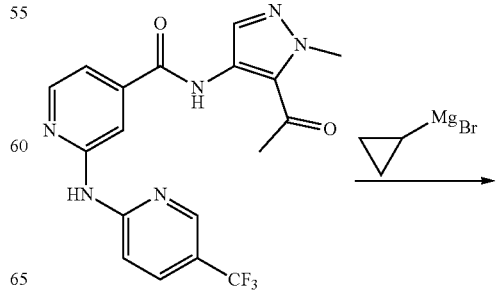

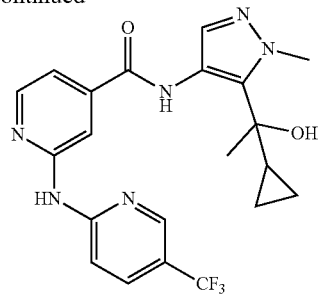

N-(5-(1-Cyclopropyl-1-hydroxyethyl)-1-methyl-1H-pyrazol-4-yl)-2-((5-(trifluoromethyl)pyridin-2-yl)amino)isonicotinamide In a 5 mL vial was N-(5-acetyl-1-methyl-1H-pyrazol-4-yl)-2-((5-(trifluoromethyl)pyridin-2-yl)amino)isonicotinamide (28.4 mg, 0.070 mmol) in Tetrahydrofuran (0.3 mL) to give a yellow suspension. Cyclopropylmagnesium bromide (0.421 mL, 0.211 mmol) was added. The vial was sealed and the resulted red solution was stirred at rt. After 30 min, LCMS showed 30~40% conversion to the desired product (M+H=447.0). Another 1 equiv. of cyclopropylmagnesium bromide was added and the reaction continued. After 3 h, LCMS showed very little improvement. The reaction mixture was diluted with EtOAc and quenched with 3 ml 0.5 N HCl. The layers were separated. The organic layer was washed with water, brine, dried and concentrated to a tan oil, which was dissolved in DMF/MeOH and purified by prep-HPLC: (7.1 mg, 22%, 8.3 mg SM recovered: 51% bosm): MS (ESI) (m/z): 447 (M+H)$^+$; $^1$H NMR (500 MHz, DMSO-d6) δ 10.52 (s, 1H), 10.07 (s, 1H), 8.68-8.57 (m, 1H), 8.46 (d, J=5.2 Hz, 1H), 8.28 (s, 1H), 8.06 (dd, J=9.1, 2.7 Hz, 1H), 7.87 (d, J=8.8 Hz, 1H), 7.71 (s, 1H), 7.31 (d, J=5.2 Hz, 1H), 5.68 (s, 1H), 3.97 (s, 3H), 1.57 (s, 3H), 1.42 (dd, J=9.7, 4.3 Hz, 1H), 0.52 (ddq, J=13.0, 8.9, 4.1 Hz, 2H), 0.43 (dd, J=8.9, 4.3 Hz, 1H), 0.39-0.32 (m, 1H).

Example 210

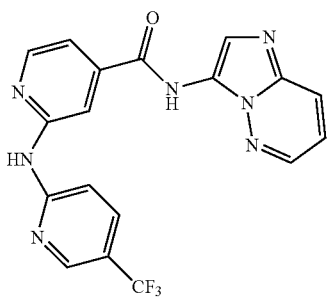 [SMILES: O=C(Nc1cnc2cccnn12)c1ccnc(Nc2ccc(C(F)(F)F)cn2)c1]

N-(Imidazo[1,2-b]pyridazin-3-yl)-2-((5-(trifluoromethyl)pyridin-2-yl)amino)isonicotinamide Followed synthesis of example 4. $^1$H NMR (500 MHz, DMSO-d$_6$) δ ppm 10.90 (br. s., 1H) 10.50 (s, 1H) 8.62 (s, 1H) 8.58-8.60 (m, 1H) 8.51 (d, J=5.19 Hz, 1H) 8.27 (s, 1H) 8.17 (d, J=9.46 Hz, 1H) 8.03-8.08 (m, 1H) 7.94 (d, J=8.85 Hz, 1H) 7.92 (s, 1H) 7.53 (d, J=5.19 Hz, 1H) 7.28 (dd, J=9.16, 4.27 Hz, 1H). MS (ESI) (m/z): 400.2 (M+H)$^+$.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:
1. A compound of formula I

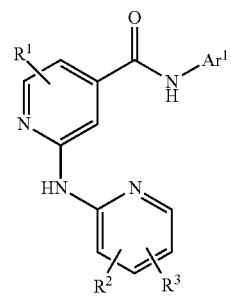

where:
R$^1$ is hydrogen, cyano, halo, alkyl, haloalkyl, alkoxy, or haloalkoxy;
R$^2$ is hydrogen, cyano, halo, alkyl, cyanoalkyl, haloalkyl, cycloalkyl, cyanocycloalkyl, (alkoxycarbonyl)alkenyl, alkoxy, haloalkoxy, alkylthio, haloalkylthio, cycloalkylthio, alkylcarbonyl, alkoxycarbonyl, aminocarbonyl, alkylsulfinyl, cycloalkylsulfinyl, phenylsulfinyl, alkyl sulfonyl, haloalkylsulfonyl, cycloalkylsulfonyl, alkylcarbonylamino, morpholinyl, SO$_2$N(R$^4$)(R$^5$);
R$^3$ is hydrogen, cyano, halo, alkyl, haloalkyl, alkoxy, or haloalkoxy;
or R$^2$ and R$^3$ taken together is —CH═CH—CH═CH—;
R$^4$ is hydrogen or alkyl;
R$^5$ is hydrogen or alkyl;
or N(R$^4$)(R$^5$) taken together is azetidinyl, pyrrolidinyl, piperidinyl, piperazinyl, morpholinyl, and is substituted with 0-4 halo or alkyl substituents;
Ar$^1$ is 3-pyridinyl, 2-pyrazinyl, 4-pyridazinyl, 4-pyrimidinyl, 4-pyrazolyl, 4-isothiazolyl, or 3-imidazopyridazinyl, and is substituted with 1 substituent selected from hydrogen, cyano, halo, alkyl, haloalkyl, hydroxyalkyl, (cycloalkyl)hydroxyalkyl, (dicycloalkyl)hydroxyalkyl, (hydroxy)haloalkyl, alkoxyalkyl, (N(R$^4$)(R$^5$))alkyl, cycloalkyl, hydroxycycloalkyl, cycloalkenyl, alkoxy, haloalkoxy, (cycloalkyl)alkoxy, ((alkyl)cycloalkyl)alkoxy, alkylcarbonyl, cycloalkylcarbonyl, tetrahydrofuranyl, (alkyl)tetrahydrofuranyl, dioxolanyl, (alkyl)dioxolanyl, (cycloalkyl)dioxolanyl, (phenyl)dioxolanyl, (dialkyl)dioxolanyl, (haloalkyl)(alkyl)dioxolanyl, (trialkyl)dioxolanyl, dihydrpyranyl, tetrahydropyranyl, hydroxytetrahydropyranyl, N(R$^4$)(R$^5$), and Ar$^2$; and is also substituted with 0-1 substituent selected from hydrogen, cyano, halo, alkyl, haloalkyl, alkoxy, and haloalkoxy;

Ar² is phenyl, pyridinyl, or pyrazolyl, and is substituted with 0-3 substituents selected from the group consisting of cyano, halo, alkyl, haloalkyl, alkoxy, and haloalkoxy;

or a pharmaceutically acceptable salt thereof.

2. A compound of claim 1 where $R^1$ is hydrogen or halo.

3. A compound of claim 1 where $R^2$ is haloalkyl.

4. A compound of claim 1 where $Ar^1$ is 3-pyridinyl substituted with 1 substituent selected from hydrogen, cyano, halo, alkyl, haloalkyl, hydroxyalkyl, (cycloalkyl)hydroxyalkyl, (dicycloalkyl)hydroxyalkyl, (hydroxy)haloalkyl, alkoxyalkyl, (N(R⁴)(R⁵)alkyl, cycloalkyl, hydroxycycloalkyl, cycloalkenyl, alkoxy, haloalkoxy, (cycloalkyl)alkoxy, ((alkyl)cycloalkyl)alkoxy, alkylcarbonyl, cycloalkylcarbonyl, tetrahydrofuranyl, (alkyl)tetrahydrofuranyl, dioxolanyl, (alkyl)dioxolanyl, (cycloalkyl)dioxolanyl, (phenyl)dioxolanyl, (dialkyl)dioxolanyl, (haloalkyl)(alkyl)dioxolanyl, (trialkyl)dioxolanyl, dihydrpyranyl, tetrahydropyranyl, hydroxytetrahydropyranyl, $N(R^4)(R^5)$, and Ar²; and is also substituted with 0-1 substituent selected from hydrogen, cyano, halo, alkyl, haloalkyl, alkoxy, and haloalkoxy.

5. A compound of claim 1 where is phenyl substituted with 0-3 substituents selected from the group consisting of cyano, halo, alkyl, haloalkyl, alkoxy, and haloalkoxy.

6. A pharmaceutical composition comprising a compound of claim 1 or a pharmaceutically acceptable salt thereof and a pharmaceutically acceptable carrier.

\* \* \* \* \*

UNITED STATES PATENT AND TRADEMARK OFFICE
CERTIFICATE OF CORRECTION

PATENT NO. : 9,718,804 B2  
APPLICATION NO. : 15/033813  
DATED : August 1, 2017  
INVENTOR(S) : Luo et al.

Page 1 of 1

It is certified that error appears in the above-identified patent and that said Letters Patent is hereby corrected as shown below:

On the Title Page

Column 2, Line 4, Other Publications:  
Delete "2-amkinothiazole" and insert -- 2-aminothiazole --.

In the Claims

Claim 1, Column 212, Lines 39-40:  
Delete "alkyl sulfonyl," and insert -- alkylsulfonyl, --.

Claim 1, Column 212, Line 63:  
Delete "dihydrpyranyl," and insert -- dihydropyranyl, --.

Claim 4, Column 213, Line 12:  
Delete "(N($R^4$)($R^5$)alkyl," and insert -- (N($R^4$)($R^5$))alkyl, --.

Claim 4, Column 213, Line 18:  
Delete "dihydrpyranyl," and insert -- dihydropyranyl, --.

Claim 5, Column 213, Line 23:  
Delete "where is phenyl" and insert -- where phenyl is --.

Signed and Sealed this  
Ninth Day of October, 2018

Andrei Iancu  
*Director of the United States Patent and Trademark Office*